US012215322B2

(12) United States Patent
Lotta et al.

(10) Patent No.: US 12,215,322 B2
(45) Date of Patent: Feb. 4, 2025

(54) TREATMENT OF LIVER DISEASE WITH MITOCHONDRIAL GLYCEROL-3-PHOSPHATE ACYLTRANSFERASE (GPAM) INHIBITORS

(71) Applicant: Regeneron Pharmaceuticals, Inc., Tarrytown, NY (US)

(72) Inventors: Luca Andrea Lotta, Tarrytown, NY (US); Niek Verweij, Tarrytown, NY (US); Colm O'Dushlaine, Tarrytown, NY (US); Jonathan Marchini, Tarrytown, NY (US); Aris Baras, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 3 days.

(21) Appl. No.: 17/680,940

(22) Filed: Feb. 25, 2022

(65) Prior Publication Data

US 2022/0307032 A1 Sep. 29, 2022

Related U.S. Application Data

(60) Provisional application No. 63/154,693, filed on Feb. 27, 2021.

(51) Int. Cl.

| | |
|---|---|
| ***C12N 15/11*** | (2006.01) |
| ***A61K 31/7088*** | (2006.01) |
| ***A61K 38/46*** | (2006.01) |
| ***A61P 1/16*** | (2006.01) |
| ***C12N 15/113*** | (2010.01) |
| ***C12Q 1/6883*** | (2018.01) |
| *C12Q 1/6827* | (2018.01) |
| *C12Q 1/6874* | (2018.01) |

(52) U.S. Cl.

CPC ...... *C12N 15/1137* (2013.01); *A61K 31/7088* (2013.01); *A61K 38/465* (2013.01); *A61P 1/16* (2018.01); *C12Q 1/6883* (2013.01); *C12N 2310/14* (2013.01); *C12N 2310/531* (2013.01); *C12Q 1/6827* (2013.01); *C12Q 1/6874* (2013.01); *C12Q 2600/156* (2013.01); *C12Q 2600/158* (2013.01)

(58) Field of Classification Search

CPC .... C12N 15/1137; C12N 2310/14; A61P 1/16

See application file for complete search history.

(56) References Cited

FOREIGN PATENT DOCUMENTS

| | | |
|---|---|---|
| WO | 2010000656 | 1/2010 |
| WO | 2019165232 | 8/2019 |
| WO | 2021252649 | 12/2021 |

OTHER PUBLICATIONS

Clemens et al., "The inhibitor of glycerol 3-phosphate acyltransferase FSG67 blunts liver regeneration after acetaminophen overdose by altering GSK3[beta] and Wnt/[beta]-catenin signaling", Food and Chemical Toxicology, 2019, 125, pp. 279-288.

International Search Report and Written Opinion mailed May 30, 2022 for International Patent Application No. PCT/US2022/017899.

*Primary Examiner* — Ekaterina Poliakova-Georgantas

(74) *Attorney, Agent, or Firm* — Armstrong Teasdale LLP

(57) ABSTRACT

The present disclosure provides methods of treating subjects having liver disease, and methods of identifying subjects having an increased risk of developing liver disease.

3 Claims, No Drawings

Specification includes a Sequence Listing.

TREATMENT OF LIVER DISEASE WITH MITOCHONDRIAL GLYCEROL-3-PHOSPHATE ACYLTRANSFERASE (GPAM) INHIBITORS

REFERENCE TO SEQUENCE LISTING

This application includes a Sequence Listing submitted electronically as a text file named 18923805801SEQ, created on Feb. 22, 2022, with a size of 269 kilobytes. The Sequence Listing is incorporated herein by reference.

FIELD

The present disclosure relates generally to the treatment of subjects having liver disease with Mitochondrial Glycerol-3-Phosphate Acyltransferase (GPAM) inhibitors, and methods of identifying subjects having an increased risk of developing liver disease.

BACKGROUND

Chronic liver disease and cirrhosis are leading causes of morbidity and mortality in the United States accounting for 38,170 deaths (1.5% of total deaths) in 2014 (Kochanek et al., Nat'l. Vital Stat. Rep., 2016, 65, 1-122). The most common etiologies of cirrhosis in the U.S. are alcoholic liver disease, chronic hepatitis C, and nonalcoholic fatty liver disease (NAFLD), together accounting for about 80% of subjects awaiting liver transplant between 2004 and 2013 (Wong et al., Gastroenterology, 2015, 148, 547-555). The estimated prevalence of NAFLD in the U.S. is between 19 and 46 percent (Browning et al., Hepatology, 2004, 40, 1387-1395; Lazo et al., Am. J. Epidemiol., 2013, 178, 38-45; and Williams et al., Gastroenterology, 2011, 140, 124-131) and is rising over time (Younossi et al., Clin. Gastroenterol. Hepatol., 2011, 9, 524-530), likely in conjunction with increased rates of obesity, its primary risk factor (Cohen et al., Science, 2011, 332, 1519-1523). While significant advances have been made in the treatment of hepatitis C, there are currently no evidence-based treatments for alcoholic or nonalcoholic liver disease and cirrhosis.

Mitochondrial glycerol-3-phosphate acyltransferase (GPAM) is a member of protein family (pfam) 01553 family of glycerolipid acyltransferases located in the outer mitochondrial membrane. GPAM uses saturated fatty acids as its substrate for the synthesis of glycerolipids. GPAM esterifies the acyl-group from acyl-ACP to the sn-1 position of glycerol-3-phosphate, an essential step in glycerolipid biosynthesis, and the first essential step in triacylglycerols (TAG) synthesis. This metabolic pathway's first step is catalyzed by the encoded enzyme. GPAM is most highly expressed in liver and adipose tissue, but is also present in many other tissues including brain, kidney, heart, and adrenal gland.

SUMMARY

The present disclosure provides methods of treating a subject having liver disease or having a risk of developing liver disease, the methods comprising administering a GPAM inhibitor to the subject.

The present disclosure also provides methods of treating a subject having fatty liver disease or liver fat or having a risk of developing fatty liver disease or liver fat, the methods comprising administering a GPAM inhibitor to the subject.

The present disclosure also provides methods of treating a subject having hepatocellular carcinoma or having a risk of developing hepatocellular carcinoma, the methods comprising administering a GPAM inhibitor to the subject.

The present disclosure also provides methods of treating a subject having liver cirrhosis or having a risk of developing liver cirrhosis, the methods comprising administering a GPAM inhibitor to the subject.

The present disclosure also provides methods of treating a subject having liver fibrosis or having a risk of developing liver fibrosis, the methods comprising administering a GPAM inhibitor to the subject.

The present disclosure also provides methods of treating a subject having simple steatosis, steatohepatitis, or nonalcoholic steatohepatitis (NASH) or having a risk of developing simple steatosis, steatohepatitis, or NASH, the methods comprising administering a GPAM inhibitor to the subject.

The present disclosure also provides methods of treating a subject with a therapeutic agent that treats or inhibits liver disease, wherein the subject is suffering from liver disease, the methods comprising the steps of: determining whether the subject has a GPAM predicted loss-of-function variant nucleic acid molecule encoding a human GPAM polypeptide by: obtaining or having obtained a biological sample from the subject; and performing or having performed a sequence analysis on the biological sample to determine if the subject has a genotype comprising the GPAM predicted loss-of-function variant nucleic acid molecule; and when the subject is GPAM reference, then administering or continuing to administer to the subject the therapeutic agent that treats or inhibits liver disease in a standard dosage amount, and administering to the subject a GPAM inhibitor; and when the subject is heterozygous for a GPAM predicted loss-of-function variant, then administering or continuing to administer to the subject the therapeutic agent that treats or inhibits liver disease in an amount that is the same as or lower than a standard dosage amount, and administering to the subject a GPAM inhibitor; wherein the presence of a genotype having the GPAM predicted loss-of-function variant nucleic acid molecule encoding the human GPAM polypeptide indicates the subject has a reduced risk of developing liver disease.

The present disclosure also provides methods of identifying a subject having an increased risk for developing liver disease, wherein the methods comprise: determining or having determined the presence or absence of a glycerol-3-phosphate acyltransferase (GPAM) predicted loss-of-function variant nucleic acid molecule encoding a human GPAM polypeptide in a biological sample obtained from the subject; wherein: when the subject is GPAM reference, then the subject has an increased risk for developing liver disease; and when the subject is heterozygous or homozygous for a GPAM predicted loss-of-function variant, then the subject has a decreased risk for developing liver disease.

The present disclosure also provides therapeutic agents that treat or inhibit liver disease for use in the treatment of liver disease in a subject having: a genomic nucleic acid molecule having a nucleotide sequence encoding a human GPAM polypeptide, wherein the nucleotide sequence comprises a guanine at a position corresponding to position 3,195 according to SEQ ID NO:2, or the complement thereof; an mRNA molecule having a nucleotide sequence encoding a human GPAM polypeptide, wherein the nucleotide sequence comprises a guanine at a position corresponding to: position 327 according to SEQ ID NO:9, or the complement thereof; position 291 according to SEQ ID NO:10, or the complement thereof; position 323 according to SEQ ID NO:11, or the complement thereof; position 326 according to SEQ ID NO:12, or the complement thereof; position 305 according to SEQ ID NO:13, or the complement thereof; or position 170 according to SEQ ID NO:14, or the complement thereof; or a cDNA molecule having a nucleotide sequence encoding a human GPAM polypeptide, wherein the nucleotide sequence comprises a guanine at a position corresponding to: position 327 according to SEQ ID NO:21, or the complement thereof; position 291 according to SEQ ID NO:22, or the complement thereof; position 323 according to SEQ ID NO:23, or the complement thereof; position 326 according to SEQ ID NO:24, or the complement thereof; position 305 according to SEQ ID NO:25, or the complement thereof; or position 170 according to SEQ ID NO:26, or the complement thereof.

The present disclosure also provides GPAM inhibitors for use in the treatment of liver disease in a subject having: a genomic nucleic acid molecule having a nucleotide sequence encoding a human GPAM polypeptide, wherein the nucleotide sequence comprises a guanine at a position corresponding to position 3,195 according to SEQ ID NO:2, or the complement thereof; an mRNA molecule having a nucleotide sequence encoding a human GPAM polypeptide, wherein the nucleotide sequence comprises a guanine at a position corresponding to: position 327 according to SEQ ID NO:9, or the complement thereof; position 291 according to SEQ ID NO:10, or the complement thereof; position 323 according to SEQ ID NO:11, or the complement thereof; position 326 according to SEQ ID NO:12, or the complement thereof; position 305 according to SEQ ID NO:13, or the complement thereof; or position 170 according to SEQ ID NO:14, or the complement thereof; or a cDNA molecule having a nucleotide sequence encoding a human GPAM polypeptide, wherein the nucleotide sequence comprises a guanine at a position corresponding to: position 327 according to SEQ ID NO:21, or the complement thereof; position 291 according to SEQ ID NO:22, or the complement thereof; position 323 according to SEQ ID NO:23, or the complement thereof; position 326 according to SEQ ID NO:24, or the complement thereof; position 305 according to SEQ ID NO:25, or the complement thereof; or position 170 according to SEQ ID NO:26, or the complement thereof.

DESCRIPTION

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the term "isolated", in regard to a nucleic acid molecule or a polypeptide, means that the nucleic acid molecule or polypeptide is in a condition other than its native environment, such as apart from blood and/or animal tissue. In some embodiments, an isolated nucleic acid molecule or polypeptide is substantially free of other nucleic acid molecules or other polypeptides, particularly other nucleic acid molecules or polypeptides of animal origin. In some embodiments, the nucleic acid molecule or polypeptide can be in a highly purified form, i.e., greater than 95% pure or greater than 99% pure. When used in this context, the term "isolated" does not exclude the presence of the same nucleic acid molecule or polypeptide in alternative physical forms, such as dimers or alternatively phosphorylated or derivatized forms.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human. In some embodiments, the human is a patient under the care of a physician.

A common missense variant in the GPAM gene associated with a decreased risk of developing liver disease in human subjects has been identified in accordance with the present disclosure. For example, a genetic alteration that changes the adenine nucleotide of position 3,195 in the human GPAM reference (see, SEQ ID NO:1) to guanine has been observed to indicate that the human having such an alteration may have a decreased risk of developing liver disease. Altogether, the genetic analyses described herein surprisingly indicate that the GPAM gene and, in particular, a variant in the GPAM gene, associates with a decreased risk of developing liver disease. Therefore, subjects that are GPAM reference that have an increased risk of developing liver disease (such as, for example, fatty liver disease (including alcoholic fatty liver disease (AFLD) and NAFLD), hepatocellular carcinoma, liver cirrhosis, liver fibrosis, simple steatosis, steatohepatitis, non-alcoholic steatohepatitis (NASH), and parenchymal liver disease) may be treated such that liver disease is prevented, the symptoms thereof are reduced, and/or development of symptoms is repressed. Accordingly, the present disclosure provides methods of leveraging the identification of such variants in subjects to identify or stratify risk in such subjects of developing liver disease, or to diagnose subjects as having an increased risk of developing liver disease, such that subjects at risk or subjects with active disease may be treated accordingly.

It has been further observed in accordance with the present disclosure that an aggregate burden of certain GPAM variants associate with a lower risk of developing liver disease (such as, for example, fatty liver disease (including AFLD and NAFLD), hepatocellular carcinoma, liver cirrhosis, liver fibrosis, simple steatosis, steatohepatitis, non-alcoholic steatohepatitis (NASH), and parenchymal liver disease). Therefore, it is believed that humans having liver disease may be treated with molecules that inhibit GPAM. Accordingly, the present disclosure provides methods for leveraging the identification of such variants, and an aggregation burden of having such variants, in subjects to identify or stratify risk in such subjects of developing liver disease, or to diagnose subjects as having liver disease, such that subjects at risk or subjects with active disease may be treated.

For purposes of the present disclosure, any particular human can be categorized as having one of three GPAM genotypes: i) GPAM reference; ii) heterozygous for a GPAM predicted loss-of-function variant; or iii) homozygous for a GPAM predicted loss-of-function variant. A human is GPAM reference when the human does not have a copy of a GPAM predicted loss-of-function variant nucleic acid molecule. A human is heterozygous for a GPAM predicted loss-of-function variant when the human has a single copy of a GPAM predicted loss-of-function variant nucleic acid molecule. A GPAM predicted loss-of-function variant nucleic acid molecule is any GPAM nucleic acid molecule (such as, a genomic nucleic acid molecule, an mRNA molecule, or a cDNA molecule) encoding a GPAM polypeptide having a partial loss-of-function, a complete loss-of-function, a predicted partial loss-of-function, or a predicted complete loss-of-function. A human who has a GPAM polypeptide having a partial loss-of-function (or predicted partial loss-of-function) is hypomorphic for GPAM. The GPAM predicted loss-of-function variant nucleic acid molecule can be any nucleic acid molecule encoding GPAM Ile43Val. GPAM Ile43Val is believed to be at least a partial predicted loss-of-function variant. A human is homozygous for a GPAM predicted loss-of-function variant when the human has two copies of a GPAM predicted loss-of-function variant nucleic acid molecule.

For subjects that are genotyped or determined to be GPAM reference, such subjects have an increased risk of developing liver disease (such as, for example, fatty liver disease (including AFLD and NAFLD), hepatocellular carcinoma, liver cirrhosis, liver fibrosis, simple steatosis, steatohepatitis, non-alcoholic steatohepatitis (NASH), and parenchymal liver disease). For subjects that are genotyped or determined to be either GPAM reference or heterozygous for a GPAM predicted loss-of-function variant, such subjects can be treated with a GPAM inhibitor.

In any of the embodiments described herein, the GPAM predicted loss-of-function variant nucleic acid molecule can be any GPAM nucleic acid molecule (such as, for example, genomic nucleic acid molecule, mRNA molecule, or cDNA molecule) encoding a GPAM polypeptide having a partial loss-of-function, a complete loss-of-function, a predicted partial loss-of-function, or a predicted complete loss-of-function. For example, the GPAM predicted loss-of-function variant nucleic acid molecule can be any nucleic acid molecule encoding GPAM Ile43Val. In any of the embodiments described herein, the GPAM variant nucleic acid molecule can be any GPAM nucleic acid molecule that is a missense variant nucleic acid molecule.

In any of the embodiments described herein, the GPAM predicted loss-of-function polypeptide can be any GPAM polypeptide having a partial loss-of-function, a complete loss-of-function, a predicted partial loss-of-function, or a predicted complete loss-of-function. In any of the embodiments described herein, the GPAM predicted loss-of-function polypeptide can be any of the GPAM polypeptides described herein including, for example, GPAM Ile43Val.

In any of the embodiments described herein, the liver disease is a fatty liver disease, including AFLD and NAFLD, hepatocellular carcinoma, liver cirrhosis, liver fibrosis, simple steatosis, steatohepatitis, NASH, or parenchymal liver disease. In some embodiments, the liver disease is a fatty liver disease. In some embodiments, the liver disease is AFLD. In some embodiments, the liver disease is NAFLD. In some embodiments, the liver disease is hepatocellular carcinoma. In some embodiments, the liver disease is liver cirrhosis. In some embodiments, the liver disease is liver fibrosis. In some embodiments, the liver disease is simple steatosis. In some embodiments, the liver disease is steatohepatitis. In some embodiments, the liver disease is NASH. In some embodiments, the liver disease is parenchymal liver disease.

In some embodiments, the liver disease is liver damage, deposition of liver fat, liver inflammation, toxic liver disease, immune liver disease, or elevated alanine aminotransferase (ALT). In some embodiments, the liver disease is liver damage. In some embodiments, the liver damage is measured by elevation of liver enzymes. In some embodiments, the liver disease is deposition of liver fat. In some embodiments, the deposition of liver fat is identified by imaging, biopsy, or other procedure. In some embodiments, the liver disease is liver inflammation. In some embodiments, the liver inflammation is identified by biopsy, imaging, or other procedure. In some embodiments, the liver disease is toxic liver disease. In some embodiments, the liver disease is immune liver disease. In some embodiments, the liver disease is elevated ALT. In some embodiments, the liver disease is due to accumulation of metals, proteinaceous material, bile acids, or other irritant or pro-inflammatory materials. In some embodiments, the liver disease is due to accumulation of metals, such as iron. In some embodiments, the liver disease is due to accumulation of proteinaceous material, such as in alpha 1 antitrypsin deficiency. In some embodiments, the liver disease is due to accumulation of bile acids. In some embodiments, the liver disease is due to accumulation of an irritant. In some embodiments, the liver disease is due to accumulation of a pro-inflammatory material.

Symptoms of liver disease include, but are not limited to, enlarged liver, fatigue, pain in the upper right abdomen, abdominal swelling (ascites), enlarged blood vessels just beneath the skin's surface, enlarged breasts in men, enlarged spleen, red palms, and yellowing of the skin and eyes (jaundice), pruritus, dark urine color, pale stool color nausea or vomiting, loss of appetite, and tendency to bruise easily. Testing for liver diseases can involve blood tests, imaging of the liver, and biopsy of the liver. An individual is at increased risk of a liver disease if the subject has at least one known risk-factor (e.g., genetic factor such as a disease-causing mutation) placing individuals with that risk factor at a statistically significant greater risk of developing the disease than individuals without the risk factor. Risk factors for liver diseases are also well known and can include, for example, excessive alcohol use, obesity, high cholesterol, high levels of triglycerides in the blood, polycystic ovary syndrome, sleep apnea, type 2 diabetes, underactive thyroid (hypothyroidism), underactive pituitary gland (hypopituitarism), and metabolic syndromes including raised blood lipids.

The present disclosure provides methods of treating a subject having liver disease, the methods comprising administering a GPAM inhibitor to the subject.

The present disclosure also provides methods of treating a subject having fatty liver disease (such as AFLD or NAFLD), the methods comprising administering a GPAM inhibitor to the subject.

The present disclosure also provides methods of treating a subject having hepatocellular carcinoma, the methods comprising administering a GPAM inhibitor to the subject.

The present disclosure also provides methods of treating a subject having liver cirrhosis, the methods comprising administering a GPAM inhibitor to the subject.

The present disclosure also provides methods of treating a subject having liver fibrosis, the methods comprising administering a GPAM inhibitor to the subject.

The present disclosure also provides methods of treating a subject having simple steatosis, steatohepatitis, or NASH, the methods comprising administering a GPAM inhibitor to the subject.

In some embodiments, the GPAM inhibitor comprises an inhibitory nucleic acid molecule. In some embodiments, the inhibitory nucleic acid molecule comprises an antisense molecule. In some embodiments, the inhibitory nucleic acid molecule comprises a small interfering RNA (siRNA) molecule. In some embodiments, the inhibitory nucleic acid molecule comprises a short hairpin RNA (shRNA) molecule. Such inhibitory nucleic acid molecules can be designed to target any region of a GPAM mRNA. In some embodiments, the inhibitory nucleic acid molecule hybridizes to a sequence within a GPAM genomic nucleic acid molecule or mRNA molecule and decreases expression of the GPAM polypeptide in a cell in the subject. In some embodiments, the GPAM inhibitor comprises an antisense RNA that hybridizes to a GPAM genomic nucleic acid molecule or mRNA molecule and decreases expression of the GPAM polypeptide in a cell in the subject. In some embodiments, the GPAM inhibitor comprises an siRNA that hybridizes to a GPAM genomic nucleic acid molecule or mRNA molecule and decreases expression of the GPAM polypeptide in a cell in the subject. In some embodiments, the GPAM inhibitor comprises an shRNA that hybridizes to a GPAM genomic nucleic acid molecule or mRNA molecule and decreases expression of the GPAM polypeptide in a cell in the subject. In some embodiments, the inhibitory nucleic acid molecule is not an siRNA molecule.

In some embodiments, the GPAM inhibitor comprises a nuclease agent that induces one or more nicks or double-strand breaks at a recognition sequence(s) or a DNA-binding protein that binds to a recognition sequence within a GPAM genomic nucleic acid molecule. The recognition sequence can be located within a coding region of the GPAM gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of the GPAM gene. For example, the recognition sequence can be located about 10, about 20, about 30, about 40, about 50, about 100, about 200, about 300, about 400, about 500, or about 1,000 nucleotides from the start codon. As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/CRISPR-associated (Cas) systems. The length of the recognition sequence can vary, and includes, for example, recognition sequences that are about 30-36 bp for a zinc finger protein or ZFN pair, about 15-18 bp for each ZFN, about 36 bp for a TALE protein or TALEN, and about 20 bp for a CRISPR/Cas guide RNA.

In some embodiments, CRISPR/Cas systems can be used to modify a GPAM genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of GPAM nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in a GPAM genomic nucleic acid molecule or it can be a nickase that creates a single-strand break in a GPAM genomic nucleic acid molecule. Additional examples of Cas proteins include, but are not limited to, Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of GPAM genomic nucleic acid molecules can be generated by contacting a cell with a Cas protein and one or more gRNAs that hybridize to one or more gRNA recognition sequences within a target genomic locus in the GPAM genomic nucleic acid molecule. For example, a gRNA recognition sequence can be located within a region of SEQ ID NO:1. The gRNA recognition sequence can also include or be proximate to a position corresponding to: position 3,195 according to SEQ ID NO:1. For example, the gRNA recognition sequence can be located from about 1000, from about 500, from about 400, from about 300, from about 200, from about 100, from about 50, from about 45, from about 40, from about 35, from about 30, from about 25, from about 20, from about 15, from about 10, or from about 5 nucleotides of a position corresponding to: position 3,195 according to SEQ ID NO:1. The gRNA recognition sequence can include or be proximate to the start codon of a GPAM genomic nucleic acid molecule or the stop codon of a GPAM genomic nucleic acid molecule. For example, the gRNA recognition sequence can be located from about 10, from about 20, from about 30, from about 40, from about 50, from about 100, from about 200, from about 300, from about 400, from about 500, or from about 1,000 nucleotides of the start codon or the stop codon.

The gRNA recognition sequences within a target genomic locus in a GPAM genomic nucleic acid molecule are located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where "N" is any nucleobase followed by two guanine ("G") nucleobases. gRNAs can transport Cas9 to anywhere in the genome for gene editing, but no editing can occur at any site other than one at which Cas9 recognizes PAM. In addition, 5'-NGA-3' can be a highly efficient non-canonical PAM for human cells. Generally, the PAM is about 2-6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10, about 2 to about 5 base pairs, or three base pairs upstream or downstream of the PAM sequence. In some embodiments (such as when Cas9 from *S. pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within a GPAM genomic nucleic acid molecule. An exemplary gRNA is a gRNA effective to direct a Cas enzyme to bind to or cleave a GPAM genomic nucleic acid molecule, wherein the gRNA comprises a DNA-targeting segment that hybridizes to a gRNA recognition sequence within the GPAM genomic nucleic acid molecule that includes or is proximate to a position corresponding to: position 3,195 according to SEQ ID NO:1. For example, a gRNA can be selected such that it hybridizes to a gRNA recognition sequence that is located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of a position corresponding to: position 3,195 according to SEQ ID NO:1. Other exemplary gRNAs comprise a DNA-targeting segment that hybridizes to a gRNA recognition sequence present within a GPAM genomic nucleic acid molecule that includes or is proximate to the start codon or the stop codon. For example, a gRNA can be selected such that it hybridizes to a gRNA recognition sequence that is located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the start codon or located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the stop codon. Suitable gRNAs can comprise from about 17 to about 25 nucleotides, from about 17 to about 23 nucleotides, from about 18 to about 22 nucleotides, or from about 19 to about 21 nucleotides. In some embodiments, the gRNAs can comprise 20 nucleotides.

Examples of suitable gRNA recognition sequences located within the human GPAM reference gene are set forth in Table 1 as SEQ ID NOs:31-44.

TABLE 1

Guide RNA Recognition Sequences Near GPAM Variation

| Strand | gRNA Recognition Sequence | SEQ ID NO: |
|---|---|---|
| - | ATGGCCTTTTCCGACTCATT | 31 |
| + | AAAGCCTAATGAGTCGGAAA | 32 |
| - | GTAAGGTTCTTACCCAGCTC | 33 |
| - | ATTAGGGTCAATAAGCAGTA | 34 |
| + | AGTCGGAAAAGGCCATTTGT | 35 |
| - | TAAGGTTCTTACCCAGCTCT | 36 |
| + | AATATTTGTCAGGGTGAGTG | 37 |
| - | GTTGCAGATCTGAAGATGGT | 38 |
| - | TACCCAGCTCTGGGGAGTGC | 39 |
| + | GGAAAGAAAGCCTAATGAGT | 40 |
| - | AAGGTTCTTACCCAGCTCTG | 41 |
| - | AGTTGCAGATCTGAAGATGG | 42 |
| + | ATTATTTCCAACTTTGTAGT | 43 |
| - | TAACAACATCTTCCAACAAA | 44 |

The Cas protein and the gRNA form a complex, and the Cas protein cleaves the target GPAM genomic nucleic acid molecule. The Cas protein can cleave the nucleic acid molecule at a site within or outside of the nucleic acid sequence present in the target GPAM genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the GPAM genomic nucleic acid molecule to which a DNA-targeting segment of a gRNA will bind.

Such methods can result, for example, in a GPAM genomic nucleic acid molecule in which a region of SEQ ID NO:1 is disrupted, the start codon is disrupted, the stop codon is disrupted, or the coding sequence is disrupted or deleted. Optionally, the cell can be further contacted with one or more additional gRNAs that hybridize to additional gRNA recognition sequences within the target genomic locus in the GPAM genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, the GPAM inhibitor comprises a small molecule. In some embodiments, the GPAM inhibitor is FSG67. In some embodiments, the GPAM inhibitor comprises: substituted or unsubstituted benzoic acid derivatives (such as, for example, 2-(alkanesulfonamido)benzoic acid, such as 4-([1,1'-biphenyl]-4-carbonyl)-2-(octane sulfonamido)benzoic acid)) (see, Outlaw et al., Med. Chem. Comm., 2014, 5, 826-830); substituted or unsubstituted 7-aminoindole derivatives (such as, for example, 7-amino-5-cyanoindoles) (see, Outlaw et al., Org. Lett., 2014, 16, 6334-6337); substituted or unsubstituted benzoic acid derivatives (such as, for example, 2-(nonylsulfonamido)benzoic acid) (see, Wydysh et al., J. Med. Chem., 2011, 52, 3317-3327); substituted or unsubstituted thiophenes and thiolactones, substituted or unsubstituted phosphonates, substituted or unsubstituted phenyls, substituted or unsubstituted benzoic acids, substituted or unsubstituted 2-, 3-, or 4-(alkanesulfonamido)benzoic acids, substituted or unsubstituted 2-, 3-, or 4-(alkanesulfonamido)benzoic acids, or 2-, 3-, or 4-(alkanesulfonamido)benzoic phosphonic acids (see, U.S. Pat. No. 9,149,445); and substituted or unsubstituted 2-(alkanesulfonamido)benzoic acids (see, PCT Publication No. WO 2019/165232).

In some embodiments, the methods of treatment further comprise detecting the presence or absence of a GPAM predicted loss-of-function variant nucleic acid molecule encoding a human GPAM polypeptide in a biological sample from the subject. As used throughout the present disclosure, a "GPAM predicted loss-of-function variant nucleic acid molecule" is any GPAM nucleic acid molecule (such as, for example, genomic nucleic acid molecule, mRNA molecule, or cDNA molecule) encoding a GPAM polypeptide having a partial loss-of-function, a complete loss-of-function, a predicted partial loss-of-function, or a predicted complete loss-of-function.

The present disclosure also provides methods of treating a subject with a therapeutic agent that treats or inhibits liver disease, wherein the subject is suffering from liver disease. In some embodiments, the methods comprise determining whether the subject has a GPAM predicted loss-of-function variant nucleic acid molecule encoding a human GPAM polypeptide by obtaining or having obtained a biological sample from the subject, and performing or having performed a sequence analysis on the biological sample to determine if the subject has a genotype comprising the GPAM predicted loss-of-function variant nucleic acid molecule. When the subject is GPAM reference, the therapeutic agent that treats or inhibits liver disease is administered or continued to be administered to the subject in a standard dosage amount, and a GPAM inhibitor is administered to the subject. When the subject is heterozygous for a GPAM predicted loss-of-function variant, the therapeutic agent that treats or inhibits liver disease is administered or continued to be administered to the subject in an amount that is the same as or lower than a standard dosage amount, and a GPAM inhibitor is administered to the subject. The presence of a genotype having the GPAM predicted loss-of-function variant nucleic acid molecule encoding the human GPAM polypeptide indicates the subject has a reduced risk of developing liver disease. In some embodiments, the subject is GPAM reference. In some embodiments, the subject is heterozygous for a GPAM predicted loss-of-function variant.

In some embodiments, the methods comprise determining the subject's aggregate burden of having a plurality of GPAM predicted loss-of-function variant genomic nucleic acid molecules, GPAM predicted loss-of-function variant mRNA molecules, and/or GPAM predicted loss-of-function variant cDNA molecules produced from the mRNA molecules, by: performing or having performed a sequence analysis on a biological sample obtained from the subject to determine the subject's aggregate burden. When the subject has a lower aggregate burden, the subject is at a higher risk of developing a liver disease and the subject is administered or continued to be administered the therapeutic agent that treats or inhibits liver disease in a standard dosage amount. When the subject has a greater aggregate burden, the subject is at a lower risk of developing a liver disease and the subject is administered or continued to be administered the therapeutic agent that treats or inhibits liver disease in an amount that is the same as or lower than the standard dosage amount. The greater the aggregate burden, the lower the risk of developing liver disease.

For subjects that are genotyped or determined to be either GPAM reference or heterozygous for a GPAM predicted loss-of-function variant, such subjects can be treated with a GPAM inhibitor, as described herein.

Detecting the presence or absence of a GPAM predicted loss-of-function variant nucleic acid molecule in a biological sample from a subject and/or determining whether a subject has a GPAM predicted loss-of-function variant nucleic acid molecule can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when the subject is GPAM reference, the subject is also administered a therapeutic agent that treats or inhibits liver disease in a standard dosage amount. In some embodiments, when the subject is heterozygous for a GPAM predicted loss-of-function variant, the subject is also administered a therapeutic agent that treats or inhibits liver disease in a dosage amount that is the same as or lower than a standard dosage amount.

In some embodiments, the treatment methods further comprise detecting the presence or absence of a GPAM predicted loss-of-function polypeptide in a biological sample from the subject. In some embodiments, when the subject does not have a GPAM predicted loss-of-function polypeptide, the subject is also administered a therapeutic agent that treats or inhibits liver disease in a standard dosage amount. In some embodiments, when the subject has a GPAM predicted loss-of-function polypeptide, the subject is also administered a therapeutic agent that treats or inhibits liver disease in a dosage amount that is the same as or lower than a standard dosage amount.

The present disclosure also provides methods of treating a subject with a therapeutic agent that treats or inhibits liver disease, wherein the subject is suffering from liver disease. In some embodiments, the method comprises determining whether the subject has a GPAM predicted loss-of-function polypeptide by obtaining or having obtained a biological sample from the subject, and performing or having performed an assay on the biological sample to determine if the subject has a GPAM predicted loss-of-function polypeptide. When the subject does not have a GPAM predicted loss-of-function polypeptide, the therapeutic agent that treats or inhibits liver disease is administered or continued to be administered to the subject in a standard dosage amount, and a GPAM inhibitor is administered to the subject. When the subject has a GPAM predicted loss-of-function polypeptide, the therapeutic agent that treats or inhibits liver disease is administered or continued to be administered to the subject in an amount that is the same as or lower than a standard dosage amount, and a GPAM inhibitor is administered to the subject. The presence of a GPAM predicted loss-of-function polypeptide indicates the subject has a reduced risk of developing liver disease. In some embodiments, the subject has a GPAM predicted loss-of-function polypeptide. In some embodiments, the subject does not have a GPAM predicted loss-of-function polypeptide.

Detecting the presence or absence of a GPAM predicted loss-of-function polypeptide in a biological sample from a subject and/or determining whether a subject has a GPAM predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell obtained from the subject.

Examples of therapeutic agents that treat or inhibit liver disease include, but are not limited to: Disulfiram, Naltrexone, Acamprosate, Prednisone, Prednisone, Azathioprine, Penicillamine, Trientine, Deferoxamine, Ciprofloxacin, Norfloxacin, Ceftriaxone, Ofloxacin, Amoxicillin-clavulanate, Phytonadione, Bumetanide, Furosemide, Hydrochlorothiazide, Chlorothiazide, Amiloride, Triamterene, Spironolactone, Octreotide, Atenolol, Metoprolol, Nadolol, Propranolol, Timolol, and Carvedilol.

Additional examples of liver disease therapeutic agents (e.g., for use in chronic hepatitis C treatment) include, but are not limited to, ribavirin, paritaprevir, simeprevir (Olysio), grazoprevir, ledipasvir, ombitasvir, elbasvir, daclatasvir (Daklinza), dasabuvir, ritonavir, sofosbuvir, velpatasvir, voxilaprevir, glecaprevir, pibrentasvir, peginterferon alfa-2a, peginterferon alfa-2b, and interferon alfa-2b.

Additional examples of liver disease therapeutic agents (e.g., for use in nonalcoholic fatty liver disease) include, but are not limited to, weight loss inducing agents such as orlistat or sibutramine; insulin sensitizing agents such as thiazolidinediones (TZDs), metformin, and meglitinides; lipid lowering agents such as statins, fibrates, and omega-3 fatty acids; antioxidants such as, vitamin E, betaine, N-Acetyl-cysteine, lecithin, silymarin, and beta-carotene; anti TNF agents such as pentoxifylline; probiotics, such as VSL #3; and cytoprotective agents such as ursodeoxycholic acid (UDCA). Other suitable treatments include ACE inhibitors/ARBs, oligofructose, and Incretin analogs.

Additional examples of liver disease therapeutic agents (e.g., for use in NASH) include, but are not limited to, OCALIVA® (obeticholic acid), Selonsertib, Elafibranor, Cenicriviroc, GR_MD_02, MGL_3196, IMM124E, arachidyl amido cholanoic acid (ARAMCHOL™), GS0976, Emricasan, Volixibat, NGM282, GS9674, Tropifexor, MN_001, LMB763, BI_1467335, MSDC_0602, PF_05221304, DF102, Saroglitazar, BMS986036, Lanifibranor, Semaglutide, Nitazoxanide, GRI_0621, EYP001, VK2809, Nalmefene, LIK066, MT_3995, Elobixibat, Namodenoson, Foralumab, SAR425899, Sotagliflozin, EDP_305, Isosabutate, Gemcabene, TERN_101, KBP_042, PF_06865571, DUR928, PF_06835919, NGM313, BMS_986171, Namacizumab, CER_209, ND_L02_s0201, RTU_1096, DRX_065, IONIS_DGAT2Rx, INT_767, NC_001, Seladepar, PXL770, TERN_201, NV556, AZD2693, SP_1373, VK0214, Hepastem, TGFTX4, RLBN1127, GKT_137831, RYI_018, CB4209-CB4211, and JH_0920.

In some embodiments, the dose of the therapeutic agents that treat or inhibit liver disease can be reduced by about 10%, by about 20%, by about 30%, by about 40%, by about 50%, by about 60%, by about 70%, by about 80%, or by about 90% for subjects that are heterozygous for a GPAM predicted loss-of-function variant (i.e., a lower than the standard dosage amount) compared to subjects that are GPAM reference (who may receive a standard dosage amount). In some embodiments, the dose of the therapeutic agents that treat or inhibit liver disease can be reduced by about 10%, by about 20%, by about 30%, by about 40%, or by about 50%. In addition, the dose of therapeutic agents that treat or inhibit liver disease in subjects that are heterozygous for a GPAM predicted loss-of-function variant can be administered less frequently compared to subjects that are GPAM reference.

Administration of the therapeutic agents that treat or inhibit liver disease and/or GPAM inhibitors can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the therapeutic agents that treat or inhibit liver disease and/or GPAM inhibitors can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

In any of the embodiments described herein, any of the therapeutic compounds described herein can be formulated into pharmaceutical compositions. Standard pharmaceutical formulation techniques are used, such as those disclosed in Remington's The Science and Practice of Pharmacy, 21st Ed., Lippincott Williams & Wilkins (2005), incorporated herein by reference in its entirety. Accordingly, the pharmaceutical compositions can comprise: a) a safe and therapeutically effective amount of a compound described herein, or a pharmaceutically acceptable salt thereof, and/or b) a pharmaceutically acceptable carrier, diluent, excipient, or combination thereof.

In any of the embodiments described herein, any of the therapeutic compounds described herein can be formulated into a single pharmaceutical composition. In some embodiments, any of the therapeutic compounds described herein can be administered in combination with one or more second pharmaceutical agents or a pharmaceutical composition comprising one or more second pharmaceutical agents.

The term "pharmaceutically acceptable carrier" or "pharmaceutically acceptable excipient" includes any and all solvents, diluents, emulsifiers, binders, buffers, dispersion media, coatings, antibacterial and antifungal agents, isotonic and absorption delaying agents and the like, or any other such compound useful in preparing pharmaceutical formulations. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, NJ Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

In some embodiments, substances which can serve as pharmaceutically-acceptable carriers or components thereof include, but are not limited to: sugars, such as lactose, glucose, and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil, and oil of theobroma; polyols such as propylene glycol, glycerine, sorbitol, mannitol, and polyethylene glycol; alginic acid; emulsifiers, such as the TWEENS; wetting agents, such as sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the subject compound can be determined depending on the manner the compound is to be administered.

The pharmaceutical compositions described herein can be provided in unit dosage form. As used herein, a "unit dosage form" is a composition containing an amount of a compound that is suitable for administration to a subject, in a single dose, according to good medical practice. The preparation of a single or unit dosage form, however, does not imply that the dosage form is administered once per day or once per course of therapy. A unit dosage form may comprise a single daily dose or a fractional sub-dose wherein several unit dosage forms are to be administered over the course of a day to complete a daily dose. In some embodiments, a unit dosage form may be administered more or less often than once daily, and may be administered more than once during a course of therapy. Such dosage forms may be administered in any manner consistent with their formulation, including orally, parenterally, and may be administered as an infusion over a period of time (e.g., from about 30 minutes to about 2-6 hours). While single administrations are specifically contemplated, the compositions administered according to the methods described herein may also be administered as a continuous infusion or via an implantable infusion pump.

In some embodiments, various oral dosage forms can be used, including solid forms such as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid, microcrystalline cellulose, carboxymethyl cellulose, and talc. Tablets may also comprise solubilizers or emulsifiers, such as poloxamers, cremophor/Kolliphor®/Lutrol®, methylcellulose, hydroxypropylmethylcellulose, or others as are known in the art. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, as desired.

Peroral (PO) compositions also include liquid solutions, emulsions, suspensions, and the like. Typical components of carriers for syrups, elixirs, emulsions and suspensions include ethanol, glycerol, propylene glycol, polyethylene glycol, liquid sucrose, sorbitol, and water. For a suspension, typical suspending agents include methyl cellulose, sodium carboxymethyl cellulose, AVICEL RC-591, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents, and colorants.

In some embodiments, the compositions may also be coated by conventional methods, typically with pH or time-dependent coatings, such that the compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes, and shellac.

In some embodiments, compositions useful for attaining systemic delivery of the subject compounds include sublingual, buccal and nasal dosage forms. Such compositions typically comprise one or more of soluble filler substances such as sucrose, sorbitol, and mannitol; and binders such as acacia, microcrystalline cellulose, carboxymethyl cellulose, and hydroxypropyl methyl cellulose. Glidants, lubricants, sweeteners, colorants, antioxidants, and flavoring agents can also be included.

In some embodiments, preservatives that can be used in the pharmaceutical compositions disclosed herein include, but are not limited to, benzalkonium chloride, PHMB, chlorobutanol, thimerosal, phenylmercuric, acetate, and phenylmercuric nitrate. A useful surfactant is, for example, Tween 80. Likewise, various useful vehicles including, but are not limited to, polyvinyl alcohol, povidone, hydroxypropyl methyl cellulose, poloxamers, carboxymethyl cellulose, hydroxyethyl cellulose, and purified water can be used.

In some embodiments, tonicity adjustors can be added as needed or convenient. They include, but are not limited to, salts, particularly sodium chloride, potassium chloride, mannitol, and glycerin, or any other suitable tonicity adjustor.

In some embodiments, various buffers and means for adjusting pH can be used. In some embodiments, the pH will be between 4 and 9. Suitable buffers include, but are not limited to, acetate buffers, citrate buffers, phosphate buffers, and borate buffers. Acids or bases may be used to adjust the pH of these formulations as needed.

In some embodiments, the compositions can comprise antioxidants including, but not limited to sodium metabi sulfite, sodium thiosulfate, acetylcysteine, butylated hydroxyanisole, and butylated hydroxytoluene.

In some embodiments, the compositions can comprise other excipient components such as chelating agents. A useful chelating agent is edetate disodium, although other chelating agents can also be used.

In some embodiments, the composition is for topical use, including for transdermal administration, creams, ointments, gels, solutions or suspensions, etc. Topical formulations can generally be comprised of a pharmaceutical carrier, co-solvent, emulsifier, penetration enhancer, preservative system, and emollient.

For intravenous administration, the compounds and compositions described herein can be dissolved or dispersed in a pharmaceutically acceptable diluent, such as a saline or dextrose solution. Suitable excipients can be included to achieve the desired pH, including but not limited to, NaOH, sodium carbonate, sodium acetate, HCl, and citric acid. In some embodiments, the pH of the final composition ranges from 2 to 8 or from 4 to 7. Antioxidant excipients can include sodium bisulfite, acetone sodium bisulfite, sodium formaldehyde, sulfoxylate, thiourea, and EDTA. Other non-limiting examples of suitable excipients found in the final intravenous composition can include sodium or potassium phosphates, citric acid, tartaric acid, gelatin, and carbohydrates such as dextrose, mannitol, and dextran. Additional acceptable excipients are described in Powell et al., PDA J. Pharm. Sci. and Tech., 1998, 52 238-311 and Nema et al., PDA J. Pharm. Sci. Tech., 2011, 65 287-332. Antimicrobial agents can also be included to achieve a bacteriostatic or fungistatic solution, including but not limited to, phenylmercuric nitrate, thimerosal, benzethonium chloride, benzalkonium chloride, phenol, cresol, and chlorobutanol.

In some embodiments, the compositions for intravenous administration can be provided to caregivers in the form of one more solids that are reconstituted with a suitable diluent such as sterile water, saline or dextrose in water shortly prior to administration. In some embodiments, the compositions are provided in solution ready to administer parenterally. In some embodiments, the compositions are provided in a solution that is further diluted prior to administration. In embodiments that include administering a combination of a compound described herein and another agent, the combination can be provided to caregivers as a mixture, or the caregivers can mix the two agents prior to administration, or the two agents can be administered separately.

The actual unit dose of the compounds described herein and/or second pharmaceutical agents described herein depends on the specific compound, and on the condition to be treated. In some embodiments, the dose can be from about 0.01 mg/kg to about 120 mg/kg or more of body weight, from about 0.05 mg/kg or less to about 70 mg/kg, from about 0.1 mg/kg to about 50 mg/kg of body weight, from about 1.0 mg/kg to about 10 mg/kg of body weight, from about 5.0 mg/kg to about 10 mg/kg of body weight, or from about 10.0 mg/kg to about 20.0 mg/kg of body weight. In some embodiments, the dose can be less than about 100 mg/kg, less than about 90 mg/kg, less than about 80 mg/kg, less than about 70 mg/kg, less than about 60 mg/kg, less than about 50 mg/kg, less than about 40 mg/kg, less than about 30 mg/kg, less than about 25 mg/kg, less than about 20 mg/kg, less than about 10 mg/kg, less than about 7.5 mg/kg, less than about 6 mg/kg, less than about 5 mg/kg, less than about 4 mg/kg, less than about 3 mg/kg, less than about 2.5 mg/kg, less than about 1 mg/kg, less than about 0.5 mg/kg, less than about 0.1 mg/kg, less than about 0.05 mg/kg, or less than about 0.005 mg/kg of body weight. In some embodiments, the actual unit dose is 0.05 mg/kg of body weight, 0.07 mg/kg of body weight, 0.1 mg/kg of body weight, 0.3 mg/kg of body weight, 1.0 mg/kg of body weight, 3.0 mg/kg of body weight, 5.0 mg/kg of body weight, 10.0 mg/kg of body weight, or 25.0 mg/kg of body weight. Thus, for administration to a 70 kg person, the dosage range would be from about 0.1 mg to 70 mg, from about 1 mg to about 50 mg, from about 0.5 mg to about 10 mg, from about 1 mg to about 10 mg, from about 2.5 mg to about 30 mg, from about 35 mg or less to about 700 mg or more, from about 7 mg to about 600 mg, from about 10 mg to about 500 mg, or from about 20 mg to about 300 mg, or from about 200 mg to about 2000 mg. In some embodiments, the actual unit dose is about 0.1 mg. In some embodiments, the actual unit dose is about 0.5 mg. In some embodiments, the actual unit dose is about 1 mg. In some embodiments, the actual unit dose is about 1.5 mg. In some embodiments, the actual unit dose is about 2 mg. In some embodiments, the actual unit dose is about 2.5 mg. In some embodiments, the actual unit dose is about 3 mg. In some embodiments, the actual unit dose is about 3.5 mg. In some embodiments, the actual unit dose is about 4 mg. In some embodiments, the actual unit dose is about 4.5 mg. In some embodiments, the actual unit dose is about 5 mg. In some embodiments the actual unit dose is about 10 mg. In some embodiments, the actual unit dose is about 25 mg. In some embodiments, the actual unit dose is about 250 mg or less. In some embodiments, the actual unit dose is about 100 mg or less. In some embodiments, the actual unit dose is about 70 mg or less.

In some embodiments, the compound dose can be from about 0.1 mg to about 100 mg, from about 0.1 mg to about 50 mg, from about 0.1 mg to about 20 mg, from about 0.1 mg to about 10 mg, from about 0.5 mg to about 100 mg, from about 0.5 mg to about 50 mg, from about 0.5 mg to about 20 mg, from about 0.5 mg to about 10 mg, from about 1 mg to about 100 mg, from about 1 mg to about 50 mg, from about 1 mg to about 20 mg, from about 1 mg to about 10 mg, from about 2.5 mg to about 50 mg, from about 2.5 mg to about 20 mg, from about 2.5 mg to about 10 mg, or from about 2.5 mg to about 5 mg. In some embodiments, the compound dose is from about 5 mg to about 300 mg, from about 5 mg to about 200 mg, from about 7.5 mg to about 200 mg, from about 10 mg to about 100 mg, from about 15 mg to about 100 mg, from about 20 mg to about 100 mg, from about 30 mg to about 100 mg, from about 40 mg to about 100 mg, from about 10 mg to about 80 mg, from about 15 mg to about 80 mg, from about 20 mg to about 80 mg, from about 30 mg to about 80 mg, from about 40 mg to about 80 mg, from about 10 mg to about 60 mg, from about 15 mg to about 60 mg, from about 20 mg to about 60 mg, from about 30 mg to about 60 mg, or from about 40 mg to about 60 mg.

In some embodiments, the compound administered is from about 20 mg to about 60 mg, from about 27 mg to about 60 mg, from about 20 mg to about 45 mg, or from about 27 mg to about 45 mg.

In some embodiments, the compound administered is from about 5 mg to about 7.5 mg, from about 5 mg to about 9 mg, from about 5 mg to about 10 mg, from about 5 mg to about 12 mg, from about 5 mg to about 14 mg, from about 5 mg to about 15 mg, from about 5 mg to about 16 mg, from about 5 mg to about 18 mg, from about 5 mg to about 20 mg, from about 5 mg to about 22 mg, from about 5 mg to about 24 mg, from about 5 mg to about 26 mg, from about 5 mg to about 28 mg, from about 5 mg to about 30 mg, from about 5 mg to about 32 mg, from about 5 mg to about 34 mg, from about 5 mg to about 36 mg, from about 5 mg to about 38 mg, from about 5 mg to about 40 mg, from about 5 mg to about 42 mg, from about 5 mg to about 44 mg, from about 5 mg to about 46 mg, from about 5 mg to about 48 mg, from about 5 mg to about 50 mg, from about 5 mg to about 52 mg, from about 5 mg to about 54 mg, from about 5 mg to about 56 mg, from about 5 mg to about 58 mg, from about 5 mg to about 60 mg, from about 10 mg to about 12 mg, from about 10 mg to about 14 mg, from about 10 mg to about 15 mg, from about 10 mg to about 16 mg, from about 10 mg to about 18 mg, from about 10 mg to about 20 mg, from about 10 mg to about 22 mg, from about 10 mg to about 24 mg, from about 10 mg to about 26 mg, from about 10 mg to about 28 mg, from about 10 mg to about 30 mg, from about 10 mg to about 32 mg, from about 10 mg to about 34 mg, from about 10 mg to about 36 mg, from about 10 mg to about 38 mg, from about 10 mg to about 40 mg, from about 10 mg to about 42 mg, from about 10 mg to about 44 mg, from about 10 mg to about 46 mg, from about 10 mg to about 48 mg, from about 10 mg to about 50 mg, from about 10 mg to about 52 mg, from about 10 mg to about 54 mg, from about 10 mg to about 56 mg, from about 10 mg to about 58 mg, from about 10 mg to about 60 mg, from about 15 mg to about 16 mg, from about 15 mg to about 18 mg, from about 15 mg to about 20 mg, from about 15 mg to about 22 mg, from about 15 mg to about 24 mg, from about 15 mg to about 26 mg, from about 15 mg to about 28 mg, from about 15 mg to about 30 mg, from about 15 mg to about 32 mg, from about 15 mg to about 34 mg, from about 15 mg to about 36 mg, from about 15 mg to about 38 mg, from about 15 mg to about 40 mg, from about 15 mg to about 42 mg, from about 15 mg to about 44 mg, from about 15 mg to about 46 mg, from about 15 mg to about 48 mg, from about 15 mg to about 50 mg, from about 15 mg to about 52 mg, from about 15 mg to about 54 mg, from about 15 mg to about 56 mg, from about 15 mg to about 58 mg, from about 15 mg to about 60 mg, from about 20 mg to about 22 mg, from about 20 mg to about 24 mg, from about 20 mg to about 26 mg, from about 20 mg to about 28 mg, from about 20 mg to about 30 mg, from about 20 mg to about 32 mg, from about 20 mg to about 34 mg, from about 20 mg to about 36 mg, from about 20 mg to about 38 mg, from about 20 mg to about 40 mg, from about 20 mg to about 42 mg, from about 20 mg to about 44 mg, from about 20 mg to about 46 mg, from about 20 mg to about 48 mg, from about 20 mg to about 50 mg, from about 20 mg to about 52 mg, from about 20 mg to about 54 mg, from about 20 mg to about 56 mg, from about 20 mg to about 58 mg, from about 20 mg to about 60 mg, from about 25 mg to about 26 mg, from about 25 mg to about 28 mg, from about 25 mg to about 30 mg, from about 25 mg to about 32 mg, from about 25 mg to about 34 mg, from about 25 mg to about 36 mg, from about 25 mg to about 38 mg, from about 25 mg to about 40 mg, from about 25 mg to about 42 mg, from about 25 mg to about 44 mg, from about 25 mg to about 46 mg, from about 25 mg to about 48 mg, from about 25 mg to about 50 mg, from about 25 mg to about 52 mg, from about 25 mg to about 54 mg, from about 25 mg to about 56 mg, from about 25 mg to about 58 mg, from about 25 mg to about 60 mg, from about 30 mg to about 32 mg, from about 30 mg to about 34 mg, from about 30 mg to about 36 mg, from about 30 mg to about 38 mg, from about 30 mg to about 40 mg, from about 30 mg to about 42 mg, from about 30 mg to about 44 mg, from about 30 mg to about 46 mg, from about 30 mg to about 48 mg, from about 30 mg to about 50 mg, from about 30 mg to about 52 mg, from about 30 mg to about 54 mg, from about 30 mg to about 56 mg, from about 30 mg to about 58 mg, from about 30 mg to about 60 mg, from about 40 mg to about 42 mg, from about 40 mg to about 44 mg, from about 40 mg to about 46 mg, from about 40 mg to about 48 mg, from about 40 mg to about 50 mg, from about 40 mg to about 52 mg, from about 40 mg to about 54 mg, from about 40 mg to about 56 mg, from about 40 mg to about 58 mg, from about 40 mg to about 60 mg, from about 45 mg to about 48 mg, from about 45 mg to about 50 mg, from about 45 mg to about 52 mg, from about 45 mg to about 54 mg, from about 45 mg to about 56 mg, from about 45 mg to about 58 mg, from about 45 mg to about 60 mg, from about 50 mg to about 52 mg, from about 50 mg to about 54 mg, from about 50 mg to about 56 mg, from about 50 mg to about 58 mg, or from about 50 mg to about 60 mg.

In some embodiments, the compound dose is greater than about 5 mg, greater than about 10 mg, greater than about 12.5 mg, greater than about 13.5 mg, greater than about 15 mg, greater than about 17.5 mg, greater than about 20 mg, greater than about 22.5 mg, greater than about 25 mg, greater than about 27 mg, greater than about 30 mg, greater than about 40 mg, greater than about 50 mg, greater than about 60 mg, greater than about 70 mg, greater than about 80 mg, greater than about 90 mg, greater than about 100 mg, greater than about 125 mg, greater than about 150 mg, or greater than about 200 mg. In some embodiments, the compound dose is less than about 5 mg, less than about 10 mg, less than about 12.5 mg, less than about 13.5 mg, less than about 15 mg, less than about 17.5 mg, less than about 20 mg, less than about 22.5 mg, less than about 25 mg, less than about 27 mg, less than about 30 mg, less than about 40 mg, less than about 50 mg, less than about 60 mg, less than about 70 mg, less than about 80 mg, less than about 90 mg, less than about 100 mg, less than about 125 mg, less than about 150 mg, or less than about 200 mg. In some embodiments, the compound dose is about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, about 200 mg, about 225 mg, about 250 mg, about 275 mg, or about 300 mg.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in liver disease, a decrease/reduction in the severity of liver disease (such as, for example, a reduction or inhibition of development or liver disease), a decrease/reduction in symptoms and liver disease-related effects, delaying the onset of symptoms and liver disease-related effects, reducing the severity of symptoms of liver disease-related effects, reducing the severity of an acute episode, reducing the number of symptoms and liver disease-related effects, reducing the latency of symptoms and liver disease-related effects, an amelioration of symptoms and liver disease-related effects, reducing secondary symptoms, reducing secondary infections, preventing relapse to liver disease, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of liver disease development/progression (such as, for example, a complete or partial avoidance/inhibition or a delay), and an increased survival time of the affected host animal, following administration of a therapeutic protocol. Treatment of liver disease encompasses the treatment of subjects already diagnosed as having any form of liver disease at any clinical stage or manifestation, the delay of the onset or evolution or aggravation or deterioration of the symptoms or signs of liver disease, and/or preventing and/or reducing the severity of liver disease.

The present disclosure also provides methods of identifying a subject having an increased risk for developing liver disease. In some embodiments, the method comprises determining or having determined in a biological sample obtained from the subject the presence or absence of a GPAM predicted loss-of-function variant nucleic acid molecule (such as a genomic nucleic acid molecule, mRNA molecule, and/or cDNA molecule) encoding a human GPAM polypeptide. When the subject lacks a GPAM predicted loss-of-function variant nucleic acid molecule (i.e., the subject is genotypically categorized as a GPAM reference), then the subject has an increased risk for developing liver disease. When the subject has a GPAM predicted loss-of-function variant nucleic acid molecule (i.e., the subject is heterozygous or homozygous for a GPAM predicted loss-of-function variant), then the subject has a decreased risk for developing liver disease.

Having a single copy of a GPAM predicted loss-of-function variant nucleic acid molecule is more protective of a subject from developing liver disease than having no copies of a GPAM predicted loss-of-function variant nucleic acid molecule. Without intending to be limited to any particular theory or mechanism of action, it is believed that a single copy of a GPAM predicted loss-of-function variant nucleic acid molecule (i.e., heterozygous for a GPAM predicted loss-of-function variant) is protective of a subject from developing liver disease, and it is also believed that having two copies of a GPAM predicted loss-of-function variant nucleic acid molecule (i.e., homozygous for a GPAM predicted loss-of-function variant) may be more protective of a subject from developing liver disease, relative to a subject with a single copy. Thus, in some embodiments, a single copy of a GPAM predicted loss-of-function variant nucleic acid molecule may not be completely protective, but instead, may be partially or incompletely protective of a subject from developing liver disease. While not desiring to be bound by any particular theory, there may be additional factors or molecules involved in the development of liver disease that are still present in a subject having a single copy of a GPAM predicted loss-of-function variant nucleic acid molecule, thus resulting in less than complete protection from the development of liver disease.

Determining whether a subject has a GPAM predicted loss-of-function variant nucleic acid molecule in a biological sample from a subject and/or determining whether a subject has a GPAM predicted loss-of-function variant nucleic acid molecule can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

The present disclosure also provides methods of identifying a subject having an increased risk of developing a liver disease wherein the methods comprise determining or having determined the subject's aggregate burden of having one or more GPAM predicted loss-of-function variant genomic nucleic acid molecules, mRNA molecules, or cDNA molecules described herein, and/or one or more GPAM predicted loss-of-function variant polypeptides described herein. The greater the aggregate burden the subject has, the lower the risk for developing a liver disease. The lower the aggregate burden the subject has, the greater the risk for developing a liver disease.

In some embodiments, the methods can further comprise determining the subject's aggregate burden of having a predicted loss-of-function variant GPAM genomic nucleic acid molecule, mRNA molecule, or cDNA molecule produced from an mRNA molecule, and/or a predicted loss-of-function variant GPAM polypeptide associated with a decreased risk of liver disease. The aggregate burden is the sum of all variants in the GPAM gene, which can be carried out in an association analysis with liver disease. In some embodiments, the subject is homozygous for one or more predicted loss-of-function variant GPAM nucleic acid molecules associated with a decreased risk of developing liver disease. In some embodiments, the subject is heterozygous for one or more predicted loss-of-function variant GPAM nucleic acid molecules associated with a decreased risk of developing liver disease. The result of the association analysis suggests that loss-of-function and missense variants of GPAM are associated with decreased risk of liver disease. In some embodiments, when a subject is identified as having an increased risk of developing a liver disease based on their aggregate burden, the subject is further treated with a therapeutic agent that treats or inhibits liver diseases and/or a GPAM inhibitor, as described herein.

In some embodiments, the subject's aggregate burden of having any one or more of GPAM predicted loss-of-function variant nucleic acid molecules represents a weighted sum of a plurality of any of the predicted loss-of-function variant nucleic acid molecules. In some embodiments, the aggregate burden is calculated using at least about 2, at least about 3, at least about 4, at least about 5, at least about 10, at least about 20, at least about 30, at least about 40, at least about 50, at least about 60, at least about 70, at least about 80, at least about 100, at least about 120, at least about 150, at least about 200, at least about 250, at least about 300, at least about 400, at least about 500, or at least about 1,000 of genetic variants associated with a liver disease. In some embodiments, when the subject has an aggregate burden above a desired threshold score, the subject has a lower or decreased risk of developing a liver disease. In some embodiments, when the subject has an aggregate burden below a desired threshold score, the subject has a greater or increased risk of developing a liver disease.

In some embodiments, the aggregate burden may be divided into quintiles, e.g., top quintile, intermediate quintile, and bottom quintile, wherein the top quintile of aggregate burden corresponds to the lowest risk group and the bottom quintile of aggregate burden corresponds to the highest risk group. In some embodiments, a subject having a greater aggregate burden comprise the highest weighted aggregate burdens, including, but not limited to the top 10%, top 20%, top 30%, top 40%, or top 50% of aggregate burdens from a subject population. In some embodiments, the genetic variants comprise the genetic variants having association with a liver disease in the top 10%, top 20%, top 30%, top 40%, or top 50% of p-value range for the association. In some embodiments, each of the identified genetic variants comprise the genetic variants having association with a liver disease with p-value of no more than about $10^{-2}$, about $10^{-3}$, about $10^{-4}$, about $10^{-5}$, about $10^{-6}$, about $10^{-7}$, about $10^{-8}$, about $10^{-9}$, about $10^{-10}$, about $10^{-11}$, about $10^{-12}$, about $10^{-13}$, about $10^{-14}$, about or $10^{-15}$. In some embodiments, the identified genetic variants comprise the genetic variants having association with a liver disease with p-value of less than $5\times10^{-8}$. In some embodiments, the identified genetic variants comprise genetic variants having association with a liver disease in high-risk subjects as compared to the rest of the reference population with odds ratio (OR) about 1.5 or greater, about 1.75 or greater, about 2.0 or greater, or about 2.25 or greater for the top 20% of the distribution; or about 1.5 or greater, about 1.75 or greater, about 2.0 or greater, about 2.25 or greater, about 2.5 or greater, or about 2.75 or greater. In some embodiments, the odds ratio (OR) may range from about 1.0 to about 1.5, from about 1.5 to about 2.0, from about 2.0 to about 2.5, from about 2.5 to about 3.0, from about 3.0 to about 3.5, from about 3.5 to about 4.0, from about 4.0 to about 4.5, from about 4.5 to about 5.0, from about 5.0 to about 5.5, from about 5.5 to about 6.0, from about 6.0 to about 6.5, or from about 6.5 to about 7.0. In some embodiments, high-risk subjects comprise subjects having aggregate burdens in the bottom decile, quintile, or tertile in a reference population.

In some embodiments, when a subject is identified as having an increased risk of developing liver disease, the subject is further treated with a therapeutic agent that treats or inhibits liver disease and/or a GPAM inhibitor, as described herein. For example, when the subject is GPAM reference, and therefore has an increased risk for developing liver disease, the subject is administered a GPAM inhibitor. In some embodiments, such a subject is also administered a therapeutic agent that treats or inhibits liver disease. In some embodiments, when the subject is heterozygous for a GPAM predicted loss-of-function variant, the subject is administered the therapeutic agent that treats or inhibits liver disease in a dosage amount that is the same as or lower than a standard dosage amount, and is also administered a GPAM inhibitor. In some embodiments, the subject is GPAM reference. In some embodiments, the subject is heterozygous for a GPAM predicted loss-of-function variant. Furthermore, when the subject has a lower aggregate burden for having a GPAM predicted loss-of-function variant nucleic acid molecule, and therefore has an increased risk for liver disease, the subject is administered a therapeutic agent that treats or inhibits liver disease. In some embodiments, when the subject has a lower aggregate burden for having a GPAM predicted loss-of-function variant nucleic acid molecule, the subject is administered the therapeutic agent that treats or inhibits liver disease in a dosage amount that is the same as or greater than the standard dosage amount administered to a subject who has a greater aggregate burden for having a GPAM predicted loss-of-function variant nucleic acid molecule.

The present disclosure also provides methods of detecting the presence or absence of a GPAM predicted loss-of-function variant genomic nucleic acid molecule in a biological sample from a subject, and/or a GPAM predicted loss-of-function variant mRNA molecule in a biological sample from a subject, and/or a GPAM predicted loss-of-function variant cDNA molecule produced from an mRNA molecule in a biological sample from a subject. It is understood that gene sequences within a population and mRNA molecules encoded by such genes can vary due to polymorphisms such as single-nucleotide polymorphisms. The sequences provided herein for the GPAM variant genomic nucleic acid molecule, GPAM variant mRNA molecule, and GPAM variant cDNA molecule are only exemplary sequences. Other sequences for the GPAM variant genomic nucleic acid molecule, variant mRNA molecule, and variant cDNA molecule are also possible.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting any GPAM variant nucleic acid molecule, preliminary processing designed to isolate or enrich the sample for the genomic DNA can be employed. A variety of techniques may be used for this purpose. When detecting the level of any GPAM variant mRNA, different techniques can be used enrich the biological sample with mRNA. Various methods to detect the presence or level of an mRNA or the presence of a particular variant genomic DNA locus can be used.

In some embodiments, detecting a human GPAM predicted loss-of-function variant nucleic acid molecule in a subject comprises assaying or analyzing a biological sample obtained from the subject to determine whether a GPAM genomic nucleic acid molecule in the biological sample, and/or a GPAM mRNA molecule in the biological sample, and/or a GPAM cDNA molecule produced from an mRNA 36molecule in the biological sample, comprises one or more variations that cause a loss-of-function (partial or complete) or are predicted to cause a loss-of-function (partial or complete).

In some embodiments, the methods of detecting the presence or absence of a GPAM predicted loss-of-function variant nucleic acid molecule (such as, for example, a genomic nucleic acid molecule, an mRNA molecule, and/or a cDNA molecule produced from an mRNA molecule) in a subject, comprise performing an assay on a biological sample obtained from the subject. The assay determines whether a nucleic acid molecule in the biological sample comprises a particular nucleotide sequence.

In some embodiments, the nucleotide sequence comprises a guanine at a position corresponding to: position 3,195 according to SEQ ID NO:2 (for genomic nucleic acid molecules), position 327 according to SEQ ID NO:9 (for mRNA molecules), or position 327 according to SEQ ID NO:21 (for cDNA molecules obtained from mRNA molecules).

In some embodiments, the nucleotide sequence comprises a guanine at a position corresponding to: position 291 according to SEQ ID NO:10 (for mRNA molecules), or position 291 according to SEQ ID NO:22 (for cDNA molecules obtained from mRNA molecules).

In some embodiments, the nucleotide sequence comprises a guanine at a position corresponding to: position 323 according to SEQ ID NO:11 (for mRNA molecules), or position 323 according to SEQ ID NO:23 (for cDNA molecules obtained from mRNA molecules).

In some embodiments, the nucleotide sequence comprises a guanine at a position corresponding to: position 326 according to SEQ ID NO:12 (for mRNA molecules), or position 326 according to SEQ ID NO:24 (for cDNA molecules obtained from mRNA molecules).

In some embodiments, the nucleotide sequence comprises a guanine at a position corresponding to: position 305 according to SEQ ID NO:13 (for mRNA molecules), or position 305 according to SEQ ID NO:25 (for cDNA molecules obtained from mRNA molecules).

In some embodiments, the nucleotide sequence comprises a guanine at a position corresponding to: position 170 according to SEQ ID NO:14 (for mRNA molecules), or position 170 according to SEQ ID NO:26 (for cDNA molecules obtained from mRNA molecules).

In some embodiments, the nucleotide sequence comprises a guanine at a position corresponding to position 3,195 according to SEQ ID NO:2, or the complement thereof.

In some embodiments, the nucleotide sequence comprises a guanine at a position corresponding to: position 327 according to SEQ ID NO:9, or the complement thereof; position 291 according to SEQ ID NO:10, or the complement thereof; position 323 according to SEQ ID NO:11, or the complement thereof; position 326 according to SEQ ID NO:12, or the complement thereof; position 305 according to SEQ ID NO:13, or the complement thereof; or position 170 according to SEQ ID NO:14, or the complement thereof.

In some embodiments, the nucleotide sequence comprises a guanine at a position corresponding to: position 327 according to SEQ ID NO:21, or the complement thereof; position 291 according to SEQ ID NO:22, or the complement thereof; position 323 according to SEQ ID NO:23, or the complement thereof; position 326 according to SEQ ID NO:24, or the complement thereof; position 305 according to SEQ ID NO:25, or the complement thereof; or position 170 according to SEQ ID NO:26, or the complement thereof.

In some embodiments, the biological sample comprises a cell or cell lysate. Such methods can further comprise, for example, obtaining a biological sample from the subject comprising a GPAM genomic nucleic acid molecule or mRNA molecule, and if mRNA, optionally reverse transcribing the mRNA into cDNA. Such assays can comprise, for example determining the identity of these positions of the particular GPAM nucleic acid molecule. In some embodiments, the method is an in vitro method.

In some embodiments, the determining step, detecting step, or sequence analysis comprises sequencing at least a portion of the nucleotide sequence of the GPAM genomic nucleic acid molecule, the GPAM mRNA molecule, or the GPAM cDNA molecule in the biological sample, wherein the sequenced portion comprises one or more variations that cause a loss-of-function (partial or complete) or are predicted to cause a loss-of-function (partial or complete).

In some embodiments, the determining step, detecting step, or sequence analysis comprises sequencing at least a portion of: the nucleotide sequence of the GPAM genomic nucleic acid molecule in the biological sample, wherein the sequenced portion comprises a position corresponding to position 3,195 according to SEQ ID NO:2, or the complement thereof; the nucleotide sequence of the GPAM mRNA molecule in the biological sample, wherein the sequenced portion comprises a position corresponding to position 327 according to SEQ ID NO:9, or the complement thereof; and/or the nucleotide sequence of the GPAM cDNA molecule produced from the mRNA in the biological sample, wherein the sequenced portion comprises a position corresponding to position 327 according to SEQ ID NO:21, or the complement thereof. When the sequenced portion of the GPAM nucleic acid molecule in the biological sample comprises a guanine at a position corresponding to: position 3,195 according to SEQ ID NO:2, position 327 according to SEQ ID NO:9, or position 327 according to SEQ ID NO:21, then the GPAM nucleic acid molecule in the biological sample is a GPAM predicted loss-of-function variant nucleic acid molecule.

In some embodiments, the determining step, detecting step, or sequence analysis comprises sequencing at least a portion of: the nucleotide sequence of the GPAM mRNA molecule in the biological sample, wherein the sequenced portion comprises a position corresponding to position 291 according to SEQ ID NO:10, or the complement thereof; and/or the nucleotide sequence of the GPAM cDNA molecule produced from the mRNA in the biological sample, wherein the sequenced portion comprises a position corresponding to position 291 according to SEQ ID NO:22, or the complement thereof. When the sequenced portion of the GPAM nucleic acid molecule in the biological sample comprises a guanine at a position corresponding to: position 291 according to SEQ ID NO:10, or position 291 according to SEQ ID NO:22, then the GPAM nucleic acid molecule in the biological sample is a GPAM predicted loss-of-function variant nucleic acid molecule.

In some embodiments, the determining step, detecting step, or sequence analysis comprises sequencing at least a portion of: the nucleotide sequence of the GPAM mRNA molecule in the biological sample, wherein the sequenced portion comprises a position corresponding to position 323 according to SEQ ID NO:11, or the complement thereof; and/or the nucleotide sequence of the GPAM cDNA molecule produced from the mRNA in the biological sample, wherein the sequenced portion comprises a position corresponding to position 323 according to SEQ ID NO:23, or the complement thereof. When the sequenced portion of the GPAM nucleic acid molecule in the biological sample comprises a guanine at a position corresponding to: position 323 according to SEQ ID NO:11, or position 323 according to SEQ ID NO:23, then the GPAM nucleic acid molecule in the biological sample is a GPAM predicted loss-of-function variant nucleic acid molecule.

In some embodiments, the determining step, detecting step, or sequence analysis comprises sequencing at least a portion of: the nucleotide sequence of the GPAM mRNA molecule in the biological sample, wherein the sequenced portion comprises a position corresponding to position 326 according to SEQ ID NO:12, or the complement thereof; and/or the nucleotide sequence of the GPAM cDNA molecule produced from the mRNA in the biological sample, wherein the sequenced portion comprises a position corresponding to position 326 according to SEQ ID NO:24, or the complement thereof. When the sequenced portion of the GPAM nucleic acid molecule in the biological sample comprises a guanine at a position corresponding to: position 326 according to SEQ ID NO:12, or position 326 according to SEQ ID NO:24, then the GPAM nucleic acid molecule in the biological sample is a GPAM predicted loss-of-function variant nucleic acid molecule.

In some embodiments, the determining step, detecting step, or sequence analysis comprises sequencing at least a portion of: the nucleotide sequence of the GPAM mRNA molecule in the biological sample, wherein the sequenced portion comprises a position corresponding to position 305 according to SEQ ID NO:13, or the complement thereof; and/or the nucleotide sequence of the GPAM cDNA molecule produced from the mRNA in the biological sample, wherein the sequenced portion comprises a position corresponding to position 305 according to SEQ ID NO:25, or the complement thereof. When the sequenced portion of the GPAM nucleic acid molecule in the biological sample comprises a guanine at a position corresponding to: position 305 according to SEQ ID NO:13, or position 305 according to SEQ ID NO:25, then the GPAM nucleic acid molecule in the biological sample is a GPAM predicted loss-of-function variant nucleic acid molecule.

In some embodiments, the determining step, detecting step, or sequence analysis comprises sequencing at least a portion of: the nucleotide sequence of the GPAM mRNA molecule in the biological sample, wherein the sequenced portion comprises a position corresponding to position 170 according to SEQ ID NO:14, or the complement thereof; and/or the nucleotide sequence of the GPAM cDNA molecule produced from the mRNA in the biological sample, wherein the sequenced portion comprises a position corresponding to position 170 according to SEQ ID NO:26, or the complement thereof. When the sequenced portion of the GPAM nucleic acid molecule in the biological sample comprises a guanine at a position corresponding to: position 170 according to SEQ ID NO:14, or position 170 according to SEQ ID NO:26, then the GPAM nucleic acid molecule in the biological sample is a GPAM predicted loss-of-function variant nucleic acid molecule.

In some embodiments, the determining step, detecting step, or sequence analysis comprises sequencing at least a portion of the nucleotide sequence of the GPAM genomic nucleic acid molecule in the biological sample, wherein the sequenced portion comprises a position corresponding to: position 3,195 according to SEQ ID NO:2, or the complement thereof, then the GPAM nucleic acid molecule in the biological sample is a GPAM predicted loss-of-function variant nucleic acid molecule.

In some embodiments, the determining step, detecting step, or sequence analysis comprises sequencing at least a portion of the nucleotide sequence of the GPAM mRNA molecule in the biological sample, wherein the sequenced portion comprises a position corresponding to: position 327 according to SEQ ID NO:9, or the complement thereof; position 291 according to SEQ ID NO:10, or the complement thereof; position 323 according to SEQ ID NO:11, or the complement thereof; position 326 according to SEQ ID NO:12, or the complement thereof; position 305 according to SEQ ID NO:13, or the complement thereof; or position 170 according to SEQ ID NO:14, or the complement thereof. When the sequenced portion of the GPAM nucleic acid molecule in the biological sample comprises a guanine at a position corresponding to: position 327 according to SEQ ID NO:9, position 291 according to SEQ ID NO:10, position 323 according to SEQ ID NO:11, position 326 according to SEQ ID NO:12, position 305 according to SEQ ID NO:13, or position 170 according to SEQ ID NO:14, then the GPAM nucleic acid molecule in the biological sample is a GPAM predicted loss-of-function variant nucleic acid molecule.

In some embodiments, the determining step, detecting step, or sequence analysis comprises sequencing at least a portion of the nucleotide sequence of the GPAM cDNA molecule in the biological sample, wherein the sequenced portion comprises a position corresponding to: position 327 according to SEQ ID NO:21, or the complement thereof; position 291 according to SEQ ID NO:22, or the complement thereof; position 323 according to SEQ ID NO:23, or the complement thereof; position 326 according to SEQ ID NO:24, or the complement thereof; position 305 according to SEQ ID NO:25, or the complement thereof; or position 170 according to SEQ ID NO:26, or the complement thereof. When the sequenced portion of the GPAM nucleic acid molecule in the biological sample comprises a guanine at a position corresponding to: position 327 according to SEQ ID NO:21, position 291 according to SEQ ID NO:22, position 323 according to SEQ ID NO:23, position 326 according to SEQ ID NO:24, position 305 according to SEQ ID NO:25, or position 170 according to SEQ ID NO:26; then the GPAM nucleic acid molecule in the biological sample is a GPAM predicted loss-of-function variant nucleic acid molecule.

In some embodiments, the determining step, detecting step, or sequence analysis comprises: a) contacting the biological sample with a primer hybridizing to a portion of the nucleotide sequence of the GPAM: genomic nucleic acid molecule that is proximate to a position corresponding to position 3,195 according to SEQ ID NO:2; mRNA molecule that is proximate to a position corresponding to position 327 according to SEQ ID NO:9; and/or cDNA molecule that is proximate to a position corresponding to position 327 according to SEQ ID NO:21; b) extending the primer at least through the position of the nucleotide sequence of the GPAM: genomic nucleic acid molecule corresponding to position 3,195 according to SEQ ID NO:2; mRNA molecule corresponding to position 327 according to SEQ ID NO:9; and/or cDNA molecule corresponding to position 327 according to SEQ ID NO:21; and c) determining whether the extension product of the primer comprises a guanine at a position corresponding to; position 3,195 according to SEQ ID NO:2, position 327 according to SEQ ID NO:9, and/or position 327 according to SEQ ID NO:21.

In some embodiments, the determining step, detecting step, or sequence analysis comprises: a) contacting the biological sample with a primer hybridizing to a portion of the nucleotide sequence of the GPAM: mRNA molecule that is proximate to a position corresponding to position 291 according to SEQ ID NO:10; and/or cDNA molecule that is proximate to a position corresponding to position 291 according to SEQ ID NO:22; b) extending the primer at least through the position of the nucleotide sequence of the GPAM: mRNA molecule corresponding to position 291 according to SEQ ID NO:10; and/or cDNA molecule corresponding to position 291 according to SEQ ID NO:22; and c) determining whether the extension product of the primer comprises a guanine at a position corresponding to: position 291 according to SEQ ID NO:10, and/or position 291 according to SEQ ID NO:22.

In some embodiments, the determining step, detecting step, or sequence analysis comprises: a) contacting the biological sample with a primer hybridizing to a portion of the nucleotide sequence of the GPAM: mRNA molecule that is proximate to a position corresponding to position 323 according to SEQ ID NO:11; and/or cDNA molecule that is proximate to a position corresponding to position 323 according to SEQ ID NO:23; b) extending the primer at least through the position of the nucleotide sequence of the GPAM: mRNA molecule corresponding to position 323 according to SEQ ID NO:11; and/or cDNA molecule corresponding to position 323 according to SEQ ID NO:23; and c) determining whether the extension product of the primer comprises a guanine at a position corresponding to: position 323 according to SEQ ID NO:11, and/or position 323 according to SEQ ID NO:23.

In some embodiments, the determining step, detecting step, or sequence analysis comprises: a) contacting the biological sample with a primer hybridizing to a portion of the nucleotide sequence of the GPAM: mRNA molecule that is proximate to a position corresponding to position 326 according to SEQ ID NO:12; and/or cDNA molecule that is proximate to a position corresponding to position 326 according to SEQ ID NO:24; b) extending the primer at least through the position of the nucleotide sequence of the GPAM: mRNA molecule corresponding to position 326 according to SEQ ID NO:12; and/or cDNA molecule corresponding to position 326 according to SEQ ID NO:24; and c) determining whether the extension product of the primer comprises a guanine at a position corresponding to: position 326 according to SEQ ID NO:12, and/or position 326 according to SEQ ID NO:24.

In some embodiments, the determining step, detecting step, or sequence analysis comprises: a) contacting the biological sample with a primer hybridizing to a portion of the nucleotide sequence of the GPAM: mRNA molecule that is proximate to a position corresponding to position 305 according to SEQ ID NO:13; and/or cDNA molecule that is proximate to a position corresponding to position 305 according to SEQ ID NO:25; b) extending the primer at least through the position of the nucleotide sequence of the GPAM: mRNA molecule corresponding to position 305 according to SEQ ID NO:13; and/or cDNA molecule corresponding to position 305 according to SEQ ID NO:25; and c) determining whether the extension product of the primer comprises a guanine at a position corresponding to: position 305 according to SEQ ID NO:13, and/or position 305 according to SEQ ID NO:25.

In some embodiments, the determining step, detecting step, or sequence analysis comprises: a) contacting the biological sample with a primer hybridizing to a portion of the nucleotide sequence of the GPAM: mRNA molecule that is proximate to a position corresponding to position 170 according to SEQ ID NO:14; and/or cDNA molecule that is proximate to a position corresponding to position 170 according to SEQ ID NO:26; b) extending the primer at least through the position of the nucleotide sequence of the GPAM: mRNA molecule corresponding to position 170 according to SEQ ID NO:14; and/or cDNA molecule corresponding to position 170 according to SEQ ID NO:26; and c) determining whether the extension product of the primer comprises a guanine at a position corresponding to: position 170 according to SEQ ID NO:14, and/or position 170 according to SEQ ID NO:26.

In some embodiments, the determining step, detecting step, or sequence analysis comprises: a) contacting the biological sample with a primer hybridizing to a portion of the nucleotide sequence of the GPAM genomic nucleic acid molecule that is proximate to a position corresponding to position 3,195 according to SEQ ID NO:2; b) extending the primer at least through the position of the nucleotide sequence of the GPAM genomic nucleic acid molecule corresponding to position 3,195 according to SEQ ID NO:2; and c) determining whether the extension product of the primer comprises a guanine at a position corresponding to position 3,195 according to SEQ ID NO:2.

In some embodiments, the determining step, detecting step, or sequence analysis comprises: a) contacting the biological sample with a primer hybridizing to a portion of the nucleotide sequence of the GPAM mRNA molecule that is proximate to a position corresponding to: position 327 according to SEQ ID NO:9, position 291 according to SEQ ID NO:10, position 323 according to SEQ ID NO:11, position 326 according to SEQ ID NO:12, position 305 according to SEQ ID NO:13, or position 170 according to SEQ ID NO:14; b) extending the primer at least through the position of the nucleotide sequence of the GPAM mRNA molecule corresponding to: position 327 according to SEQ ID NO:9, position 291 according to SEQ ID NO:10, position 323 according to SEQ ID NO:11, position 326 according to SEQ ID NO:12, position 305 according to SEQ ID NO:13, or position 170 according to SEQ ID NO:14; and c) determining whether the extension product of the primer comprises a guanine at a position corresponding to: position 327 according to SEQ ID NO:9, position 291 according to SEQ ID NO:10, position 323 according to SEQ ID NO:11, position 326 according to SEQ ID NO:12, position 305 according to SEQ ID NO:13, or position 170 according to SEQ ID NO:14.

In some embodiments, the determining step, detecting step, or sequence analysis comprises: a) contacting the biological sample with a primer hybridizing to a portion of the nucleotide sequence of the GPAM cDNA molecule that is proximate to a position corresponding to: position 327 according to SEQ ID NO:21, position 291 according to SEQ ID NO:22, position 323 according to SEQ ID NO:23, position 326 according to SEQ ID NO:24, position 305 according to SEQ ID NO:25, or position 170 according to SEQ ID NO:26; b) extending the primer at least through the position of the nucleotide sequence of the GPAM cDNA molecule corresponding to: position 327 according to SEQ ID NO:21, position 291 according to SEQ ID NO:22, position 323 according to SEQ ID NO:23, position 326 according to SEQ ID NO:24, position 305 according to SEQ ID NO:25, or position 170 according to SEQ ID NO:26; and c) determining whether the extension product of the primer comprises a guanine at a position corresponding to: position 327 according to SEQ ID NO:21, position 291 according to SEQ ID NO:22, position 323 according to SEQ ID NO:23, position 326 according to SEQ ID NO:24, position 305 according to SEQ ID NO:25, or position 170 according to SEQ ID NO:26.

In some embodiments, the assay comprises sequencing the entire nucleic acid molecule. In some embodiments, only a GPAM genomic nucleic acid molecule is analyzed. In some embodiments, only a GPAM mRNA is analyzed. In some embodiments, only a GPAM cDNA obtained from GPAM mRNA is analyzed.

In some embodiments, the determining step, detecting step, or sequence analysis comprises: a) amplifying at least a portion of the nucleic acid molecule that encodes the human GPAM polypeptide, wherein the amplified portion comprises a guanine at a position corresponding to: position 3,195 according to SEQ ID NO:2, or the complement thereof; position 327 according to SEQ ID NO:9, or the complement thereof; and/or position 327 according to SEQ ID NO:21, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a guanine at a position corresponding to: position 3,195 according to SEQ ID NO:2, or the complement thereof; position 327 according to SEQ ID NO:9, or the complement thereof; and/or position 327 according to SEQ ID NO:21, or the complement thereof; and d) detecting the detectable label.

In some embodiments, the determining step, detecting step, or sequence analysis comprises: a) amplifying at least a portion of the nucleic acid molecule that encodes the human GPAM polypeptide, wherein the amplified portion comprises a guanine at a position corresponding to: position 291 according to SEQ ID NO:10, or the complement thereof; and/or position 291 according to SEQ ID NO:22, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a guanine at a position corresponding to: position 291 according to SEQ ID NO:10, or the complement thereof; and/or position 291 according to SEQ ID NO:22, or the complement thereof; and d) detecting the detectable label.

In some embodiments, the determining step, detecting step, or sequence analysis comprises: a) amplifying at least a portion of the nucleic acid molecule that encodes the human GPAM polypeptide, wherein the amplified portion comprises a guanine at a position corresponding to: position 323 according to SEQ ID NO:11, or the complement thereof; and/or position 323 according to SEQ ID NO:23, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a guanine at a position corresponding to: position 323 according to SEQ ID NO:11, or the complement thereof; and/or position 323 according to SEQ ID NO:23, or the complement thereof; and d) detecting the detectable label.

In some embodiments, the determining step, detecting step, or sequence analysis comprises: a) amplifying at least a portion of the nucleic acid molecule that encodes the human GPAM polypeptide, wherein the amplified portion comprises a guanine at a position corresponding to: position 326 according to SEQ ID NO:12, or the complement thereof; and/or position 326 according to SEQ ID NO:24, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a guanine at a position corresponding to: position 326 according to SEQ ID NO:12, or the complement thereof; and/or position 326 according to SEQ ID NO:24, or the complement thereof; and d) detecting the detectable label.

In some embodiments, the determining step, detecting step, or sequence analysis comprises: a) amplifying at least a portion of the nucleic acid molecule that encodes the human GPAM polypeptide, wherein the amplified portion comprises a guanine at a position corresponding to: position 305 according to SEQ ID NO:13, or the complement thereof; and/or position 305 according to SEQ ID NO:25, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a guanine at a position corresponding to: position 305 according to SEQ ID NO:13, or the complement thereof; and/or position 305 according to SEQ ID NO:25, or the complement thereof; and d) detecting the detectable label.

In some embodiments, the determining step, detecting step, or sequence analysis comprises: a) amplifying at least a portion of the nucleic acid molecule that encodes the human GPAM polypeptide, wherein the amplified portion comprises a guanine at a position corresponding to: position 170 according to SEQ ID NO:14, or the complement thereof; and/or position 170 according to SEQ ID NO:26, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a guanine at a position corresponding to: position 170 according to SEQ ID NO:14, or the complement thereof; and/or position 170 according to SEQ ID NO:26, or the complement thereof; and d) detecting the detectable label.

In some embodiments, the determining step, detecting step, or sequence analysis comprises: a) amplifying at least a portion of the nucleic acid molecule that encodes the human GPAM polypeptide, wherein the amplified portion comprises a guanine at a position corresponding to position 3,195 according to SEQ ID NO:2, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a guanine at a position corresponding to position 3,195 according to SEQ ID NO:2, or the complement thereof; and d) detecting the detectable label.

In some embodiments, the determining step, detecting step, or sequence analysis comprises: a) amplifying at least a portion of the nucleic acid molecule that encodes the human GPAM polypeptide, wherein the amplified portion comprises a guanine at a position corresponding to: position 327 according to SEQ ID NO:9, or the complement thereof; position 291 according to SEQ ID NO:10, or the complement thereof; position 323 according to SEQ ID NO:11, or the complement thereof; position 326 according to SEQ ID NO:12, or the complement thereof; position 305 according to SEQ ID NO:13, or the complement thereof; or position 170 according to SEQ ID NO:14, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a guanine at a position corresponding to: position 327 according to SEQ ID NO:9, or the complement thereof; position 291 according to SEQ ID NO:10, or the complement thereof; position 323 according to SEQ ID NO:11, or the complement thereof; position 326 according to SEQ ID NO:12, or the complement thereof; position 305 according to SEQ ID NO:13, or the complement thereof; or position 170 according to SEQ ID NO:14, or the complement thereof; and d) detecting the detectable label.

In some embodiments, the determining step, detecting step, or sequence analysis comprises: a) amplifying at least a portion of the nucleic acid molecule that encodes the human GPAM polypeptide, wherein the amplified portion comprises a guanine at a position corresponding to: position 327 according to SEQ ID NO:21, or the complement thereof; position 291 according to SEQ ID NO:22, or the complement thereof; position 323 according to SEQ ID NO:23, or the complement thereof; position 326 according to SEQ ID NO:24, or the complement thereof; position 305 according to SEQ ID NO:25, or the complement thereof; or position 170 according to SEQ ID NO:26, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a guanine at a position corresponding to: position 327 according to SEQ ID NO:21, or the complement thereof; position 291 according to SEQ ID NO:22, or the complement thereof; position 323 according to SEQ ID NO:23, or the complement thereof; position 326 according to SEQ ID NO:24, or the complement thereof; position 305 according to SEQ ID NO:25, or the complement thereof; or position 170 according to SEQ ID NO:26, or the complement thereof; and d) detecting the detectable label.

In some embodiments, the nucleic acid molecule is mRNA and the determining step further comprises reverse-transcribing the mRNA into a cDNA prior to the amplifying step.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a guanine at a position corresponding to: position 3,195 according to SEQ ID NO:2, or the complement thereof; position 327 according to SEQ ID NO:9, or the complement thereof; and/or position 327 according to SEQ ID NO:21, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a guanine at a position corresponding to: position 291 according to SEQ ID NO:10, or the complement thereof; and/or position 291 according to SEQ ID NO:22, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a guanine at a position corresponding to: position 323 according to SEQ ID NO:11, or the complement thereof; and/or position 323 according to SEQ ID NO:23, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a guanine at a position corresponding to: position 326 according to SEQ ID NO:12, or the complement thereof; and/or position 326 according to SEQ ID NO:24, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a guanine at a position corresponding to: position 305 according to SEQ ID NO:13, or the complement thereof; and/or position 305 according to SEQ ID NO:25, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a guanine at a position corresponding to: position 170 according to SEQ ID NO:14, or the complement thereof; and/or position 170 according to SEQ ID NO:26, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a guanine at a position corresponding to position 3,195 according to SEQ ID NO:2, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a guanine at a position corresponding to: position 327 according to SEQ ID NO:9, or the complement thereof; position 291 according to SEQ ID NO:10, or the complement thereof; position 323 according to SEQ ID NO:11, or the complement thereof; position 326 according to SEQ ID NO:12, or the complement thereof; position 305 according to SEQ ID NO:13, or the complement thereof; or position 170 according to SEQ ID NO:14, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a guanine at a position corresponding to: position 327 according to SEQ ID NO:21, or the complement thereof; position 291 according to SEQ ID NO:22, or the complement thereof; position 323 according to SEQ ID NO:23, or the complement thereof; position 326 according to SEQ ID NO:24, or the complement thereof; position 305 according to SEQ ID NO:25, or the complement thereof; or position 170 according to SEQ ID NO:26, or the complement thereof; and detecting the detectable label.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the subject.

In some embodiments, the assay comprises contacting the biological sample with a primer or probe, such as an alteration-specific primer or alteration-specific probe, that specifically hybridizes to a GPAM variant genomic sequence, variant mRNA sequence, or variant cDNA sequence and not the corresponding GPAM reference sequence under stringent conditions, and determining whether hybridization has occurred.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising a GPAM variant genomic nucleic acid molecule, variant mRNA molecule, or variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

In some embodiments, to determine whether a GPAM nucleic acid molecule (genomic nucleic acid molecule, mRNA molecule, or cDNA molecule), or complement thereof, within a biological sample comprises a nucleotide sequence comprising a guanine at a position corresponding to position 3,195 according to SEQ ID NO:2 (genomic nucleic acid molecule), or a guanine at a position corresponding to position 327 according to SEQ ID NO:9 (mRNA molecule), or a guanine at a position corresponding to position 327 according to SEQ ID NO:21 (cDNA molecule), the biological sample can be subjected to an amplification method using a primer pair that includes a first primer derived from the 5' flanking sequence adjacent to a guanine at a position corresponding to position 3,195 according to SEQ ID NO:2, or a guanine at a position corresponding to position 327 according to SEQ ID NO:9, or a guanine at a position corresponding to position 327 according to SEQ ID NO:21, and a second primer derived from the 3' flanking sequence adjacent to a guanine at a position corresponding to position 3,195 according to SEQ ID NO:2, or a guanine at a position corresponding to position 327 according to SEQ ID NO:9, or a guanine at a position corresponding to position 327 according to SEQ ID NO:21 to produce an amplicon that is indicative of the presence of the SNP at positions encoding a guanine at a position corresponding to position 3,195 according to SEQ ID NO:2, or a guanine at a position corresponding to position 327 according to SEQ ID NO:9, or a guanine at a position corresponding to position 327 according to SEQ ID NO:21. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a guanine at a position corresponding to position 3,195 according to SEQ ID NO:2, or a guanine at a position corresponding to position 327 according to SEQ ID NO:9, or a guanine at a position corresponding to position 327 according to SEQ ID NO:21, and at least 1, 2, 3, 4, 5, 6, 7, 8, 9, 10, or more nucleotides on each side of positions comprising a guanine at a position corresponding to position 3,195 according to SEQ ID NO:2, or a guanine at a position corresponding to position 327 according to SEQ ID NO:9, or a guanine at a position corresponding to position 327 according to SEQ ID NO:21.

In some embodiments, to determine whether a GPAM nucleic acid molecule (mRNA molecule or cDNA molecule), or complement thereof, within a biological sample comprises a guanine at a position corresponding to position 291 according to SEQ ID NO:10 (mRNA molecule), or a guanine at a position corresponding to position 291 according to SEQ ID NO:22 (cDNA molecule), the biological sample can be subjected to an amplification method using a primer pair that includes a first primer derived from the 5' flanking sequence adjacent to a guanine at a position corresponding to position 291 according to SEQ ID NO:10, or a guanine at a position corresponding to position 291 according to SEQ ID NO:22, and a second primer derived from the 3' flanking sequence adjacent to a guanine at a position corresponding to position 291 according to SEQ ID NO:10, or a guanine at a position corresponding to position 291 according to SEQ ID NO:22 to produce an amplicon that is indicative of the presence of the SNP at positions encoding a guanine at a position corresponding to position 291 according to SEQ ID NO:10, or a guanine at a position corresponding to position 291 according to SEQ ID NO:22. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs.

Optionally, the primer pair flanks a region including positions comprising a guanine at a position corresponding to position 291 according to SEQ ID NO:10, or a guanine at a position corresponding to position 291 according to SEQ ID NO:22, and at least 1, 2, 3, 4, 5, 6, 7, 8, 9, 10, or more nucleotides on each side of positions comprising a guanine at a position corresponding to position 291 according to SEQ ID NO:10, or a guanine at a position corresponding to position 291 according to SEQ ID NO:22.

In some embodiments, to determine whether a GPAM nucleic acid molecule (mRNA molecule or cDNA molecule), or complement thereof, within a biological sample comprises a nucleotide sequence comprising a guanine at a position corresponding to position 323 according to SEQ ID NO:11 (mRNA molecule), or a guanine at a position corresponding to position 323 according to SEQ ID NO:23 (cDNA molecule), the biological sample can be subjected to an amplification method using a primer pair that includes a first primer derived from the 5' flanking sequence adjacent to a guanine at a position corresponding to position 323 according to SEQ ID NO:11, or a guanine at a position corresponding to position 323 according to SEQ ID NO:23, and a second primer derived from the 3' flanking sequence adjacent to a guanine at a position corresponding to position 323 according to SEQ ID NO:23 to produce an amplicon that is indicative of the presence of the SNP at positions encoding a guanine at a position corresponding to position 323 according to SEQ ID NO:11, or a guanine at a position corresponding to position 323 according to SEQ ID NO:23. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a guanine at a position corresponding to position 323 according to SEQ ID NO:11, or a guanine at a position corresponding to position 323 according to SEQ ID NO:23, and at least 1, 2, 3, 4, 5, 6, 7, 8, 9, 10, or more nucleotides on each side of positions comprising a guanine at a position corresponding to position 323 according to SEQ ID NO:11, or a guanine at a position corresponding to position 323 according to SEQ ID NO:23.

In some embodiments, to determine whether a GPAM nucleic acid molecule (mRNA molecule or cDNA molecule), or complement thereof, within a biological sample comprises a nucleotide sequence comprising a guanine at a position corresponding to position 326 according to SEQ ID NO:12 (mRNA molecule), or a guanine at a position corresponding to position 326 according to SEQ ID NO:24 (cDNA molecule), the biological sample can be subjected to an amplification method using a primer pair that includes a first primer derived from the 5' flanking sequence adjacent to a guanine at a position corresponding to position 326 according to SEQ ID NO:12, or a guanine at a position corresponding to position 326 according to SEQ ID NO:24, and a second primer derived from the 3' flanking sequence adjacent to a guanine at a position corresponding to position 326 according to SEQ ID NO:12, or a guanine at a position corresponding to position 326 according to SEQ ID NO:24 to produce an amplicon that is indicative of the presence of the SNP at positions encoding a guanine at a position corresponding to position 326 according to SEQ ID NO:12, or a guanine at a position corresponding to position 326 according to SEQ ID NO:24. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a guanine at a position corresponding to position 326 according to SEQ ID NO:12, or a guanine at a position corresponding to position 326 according to SEQ ID NO:24, and at least 1, 2, 3, 4, 5, 6, 7, 8, 9, 10, or more nucleotides on each side of positions comprising a guanine at a position corresponding to position 326 according to SEQ ID NO:12, or a guanine at a position corresponding to position 326 according to SEQ ID NO:24.

In some embodiments, to determine whether a GPAM nucleic acid molecule (mRNA molecule or cDNA molecule), or complement thereof, within a biological sample comprises a nucleotide sequence comprising a guanine at a position corresponding to position 305 according to SEQ ID NO:13 (mRNA molecule), or a guanine at a position corresponding to position 305 according to SEQ ID NO:25 (cDNA molecule), the biological sample can be subjected to an amplification method using a primer pair that includes a first primer derived from the 5' flanking sequence adjacent to a guanine at a position corresponding to position 305 according to SEQ ID NO:13, or a guanine at a position corresponding to position 305 according to SEQ ID NO:25, and a second primer derived from the 3' flanking sequence adjacent to a guanine at a position corresponding to position 305 according to SEQ ID NO:13, or a guanine at a position corresponding to position 305 according to SEQ ID NO:25 to produce an amplicon that is indicative of the presence of the SNP at positions encoding a guanine at a position corresponding to position 305 according to SEQ ID NO:13, or a guanine at a position corresponding to position 305 according to SEQ ID NO:25. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a guanine at a position corresponding to position 305 according to SEQ ID NO:13, or a guanine at a position corresponding to position 305 according to SEQ ID NO:25, and at least 1, 2, 3, 4, 5, 6, 7, 8, 9, 10, or more nucleotides on each side of positions comprising a guanine at a position corresponding to position 305 according to SEQ ID NO:13, or a guanine at a position corresponding to position 305 according to SEQ ID NO:25.

In some embodiments, to determine whether a GPAM nucleic acid molecule (mRNA molecule or cDNA molecule), or complement thereof, within a biological sample comprises a nucleotide sequence comprising a guanine at a position corresponding to position 170 according to SEQ ID NO:14 (mRNA molecule), or a guanine at a position corresponding to position 170 according to SEQ ID NO:26 (cDNA molecule), the biological sample can be subjected to an amplification method using a primer pair that includes a first primer derived from the 5' flanking sequence adjacent to a guanine at a position corresponding to position 170 according to SEQ ID NO:14, or a guanine at a position corresponding to position 170 according to SEQ ID NO:26, and a second primer derived from the 3' flanking sequence adjacent to a guanine at a position corresponding to position 170 according to SEQ ID NO:14, or a guanine at a position corresponding to position 170 according to SEQ ID NO:26 to produce an amplicon that is indicative of the presence of the SNP at positions encoding a guanine at a position corresponding to position 170 according to SEQ ID NO:14, or a guanine at a position corresponding to position 170 according to SEQ ID NO:26. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a guanine at a position corresponding to position 170 according to SEQ ID NO:14, or a guanine at a position corresponding to position 170 according to SEQ ID NO:26, and at least 1, 2, 3, 4, 5, 6, 7, 8, 9, 10, or more nucleotides on each side of positions comprising a guanine at a position corresponding to position 170 according to SEQ ID NO:14, or a guanine at a position corresponding to position 170 according to SEQ ID NO:26.

Similar amplicons can be generated from the mRNA and/or cDNA sequences. PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using known guidelines.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M $Na^+$ ion, typically about 0.01 to 1.0 M $Na^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure also provides methods of detecting the presence of a human GPAM predicted loss-of-function polypeptide comprising performing an assay on a sample obtained from a subject to determine whether a GPAM polypeptide in the subject contains one or more variations that causes the polypeptide to have a loss-of-function (partial or complete) or predicted loss-of-function (partial or complete). The GPAM predicted loss-of-function polypeptide can be any of the GPAM truncated variant polypeptides described herein. In some embodiments, the methods detect the presence of GPAM Ile43Val.

In some embodiments, the methods comprise performing an assay on a sample obtained from a subject to determine whether a GPAM polypeptide in the sample comprises a valine at a position corresponding to position 43 according to SEQ ID NO:29. In some embodiments, the methods comprise performing an assay on a sample obtained from a subject to determine whether a GPAM polypeptide in the sample comprises a valine at a position corresponding to position 43 according to SEQ ID NO:30.

In some embodiments, the detecting step comprises sequencing at least a portion of the polypeptide that comprises a position corresponding to position 43 according to SEQ ID NO:29, SEQ ID NO:27, or SEQ ID NO:28. In some embodiments, the detecting step comprises sequencing at least a portion of the polypeptide that comprises a position corresponding to position 43 according to SEQ ID NO:30, SEQ ID NO:27, or SEQ ID NO:28.

In some embodiments, the detecting step comprises an immunoassay for detecting the presence of a polypeptide that comprises a position corresponding to position 43 according to SEQ ID NO:29, SEQ ID NO:27, or SEQ ID NO:28. In some embodiments, the detecting step comprises an immunoassay for detecting the presence of a polypeptide that comprises a position corresponding to position 43 according to SEQ ID NO:30, SEQ ID NO:27, or SEQ ID NO:28.

In some embodiments, when the subject does not have a GPAM predicted loss-of-function polypeptide, then the subject has an increased risk for developing liver disease. In some embodiments, when the subject has a GPAM predicted loss-of-function polypeptide, then the subject has a decreased risk for developing liver disease.

The present disclosure also provides isolated nucleic acid molecules that hybridize to GPAM variant genomic nucleic acid molecules, GPAM variant mRNA molecules, and/or GPAM variant cDNA molecules (such as any of the genomic variant nucleic acid molecules, mRNA variant molecules, and cDNA variant molecules disclosed herein). In some embodiments, the isolated nucleic acid molecules hybridize to a portion of the GPAM nucleic acid molecule that includes a position corresponding to: position 3,195 according to SEQ ID NO:2, position 327 according to SEQ ID NO:9, or position 327 according to SEQ ID NO:21. In some embodiments, the isolated nucleic acid molecules hybridize to a portion of the GPAM nucleic acid molecule that includes a position corresponding to: position 291 according to SEQ ID NO:10, or position 291 according to SEQ ID NO:22. In some embodiments, the isolated nucleic acid molecules hybridize to a portion of the GPAM nucleic acid molecule that includes a position corresponding to: position 323 according to SEQ ID NO:11, or position 323 according to SEQ ID NO:23. In some embodiments, the isolated nucleic acid molecules hybridize to a portion of the GPAM nucleic acid molecule that includes a position corresponding to: position 326 according to SEQ ID NO:12, or position 326 according to SEQ ID NO:24. In some embodiments, the isolated nucleic acid molecules hybridize to a portion of the GPAM nucleic acid molecule that includes a position corresponding to: position 305 according to SEQ ID NO:13, or position 305 according to SEQ ID NO:25. In some embodiments, the isolated nucleic acid molecules hybridize to a portion of the GPAM nucleic acid molecule that includes a position corresponding to: position 170 according to SEQ ID NO:14, or position 170 according to SEQ ID NO:26.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In some embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules consist of or comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In some embodiments, the isolated nucleic acid molecules consist of or comprise from about 18 to about 30 nucleotides. In some embodiments, the isolated nucleic acid molecules comprise or consist of at least about 15 nucleotides to at least about 35 nucleotides.

In some embodiments, such isolated nucleic acid molecules hybridize to GPAM variant nucleic acid molecules (such as genomic nucleic acid molecules, mRNA molecules, and/or cDNA molecules) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to GPAM variant genomic nucleic acid molecules, GPAM variant mRNA molecules, and/or GPAM variant cDNA molecules. In some embodiments, the isolated nucleic acid molecules consist of or comprise from about 15 to about 100 nucleotides, or from about 15 to about 35 nucleotides. In some embodiments, the isolated nucleic acid molecules consist of or comprise from about 15 to about 100 nucleotides. In some embodiments, the isolated nucleic acid molecules consist of or comprise from about 15 to about 35 nucleotides.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human GPAM polypeptide, wherein the portion comprises a position corresponding to: position 3,195 according to SEQ ID NO:2, or the complement thereof; position 327 according to SEQ ID NO:9, or the complement thereof; or position 327 according to SEQ ID NO:21, or the complement thereof. In some embodiments, the alteration-specific probe or alteration-specific primer comprises a nucleotide sequence which is complementary to a portion of a nucleotide sequence comprising positions corresponding to: positions 3,195-3,197 according to SEQ ID NO:2, or the complement thereof; positions 327-329 according to SEQ ID NO:9, or the complement thereof; and/or positions 327-329 according to SEQ ID NO:21, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human GPAM polypeptide, wherein the portion comprises a position corresponding to: position 291 according to SEQ ID NO:10, or the complement thereof; or position 291 according to SEQ ID NO:22, or the complement thereof. In some embodiments, the alteration-specific probe or alteration-specific primer comprises a nucleotide sequence which is complementary to a portion of a nucleotide sequence comprising positions corresponding to: positions 291-293 according to SEQ ID NO:10, or the complement thereof; and/or positions 291-293 according to SEQ ID NO:22, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human GPAM polypeptide, wherein the portion comprises a position corresponding to: position 323 according to SEQ ID NO:11, or the complement thereof; or position 323 according to SEQ ID NO:23, or the complement thereof. In some embodiments, the alteration-specific probe or alteration-specific primer comprises a nucleotide sequence which is complementary to a portion of a nucleotide sequence comprising positions corresponding to: positions 323-325 according to SEQ ID NO:11, or the complement thereof; and/or positions 323-325 according to SEQ ID NO:23, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human GPAM polypeptide, wherein the portion comprises a position corresponding to: position 326 according to SEQ ID NO:12, or the complement thereof; or position 326 according to SEQ ID NO:24, or the complement thereof. In some embodiments, the alteration-specific probe or alteration-specific primer comprises a nucleotide sequence which is complementary to a portion of a nucleotide sequence comprising positions corresponding to positions 326-328 according to SEQ ID NO:12, or the complement thereof; and/or positions 326-328 according to SEQ ID NO:24, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human GPAM polypeptide, wherein the portion comprises a position corresponding to: position 305 according to SEQ ID NO:13, or the complement thereof; or position 305 according to SEQ ID NO:25, or the complement thereof. In some embodiments, the alteration-specific probe or alteration-specific primer comprises a nucleotide sequence which is complementary to a portion of a nucleotide sequence comprising positions corresponding to: positions 305-307 according to SEQ ID NO:13, or the complement thereof; and/or positions 305-307 according to SEQ ID NO:25, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human GPAM polypeptide, wherein the portion comprises a position corresponding to: position 170 according to SEQ ID NO:14, or the complement thereof; or position 170 according to SEQ ID NO:26, or the complement thereof. In some embodiments, the alteration-specific probe or alteration-specific primer comprises a nucleotide sequence which is complementary to a portion of a nucleotide sequence comprising positions corresponding to: positions 170-172 according to SEQ ID NO:14, or the complement thereof; and/or positions 170-172 according to SEQ ID NO:26, or the complement thereof.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect a nucleotide variation within any of the GPAM variant genomic nucleic acid molecules, GPAM variant mRNA molecules, and/or GPAM variant cDNA molecules disclosed herein. The primers described herein can be used to amplify GPAM variant genomic nucleic acid molecules, GPAM variant mRNA molecules, or GPAM variant cDNA molecules, or a fragment thereof.

The present disclosure also provides pairs of primers comprising any of the primers described above. For example, if one of the primers' 3'-ends hybridizes to an adenine at a position corresponding to position 3,195 according to SEQ ID NO:1 (rather than guanine) in a particular GPAM nucleic acid molecule, then the presence of the amplified fragment would indicate the presence of a GPAM reference genomic nucleic acid molecule.

Conversely, if one of the primers' 3'-ends hybridizes to a guanine at a position corresponding to position 3,195 according to SEQ ID NO:2 (rather than adenine) in a particular GPAM nucleic acid molecule, then the presence of the amplified fragment would indicate the presence of the GPAM variant genomic nucleic acid molecule. In some embodiments, the nucleotide of the primer complementary to the guanine at a position corresponding to position 3,195 according to SEQ ID NO:2 can be at the 3' end of the primer. In addition, if one of the primers' 3'-ends hybridizes to an adenine at a position corresponding to position 327 according to SEQ ID NO:3 (rather than guanine) in a particular GPAM nucleic acid molecule, then the presence of the amplified fragment would indicate the presence of a GPAM reference mRNA molecule. Conversely, if one of the primers' 3'-ends hybridizes to a guanine at a position corresponding to position 327 according to SEQ ID NO:9 (rather than adenine) in a particular GPAM mRNA molecule, then the presence of the amplified fragment would indicate the presence of the GPAM variant mRNA molecule. In some embodiments, the nucleotide of the primer complementary to the guanine at a position corresponding to position 327 according to SEQ ID NO:9 can be at the 3' end of the primer. In addition, if one of the primers' 3'-ends hybridizes to an adenine at a position corresponding to position 327 according to SEQ ID NO:15 (rather than guanine) in a particular GPAM nucleic acid molecule, then the presence of the amplified fragment would indicate the presence of a GPAM reference cDNA molecule. Conversely, if one of the primers' 3'-ends hybridizes to a guanine at a position corresponding to position 327 according to SEQ ID NO:21 (rather than adenine) in a particular GPAM cDNA molecule, then the presence of the amplified fragment would indicate the presence of the GPAM variant cDNA molecule. In some embodiments, the nucleotide of the primer complementary to the guanine at a position corresponding to position 327 according to SEQ ID NO:21 can be at the 3' end of the primer.

In addition, if one of the primers' 3'-ends hybridizes to an adenine at a position corresponding to position 291 according to SEQ ID NO:4 (rather than guanine) in a particular GPAM nucleic acid molecule, then the presence of the amplified fragment would indicate the presence of a GPAM reference mRNA molecule. Conversely, if one of the primers' 3'-ends hybridizes to a guanine at a position corresponding to position 291 according to SEQ ID NO:10 (rather than adenine) in a particular GPAM mRNA molecule, then the presence of the amplified fragment would indicate the presence of the GPAM variant mRNA molecule. In some embodiments, the nucleotide of the primer complementary to the guanine at a position corresponding to position 291 according to SEQ ID NO:10 can be at the 3' end of the primer. In addition, if one of the primers' 3'-ends hybridizes to an adenine at a position corresponding to position 291 according to SEQ ID NO:16 (rather than guanine) in a particular GPAM nucleic acid molecule, then the presence of the amplified fragment would indicate the presence of a GPAM reference cDNA molecule. Conversely, if one of the primers' 3'-ends hybridizes to a guanine at a position corresponding to position 291 according to SEQ ID NO:22 (rather than adenine) in a particular GPAM cDNA molecule, then the presence of the amplified fragment would indicate the presence of the GPAM variant cDNA molecule. In some embodiments, the nucleotide of the primer complementary to the guanine at a position corresponding to position 291 according to SEQ ID NO:22 can be at the 3' end of the primer.

In addition, if one of the primers' 3'-ends hybridizes to an adenine at a position corresponding to position 323 according to SEQ ID NO:5 (rather than guanine) in a particular GPAM nucleic acid molecule, then the presence of the amplified fragment would indicate the presence of a GPAM reference mRNA molecule. Conversely, if one of the primers' 3'-ends hybridizes to a guanine at a position corresponding to position 323 according to SEQ ID NO:11 (rather than adenine) in a particular GPAM mRNA molecule, then the presence of the amplified fragment would indicate the presence of the GPAM variant mRNA molecule. In some embodiments, the nucleotide of the primer complementary to the guanine at a position corresponding to position 323 according to SEQ ID NO:11 can be at the 3' end of the primer. In addition, if one of the primers' 3'-ends hybridizes to an adenine at a position corresponding to position 323 according to SEQ ID NO:17 (rather than guanine) in a particular GPAM nucleic acid molecule, then the presence of the amplified fragment would indicate the presence of a GPAM reference cDNA molecule. Conversely, if one of the primers' 3'-ends hybridizes to a guanine at a position corresponding to position 323 according to SEQ ID NO:23 (rather than adenine) in a particular GPAM cDNA molecule, then the presence of the amplified fragment would indicate the presence of the GPAM variant cDNA molecule. In some embodiments, the nucleotide of the primer complementary to the guanine at a position corresponding to position 323 according to SEQ ID NO:23 can be at the 3' end of the primer.

In addition, if one of the primers' 3'-ends hybridizes to an adenine at a position corresponding to position 326 according to SEQ ID NO:6 (rather than guanine) in a particular GPAM nucleic acid molecule, then the presence of the amplified fragment would indicate the presence of a GPAM reference mRNA molecule. Conversely, if one of the primers' 3'-ends hybridizes to a guanine at a position corresponding to position 326 according to SEQ ID NO:12 (rather than adenine) in a particular GPAM mRNA molecule, then the presence of the amplified fragment would indicate the presence of the GPAM variant mRNA molecule. In some embodiments, the nucleotide of the primer complementary to the guanine at a position corresponding to position 326 according to SEQ ID NO:12 can be at the 3' end of the primer. In addition, if one of the primers' 3'-ends hybridizes to an adenine at a position corresponding to position 326 according to SEQ ID NO:18 (rather than guanine) in a particular GPAM nucleic acid molecule, then the presence of the amplified fragment would indicate the presence of a GPAM reference cDNA molecule. Conversely, if one of the primers' 3'-ends hybridizes to a guanine at a position corresponding to position 326 according to SEQ ID NO:24 (rather than adenine) in a particular GPAM cDNA molecule, then the presence of the amplified fragment would indicate the presence of the GPAM variant cDNA molecule. In some embodiments, the nucleotide of the primer complementary to the guanine at a position corresponding to position 326 according to SEQ ID NO:24 can be at the 3' end of the primer.

In addition, if one of the primers' 3'-ends hybridizes to an adenine at a position corresponding to position 305 according to SEQ ID NO:7 (rather than guanine) in a particular GPAM nucleic acid molecule, then the presence of the amplified fragment would indicate the presence of a GPAM reference mRNA molecule. Conversely, if one of the primers' 3'-ends hybridizes to a guanine at a position corresponding to position 305 according to SEQ ID NO:13 (rather than adenine) in a particular GPAM mRNA molecule, then the presence of the amplified fragment would indicate the presence of the GPAM variant mRNA molecule. In some embodiments, the nucleotide of the primer complementary to the guanine at a position corresponding to position 305 according to SEQ ID NO:13 can be at the 3' end of the primer. In addition, if one of the primers' 3'-ends hybridizes to an adenine at a position corresponding to position 305 according to SEQ ID NO:19 (rather than guanine) in a particular GPAM nucleic acid molecule, then the presence of the amplified fragment would indicate the presence of a GPAM reference cDNA molecule. Conversely, if one of the primers' 3'-ends hybridizes to a guanine at a position corresponding to position 305 according to SEQ ID NO:25 (rather than adenine) in a particular GPAM cDNA molecule, then the presence of the amplified fragment would indicate the presence of the GPAM variant cDNA molecule. In some embodiments, the nucleotide of the primer complementary to the guanine at a position corresponding to position 305 according to SEQ ID NO:25 can be at the 3' end of the primer.

In addition, if one of the primers' 3'-ends hybridizes to an adenine at a position corresponding to position 170 according to SEQ ID NO:8 (rather than guanine) in a particular GPAM nucleic acid molecule, then the presence of the amplified fragment would indicate the presence of a GPAM reference mRNA molecule. Conversely, if one of the primers' 3'-ends hybridizes to a guanine at a position corresponding to position 170 according to SEQ ID NO:14 (rather than adenine) in a particular GPAM mRNA molecule, then the presence of the amplified fragment would indicate the presence of the GPAM variant mRNA molecule. In some embodiments, the nucleotide of the primer complementary to the guanine at a position corresponding to position 170 according to SEQ ID NO:14 can be at the 3' end of the primer. In addition, if one of the primers' 3'-ends hybridizes to an adenine at a position corresponding to position 170 according to SEQ ID NO:20 (rather than guanine) in a particular GPAM nucleic acid molecule, then the presence of the amplified fragment would indicate the presence of a GPAM reference cDNA molecule. Conversely, if one of the primers' 3'-ends hybridizes to a guanine at a position corresponding to position 170 according to SEQ ID NO:26 (rather than adenine) in a particular GPAM cDNA molecule, then the presence of the amplified fragment would indicate the presence of the GPAM variant cDNA molecule. In some embodiments, the nucleotide of the primer complementary to the guanine at a position corresponding to position 170 according to SEQ ID NO:26 can be at the 3' end of the primer.

In the context of the disclosure "specifically hybridizes" means that the probe or primer (such as, for example, the alteration-specific probe or alteration-specific primer) does not hybridize to a nucleic acid sequence encoding a GPAM reference genomic nucleic acid molecule, a GPAM reference mRNA molecule, and/or a GPAM reference cDNA molecule.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The nucleotide sequence of a GPAM reference genomic nucleic acid molecule is set forth in SEQ ID NO:1. Referring to SEQ ID NO:1, position 3,195 is an adenine.

A variant genomic nucleic acid molecule of GPAM exists, wherein the adenine at position 3,195 is replaced with a guanine. The nucleotide sequence of this GPAM variant genomic nucleic acid molecule is set forth in SEQ ID NO:2.

The nucleotide sequence of a GPAM reference mRNA molecule is set forth in SEQ ID NO:3. Referring to SEQ ID NO:3, position 327 is an adenine. The nucleotide sequence of another GPAM reference mRNA molecule is set forth in SEQ ID NO:4. Referring to SEQ ID NO:4, position 291 is an adenine. The nucleotide sequence of another GPAM reference mRNA molecule is set forth in SEQ ID NO:5. Referring to SEQ ID NO:5, position 323 is an adenine. The nucleotide sequence of another GPAM reference mRNA molecule is set forth in SEQ ID NO:6. Referring to SEQ ID NO:6, position 326 is an adenine. The nucleotide sequence of another GPAM reference mRNA molecule is set forth in SEQ ID NO:7. Referring to SEQ ID NO:7, position 305 is an adenine. The nucleotide sequence of another GPAM reference mRNA molecule is set forth in SEQ ID NO:8. Referring to SEQ ID NO:8, position 170 is an adenine.

A variant mRNA molecule of GPAM exists, wherein the adenine at position 327 is replaced with guanine. The nucleotide sequence of this GPAM variant mRNA molecule is set forth in SEQ ID NO:9.

Another variant mRNA molecule of GPAM exists, wherein the adenine at position 291 is replaced with guanine. The nucleotide sequence of this GPAM variant mRNA molecule is set forth in SEQ ID NO:10.

Another variant mRNA molecule of GPAM exists, wherein the adenine at position 323 is replaced with guanine. The nucleotide sequence of this GPAM variant mRNA molecule is set forth in SEQ ID NO:11.

Another variant mRNA molecule of GPAM exists, wherein the adenine at position 326 is replaced with guanine. The nucleotide sequence of this GPAM variant mRNA molecule is set forth in SEQ ID NO:12.

Another variant mRNA molecule of GPAM exists, wherein the adenine at position 305 is replaced with guanine. The nucleotide sequence of this GPAM variant mRNA molecule is set forth in SEQ ID NO:13.

Another variant mRNA molecule of GPAM exists, wherein the adenine at position 170 is replaced with guanine. The nucleotide sequence of this GPAM variant mRNA molecule is set forth in SEQ ID NO:14.

The nucleotide sequence of a GPAM reference cDNA molecule is set forth in SEQ ID NO:15. Referring to SEQ ID NO:15, position 327 is an adenine. The nucleotide sequence of another GPAM reference cDNA molecule is set forth in SEQ ID NO:16. Referring to SEQ ID NO:16, position 291 is an adenine. The nucleotide sequence of another GPAM reference cDNA molecule is set forth in SEQ ID NO:17. Referring to SEQ ID NO:17, position 323 is an adenine. The nucleotide sequence of another GPAM reference cDNA molecule is set forth in SEQ ID NO:18. Referring to SEQ ID NO:18, position 326 is an adenine. The nucleotide sequence of another GPAM reference cDNA molecule is set forth in SEQ ID NO:19. Referring to SEQ ID NO:19, position 305 is an adenine. The nucleotide sequence of another GPAM reference cDNA molecule is set forth in SEQ ID NO:20. Referring to SEQ ID NO:20, position 170 is an adenine.

A variant cDNA molecule of GPAM exists, wherein the adenine at position 327 is replaced with guanine. The nucleotide sequence of this GPAM variant cDNA molecule is set forth in SEQ ID NO:21.

Another variant cDNA molecule of GPAM exists, wherein the adenine at position 291 is replaced with guanine. The nucleotide sequence of this GPAM variant cDNA molecule is set forth in SEQ ID NO:22.

Another variant cDNA molecule of GPAM exists, wherein the adenine at position 323 is replaced with guanine. The nucleotide sequence of this GPAM variant cDNA molecule is set forth in SEQ ID NO:23.

Another variant cDNA molecule of GPAM exists, wherein the adenine at position 326 is replaced with guanine. The nucleotide sequence of this GPAM variant cDNA molecule is set forth in SEQ ID NO:24.

Another variant cDNA molecule of GPAM exists, wherein the adenine at position 305 is replaced with guanine. The nucleotide sequence of this GPAM variant cDNA molecule is set forth in SEQ ID NO:25.

Another variant cDNA molecule of GPAM exists, wherein the adenine at position 170 is replaced with guanine. The nucleotide sequence of this GPAM variant cDNA molecule is set forth in SEQ ID NO:26.

The genomic nucleic acid molecules, mRNA molecules, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible.

Also provided herein are functional polynucleotides that can interact with the disclosed nucleic acid molecules. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be within a vector or as an exogenous donor sequence comprising the isolated nucleic acid molecule and a heterologous nucleic acid sequence. The isolated nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3XFLAG, 6Xhis or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The disclosed nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophore-labeled nucleotides.

The nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthine-9-yl (1), and 2-aminoadenine-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, $—O[(CH_2)_nO]_mCH_3$, $—O(CH_2)_nOCH_3$, $—O(CH_2)_nNH_2$, $—O(CH_2)_nCH_3$, $—O(CH_2)_n—ONH_2$, and $—O(CH_2)_nON[(CH_2)_nCH_3)]_2$, where n and m are from 1 to about 10. Other modifications at the 2' position include, but are not limited to, $C_{1-10}$alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as $CH_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

The present disclosure also provides vectors comprising any one or more of the nucleic acid molecules disclosed herein. In some embodiments, the vectors comprise any one or more of the nucleic acid molecules disclosed herein and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

Desired regulatory sequences for mammalian host cell expression can include, for example, viral elements that direct high levels of polypeptide expression in mammalian cells, such as promoters and/or enhancers derived from retroviral LTRs, cytomegalovirus (CMV) (such as, for example, CMV promoter/enhancer), Simian Virus 40 (SV40) (such as, for example, SV40 promoter/enhancer), adenovirus, (such as, for example, the adenovirus major late promoter (AdMLP)), polyoma and strong mammalian promoters such as native immunoglobulin and actin promoters. Methods of expressing polypeptides in bacterial cells or fungal cells (such as, for example, yeast cells) are also well known. A promoter can be, for example, a constitutively active promoter, a conditional promoter, an inducible promoter, a temporally restricted promoter (such as, for example, a developmentally regulated promoter), or a spatially restricted promoter (such as, for example, a cell-specific or tissue-specific promoter).

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

The present disclosure also provides compositions comprising any one or more of the isolated nucleic acid molecules, genomic nucleic acid molecules, mRNA molecules, and/or cDNA molecules disclosed herein. In some embodiments, the composition is a pharmaceutical composition. In some embodiments, the compositions comprise a carrier and/or excipient. Examples of carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence (such as, for example, SEQ ID NO:1, SEQ ID NO:3, or SEQ ID NO:15). In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

For example, a nucleic acid molecule comprising a nucleotide sequence encoding a human GPAM polypeptide, wherein the nucleotide sequence comprises a guanine at a position corresponding to position 3,195 according to SEQ ID NO:2 means that if the nucleotide sequence of the GPAM genomic nucleic acid molecule is aligned to the sequence of SEQ ID NO:2, the GPAM sequence has a guanine residue at the position that corresponds to position 3,195 of SEQ ID NO:2. The same applies for mRNA molecules comprising a nucleotide sequence encoding a human GPAM polypeptide, wherein the nucleotide sequence comprises a guanine at a position corresponding to position 327 according to SEQ ID NO:9, and cDNA molecules comprising a nucleotide sequence encoding a human GPAM polypeptide, wherein the nucleotide sequence comprises a guanine at a position corresponding to position 327 according to SEQ ID NO:21. In other words, these phrases refer to a nucleic acid molecule encoding a GPAM polypeptide, wherein the genomic nucleic acid molecule has a nucleotide sequence that comprises a guanine residue that is homologous to the guanine residue at position 3,195 of SEQ ID NO:2 (or wherein the mRNA molecule has a nucleotide sequence that comprises a guanine residue that is homologous to the guanine residue at position 327 of SEQ ID NO:9, or wherein the cDNA molecule has a nucleotide sequence that comprises a guanine residue that is homologous to the guanine residue at position 327 of SEQ ID NO:21). Herein, such a sequence is also referred to as "GPAM sequence with the Ile43Val alteration" or "GPAM sequence with the Ile43Val variation" referring to genomic nucleic acid molecules (or "GPAM sequence with the A327G alteration" or "GPAM sequence with the A327G variation" referring to mRNA molecules, and "GPAM sequence with the A327G alteration" or "GPAM sequence with the A327G variation" referring to cDNA molecules).

As described herein, a position within a GPAM genomic nucleic acid molecule that corresponds to position 3,195 according to SEQ ID NO:2, for example, can be identified by performing a sequence alignment between the nucleotide sequence of a particular GPAM nucleic acid molecule and the nucleotide sequence of SEQ ID NO:2. A variety of computational algorithms exist that can be used for performing a sequence alignment to identify a nucleotide position that corresponds to, for example, position 3,195 in SEQ ID NO:2. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence alignments may be performed. However, sequences can also be aligned manually.

The amino acid sequence of a GPAM reference polypeptide is set forth in SEQ ID NO:27. Referring to SEQ ID NO:27, the GPAM reference polypeptide is 828 amino acids in length. Referring to SEQ ID NO:27, position 43 is isoleucine. The amino acid sequence of another GPAM reference polypeptide is set forth in SEQ ID NO:28. Referring to SEQ ID NO:28, the GPAM reference polypeptide is 710 amino acids in length. Referring to SEQ ID NO:28, position 43 is isoleucine.

A GPAM variant polypeptide exists, the amino acid sequence of which is set forth in SEQ ID NO:29. Referring to SEQ ID NO:29, the GPAM variant polypeptide is 828 amino acids in length. Referring to SEQ ID NO:29, position 43 is valine.

Another GPAM variant polypeptide exists, the amino acid sequence of which is set forth in SEQ ID NO:30. Referring to SEQ ID NO:30, the GPAM variant polypeptide is 710 amino acids in length. Referring to SEQ ID NO:30, position 43 is valine.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

The present disclosure also provides therapeutic agents that treat or inhibit liver disease for use in the treatment of liver disease (or for use in the preparation of a medicament for treating liver disease) in a subject, wherein the subject has any of the genomic nucleic acid molecules, mRNA molecules, and/or cDNA molecules encoding a human GPAM polypeptide described herein. The therapeutic agents that treat or inhibit liver disease can be any of the therapeutic agents that treat or inhibit liver disease described herein.

In some embodiments, the subject comprises: a genomic nucleic acid molecule having a nucleotide sequence encoding a human GPAM polypeptide, wherein the nucleotide sequence comprises a guanine at a position corresponding to position 3,195 according to SEQ ID NO:2, or the complement thereof; an mRNA molecule having a nucleotide sequence encoding a human GPAM polypeptide, wherein the nucleotide sequence comprises a guanine at a position corresponding to position 327 according to SEQ ID NO:9, or the complement thereof; a cDNA molecule having a nucleotide sequence encoding a human GPAM polypeptide, wherein the nucleotide sequence comprises a guanine at a position corresponding to position 327 according to SEQ ID NO:21, or the complement thereof; or a GPAM polypeptide that comprises a valine at a position corresponding to position 43 according to SEQ ID NO:29.

In some embodiments, the subject comprises: an mRNA molecule having a nucleotide sequence encoding a human GPAM polypeptide, wherein the nucleotide sequence comprises a guanine at a position corresponding to position 291 according to SEQ ID NO:10, or the complement thereof; a cDNA molecule having a nucleotide sequence encoding a human GPAM polypeptide, wherein the nucleotide sequence comprises a guanine at a position corresponding to position 291 according to SEQ ID NO:22, or the complement thereof; or a GPAM polypeptide that comprises a valine at a position corresponding to position 43 according to SEQ ID NO:30.

In some embodiments, the subject comprises: an mRNA molecule having a nucleotide sequence encoding a human GPAM polypeptide, wherein the nucleotide sequence comprises a guanine at a position corresponding to position 323 according to SEQ ID NO:11, or the complement thereof; or a cDNA molecule having a nucleotide sequence encoding a human GPAM polypeptide, wherein the nucleotide sequence comprises a guanine at a position corresponding to position 323 according to SEQ ID NO:23, or the complement thereof.

In some embodiments, the subject comprises: an mRNA molecule having a nucleotide sequence encoding a human GPAM polypeptide, wherein the nucleotide sequence comprises a guanine at a position corresponding to position 326 according to SEQ ID NO:12, or the complement thereof; or a cDNA molecule having a nucleotide sequence encoding a human GPAM polypeptide, wherein the nucleotide sequence comprises a guanine at a position corresponding to position 326 according to SEQ ID NO:24, or the complement thereof.

In some embodiments, the subject comprises: an mRNA molecule having a nucleotide sequence encoding a human GPAM polypeptide, wherein the nucleotide sequence comprises a guanine at a position corresponding to position 305 according to SEQ ID NO:13, or the complement thereof; a or cDNA molecule having a nucleotide sequence encoding a human GPAM polypeptide, wherein the nucleotide sequence comprises a guanine at a position corresponding to position 305 according to SEQ ID NO:25, or the complement thereof.

In some embodiments, the subject comprises: an mRNA molecule having a nucleotide sequence encoding a human GPAM polypeptide, wherein the nucleotide sequence comprises a guanine at a position corresponding to position 170 according to SEQ ID NO:14, or the complement thereof; or a cDNA molecule having a nucleotide sequence encoding a human GPAM polypeptide, wherein the nucleotide sequence comprises a guanine at a position corresponding to position 170 according to SEQ ID NO:26, or the complement thereof.

The present disclosure also provides GPAM inhibitors for use in the treatment of liver disease (or for use in the preparation of a medicament for treating liver disease) in a subject, wherein the subject has any of the genomic nucleic acid molecules, mRNA molecules, and/or cDNA molecules encoding a human GPAM polypeptide described herein. The GPAM inhibitors can be any of the GPAM inhibitors described herein.

In some embodiments, the subject comprises: a genomic nucleic acid molecule having a nucleotide sequence encoding a human GPAM polypeptide, wherein the nucleotide sequence comprises a guanine at a position corresponding to position 3,195 according to SEQ ID NO:2, or the complement thereof; an mRNA molecule having a nucleotide sequence encoding a human GPAM polypeptide, wherein the nucleotide sequence comprises a guanine at a position corresponding to position 327 according to SEQ ID NO:9, or the complement thereof; a cDNA molecule having a nucleotide sequence encoding a human GPAM polypeptide, wherein the nucleotide sequence comprises a guanine at a position corresponding to position 327 according to SEQ ID NO:21, or the complement thereof; or a GPAM polypeptide that comprises a valine at a position corresponding to position 43 according to SEQ ID NO:29. The GPAM inhibitors can be any of the GPAM inhibitors described herein.

In some embodiments, the subject comprises: an mRNA molecule having a nucleotide sequence encoding a human GPAM polypeptide, wherein the nucleotide sequence comprises a guanine at a position corresponding to position 291 according to SEQ ID NO:10, or the complement thereof; a cDNA molecule having a nucleotide sequence encoding a human GPAM polypeptide, wherein the nucleotide sequence comprises a guanine at a position corresponding to position 291 according to SEQ ID NO:22, or the complement thereof; or a GPAM polypeptide that comprises a valine at a position corresponding to position 43 according to SEQ ID NO:30.

In some embodiments, the subject comprises: an mRNA molecule having a nucleotide sequence encoding a human GPAM polypeptide, wherein the nucleotide sequence comprises a guanine at a position corresponding to position 323 according to SEQ ID NO:11, or the complement thereof; or a cDNA molecule having a nucleotide sequence encoding a human GPAM polypeptide, wherein the nucleotide sequence comprises a guanine at a position corresponding to position 323 according to SEQ ID NO:23, or the complement thereof.

In some embodiments, the subject comprises: an mRNA molecule having a nucleotide sequence encoding a human GPAM polypeptide, wherein the nucleotide sequence comprises a guanine at a position corresponding to position 326 according to SEQ ID NO:12, or the complement thereof; or a cDNA molecule having a nucleotide sequence encoding a human GPAM polypeptide, wherein the nucleotide sequence comprises a guanine at a position corresponding to position 326 according to SEQ ID NO:24, or the complement thereof.

In some embodiments, the subject comprises: an mRNA molecule having a nucleotide sequence encoding a human GPAM polypeptide, wherein the nucleotide sequence comprises a guanine at a position corresponding to position 305 according to SEQ ID NO:13, or the complement thereof; or a cDNA molecule having a nucleotide sequence encoding a human GPAM polypeptide, wherein the nucleotide sequence comprises a guanine at a position corresponding to position 305 according to SEQ ID NO:25, or the complement thereof.

In some embodiments, the subject comprises: an mRNA molecule having a nucleotide sequence encoding a human GPAM polypeptide, wherein the nucleotide sequence comprises a guanine at a position corresponding to position 170 according to SEQ ID NO:14, or the complement thereof; or a cDNA molecule having a nucleotide sequence encoding a human GPAM polypeptide, wherein the nucleotide sequence comprises a guanine at a position corresponding to position 170 according to SEQ ID NO:26, or the complement thereof.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: Loss of Function of the Gene Encoding Glycerol-3-Phosphate Acyltransferase, Mitochondrial (GPAM) is Associated with Lower Liver Fat, Lower ALT, and Protection Against Liver Disease To identify genetic factors contributing to chronic liver disease, imputed genotype data, exome sequence data, and magnetic resonance imaging (MRI) derived phenotypes were analyzed on 40,058 participants of the UK Biobank cohort (UKB). Statistically significant findings were subsequently evaluated for their relationship with liver injury as measured by ALT, a widely used measure of liver damage. Associations with metabolic phenotypes, diagnosis of chronic liver disease, type 2 diabetes, and coronary artery disease were also estimated. This analysis included 597,856 participants of European ancestry in the UK Biobank cohort (UKB), the Geisinger Health System MyCode Community Health Initiative cohort study (GHS) and Mount Sinai's BioMe Personalized Medicine Cohort (SINAI).

Genome wide analysis studies (GWAS) of MRI derived phenotypes were carried out using an imputed dataset of 11,914,698 variants and 37,250 individuals of European ancestry participating in UKB. Outcomes phenotypes included proton density fat fraction (PDFF), a measure of hepatic fat content, extracellular fluid fraction (ECF), a proxy for liver fibrosis and inflammation and iron corrected T1 measurements (cT1). PDFF is defined as the ratio of density of mobile protons from fat (triglycerides) and the total density of protons from mobile triglycerides and mobile water and reflects the concentration of fat within a tissue. ECF and cT1 measure the increases in extracellular tissue fluids that occur in response to inflammation and fibrosis.

The GWAS for PDFF identified 19 associations at the genome-wide level of statistical significance ($p<5\times10^{-8}$). One locus comprised rs2792751 (T→C, alternative allele frequency of 73%), encoding for a common missense variation changing an isoleucine into a valine at the 43rd amino acid of the encoded GPAM protein (Ile43Val). Ile43Val was in near perfect linkage disequilibrium ($r^2=0.99$) with the sentinel genetic variant (i.e., the variant with the lowest p-value for association) for PDFF at the GPAM locus in the European population. Ile43Val was significantly associated with lower PDFF levels at $P<6.9\times10^{-6}$ as shown in Table 2.

TABLE 2

Association of Ile43Val and GPAM pLOF burden with liver fat content as measured by magnetic resonance imaging (MRI) derived proton density fat fraction (PDFF) in the UKB

| Genetic exposure | Outcome | Per allele beta (95% confidence interval) | P-value | Genotype counts, RR\|RA\|AA genotypes | AAF, fraction of 1 |
|---|---|---|---|---|---|
| p.Ile43Val | PDFF | −0.05 (−0.06, −0.04) SD | 6.9E−16 | 2,849\|14,700\|19,701 | 0.73 |
| pLOF; AAF < 1% | PDFF | −0.34 (−0.64, −0.04) SD | 0.024 | 35,252\|22\|0 | 0.0003 |

Note:
PDFF, proton density fat fraction; RR, number of individuals carrying no alternative variant allele (homozygous non-carriers); RA, number of individuals carrying a single alternative variant allele (heterozygous carriers); AA, number of individuals carrying alternative variant alleles in both copies of the gene (homozygous carriers); The alternative allele is the allele causing loss of function or change in amino acid following human genome sequence reference build 38 and HGVS protein sequence nomenclature; AAF, the alternative allele frequency; SD, standard deviation units.

Using exome sequence data, the association for the burden of rare (AAF<1%) predicted loss-of-function (pLOF) variants in GPAM gene with liver fat as measured by PDFF at liver MRI was estimated. In this analysis, pLOF variants in GPAM were associated with lower PDFF levels at p=0.024 as shown in Table 2.

A meta-analysis of genetic association studies was then carried out to identify genes associated with ALT, a biomarker of liver damage. The Ile43Val variant at the GPAM locus was found to be associated with lower ALT levels at $P<4.20\times10^{-54}$ as shown in Table 3 and to be in perfect linkage disequilibrium (r2>0.99) with the sentinel variant at this locus.

TABLE 3

The GPAM Ile43Val allele and the burden of protein-truncating variants in GPAM are associated with lower circulating ALT levels. Results are shown both in units of standard deviation, and in the original clinical units (international units/liter)

| Genetic exposure | Outcome | Per allele beta (95% confidence interval) | P-value | Genotype counts, RR\|RA\|AA genotypes | AAF, fraction of 1 |
|---|---|---|---|---|---|
| p.Ile43Val | ALT | −0.03 (−0.04, −0.03) SD<br>−0.41 (−0.55, −0.41) U/L | 2.7E−55 | 43,024\|220,632\|287,173 | 0.72 |
| pLOF; AAF < 1% | ALT | −0.27 (−0.38, −0.16) SD<br>−3.69 (−5.19, −2.19) U/L | 2.50E−06 | 518,035\|276\|0 | 0.00027 |

Note:
RR, number of individuals carrying no alternative variant allele (homozygous non-carriers); RA, number of individuals carrying a single alternative variant allele (heterozygous carriers); AA, number of individuals carrying alternative variant alleles in both copies of the gene (homozygous carriers); the alternative allele is the allele causing loss of function or change in amino acid following human genome sequence reference build 38 and HGVS protein sequence nomenclature; AAF, alternative allele frequency; SD, standard deviation units; U/L, units per liter.

Using exome sequence data, the association for the burden of rare (AAF<1%) predicted loss-of-function (pLOF) variants in GPAM gene with ALT was estimated. In this analysis, pLOF variants in GPAM were strongly associated with reduced circulating ALT levels at $p=2.5\times10^{-06}$ as shown in Table 3. The patterns of association described in Table 2 and Table 3 of Ile43Val and the GPAM pLOF burden indicates that Ile43Val is likely to cause loss of function of GPAM.

Table 4 shows that Ile43Val is associated with reduced measures of liver inflammation as measured on the MRI in UKB. These results, together with results in Table 2 and Table 3 indicate that loss of function of GPAM is associated with lower liver inflammation. Carriers of GPAM pLOF variants had numerically lower levels of liver inflammation at imaging, but the statistical power is limited to detect significant associations between the GPAM pLOF burden and liver inflammation based on the observed effects for Ile43Val and low frequency of GPAM pLOF variants.

TABLE 4

Significant association between Ile43Val and liver imaging phenotypes in the UKB indicating liver inflammation

| Genetic exposure | Outcome | Per allele beta (95% confidence interval) | P-value | Genotype counts, RR\|RA\|AA genotypes | AAF |
|---|---|---|---|---|---|
| p.Ile43Val | cT1 | −0.03 (−0.05, −0.02) SD | 3.00E−05 | 2,981\|15,324\|20,540 | 0.73 |
| p.Ile43Val | cT1* | −0.03 (−0.05, −0.02) SD | 1.50E−06 | 2,849\|14,700\|19,701 | 0.73 |
| p.Ile43Val | ECF | −0.03 (−0.05, −0.02) SD | 3.20E−05 | 2,981\|15,324\|20,540 | 0.73 |

TABLE 4-continued

Significant association between Ile43Val and liver imaging phenotypes in the UKB indicating liver inflammation

| Genetic exposure | Outcome | Per allele beta (95% confidence interval) | P-value | Genotype counts, RR\|RA\|AA genotypes | AAF |
|---|---|---|---|---|---|
| p.Ile43Val | ECF* | −0.03 (−0.05, −0.02) SD | 1.80E−06 | 2,849\|14,700\|19,701 | 0.73 |
| pLOF; AAF < 1% | cT1 | −0.36 (−0.76, 0.03) SD | 0.073 | 36,738\|22\|0 | 0.0003 |
| pLOF; AAF < 1% | cT1* | −0.28 (−0.65, 0.08) SD | 0.13 | 35,252\|22\|0 | 0.00031 |
| pLOF; AAF < 1% | ECF | −0.36 (−0.75, 0.04) SD | 0.076 | 36,738\|22\|0 | 0.0003 |
| pLOF; AAF < 1% | ECF* | −0.28 (−0.64, 0.09) SD | 0.14 | 35,252\|22\|0 | 0.00031 |

Note:
*indicates that the phenotype was adjusted for technical covariates including BMI, alcohol usage, and diabetes; ECF indicates extracellular fluid; T1 indicates the time constant for recovery of longitudinal magnetization, it is a measure of how quickly the net magnetization recovers to its ground state, which is influenced by the strength of the magnetic field and tissue composition such as fat and/or iron in the tissue; cT1 = T1 corrected for the effects of liver iron content which result in T1 values being underestimated. RR, number of individuals carrying no alternative variant allele (homozygous non-carriers); RA, number of individuals carrying a single alternative variant allele (heterozygous carriers); AA, number of individuals carrying alternative variant alleles in both copies of the gene (homozygous carriers); The alternative allele is the allele causing loss of function or change in amino acid following human genome sequence reference build 38 and HGVS protein sequence nomenclature; AAF indicates the alternative allele frequency; SD indicates standard deviation units.

Table 5 and Table 6 shows associations between Ile43Val and multiple cardio-metabolic phenotypes, including lower HbA1c, lower apolipoprotein B, lower LDL-C, lower waist-hip ratio (adjust for BMI, WHRadjBMI), lower blood pressure, higher body mass index (BMI) and higher triglycerides. The variant was not associated with risk of type 2 diabetes or coronary artery disease.

TABLE 5

The Ile43Val variant in GPAM is associated with cardiovascular and metabolic continuous phenotypes. The results are from an inverse variance weighted meta-analysis in the GHS and UKB cohorts

| Outcome | Per allele Effect (95% confidence interval) | P-value | Genotype counts, RR\|RA\|AA genotypes | AAF |
|---|---|---|---|---|
| LDL-C | −0.02 (−0.03, −0.02) SD | 3.30E−36 | 41,427\|213,197\|277,973 | 0.72 |
| HDL-C | −0.04 (−0.04, −0.04) SD | 6.63E−84 | 38,698\|198,885\|259,316 | 0.72 |
| Triglycerides | 0.02 (0.01, 0.02) SD | 3.40E−20 | 41,539\|213,753\|278,608 | 0.72 |
| SBP | −0.01 (−0.01,−0.00) SD | 7.30E−05 | 43,830\|224,050\|290,153 | 0.72 |
| DBP | −0.01 (−0.01,−0.00) SD | 0.0029 | 43,553\|222,394\|287,977 | 0.72 |
| BMI | 0.01 (0.01, 0.01) SD | 2.90E−06 | 43,185\|220,899\|286,632 | 0.72 |
| WHRadjBMI | −0.01 (−0.01,−0.00) SD | 1.60E−05 | 65,480\|341,623\|450,945 | 0.72 |
| Glucose | 0.00 (−0.00, 0.01) SD | 0.20 | 38,189\|196,338\|256,154 | 0.72 |
| HbA1c | 0.01 (0.00, 0.01) SD | 0.0015 | 39,447\|203,863\|266,500 | 0.72 |

Note:
LDL-C indicates low-density lipoprotein cholesterol, HDL-C indicates high-density lipoprotein cholesterol, SBP indicates systolic blood pressure, DBP indicates diastolic blood pressure, BMI indicates body mass index, WHRadjBMI indicates waist hip ratio adjusted BMI, HbA1c indicates hemoglobin A1c, CAD indicates coronary artery disease; RR, number of individuals carrying no alternative variant allele (homozygous non-carriers); RA, number of individuals carrying a single alternative variant allele (heterozygous carriers); AA, number of individuals carrying alternative variant alleles in both copies of the gene (homozygous carriers); The alternative allele is the allele causing loss of function or change in amino acid following human genome sequence reference build 38 and HGVS protein sequence nomenclature; AAF indicates the alternative allele frequency; SD indicates standard deviation units.

TABLE 6

The variant Ile43Val in GPAM is not associated with risk of type 2 diabetes or coronary artery disease. The results are from an inverse variance weighted meta-analysis in the GHS and UKB cohorts

| Outcome | Per allele odds ratio (95% CI) for the outcome | p-value | Genotype counts, RR\|RA\|AA genotypes in the case and control groups | AAF, fraction of 1 |
|---|---|---|---|---|
| Type 2 diabetes | 1.01 (0.99, 1.02) OR | 0.26 | Cases: 4,245\|21,062\|27,191<br>Controls: 38,531\|199,011\|259,679 | 0.72 |

TABLE 6-continued

The variant Ile43Val in GPAM is not associated with risk of type 2 diabetes or coronary artery disease. The results are from an inverse variance weighted meta-analysis in the GHS and UKB cohorts

| Outcome | Per allele odds ratio (95% CI) for the outcome | p-value | Genotype counts, RR\|RA\|AA genotypes in the case and control groups | AAF, fraction of 1 |
|---|---|---|---|---|
| CAD | 0.99 (0.98, 1.01) OR | 0.24 | Cases: 4,977\|25,413\|32,086<br>Controls: 25,319\|128,167\|165,470 | 0.72 |

Note:
CAD indicates coronary artery disease; RR, number of individuals carrying no alternative variant allele (homozygous non-carriers); RA, number of individuals carrying a single alternative variant allele (heterozygous carriers); AA, number of individuals carrying alternative variant alleles in both copies of the gene (homozygous carriers); The alternative allele is the allele causing loss of function or change in amino acid following human genome sequence reference build 38 and HGVS protein sequence nomenclature; AAF indicates the alternative allele frequency; SD indicates standard deviation units.

Table 7 shows that Ile43Val in GPAM is also strongly associated with protection against liver diseases diagnoses, including parenchymal liver disease, alcoholic, non-alcoholic liver disease, liver fibrosis, cirrhosis of the liver and viral hepatitis. These results, together with the results in Table 2 and Table 3, indicate that loss-of-function of GPAM protects against various chronic liver diseases and viral hepatitis.

TABLE 7

Association of Ile43Val with clinical diagnoses of liver disease in a meta-analysis of the UKB, GHS and SINAI

| Outcome | Per allele Effect OR (95% confidence interval) | P-value | Genotype counts, RR\|RA\|AA genotypes | AAF |
|---|---|---|---|---|
| Parenchymal liver disease | 0.91 (0.88, 0.93) | 1.60E−13 | Cases: 1,435\|6,619\|7,660<br>Controls: 32,620\|166,799\|219,527 | 0.71 |
| Non-alcoholic liver disease | 0.90 (0.88, 0.93) | 7.20E−13 | Cases: 1,261\|5,520\|6,429<br>Controls: 30,928\|158,266\|208,098 | 0.71 |
| Liver disease (any) | 0.93 (0.91, 0.95) | 2.20E−12 | Cases: 2,016\|9,682\|11,366<br>Controls: 32,620\|166,799\|219,527 | 0.72 |
| Liver fibrosis or cirrhosis | 0.85 (0.81, 0.90) | 7.80E−10 | Cases: 341\|1,583\|1,673<br>Controls: 30,928\|158,266\|208,098 | 0.71 |
| Non-alcoholic fatty liver disease and steatosis hepatitis | 0.89 (0.86, 0.93) | 1.60E−09 | Cases: 710\|3,084\|3,575<br>Controls: 30,615\|156,760\|206,236 | 0.72 |
| Liver cirrhosis | 0.86 (0.81, 0.90) | 4.20E−09 | Cases: 318\|1,519\|1,592<br>Controls: 30,928\|158,266\|208,098 | 0.71 |
| Non-alcoholic liver fibrosis or cirrhosis | 0.85 (0.81, 0.90) | 6.80E−09 | Cases: 307\|1,365\|1,452<br>Controls: 30,927\|158,265\|208,095 | 0.71 |
| Non-alcoholic liver cirrhosis | 0.85 (0.81, 0.90) | 2.40E−08 | Cases: 284\|1,298\|1,365<br>Controls: 30,905\|158,181\|207,993 | 0.71 |
| Alcoholic liver disease | 0.87 (0.81, 0.93) | 6.70E−05 | Cases: 164\|846\|946<br>Controls: 30,016\|154,665\|204,484 | 0.72 |
| Alcoholic liver cirrhosis | 0.84 (0.77, 0.91) | 7.90E−05 | Cases: 104\|516\|546<br>Controls: 30,016\|154,665\|204,484 | 0.72 |
| Viral hepatitis | 0.94 (0.90, 0.99) | 0.010 | Cases: 396\|1,912\|2,147<br>Controls: 31,787\|162,679\|213,578 | 0.71 |

Note:
RR, number of individuals carrying no alternative variant allele (homozygous non-carriers); RA, number of individuals carrying a single alternative variant allele (heterozygous carriers); AA, number of individuals carrying alternative variant alleles in both copies of the gene (homozygous carriers); The alternative allele is the allele causing loss of function or change in amino acid following human genome sequence reference build 38 and HGVS protein sequence nomenclature; AAF indicates the alternative allele frequency; SD indicates standard deviation units; OR indicates odds ratio.

The associations between the burden of loss-of-function variants and PDFF or ALT was driven by multiple missense and loss-of-function variants in GPAM. Table 8 contains all individual variants that were used in the association.

TABLE 8

Chr:position:ref:alt indicates the position of the genetic variant on chromosome (chr) with reference (ref) and it's alternative (alt) allele on build 38 of the Genome Reference Consortium. Protein changes follow the recommendation of the Human Genome Variation Society and correspond to each to the Ensembl transcript IDs, hgvsp (protein change) is given in case of a protein coding variant, hgvsc (cDNA change) is given in case of a splice variant

| Genomic coordinates, chr:position:ref:alt | Transcript IDs | Protein or cDNA change |
|---|---|---|
| 10:112153594:G:A | ENST00000348367 | hgvsp: p.Arg815* |
| 10:112153667:C:T | ENST00000348367 | hgvsc: c.2371 − 1G > A |
| 10:112153668:T:C | ENST00000348367 | hgvsc: c.2371 − 2A > G |
| 10:112157390:C:T | ENST00000348367, ENST00000369425 | hgvsc: c.1981 − 1G > A, c.1981 − 1G > A |
| 10:112158315:C:T | ENST00000348367, ENST00000369425 | hgvsc: c.1980 + 1G > A, c.1980 + 1G > A |
| 10:112159909:AC:A | ENST00000348367, ENST00000369425 | hgvsc: c.1902 + 1delG, c.1902 + 1delG |
| 10:112159915:G:T | ENST00000348367, ENST00000369425 | hgvsp: p.Ser633*, p.Ser633* |
| 10:112159955:CCG:C | ENST00000348367, ENST00000369425 | hgvsp: p.Ala619fs, p.Ala619fs |
| 10:112160868:C:A | ENST00000348367, ENST00000369425 | hgvsp: p.Gly499*, p.Gly499* |
| 10:112163743:G:A | ENST00000348367, ENST00000369425 | hgvsp: p.Arg461*, p.Arg461* |
| 10:112166434:G:A | ENST00000348367, ENST00000369425 | hgvsp: p.Arg397*, p.Arg397* |
| 10:112166474:TCTTG:T | ENST00000348367, ENST00000369425 | hgvsp: p.Ala382fs, p.Ala382fs |
| 10:112168400:GACAGAGTATCT:G | ENST00000348367, ENST00000369425 | hgvsp: p.Asp337fs, p.Asp337fs |
| 10:112168506:G:A | ENST00000348367, ENST00000369425 | hgvsp: p.Arg305*, p.Arg305* |
| 10:112168915:G:A | ENST00000348367, ENST00000369425 | hgvsp: p.Arg278*, p.Arg278* |
| 10:112175598:A:T | ENST00000348367, ENST00000369425 | hgvsc: c.413 + 2T > A, c.413 + 2T > A |
| 10:112177984:CT:C | ENST00000348367, ENST00000369425 | hgvsp: p.Arg100fs, p.Arg100fs |
| 10:112177986:TG:T | ENST00000348367, ENST00000369425 | hgvsp: p.Thr99fs, p.Thr99fs |
| 10:112181719:GT:G | ENST00000348367, ENST00000369425 | hgvsp: p.Tyr22fs, p.Tyr22fs |
| 10:112181729:G:C | ENST00000348367, ENST00000369425 | hgvsp: p.Ser19*, p.Ser19* |
| 10:112156032:G:A | ENST00000348367 | hgvsp: p.Gln715* |
| 10:112158343:GA:G | ENST00000348367, ENST00000369425 | hgvsp: p.Ile651fs, p.Ile651fs |
| 10:112160010:AC:A | ENST00000348367, ENST00000369425 | hgvsp: p.Gly601fs, p.Gly601fs |
| 10:112161731:C:CT | ENST00000348367, ENST00000369425 | hgvsp: p.Ser477fs, p.Ser477fs |
| 10:112163779:TG:T | ENST00000348367, ENST00000369425 | hgvsp: p.Ile449fs, p.Ile449fs |
| 10:112163790:CT:C | ENST00000348367, ENST00000369425 | hgvsp: p.Arg445fs, p.Arg445fs |
| 10:112166419:G:A | ENST00000348367, ENST00000369425 | hgvsp: p.Gln402*, p.Gln402* |
| 10:112166455:G:A | ENST00000348367, ENST00000369425 | hgvsp: p.Arg390*, p.Arg390* |
| 10:112166517:T:A | ENST00000348367, ENST00000369425 | hgvsc: c.1108 − 2A > T, c.1108 − 2A > T |
| 10:112168309:TA:T | ENST00000348367, ENST00000369425 | hgvsc: c.1107 + 2delT, c.1107 + 2delT |
| 10:112168351:A:T | ENST00000348367, ENST00000369425 | hgvsp: p.Tyr356*, p.Tyr356* |
| 10:112168503:G:A | ENST00000348367, ENST00000369425 | hgvsp: p.Gln306*, p.Gln306* |
| 10:112168953:C:T | ENST00000348367, ENST00000369425 | hgvsc: c.795 − 1G > A, c.795 − 1G > A |
| 10:112173052:AC:A | ENST00000348367, ENST00000369425 | hgvsp: p.Val192fs, p.Val192fs |
| 10:112173717:AC:A | ENST00000348367, ENST00000369425 | hgvsp: p.Val181fs, p.Val181fs |
| 10:112173846:C:T | ENST00000348367, ENST00000369425 | hgvsc: c.414 − 1G > A, c.414 − 1G > A |

TABLE 8-continued

Chr:position:ref:alt indicates the position of the genetic variant on chromosome (chr) with reference (ref) and it's alternative (alt) allele on build 38 of the Genome Reference Consortium. Protein changes follow the recommendation of the Human Genome Variation Society and correspond to each to the Ensembl transcript IDs, hgvsp (protein change) is given in case of a protein coding variant, hgvsc (cDNA change) is given in case of a splice variant

| Genomic coordinates, chr:position:ref:alt | Transcript IDs | Protein or cDNA change |
|---|---|---|
| 10:112173847:T:C | ENST00000348367, ENST00000369425 | hgvsc: c.414 − 2A > G, c.414 − 2A > G |
| 10:112175661:G:A | ENST00000348367, ENST00000369425 | hgvsp: p.Arg118*, p.Arg118* |
| 10:112177985:TTG:T | ENST00000348367, ENST00000369425 | hgvsp: p.Thr99fs, p.Thr99fs |
| 10:112181683:C:T | ENST00000348367, ENST00000369425 | hgvsp: p.Trp34*, p.Trp34* |
| 10:112181784:T:C | ENST00000348367, ENST00000369425 | hgvsp: p.Met1?, p.Met1? |
| 10:112153559:CACAAA:C | ENST00000348367 | hgvsp: p.Phe825fs |
| 10:112153575:TA:T | ENST00000348367 | hgvsp: p.Tyr821fs |
| 10:112153591:G:A | ENST00000348367 | hgvsp: p.Gln816* |
| 10:112153603:G:A | ENST00000348367 | hgvsp: p.Gln812* |
| 10:112153631:AAC:A | ENST00000348367 | hgvsp: p.Val802fs |
| 10:112154628:C:T | ENST00000348367 | hgvsc: c.2370 + 1G > A |
| 10:112154636:TC:T | ENST00000348367 | hgvsp: p.Asp788fs |
| 10:112154678:GC:G | ENST00000348367 | hgvsp: p.Ala774fs |
| 10:112155862:A:T | ENST00000348367 | hgvsc: c.2311 + 2T > A |
| 10:112155899:AG:A | ENST00000348367 | hgvsp: p.Leu759fs |
| 10:112156055:T:C | ENST00000348367 | hgvsc: c.2122 − 2A > G |
| 10:112157247:A:T | ENST00000348367 | hgvsc: c.2121 + 2T > A |
| 10:112157266:G:A | ENST00000348367, ENST00000369425 | hgvsp: p.Arg702*, p.Arg702* |
| 10:112157273:C:CT | ENST00000348367, ENST00000369425 | hgvsp: p.Glu700fs, p.Glu700fs |
| 10:112157338:T:A | ENST00000348367, ENST00000369425 | hgvsp: p.Lys678*, p.Lys678* |
| 10:112157371:TATCTTCCTGG:T | ENST00000348367, ENST00000369425 | hgvsp: p.Asp663fs, p.Asp663fs |
| 10:112158319:TG:T | ENST00000348367, ENST00000369425 | hgvsp: p.Ala659fs, p.Ala659fs |
| 10:112158326:GT:G | ENST00000348367, ENST00000369425 | hgvsp: p.Thr657fs, p.Thr657fs |
| 10:112158367:G:T | ENST00000348367, ENST00000369425 | hgvsp: p.Cys643*, p.Cys643* |
| 10:112158375:G:A | ENST00000348367, ENST00000369425 | hgvsp: p.Gln641*, p.Gln641* |
| 10:112159915:G:C | ENST00000348367, ENST00000369425 | hgvsp: p.Ser633*, p.Ser633* |
| 10:112159941:G:T | ENST00000348367, ENST00000369425 | hgvsp: p.Tyr624*, p.Tyr624* |
| 10:112160010:A:AC | ENST00000348367, ENST00000369425 | hgvsp: p.Pro602fs, p.Pro602fs |
| 10:112160603:C:A | ENST00000348367, ENST00000369425 | hgvsc: c.1759 + 1G > T, c.1759 + 1G > T |
| 10:112160620:GAT:G | ENST00000348367, ENST00000369425 | hgvsp: p.Ile581fs, p.Ile581fs |
| 10:112160685:TG:T | ENST00000348367, ENST00000369425 | hgvsp: p.Ser560fs, p.Ser560fs |
| 10:112160685:T:TG | ENST00000348367, ENST00000369425 | hgvsp: p.Ser560fs, p.Ser560fs |
| 10:112160694:T:TA | ENST00000348367, ENST00000369425 | hgvsp: p.Ile557fs, p.Ile557fs |
| 10:112160786:G:T | ENST00000348367, ENST00000369425 | hgvsp: p.Ser526*, p.Ser526* |
| 10:112160854:GGA:G | ENST00000348367, ENST00000369425 | hgvsp: p.Ser503fs, p.Ser503fs |
| 10:112161666:C:T | ENST00000348367, ENST00000369425 | hgvsc: c.1494 + 1G > A, c.1494 + 1G > A |
| 10:112161739:T:A | ENST00000348367, ENST00000369425 | hgvsc: c.1424 − 2A > T, c.1424 − 2A > T |
| 10:112163718:GC:G | ENST00000348367, ENST00000369425 | hgvsp: p.Ala469fs, p.Ala469fs |
| 10:112163744:TA:T | ENST00000348367, ENST00000369425 | hgvsp: p.Leu460fs, p.Leu460fs |
| 10:112163748:G:GT | ENST00000348367, ENST00000369425 | hgvsp: p.Ser459fs, p.Ser459fs |

TABLE 8-continued

Chr:position:ref:alt indicates the position of the genetic variant on chromosome (chr) with reference (ref) and it's alternative (alt) allele on build 38 of the Genome Reference Consortium. Protein changes follow the recommendation of the Human Genome Variation Society and correspond to each to the Ensembl transcript IDs, hgvsp (protein change) is given in case of a protein coding variant, hgvsc (cDNA change) is given in case of a splice variant

| Genomic coordinates, chr:position:ref:alt | Transcript IDs | Protein or cDNA change |
|---|---|---|
| 10:112163796:TC:T | ENST00000348367, ENST00000369425 | hgvsp: p.Glu443fs, p.Glu443fs |
| 10:112163812:TG:T | ENST00000348367, ENST00000369425 | hgvsp: p.Ser438fs, p.Ser438fs |
| 10:112164527:TG:T | ENST00000348367, ENST00000369425 | hgvsp: p.Ser435fs, p.Ser435fs |
| 10:112164527:TGAAG:T | ENST00000348367, ENST00000369425 | hgvsp: p.Pro434fs, p.Pro434fs |
| 10:112164528:GA:G | ENST00000348367, ENST00000369425 | hgvsp: p.Ser435fs, p.Ser435fs |
| 10:112164528:G:T | ENST00000348367, ENST00000369425 | hgvsp: p.Ser435*, p.Ser435* |
| 10:112164538:TA:T | ENST00000348367, ENST00000369425 | hgvsp: p.Ile432fs, p.Ile432fs |
| 10:112164541:CT:C | ENST00000348367, ENST00000369425 | hgvsp: p.Ala431fs, p.Ala431fs |
| 10:112164542:TG:T | ENST00000348367, ENST00000369425 | hgvsp: p.Pro430fs, p.Pro430fs |
| 10:112164558:TC:T | ENST00000348367, ENST00000369425 | hgvsp: p.Glu425fs, p.Glu425fs |
| 10:112164561:AG:A | ENST00000348367, ENST00000369425 | hgvsp: p.Leu424fs, p.Leu424fs |
| 10:112164597:CT:C | ENST00000348367, ENST00000369425 | hgvsp: p.Ser412fs, p.Ser412fs |
| 10:112164601:CT:C | ENST00000348367, ENST00000369425 | hgvsp: p.Glu411fs, p.Glu411fs |
| 10:112164607:AT:A | ENST00000348367, ENST00000369425 | hgvsp: p.Glu408fs, p.Glu408fs |
| 10:112164611:C:T | ENST00000348367, ENST00000369425 | hgvsc: c.1222 − 1G > A, c.1222 − 1G > A |
| 10:112164612:T:C | ENST00000348367, ENST00000369425 | hgvsc: c.1222 − 2A > G, c.1222 − 2A > G |
| 10:112166409:GA:G | ENST00000348367, ENST00000369425 | hgvsp: p.Ser405fs, p.Ser405fs |
| 10:112166443:CAT:C | ENST00000348367, ENST00000369425 | hgvsp: p.Tyr393fs, p.Tyr393fs |
| 10:112166497:C:CA | ENST00000348367, ENST00000369425 | hgvsp: p.Glu376fs, p.Glu376fs |
| 10:112166516:CT:C | ENST00000348367, ENST00000369425 | hgvsc: c.1108 − 2delA, c.1108 − 2delA |
| 10:112168327:G:T | ENST00000348367, ENST00000369425 | hgvsp: p.Tyr364*, p.Tyr364* |
| 10:112168335:CT:C | ENST00000348367, ENST00000369425 | hgvsp: p.Gly362fs, p.Gly362fs |
| 10:112168411:TAC:T | ENST00000348367, ENST00000369425 | hgvsp: p.Val336fs, p.Val336fs |
| 10:112168857:TG:T | ENST00000348367, ENST00000369425 | hgvsp: p.His297fs, p.His297fs |
| 10:112168872:TA:T | ENST00000348367, ENST00000369425 | hgvsp: p.Tyr292fs, p.Tyr292fs |
| 10:112168918:G:A | ENST00000348367, ENST00000369425 | hgvsp: p.Arg277*, p.Arg277* |
| 10:112168937:CT:C | ENST00000348367, ENST00000369425 | hgvsp: p.Lys270fs, p.Lys270fs |
| 10:112168939:T:A | ENST00000348367, ENST00000369425 | hgvsp: p.Lys270*, p.Lys270* |
| 10:112172190:TG:T | ENST00000348367, ENST00000369425 | hgvsp: p.Pro262fs, p.Pro262fs |
| 10:112172968:G:T | ENST00000348367, ENST00000369425 | hgvsc: c.657 + 2C > A, c.657 + 2C > A |
| 10:112172968:G:C | ENST00000348367, ENST00000369425 | hgvsc: c.657 + 2C > G, c.657 + 2C > G |
| 10:112172972:CA:C | ENST00000348367, ENST00000369425 | hgvsp: p.Glu219fs, p.Glu219fs |
| 10:112172976:TG:T | ENST00000348367, ENST00000369425 | hgvsp: p.Ala217fs, p.Ala217fs |
| 10:112173035:TG:T | ENST00000348367, ENST00000369425 | hgvsp: p.Phe197fs, p.Phe197fs |

TABLE 8-continued

Chr:position:ref:alt indicates the position of the genetic variant on chromosome (chr) with reference (ref) and it's alternative (alt) allele on build 38 of the Genome Reference Consortium. Protein changes follow the recommendation of the Human Genome Variation Society and correspond to each to the Ensembl transcript IDs, hgvsp (protein change) is given in case of a protein coding variant, hgvsc (cDNA change) is given in case of a splice variant

| Genomic coordinates, chr:position:ref:alt | Transcript IDs | Protein or cDNA change |
|---|---|---|
| 10:112173050:GCACC:G | ENST00000348367, ENST00000369425 | hgvsp: p.Trp191fs, p.Trp191fs |
| 10:112173056:AC:A | ENST00000348367, ENST00000369425 | hgvsp: p.Trp191fs, p.Trp191fs |
| 10:112173058:CCAGT:C | ENST00000348367, ENST00000369425 | hgvsp: p.Thr189fs, p.Thr189fs |
| 10:112173067:C:A | ENST00000348367, ENST00000369425 | hgvsc: c.561 − 1G > T, c.561 − 1G > T |
| 10:112173733:C:A | ENST00000348367, ENST00000369425 | hgvsp: p.Glu176*, p.Glu176* |
| 10:112175598:A:G | ENST00000348367, ENST00000369425 | hgvsc: c.413 + 2T > C, c.413 + 2T > C |
| 10:112175599:C:T | ENST00000348367, ENST00000369425 | hgvsc: c.413 + 1G > A, c.413 + 1G > A |
| 10:112175680:G:C | ENST00000348367, ENST00000369425 | hgvsp: p.Tyr111*, p.Tyr111* |
| 10:112177983:C:A | ENST00000348367, ENST00000369425 | hgvsc: c.299 + 1G > T, c.299 + 1G > T |
| 10:112178039:TG:T | ENST00000348367, ENST00000369425 | hgvsp: p.Ser82fs, p.Ser82fs |
| 10:112178058:C:G | ENST00000348367, ENST00000369425 | hgvsc: c.226 − 1G > C, c.226 − 1G > C |
| 10:112178058:C:A | ENST00000348367, ENST00000369425 | hgvsc: c.226 − 1G > T, c.226 − 1G > T |
| 10:112178059:T:C | ENST00000348367, ENST00000369425 | hgvsc: c.226 − 2A > G, c.226 − 2A > G |
| 10:112180473:C:T | ENST00000348367, ENST00000369425 | hgvsp: p.Trp75*, p.Trp75* |
| 10:112180580:T:A | ENST00000348367, ENST00000369425 | hgvsp: p.Arg40*, p.Arg40* |
| 10:112180597:T:C | ENST00000348367, ENST00000369425 | hgvsc: c.103 − 2A > G, c.103 − 2A > G |
| 10:112181681:AC:A | ENST00000348367, ENST00000369425 | hgvsc: c.102 + 1delG, c.102 + 1delG |
| 10:112181691:CACTT:C | ENST00000348367, ENST00000369425 | hgvsp: p.Ser31fs, p.Ser31fs |
| 10:112181694:TTG:T | ENST00000348367, ENST00000369425 | hgvsp: p.Thr30fs, p.Thr30fs |
| 10:112181709:G:A | ENST00000348367, ENST00000369425 | hgvsp: p.Arg26*, p.Arg26* |
| 10:112181710:AC:A | ENST00000348367, ENST00000369425 | hgvsp: p.Gly25fs, p.Gly25fs |
| 10:112181729:G:T | ENST00000348367, ENST00000369425 | hgvsp: p.Ser19*, p.Ser19* |
| 10:112181734:TG:T | ENST00000348367, ENST00000369425 | hgvsp: p.Pro17fs, p.Pro17fs |
| 10:112181740:A:C | ENST00000348367, ENST00000369425 | hgvsp: p.Tyr15*, p.Tyr15* |
| 10:112181757:TA:T | ENST00000348367, ENST00000369425 | hgvsp: p.Thr10fs, p.Thr10fs |
| 10:112181780:TCC:T | ENST00000348367, ENST00000369425 | hgvsp: p.Met1fs, p.Met1fs |
| 10:112181783:A:C | ENST00000348367, ENST00000369425 | hgvsp: p.Met1?, p.Met1? |
| 10:112181815:T:C | ENST00000348367, ENST00000369425 | hgvsc: c.−29 − 2A > G, c.−29 − 2A > G |
| 10:112153552:A:G | ENST00000348367 | hgvsp: p.Ter829Glnext*? |
| 10:112157248:C:A | ENST00000348367 | hgvsc: c.2121 + 1G > T |
| 10:112157343:C:T | ENST00000348367, ENST00000369425 | hgvsp: p.Trp676*, p.Trp676* |
| 10:112160805:CACGAGCCAGG:C | ENST00000348367, ENST00000369425 | hgvsp: p.Leu517fs, p.Leu517fs |
| 10:112168525:C:T | ENST00000348367, ENST00000369425 | hgvsc: c.895 − 1G > A, c.895 − 1G > A |
| 10:112172320:T:C | ENST00000348367, ENST00000369425 | hgvsc: c.658 − 2A > G, c.658 − 2A > G |
| 10:112173037:AAC:A | ENST00000348367, ENST00000369425 | hgvsp: p.Phe197fs, p.Phe197fs |
| 10:112164564:G:GA | ENST00000348367, ENST00000369425 | hgvsp: p.Ser423fs, p.Ser423fs |

TABLE 8-continued

Chr:position:ref:alt indicates the position of the genetic variant on chromosome (chr) with reference (ref) and it's alternative (alt) allele on build 38 of the Genome Reference Consortium. Protein changes follow the recommendation of the Human Genome Variation Society and correspond to each to the Ensembl transcript IDs, hgvsp (protein change) is given in case of a protein coding variant, hgvsc (cDNA change) is given in case of a splice variant

| Genomic coordinates, chr:position:ref:alt | Transcript IDs | Protein or cDNA change |
|---|---|---|
| 10:112166441:AC:A | ENST00000348367, ENST00000369425 | hgvsp: p.Gly394fs, p.Gly394fs |
| 10:112168850:T:TA | ENST00000348367, ENST00000369425 | hgvsc: c.894 + 2_894 + 3insT, c.894 + 2_894 + 3insT |
| 10:112172202:AT:A | ENST00000348367, ENST00000369425 | hgvsp: p.Asn258fs, p.Asn258fs |
| 10:112173754:TC:T | ENST00000348367, ENST00000369425 | hgvsp: p.Ala170fs, p.Ala170fs |
| 10:112173790:G:A | ENST00000348367, ENST00000369425 | hgvsp: p.Gln157*, p.Gln157* |
| 10:112181682:C:T | ENST00000348367, ENST00000369425 | hgvsc: c.102 + 1G > A, c.102 + 1G > A |
| 10:112181814:C:A | ENST00000348367, ENST00000369425 | hgvsc: c.−29 − 1G > T, c.−29 − 1G > T |
| 10:112155956:TG:T | ENST00000348367 | hgvsp: p.His740fs |
| 10:112158327:TA:T | ENST00000348367, ENST00000369425 | hgvsp: p.Thr657fs, p.Thr657fs |
| 10:112158363:C:A | ENST00000348367, ENST00000369425 | hgvsp: p.Glu645*, p.Glu645* |
| 10:112160869:C:T | ENST00000348367, ENST00000369425 | hgvsc: c.1495 − 1G > A, c.1495 − 1G > A |
| 10:112163818:T:C | ENST00000348367, ENST00000369425 | hgvsc: c.1308 − 2A > G, c.1308 − 2A > G |
| 10:112166400:A:T | ENST00000348367, ENST00000369425 | hgvsc: c.1221 + 2T > A, c.1221 + 2T > A |
| 10:112166401:C:T | ENST00000348367, ENST00000369425 | hgvsc: c.1221 + 1G > A, c.1221 + 1G > A |
| 10:112168951:TA:T | ENST00000348367, ENST00000369425 | hgvsp: p.Ser265fs, p.Ser265fs |
| 10:112168954:T:C | ENST00000348367, ENST00000369425 | hgvsc: c.795 − 2A > G, c.795 − 2A > G |
| 10:112178004:A:T | ENST00000348367, ENST00000369425 | hgvsp: p.Tyr93*, p.Tyr93* |
| 10:112178005:TA:T | ENST00000348367, ENST00000369425 | hgvsp: p.Tyr93fs, p.Tyr93fs |

Participating Cohorts:

Genetic association studies were performed in the United Kingdom Biobank (UKB) cohort (Bycroft et al., 2018, doi:10.1038/s41586-018-0579-z; Van Hout et al., 2020, doi: 10.1038/s41586-020-2853-0), the MyCode Community Health Initiative cohort from the Geisinger Health System (GHS) (Carey et al., 2016, doi:10.1038/gim.2015.187) and Mount Sinai's BioMe Personalized Medicine Cohort (SINAI) (Gottesman et al., 2013, doi:10.1038/gim.2013.72).

The UKB is a population-based cohort study of people aged between 40 and 69 years recruited through 22 testing centers in the UK between 2006-2010. A total of 430,998 European ancestry participants from UKB with available whole-exome sequencing and phenotype data were included. The GHS MyCode study is a health system-based cohort of patients from Central and Eastern Pennsylvania (USA) recruited in 2007-2019. A total of 136,239 European ancestry participants from GHS with available whole-exome sequencing and phenotype data were included. Mount Sinai's BioMe Personalized Medicine Cohort (SINAI) is an electronic health record-linked clinical care cohort of 30,619 individuals. These individuals are from diverse ancestries and characterized by a broad spectrum of biomedical traits.

Liver MRI Phenotypes:

A subset of 40,058 individuals participating in UKB underwent imaging sessions of liver magnetic resonance imaging (MRI) (Littlejohns et al., 2020, doi:10.1038/s41467-020-15948-9). The majority of UK Biobank participants selected for liver MRI underwent two acquisitions, one for estimating fat content and the other a quantitative T1 mapping sequence. For the former, approximately 10,000 subjects were imaged under a Dixon gradient echo protocol; in 2016, the acquisition protocol for measurement of fat fraction was updated to the IDEAL sequence (Iterative Decomposition of water and fat with Echo Asymmetry and Least-squares estimation). Data from this acquisition are provided as a series of complex-valued 2D images per subject. The in-plane pixel size is 2.5×2.5 mm; slice thickness is 6 mm. The latter protocol, "ShMOLLI" (Shortened Modified Look-Locker Inversion recovery), has been consistent throughout the study. Data for this acquisition are provided as one real-valued 2D pre-computed T1 map per subject. The in-plane pixel size is 1.15×1.15 mm; slice thickness is 8 mm. Both MRI datasets were acquired at the same 2D cross-section per subject, intended to be through the porta hepatis. All images were acquired on a Siemens MAGNETOM Aera 1.5T clinical MRI scanner.

Measurements of PDFF, ECF, T1 and corrected T1 were obtained by applying pre-defined mathematical models after segmenting the liver on liver MRI images (Hernando et al., 2012, doi:10.1002/mrm.23044; Wood et al., 2005, doi: 10.1182/blood-2004-10-3982; Tunnicliffe et al., 2017, doi: 10.1002/jmri.25392). Three distinct phenotypes were derived from two abdominal MRIs acquisition, one for estimating fat content and the other a quantitative T1 mapping sequence: proton density fat fraction (PDFF), and extracellular fluid fraction (ECF, a proxy for liver fibrosis and inflammation). PDFF was estimated as the fraction of fat signal relative to total fat plus water signal. ECF was estimated by interpolation from their published Table containing grid points of a non-linear numerical model describing ECF as a function of T1 (from ShMOLLI MRI) and hepatic iron content (from IDEAL MRI), correcting for field strength.

Pixels belonging to the liver were segmented using a thresholding approach, Li thresholding for PDFF maps to identify liver tissue, and Otsu thresholding for T1 maps to exclude larger vessels. To obtain a summary measure of each trait per subject, all pixels within the liver were averaged for each parametric map.

All traits were deconfounded by residualizing the traits with the following covariates: sex, age, age-squared, top 20 principal components for ancestry, age*sex, imaging center, imaging protocol. Additional covariates (referred to as 'extra' here), were BMI, $BMI^2$, 7 binary alcohol variables (daily, 1-2 times per week, 3-4 times per week, 1-3 times per month, special occasions, previous, current), 2 binary weight gain variables (weight gain in last year, weight loss in last year) and 5 binary disease variables (diabetes, heart attack, angina, stroke, high blood pressure).

Phenotype Definitions:

Clinical laboratory measurements for ALT, LDL-C, HDL-C, triglycerides, BMI, waist, hip, glucose and Hb1Ac were extracted from electronic health records (EHRs) of participants from GHS or measured from blood at UKB recruitment centers. For GHS, median values were calculated for all participants with two or more measurements. In UKB, ALT, LDL-C, HDL-C, triglyceride and glucose were measured by IFCC (International Federation of Clinical Chemistry) analysis on a Beckman Coulter AU5800 at the baseline visit of the study and averaged in case of multiple measurements. Hb1Ac was measured by HPLC using a Bio-Rad VARIANT II Turbo. Prior to genetic association analysis, continues phenotype values were transformed by the inverse standard normal function, applied within each ancestry group and separately in men and women.

In GHS, UKB and SINAI, disease outcomes were defined according to the International Classification of Diseases, Ninth and Tenth Revision (ICD-9 and ICD-t) and Read codes stored in EHRs, and self-reports were used when available; all of which and combined into single variables to classify individuals into cases or controls. Individuals with type 2 diabetes were identified using a previously described algorithm (Eastwood et al., 2016, doi:10.1371/journal.pone.0162388). Individuals with coronary artery disease or liver diseases were identified as described in Table 9, combining EHR records, self-reports and ALT measurements.

TABLE 9

Individuals with or without disease were identified in GHS, UKB and SINAI using EHR records and self-reports. OPCS4 codes (operation procedures), f.20002 (self-reported disease) and f.20004 (self-reported operation procedures) variables were specific to UKB. In each cohort, EHR records with ICD-9 or read codes were translated to ICD-10 codes

| | Case definition | Control exclusion |
|---|---|---|
| Parenchymal liver disease | ICD10:<br>K70, K71, K72, K73, K74, K753, K753, K752, K754, K758, K759, K760, K767, K7681<br>OPCS4: G10, G144, J01<br>f.20002: 1604, 1158, 1141 | ICD10:<br>K70, K71, K72, K73, K74, K75, K76, K77, I81, I85, I982, I983, I864, T864, Z944, C220<br>OPCS4: G10, G144, J01<br>f.20002: 1604, 1158, 1141<br>ALT: >33 IU/L for men and >24 IU/L for women |
| Non-alcoholic liver disease | ICD10: K746, K758, K760 | See Parenchymal liver disease |
| Non-alcoholic liver disease (broad) | ICD10:<br>K721, K740, K741, K742, K746, K758, K760 | See Parenchymal liver disease |
| Liver disease (any) | ICD10: K70, K71, K72, K73, K74, K75, K76, K77, I81, I85, I982, I983, I864, T864, Z944, C220<br>OPCS4: G10, G144, J01<br>f.20002: 1604, 1158, 1141 | See Parenchymal liver disease |
| Liver fibrosis or cirrhosis (agnostic) | ICD10:<br>K703, K704, K717, K721, K746, K702, K740, K741, K742 | See Parenchymal liver disease |
| Non-alcoholic fatty liver disease and steatosis hepatitis | ICD10: K760, K7581 | See Parenchymal liver disease |
| Liver cirrhosis | ICD10: K703, K704, K717, K721, K746 | See Parenchymal liver disease |
| Non-alcoholic Liver fibrosis or cirrhosis | ICD10: K721, K740, K741, K742, K746 | See Parenchymal liver disease |
| Non-alcoholic liver cirrhosis | ICD10: K746 | See Parenchymal liver disease |
| Alcoholic liver disease | ICD10: K70 | See Parenchymal liver disease |

TABLE 9-continued

Individuals with or without disease were identified in GHS, UKB and SINAI using EHR records and self-reports. OPCS4 codes (operation procedures), f.20002 (self-reported disease) and f.20004 (self-reported operation procedures) variables were specific to UKB. In each cohort, EHR records with ICD-9 or read codes were translated to ICD-10 codes

| | Case definition | Control exclusion |
|---|---|---|
| Alcoholic liver cirrhosis | ICD10: K703, K704 | See Parenchymal liver disease |
| Viral hepatitis | ICD10: K746, K758, K760 | See Parenchymal liver disease |
| Coronary artery disease | ICD10: Z955, I248, I249, I241, I251, I255, I258, I259, I21, I22, I23, I252, I256, Z951<br>OPSC4: K471, K49, K502, K75, K40, K41, K44, K45, K46<br>f.20002: 1075<br>f.20004: 1070, 1095, 1523<br>EHR: CABG or stenosis from Cath-lab records. | Family history of heart disease based on ICD10: Z824<br>self-reports in UK Biobank (fields 20107, 20110 and 20111) |

Genotype Data:

High coverage whole exome sequencing was performed as previously described (Science, 2016, 354: aaf6814; and Nature, 2020; 586, 749-756) and as summarized below. NimbleGen probes (VCRome; for part of the GHS cohort) or a modified version of the xGen design available from Integrated DNA Technologies (IDT; for the rest of GHS and other cohorts) were used for target sequence capture of the exome. A unique 6 base pair (bp) barcode (VCRome) or 10 bp barcode (IDT) was added to each DNA fragment during library preparation to facilitate multiplexed exome capture and sequencing. Equal amounts of sample were pooled prior to exome capture. Sequencing was performed using 75 bp paired-end reads on Illumina v4 HiSeq 2500 (for part of the GHS cohort) or NovaSeq (for the rest of GHS and other cohorts) instruments. Sequencing had a coverage depth (i.e., number of sequence-reads covering each nucleotide in the target areas of the genome) sufficient to provide greater than 20× coverage over 85% of targeted bases in 96% of VCRome samples and 20× coverage over 90% of targeted bases in 99% of IDT samples. Data processing steps included sample de-multiplexing using Illumina software, alignment to the GRCh38 Human Genome reference sequence including generation of binary alignment and mapping files (BAM), processing of BAM files (e.g., marking of duplicate reads and other read mapping evaluations). Variant calling was performed using the GLNexus system (DOI: 10.1101/343970). Variant mapping and annotation were based on the GRCh38 Human Genome reference sequence and Ensembl v85 gene definitions using the snpEff software. The snpEff predictions that involve protein-coding transcripts with an annotated start and stop were then combined into a single functional impact prediction by selecting the most deleterious functional effect class for each gene. The hierarchy (from most to least deleterious) for these annotations was frameshift, stop-gain, stop-loss, splice acceptor, splice donor, stop-lost, in-frame indel, missense, other annotations. Predicted LOF genetic variants included: a) insertions or deletions resulting in a frameshift, b) insertions, deletions or single nucleotide variants resulting in the introduction of a premature stop codon or in the loss of the transcription start site or stop site, and c) variants in donor or acceptor splice sites. Missense variants were classified for likely functional impact according to the number of in silico prediction algorithms that predicted deleteriousness using SIFT (Adzhubei et al., Nat. Methods, 2010, 7, 248-9) and Polyphen2_HVAR (Adzhubei et al., Nat. Methods, 2010, 7, 248-9), LRT (Chun et al., Genome Res., 2009, 19, 1553-61) and MutationTaster (Schwarz et al., Nat. Methods, 2010, 7, 575-6). For each gene, the alternative allele frequency (AAF) and functional annotation of each variant determined inclusion into these 7 gene burden exposures: 1) pLOF variants with AAF<1%; 2) pLOF or missense variants predicted deleterious by 5/5 algorithms with AAF<1%; 3) pLOF or missense variants predicted deleterious by 5/5 algorithms with AAF<0.1%; 4) pLOF or missense variants predicted deleterious by at least 1/5 algorithms with AAF<1%; 5) pLOF or missense variants predicted deleterious by at least 1/5 algorithms with AAF<0.1%; 6) pLOF or any missense with AAF<1%; 7) pLOF or any missense variants with AAF<0.1%.

Association Analysis of Gene Burden of Rare Loss of Function Variation:

Association between the burden of rare predicted loss-of-function or missense variants in a given gene and phenotype was examined by fitting a linear (for quantitative traits) or firth bias-corrected logistic (for binary traits) regression model adjusted for a polygenic score that approximates a genomic kinship matrix using REGENIE v1.0 (doi: world wide web at “doi.org/10.1101/2020.06.19.162354”). Analyses were stratified by ancestry and adjusted for age, age$^2$, sex, age-by-sex and age$^2$-by-sex interaction terms, experimental batch-related covariates, 10 common variant-derived principal components, and 20 rare variant-derived principal components. Results across cohorts for each variant-phenotype association were combined using fixed effects inverse variance weighted meta-analysis. In gene burden tests, all individuals are labeled as heterozygotes if they carry one or more qualifying rare variant (as described above based on frequency and functional annotation) and as homozygotes if they carry any qualifying variant in the homozygous state. This “composite genotype” is then used to test for association.

GWAS of Common Variants:

Associated common variants were identified by performing a genome-wide association study including over 12 million common-to-low-frequency genetic variants imputed using the Haplotype Reference Consortium panel. In the GHS study, imputation was performed separately in samples genotyped with the Illumina Human Omni Express Exome array (OMNI set) and the Global Screening array (GSA set). Dosage data from imputed variants were then merged across the two GHS sets, to obtain a combined dataset for association analysis. Genome-wide association analyses were performed in GHS and UKB separately by fitting whole genome regression models using REGENIE (Mbatchou et al., 2020, doi:10.1101/2020.06.19.162354). As described above for burden tests, within each cohort analyses were stratified by ancestry and adjusted for age, age$^2$, sex, age-by-sex and age$^2$-by-sex interaction terms, experimental batch-related covariates, and 10 common variant-derived principal components. Results from the UKB and GHS analyses were then combined by inverse variance-weighted meta-analysis to obtain a genome-wide meta-analysis in the European subset of the discovery cohorts.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

What is claimed is:

1. A method of treating a subject having liver disease or at risk of having liver disease, having fatty liver disease or at risk of having fatty liver disease, having hepatocellular carcinoma or at risk of having hepatocellular carcinoma, having liver cirrhosis or at risk of having liver cirrhosis, having liver fibrosis or at risk of having liver fibrosis, and/or having simple steatosis, steatohepatitis, or non-alcoholic steatohepatitis (NASH) or at risk of having simple steatosis, steatohepatitis, or NASH, the method comprising administering a glycerol-3-phosphate acyltransferase (GPAM) inhibitor to the subject, wherein:

the GPAM inhibitor comprises an antisense nucleic acid molecule, a small interfering RNA (siRNA), or a short hairpin RNA (shRNA) that hybridizes to a GPAM mRNA; and the subject is heterozygous for a GPAM predicted loss-of-function variant mRNA molecule comprising SEQ ID NO: 10, SEQ ID NO: 11, SEQ ID NO: 12, SEQ ID NO: 13, and/or SEQ ID NO: 14.

2. The method according to claim 1, wherein the fatty liver disease is alcoholic fatty liver disease (AFLD) or nonalcoholic fatty liver disease (NAFLD).

3. The method according to claim 1, wherein the subject is heterozygous for a GPAM predicted loss-of-function variant mRNA molecule comprising SEQ ID NO: 10.

* * * * *

SEQUENCE LISTING

```
<160> NUMBER OF SEQ ID NOS: 44

<210> SEQ ID NO 1
<211> LENGTH: 33901
<212> TYPE: DNA
<213> ORGANISM: homo sapien

<400> SEQUENCE: 1

gcgccactgc agctggcatt ggccgggact ggaagtgcgg gcttctgcag cagccgaagc      60
tggagctgct agggtgcgaa ctgccagggc aggtgtgggc tgcgggaggc tactcgggcc     120
gggagcgccg ggacaagtgc atggaggtgg tgcgactcct gcaagttgct ggggcagtcg     180
tgtcccctat tccctgacac ccgagctccg gtcttctccc tgagaaatcg gtcgggctcg     240
tgcaggggtg gggatcagga ttcatctctc ctggggagac tgcgctgggg catgggttcc     300
cctgggttgg aaggagtcct tatggactca gtcccctaag tatctgcacg cgcggaggcg     360
ccgccagcca gcccgcctgg gtccctaggg aacattgagg cagtaagggg tactctgaga     420
gcagccggta tgctggagat aattaatgac agcgttacca ttgattggac tgagcgctca     480
ctgtgtgtta cacactgtgg tagacccttt gtttatatta ttccgtcctc tcaacaatcc     540
aggaggttaa gagctatcat tctgcccatt ttccagatgg gaaaactaag gcatagaagt     600
taaccaactt atggtaataa aaaatcacac agatggtaag cagtggaaga tttaaacctc     660
acagctggtc ttccagcctc tgtccttttc agatcctcta gtcagcttct ctcagcgcat     720
gctgctggct ggtgcctctg ggatattgct tctttattac tccttgacct agagcgaact     780
gtgcggaggg aggaagtgca aaacgtggac ctcctgttgg cacaaacgag cctctttgtc     840
ctctcctcat cctctcttca cttcattttc tcaggcagca gcggctcccc tgttgtatgg     900
acattctgca cccgaaactg atagctgagt cctgaagttt tatgttatga aacagaagaa     960
ctttcatccc aggtgcattg gtttattctc tcccctagcc tgttatgtta gattgtactt    1020
atgttaaatt tttaaggaca taggtggtta tgccgagaat aacagtgact gtagccaacc    1080
catgtgggga ttgtaaagaa attggaatat gccttccaaa ggaacactgt taatctagac    1140
atgacctttc aggattttaa aggaataatt ttaggccagg tgagaaacag ccaaaagcaa    1200
aaataatgtg aggctagaga ttatgtttga aagtttttat attttggatt aatatctatt    1260
ctaggagttt actcttagtg aatctttttc cttagggtag aaaaaagctt atcgaaaagg    1320
atgaaaactt atacatcaga tatttcaaaa tagtgtgctt ttctttcaga gctttgtagc    1380
tttgtattac ctttgtatta aaagtgaaaa tgttctttta ggacatcaca agaaaattaa    1440
gatcttaatt taagtacggg aacttaaggg gtgccctaat tgccttaatt aaataaacat    1500
gccttccttc tgccaggaac tattcaatta acaaaaatga aataagaata agctcttatt    1560
ttcatttgca aatgactatt catagctatt ttgtttggat acaattcata gctattttgt    1620
ttggatacta ttttgtttgc atactatgtt ttgtttggat actattcata gctattttgt    1680
```

-continued

```
gtggatacaa aggatacaat gttgtatcct tatatattca ggaagtctta gaatacaaat   1740
gctgattttt tttttttcta gtcagggaag cctaactgtg ttcatataaa cacatcaaag   1800
tcagttttta ccttgtgact caacatggta gaagtctgtc agttcatgtg atatcccatt   1860
gtggagcaaa gtaatgtaga aatcagaatt ttgagttcta gtatttactc tctcgattcc   1920
ttgttaattt aaatggtacc tattttttat agcacatgat ttgggaatta cactttgtga   1980
catggatgaa tctgcactga cccttggtac aatagatgtt tcttatctgc cacattcatc   2040
agaatacagt gttggtcgat gtaagcacac aagtgaggaa tgggtaagtt taggataaga   2100
gttaaaagca ctcagcctaa aaatgttcat ttcaatgatg tttatgaagg tgcaaatact   2160
ggcagcaaca taatatcaca tcaagattaa tagctacaga aactggtatg tttatgaagc   2220
ctaataaaaa attttatggc attatattgg gaagaaaaaa tggttagaaa atttatgtac   2280
actgattatg ttagaaaaca aaataatcat tttgcatagg aaaaaaaccc tagtagtagt   2340
tttgggtcgg taagaaattt ttttttcttt ctttctcttg gtatgtactt tccatgagtt   2400
atacttgaaa agcatgaatt ttataataga agtaaacttt aaaaaattag gaacttatag   2460
tatgaattca atccaaaagg cgtacatttt cttggattgt ttttcctatt tcaatataac   2520
atgacgtatt ttaaatatct taattgtctt tatataaaaa atggtggggt ttttttttt    2580
gcttaatttt gagaatgtta tatctgtata acagagatgt gagcaactga gctcaaagtt   2640
aagcattttt agaatagaag agcaaggttt gaccctaatt gaatagtata gctataattt   2700
aagttctggt ctttaagttc ccttgataag ataaaggaat gttatataag tttacctgtt   2760
ttttatttaa agtaaaatta taaaaacttg ctcactatgt aaggccttta tagttctgta   2820
gtgcgactgt gtgatttaaa agggggtaag gttaattgtt agactagaga tccaggagtc   2880
tgaattgatt tatctagctg tcagaagtct gtttgacctt ctacaattta gtttttaaat   2940
ttttgaatac tgccttcagt gtgtagctat tactatcctt gggtgctcag cttttgctta   3000
tgtggtaagc ttttatccaa gtgttgatca tggagggagt acttaaatga aaatcaccca   3060
gaatatgcca taagttttc ttctgttcaa aatactttag attttgagat caagtagaca    3120
agtattctct tgccatttag aaactatatt tttttcttaa tatttgtcag ggtgagtgtg   3180
gctttagacc caccatcttc agatctgcaa ctttaaaatg gaaagaaagc ctaatgagtc   3240
ggaaaaggcc atttgttgga agatgttgtt actcctgcac tccccagagc tgggtaagaa   3300
ccttactgct tattgaccct aatactcagc ataaaatatt atttccaact ttgtagtagg   3360
cagtcttatt ggactaaatt cactttcaga acagagaccc atgtttatga accaaatatt   3420
tcaagtaaag atgttgacac actttttctt tccatttatt tattcagtaa atattggtcc   3480
cataattgat actaggtaac attctagttc ttttgaggtt ttagtaggat tttaaggggg   3540
agagtagatc ttacttttgg ttaagtcttc aaaggagtta gtgggaacct tcatgaactt   3600
ttaggtgttg aactttagca cttaacatta aaattctagc aagataagaa agagataatg   3660
ggacagaata agaagttaaa gctgtgactt tgctctgagc ctttgctaat ggaaggtgtc   3720
tgttgacttt gtgatagtga aagattgtca ctaaaatgtt agaatgaaga tttaagagag   3780
tgtatatggg tttgttgttt gtattttggt gaaaaaacac aagccatgca atatcttttg   3840
cattacagtg cagtctttga gaagagccaa gtgggtgaga ggtatatttt cggtggtagt   3900
tgaagagaag gacaaattag cacaggaaca agaacttcac gtagttgtgt ttgaaggcag   3960
tagaattgcc ttttaaaagt catatctgga tgttaagctc tctctgggat ccagttatta   4020
```

-continued ggatgaagaa attctgccgt ttaagtgcct gccatttata gaggttgctt gtaacttgtg 4080
tggctaggta attgtgctgt gtgaattttc tactcaaggt tggtttggca gaaagtagaa 4140
ttctgagtct ggtataaagg ggtttactaa catgggagag atttgtgtgg aacccaagca 4200
gtttatgtta aatgttcaga tctgctgaag aatgtcttgt tataaatatt gcttctttta 4260
aaccacaact accttgttgc aagaatttgg tagaattcaa gaatcacaga aatttctagc 4320
ctaggagtaa agctagttca gattaatagg tcacttgaaa tcaagattta aacagaatgt 4380
cattttcttt ttagatctga catctagtct aattctaatt ttgaatactt aaaacaataa 4440
ctacaatgtg ttcttaagtc agagggtata ggaaataatt tggtggtggt aatggtttgg 4500
agtaaagggt aaaggtagat agtacaacag acaattgatt tttgccctac tatagtacct 4560
gatggagttg aacttgatct tgaattactt ccatgacatg atcatttaaa ataatttgtt 4620
taaaaatgtt tttattggta actgtataat atttgctatc ttttctctga aatcgtattt 4680
tccttttctc taaagagatt ccacttaagt agttttatat ttgttgaggg aacattgtgc 4740
tttttcagca tttaagtgtg gaacagttac ctttttgccc atattgataa agctatagac 4800
tatcttttca gcaaagctat ctctggatta tctttcaaga tcacatgtaa agagggtgac 4860
cagtagacag acgatttctc attaaatgga cagttattta ggggtaatag aaagaccata 4920
ctctttagat caagacataa gattgaatcc taaacctctc ccggtcttag tttctcacct 4980
agaaaatggt gataactctt ttgtgtcagg gattttggga gatttagtaa gcaacaataa 5040
ctgcatggta cttagcgtgg tctttgtatt ttgggaaaac tgaaatctct gacattcttg 5100
tagcttcact tctttcaggg tggagatgag gagtcaagca gcaaggggta ctgtttcctt 5160
tggttttaag gtggtttgtt tgtttgtttg tttttttgttt ttgtttttgt tttttttgaga 5220 tggagtcttg ctttgtcgcc caggctggag tacaatggca tcgtgttggc tcactgcaac 5280
ctccgtctct taggttcaag caattctcct gcctcagcct cccaagtagc tgggattaca 5340
ggcaccgacc accacaccca gctaattttt atatttttgg tagagacgga gtttcaccat 5400
gttggccagg ctggtctcaa actaatgacc tcaggtgatc tgcccgcttc ggcctcccaa 5460
agtgctgaga ttacgggtgt gagccactgc gcctggctag ttttaagatt tttaaagatga 5520 attttgagtt tatgacattc tttgaaggct aaaaagtact tttcaataaa actttttttct 5580 tccctaagat ttttgaggca atatctgttt ttatgcttga tattaaagtt atcaagaact 5640
cataatgaga gctcttcacc gtcaatctag ttgtgtattt atgtctacat ttactttgtt 5700
ttatatagga caaatttttc aaccccagta tcccgtcttt gggtttgcgg aatgttattt 5760
atatcaatga aactcacaca aggtaaaaag aaatttctta tgtttttaat acatctcaaa 5820
agaaaaactt cataataatc agttaacaca ctttaagctg aattgctttg cattactgag 5880
agtgaataga atatgagttt ctgacacaag agagattatc tgaaaattgg aagcagtata 5940
gccacagaga gaactattac tgttaccact tgtgtactta cagataattt caggggagtg 6000
tagatgtcac ttagaatgtt ctttgactta tattgatttg catatgaagt atgccaaaat 6060
gtgggaaata tttgtctgag aagaccggta ggtttgaatc tcttatgatt tattatgact 6120
atttaatact taaaaaaagt ataaattatt gaaatctgcc caatctgtag ggtgttaaaa 6180
gacattttct ctgttgagca aatgttgttt gagttactat ttacccaaga ctttacttag 6240
agttcttaca atttctaggc atatggggat aggcttgtaa gcaccagtgt gagagaaaaa 6300
ggtctttgtt ttatctgact ctaggccagg ggacagggaa ggagggtcga aaggttgtgt 6360
gaatgtctgt gaggcaagag aatcagtagc caaatgctag cagtccttgt aattctaaaa 6420

```
atagatacct ggagtaggca ggcagatagg ctcagatgag aaatacttga aattctatga   6480
aaattagtgc aagaaatcaa ctacttgaag cccttatgat attacttctc ataatttgat   6540
gatgagatca catatgagaa tgataatact tggatatata gtaaactttt aaaaatagaa   6600
cttaagtcta agtacatgag cagatcattc ccaggctgct ggtctctctc tctctctctt   6660
ttaaatttgc atttaaattt aaatttaaaa aagaggggag agactttggt ccgttgaatt   6720
tttttgata agatgataag atcctaagaa aagggatctc agagtcttcc ttatgtaagt   6780
agatatttta tatataaagc caagaggttt gtttcttgcc ctcaattaga gacagttaag   6840
gaaaatcgca tttgctatga tgacgaggca gaatgaaact attcagtgaa ataagctgca   6900
tgttcagcta tttacttctt ctgtgtattc tatgaagcaa agcctaaaac atttttacac   6960
attcacatag agtcacacac tctgtcactg tcacactcat gcacatgtgc gcacacacac   7020
acaatgcttt cagtcagttg caaagggatt tcatagagag cttggacttt gtacatacca   7080
ataatatttc tgaaaatgtt gactgaagga ggagtttagg attaacattt aatatattgg   7140
gccaaatttt tggaagattt agacaaagga agggaggaag aaaaagagaa tggcaggaag   7200
gagaggtgaa gaaataggtg attcataaac agttctcttt caagttactt tttctctatt   7260
gagggtattc tgggtctttt cagagttact gaattgataa taataatgtg atatcatgta   7320
atcattacaa atgttttcaa agtattacat aatgaaagct tgtagcattc ttattctgaa   7380
actcatctct ccatcctccc atctaaacac cacatagtca tttataactg acaggaatat   7440
gttctatccc tcaggtgtat ttaaaatgtg aagggggaaa aagtgagaaa ttctggcttc   7500
gttagcctag agtacaaata tttagatcat gcttgacttc tttcaactga tctgccttgt   7560
caattcaatt agagaatcag tgattatctt aggaaaaaac aaacaaaaac ttaacaaaaa   7620
aaattagtct ttgatcatag gaaaagactt ccaaatttat ctttttatag cccatagcta   7680
taaatataag ctgtatggtt tatcagaata gatatagctt atatatagca ttaaacattt   7740
ttgccttttt aatggtatta ataaagccag atgttcttat ttcttttgtt ttcatattag   7800
ggttattcgg cacagtaaca ctattcaaac attaatacac aaattccaag tttcagtttt   7860
agctgagagt acatgaataa aattggctgc acaacattct gaactactaa ggagaatttg   7920
ctgtaggaga accctaaatc tcagaaagag atgacattag gctttgtttt tatgggcgga   7980
aaattagttt atgatttaag caacttgttt taggggtacc tctaatactt ctctgctaaa   8040
tcattttcac agacaccgcg gatggcttgc aagacgcctt tcttacgttc tttttattca   8100
agagcgagat gtgcataagg gcatgtttgc caccaatgtg actgaaaatg tgctgaacag   8160
cagtaggtaa gggcggggca aggtgtaaag gtgggaagag gcagggatgg gcggtaggag   8220
tgggaggggg aagtaattct tagtaacctt tagtttctct gggactgtgt ctcaagaagt   8280
gttcacattt ccaaacatta aatgttaagc tccaaaggaa actaaagaaa ggcaggagaa   8340
caggtgcttt ggtgacagtg ccatgtggga atagcagcct tgttttatgg attaataatt   8400
gaatgggttt ctaaaacatg aaaggcaaat aagagttcag agatgcacat atttccagag   8460
ttctctgctt tctgtaatat aaatgttgga gacattgtat ttcctatttt atagccgaaa   8520
gagaattgag tttgatattt ttgccagtta ctgagtatct aggtacaaat tcttgtactg   8580
gaaagtcatt gctagaaatc ttaacagaat gaattactgc ctttgctctt acaggagctt   8640
gcttacaata ggaaagactg attggaactc aggtggaatg gggaaataaa tattctagaa   8700
tatgggagtt tgggtgaaga tgttccaaac tcccgtactc tagaatattg attctagagt   8760
```

-continued

```
actggcctca ttggtgtggc cagtttcaga gatctacctg gatttgggga gcaggagacc   8820
agggtgaatt aaaaggctgc tttaaattca taagtgtcat ctgtagactc ttcgttatgt   8880
ttgttaaggc ctgaacaatg ctggcacata atatgtactc aagaaatact tctcgaatgg   8940
atgagtgagt agttgataat ggaggtgcat cagtcatggt aatgacgtgt agaaacattc   9000
ctggtcagaa tgcaatgaat gctttttagg gaatagactt ggggggcatc agtgtcctgt   9060
ggtattggtc tttttgtatt agtgaattat ggggctatgt ggaattttgc tgtacttcac   9120
tagtccaaaa tcagcaccac tgggataaaa cacaattatg tgaaattctt agattattat   9180
atattctgtt ttcttgttaa aaccttcaag tacatttatt tcatccagat gttttgacta   9240
gtaactggga tgttagaagt ggtttaagga ggttgaacct catgctttct cccctaagtc   9300
agctggaaga tttataaaac tggattaaat gtttcctttt atctcactgc ttattattct   9360
gtgctgtgct cttttgatct tgagctgtgc cttttaaaaa ttactggttt gagttgaaaa   9420
aatttgtaaa tatttatgac catttttggt ccctcccaga gttttacata tagttttact   9480
aatggagtca caatacaaat taaaagtaaa ttaagtcttc aaaagaaaaa tcacacatta   9540
atttggtagt agacttttgg atacctctga attatatgcc taaagggata acctttcttt   9600
ttctctcttc tgctagagta caatttcgtg tccctcatac tttaatggga acattcaaat   9660
tcacccagta aatttgaatt aaattcttag tctgctttcc agattcctca gagattcatt   9720
gatttaggaa tatagtattc ttaatattta atagatagcc agaaagagca cttctagctt   9780
gagcttattc tttcatgtta ccgcatttta aagagaacat acattttgtt ttgtgattta   9840
cagctgcagt ttagaaaata ctgaatacag aatgtagtat agaaacaatt acattgtctc   9900
tttttccatt ttcataccag agtacaagag gcaattgcag aagtggctgc tgaattaaac   9960
cctgatggtt ctgcccagca gcaatcaaaa gccgttaaca aagtgaaaaa gaaagctaaa  10020
aggattcttc aagaaatggt tgccactgtc tcaccggcaa tgatcaggta ttaaaaggca  10080
aggcagaaag ctttcaatca cagccatgct gatttgagca aataagactg aattattgaa  10140
ctttcctagc acagttctct ttgtccaaaa gatgttttaa tgaatcctga tattaaatta  10200
aactcttctt atattcttat tcagctttcg tgcaaagtag cactgtggta ggcttgaagg  10260
tgccttcata tctgttaatt gatagcagcc aatgtattac tactaacatc tgctcaccta  10320
gactgcttgt gaatcaactt tcacgtatct gagtcataaa aggagtggtt tgtgtacatc  10380
agagggatca ttctgctcac taaatattca ttcgccttgg tcatttgctt ctgcagtata  10440
aaatgttatt agagtgaact atgactgtag tctataataa atggatactt ctgtaagtag  10500
tatatatata tataaaatta gctctagttc agcaattcag acatacgtgc atgcatgtgc  10560
acacacacta agtcatttac aagtactttg aggttgtagg tccataaatt taagtagaca  10620
gaagtcaact gtatgtgctt gtatgtaaaa ataacgtgtg ttcatttatg ttgttttttt  10680
tgtttgtact ttgtttcaga ctgactgggt gggtgctgct aaaactgttc aacagcttct  10740
tttggaacat tcaaattcac aaaggtcaac ttgagatggt taaagctgca actgaggcaa  10800
gaatttctgt gaatctatta ccccattttc ccctcaattg tagagtggtt ttagggttct  10860
tgtggaaatg ttttcttgtg tactgtgatg tatttcaacc catttggaag atttccctca  10920
tttatgataa cttcaatagc tgtgtatttg gggaggagaa atgagataca ggagtactta  10980
ctagcaatat gcaggattcc ttttgtaagt taccttgcaa caaccctgaa aatctggtag  11040
aacaatccct attttgtaga tgaagcaata gagacacaga tagataaata ggttgtctca  11100
agtggcagat aataagtgac ttgccctgga tttcaaatca aaccaagcct gactccaaaa  11160
```

-continued cctgtgctct ttttatatca gtggagctgc ttctcagaaa gggtataggt caactggaac 11220
tcttgattgc tcttcttccc ccaacttatt tctgttgtta tagttgctct ttttcttttt 11280
agctcagaaa gtattacatt gaaggaagtt cctattattg gaaaatgttt ttaaagagtg 11340
agtcactgat tagccagtgt ttgagtgact ctagccaaat atgcagttgc aaagtgtgat 11400
tgaattttac atttgagttt taaatttggc atttttccct ttgctagacg aatttgccgc 11460
ttctgtttct accagttcat agatcccata ttgactatct gctgctcact ttcattctct 11520
tctgccataa catcaaagca ccatacattg cttcaggcaa taatctcaac atcccaatct 11580
tcaggtaaga tgagcttatt ttggaattta aggaattaaa aagattatgt tttgaatttt 11640 aatttttaa attatagctt tcgatatgtt attgtaaaga tgacattagc ctttttttctt 11700 ttattataaa agtgatacat agttattgtg taaaatttgg agagtgcaaa aatgcattaa 11760
gactatcatc attatttata tattttatat gggatacttg gtgaactgtg actacctaaa 11820
ctttatgggc attgtttatc aaatagataa aaggcaatta gaaaggcaag atagcaaatt 11880
accataccag gctcagcagt agggagttgt ttggtggagg agggggcagt gaagtgggag 11940
aagggttagt gatataaaga caaccatacc tgttactttg acctcataat ttagtagagc 12000
tagaaccact taaaaagtac aatatcatgt gaaaggtatg ttttagaggt tttcaccttt 12060
tgaaaggttt tttagaggtt ttcctcaatg cgttccattc aggggaaata gtatgtgcaa 12120
atgcggagag atacaggagc atggtatggt tgggaagtga tggacaattg ggtaaggtgg 12180
gaatatggga tgcattagga aggatcagag actggaggtg gtagctgtgt aggtagtgaa 12240
agctggatca aaacaatttc taagccaaga gattagagtc tgtcctgtac ttgagaaatg 12300
acatgttcag gtttgtattt tgaaaggtca ttctggatta gaaagaatga aatcaattct 12360
gcttccatta ggatagttca ggcagaagat aatggaggtt taaattgtag tattgttttt 12420
ggacaggagg gcatagattt aaaaagtact tagtagctcg aatttaaaga cccagtgcta 12480
gtccctatgg gggctcaata gagggggaga ggaaggagca agattcccag gtgtttacca 12540
cctaggaaac tgggtaggtg gtaggtctga tcaccaacaa agaattggtg aggaactggt 12600
tgagctggtt tgggaaatta aaagtttcaa acctgaaagg acaaagcatc tctaaggtca 12660
gctctgtggg tagagagtgg ataaaaggag catgaattta gaaagagact ggaaggaaag 12720
tgggctggca ggttgtgcag gtggagcttc acaagatggc cttcgtcacc tttgtgtgct 12780
gtgtcctcag tatcacagtc taaggagctc cttcttaatc ccttggttca gagttctata 12840
ggctttcaga gttctgtagc taaccagact cttgtgaccc aactgaagag aagccatgga 12900
ttcatgcagt cagtgatatt tatccagctg tgctttagac aagagagaac aaaatatata 12960
gtccttgcct tcacatagct taatggataa tgtagacaga cagctagctg taatagcgtg 13020
tgatatgatt ctacagggta gatgtgcttt tccaggaatt agaatatctg tgtttgctct 13080
ccaggggacc tctctccagg aacaaggaac cgggaaactg aattagaaag tcatcaggaa 13140
gtttctggtg ggcacagact tagagggaag aggactattc cactggggct ctagagaagc 13200
cttgcttctc ttgtaattag aatatttcct atacccattt ccttcacatt tggttctcaa 13260
ttaggatttc ttggaactgc ttaataaaca ctgataattt tttgtaatcc aacttccctt 13320
tcatggactc tatgccagtg actgtgtagc tcacctgtcc ttcagacaca gcaggctgta 13380
gttagcccag cctgtttttg tgcagctttc ttttgttaca tgacagtcta cccattcaca 13440
aaccacttct caggtgttat ttttgtggat ggctcatctc attcatttta ttctgcagag 13500

-continued

```
ttttactctc aaagagtgat actaagcttt ggcaacacct tactgtggcc tccttctatt  13560
tactgtagag cagtggtccc caaccttttt ggcatcaggg accagtttca tggaagacaa  13620
tttccacaga ccatgggggt ggggaggatg gttttgggat gattcaagca tgttacattt  13680
attgtgcact ttatttctat tattattact ttgtaatata taaagaaata attatacaac  13740
tcatcataat gtagaatcac tagacggtcc caactggggg tgataggaga cagtgacaga  13800
tcatcaggca ttagattctc ataaggaatg cacaacctag atccctcatg ggcagatgtg  13860
cagttcacaa taggatttgc gctcctatcc tatgagaatc taatgctgtt gctgatctga  13920
caggaggcgg agctcagagg gtaatgcaag tgatggggaa tggctgtaaa tatagatgaa  13980
gctttgcttg cttgcctgcc actcatctcc tgctgtgtgg cccggttcct aacaggccgg  14040
ggaccggtat tggtccgtgg ccccggggtt tgggaccact gctgtagagg ataccaaaaa  14100
tatatattaa tgtttatgtt agtatcactc tacttgaaaa gaataggagg ctgtgagttt  14160
ggaaagattg acttagacag tttcaacttc atatcaaaat tagtgttgta gaaagagaca  14220
tagggttagg aaaagaatcg ttttatgcct gtgtatgtgc aaatgaagca catttttgtt  14280
tcatgttttg gaaagatggt tatgcttggt ttcagttgga taaaattgtt tttgtctcac  14340
aaggatcctc tgtaaacaat aattatttga gaaaatttcc cccaaggagc tttcgtaata  14400
aacatcatat tcattttgta gtaaacatgc catgcgcaaa tttcagaatg tctaagggtc  14460
agtgtcttga gaccctgggc aggattttaa aatttagaag tgttctataa tcctcttaaa  14520
atctatacta tcatttttac gggtaatatg tcatgcaaac tccttttggc ttggaacaga  14580
tataatagag gctcattata cacagtgata tcccaaagac tgatgaacaa tgtaaatgac  14640
tgaaacatgt cgataatatg gaaaatgaaa aaaatgcctg catttttact gtcagctgct  14700
caaacggcac atatggcttg tatccacttg gcaaatgttt tcaattaact tggaatgtga  14760
gtattctttt tacatttttc tttgtaaata attcatgtat tctgaattta tagtaccttg  14820
atccataagc ttgggggctt cttcatacga cgaaggctcg atgaaacacc agatggacgg  14880
aaagatgttc tctatagagc tttgctccat ggggtatgtg tgatctctaa ttatccttag  14940
ggacattgtg ttggttatca cagtggaagg aaaaatgact cttttgagtt gagattttta  15000
aaaactgctc tttgagtaac tggagtgatt attgcttgag tttggtaatt tgttgttgtt  15060
gttgttgttg ttattaccaa aatatagcat tggaggagct gttttattag tgtgaataag  15120
atactttgtc agtagtgaag ttatcgtttt ttctgttttg cttttaaaga tttaattttt  15180
ctgagctcat tctaagttga gtggtcttga atgtatgttt tactttcttc ttatatccca  15240
gcatatagtt gaattacttc gacagcagca attcttggag atcttcctgg aaggcacacg  15300
ttctaggagt ggaaaaacct cttgtgctcg ggcaggactt ttgtcagttg tggtagatac  15360
tctgtctacc aatgtcatcc cagacatctt gataatacct gttggaatct cctatgatcg  15420
cattatcgaa ggtcactaca atggtgaaca actggtaagg gtacctacac aaaagttttc  15480
tttgcttatc aagtctttta gatttaactt ttagaattta catttgcttt tagaattaag  15540
aatttttttt ggtactccct atgtttaaag cactgtatga aatgtgattg gatgggcatg  15600
gtgagtagct ttcatgccct atctttaact tgattggtag tgcttatgtg gtgttttctt  15660
gagcttggca gaagtgacct ggttagattt atcagtgccg accttggtca tgggattggg  15720
aagtgggaga agacttgcca ccgtgttgcc atctctgctg tggaaggtta tctgcggttt  15780
gttctcccca gggcttaatg aatatgtgca tattttaaat tgggcttgaa gaacttgtgg  15840
ggtcatgttg gcaaaaacac ctacagatta atttgagagg tagcaatgac tttttcagta  15900
```

```
taccttttta ttgaagtata atagttacaa aagagtatat aaatcatagg catgtagctt  15960
gaattatcac aaagtgaata catctatgca actagcaccc agatcaagga acaatattac  16020
caggaccttt gaaaccctcc ttgtgcttct cctatcatca tccccgcaag ggtaatgatt  16080
aatttcattt cttacagact gggttagttt tgcatatttt tgcacttacg taaattggat  16140
aacatgtggt ctgtacgcat ctggtttcct ttgcttaagc aggtgtttgt gagattcatc  16200
cacattgttg catgtagtct attccttctc atagctgtgt agtattccag tgtatggtat  16260
accataattt attctactgt taacaaaatg tttggctgta atcattcttg gatatttttt  16320
cttgatgacc atatatattc attttgttgg gtatgtgcct aggagaagaa ctgatgggtc  16380
ttaaaaaata tgtattttca gctttagtag gtactgccaa ccactttatc agaatggttt  16440
taccagctta ccactccagt cagcagttag agttcaagag gaatttagtt ttgttcttat  16500
ttattgtgga aattttggct gaggtactta tttcaagctt acggctccag acatgtcaga  16560
aattcaagga cgtctgacaa tcagaggctt tagaaattaa gtgataggct tacaaattaa  16620
gtgatatgat ctgtatgaca ctcttctcct tgtgttctat gaatctgtcc ttgatgtata  16680
ccctactcat cctgactgtg tctcacgagt tcatatctga gtctgtgtcc gttatatgtc  16740
ctgtcattgt gccttatgtg taatagatac taggtattta ctgaatgaat actcagctca  16800
aaggccactg taaggctgga tttgcaatta cttgcctaat attagacatt tagactctgg  16860
tgatcatcag acctcagata aatggcctct ttgatgtttt attcttgttt aagaaccaca  16920
gaagttttcc aggctatgtc attttttcct tcattagttt gcaattgtat ttttgtgaat  16980
tgtgtgaaca tgatactaaa tgaaatagta ttaaatgttt tgtttttcat tgactgaatt  17040
ccatctccca atgacatgat tacatctttg aatactaaac gttttctgac aggccgcagt  17100
taatgattac ctcctttcct tcttcattca ttgttcttct tcaagatgaa cttacagttt  17160
ccataaaaca agttattctg tggataatag aatgtttgtg tatgtgttgg ctttatttct  17220
caccatgtta ttctcactat tggaatttag ggcaaaccta agaagaatga gagcctgtgg  17280
agtgtagcaa gaggtgttat tagaatgtta cgaaaaaact atggttgtgt ccgagtggat  17340
tttgcacagc cattttcctt aaaggtgagt gtctgttgaa atgaaaccat gttgaagcat  17400
ctacctggag tcaggaggct ccagtgctga ctcttaacag cacctctctg tgtgacttgg  17460
ggctgcagtt tgctctcctg taaaatgagg actatgataa aggtggtgtt gcctaaattt  17520
ttccacaaaa tttgcctatt gacaaaggag agtgagtatc tgtttttggg agatatcagg  17580
ctcgacattt attgctatta ttattttttt ttaattcatg accatctaag gggaacaaaa  17640
aacaggtaga aggaataagt tttagtattt gatagtacag tagggaaatt atagttagca  17700
gtaatttatt gtatatttca aaataactaa aagagaagaa ttgtaatatt cccaaccccc  17760
cacaaaaagc taagtgtttg aggtgatggt tatcccaatt accctgattt tatcattaca  17820
cattgtatat agatatcaaa atatcacatg taccccaaaa tatgtacaag tattatatat  17880
caattaaccc caaaagtcaa aaaaattttg agatggatga atgaataaat gaataaataa  17940
ttgtaaaaaa ataaaaattc atgggaatct tgcatgtgcc tttataatac gtatttatat  18000
cttatgtttc aaaattgcct ttaggggaaa tttttccaaa cacctcccct aaaagctggg  18060
taactttttt tttgagacgg agtttcatgt tcttgtagcc caggctggag tgcagtggcg  18120
aaatctcagc tcactgcaac ctctgccccc taggttcaag caattctcct gcgtcagcct  18180
cctaagtagc tgggattaca ggtgcccgct accacacctg gctaattttt gtatttttag  18240
```

-continued

```
tagagacggg gtttcaccat gttggccagg ctggcctcaa acttctgacc tcaggtgatc  18300
tgcccgcctc ctcatctgcc tcccaaagtg ctgggattac aggtgtgagc cacttcgggc  18360
agccaaagct gggtgaattt gacaggataa tgctctctat gtcctattgt gtagaatcca  18420
gtacccacac atcccaaagg atagtgccat cctcattgaa agtctgggac tggcaggtcc  18480
ctgaggccct tgctggttta aattcttaag gtattcaaat tgtaaaggag aaggagaaaa  18540
atgggtacag aagtagggag cccagggata aggagcagaa ggtcccgcct ctccttttat  18600
tctacttcct ggcttaactt taagagattc cagctgctgt ggtagatgct tgctaacctt  18660
aaatgctttg atcttttaga accttatcat ttcttgccac tttctttctc tttatttttt  18720
aaatggtcac atagcttctc tgtcttgtta tgatttgctt ttagattgag gttcttttga  18780
aaataatgtg acccttgggt tgccagattt ttttaagtat gattatgtct atcatcacta  18840
ttaatgatat taagaatgtc agttttatga tgatgtgtga gaaaagttaa aaatttcttt  18900
taattttaaa atgattttgt ttaagcatcc tattctttgt gtcttcagtg ttcaagttca  18960
gtttcatgct tagcagcatt ctgtgaatca ttctggactt ctgaagacag tttaggatat  19020
agaaagtatt tcccatgctc tatagcatgg cttatttcat aaacaactcc cttttaacct  19080
ttggaagatg aaattacatt ttatatgttg gtgcgaaagt gagggtaaat gatcatgttg  19140
tgttttttttc tccaggaata tttagaaagc caaagtcaga aaccggtgtc tgctctactt  19200
tccctggagc aagcgttgtt accagctata cttccttcaa ggtaaaattt gtagaattgt  19260
ttaatgctaa tcaagctacc aaacatctgt tatttcttgt attgcataga ttaaccttat  19320
taaaaatgcg cacattctta ttttcacttc ttaagtaact tttctcttag tccaataagg  19380
gatattgaga tgacatgttt tcatattagt ttggaagttt ttaattattt gcttataact  19440
ttttgatttt gtgactcata taggagttct taattgattt atgctttttg aatgcttgaa  19500
ctgagttttt ttggtagtag gttatgcata ttgtatgtaa gtgaaccata tgaaagaatt  19560
ttgctgtttg aatttttcgg aattcaaatt gaattcaaat tgaattttaa cttagagaaa  19620
ttgaatatga agcctttcct ttaatatgtg gaagtgttga attttcagaa atgttttaaa  19680
ataaggcatc ttgaattatg tattctttct gccagtggtt ttggaagtgg tgtatcaaca  19740
gactatttag tcataactaa ataacatgtt ttggccaggc cataatgtag tatattatgg  19800
aggaaaataa gccatagaaa taatctgttt gtggtttaaa tttaaaatat atagtaattt  19860
aaagtatcta attcatttaa agatcagttc cacatggttt gccttgtaaa agagtgcggt  19920
tgtgtgttga tttttgaaac actttttaga cccagtgatg ctgctgatga aggtagagac  19980
acgtccatta atgagtccag aaatgcaaca gatgaatccc tacgaaggag gttgattgca  20040
aatctggctg agcatattct attcagtaag tagaatacca gactctttaa ttctacaatt  20100
tagattcatc atggtatggt gcaaactata cagattttgg aatctgctga ggttagtttc  20160
cacttctatt aattcacagg tggtgatagg taagttatta gaaagaaggt gataccgtga  20220
ggatttgaga taattggagt taaacatctt atacagtgtc tggtaattag taggtgttca  20280
tgtggtagtt gttgtacttt ttaaaaatag ttattattaa aatgatttgt tgcctctgtt  20340
gctcattaat gtgttttatt tgaactactt gaactaattt gtggtacaac gtctagattt  20400
atagttgcat gtccatttct cctttgaccc catgagtttt tgtaatgcag caaatatgag  20460
tggccttgta taaagctttg ccttagccgt ggagaataca aaatgaataa ttaatggttc  20520
tgaactcaat gagcttatgt tcttgtcagt gggatggtta tacacaaata attaaagtga  20580
acctagagag gagaggagtg tgagttcact gcaggaccag tcttctttaa gttccaagct  20640
```

-continued

```
gtacaattgt gtactgttgt ggaggctgct ttaaaatccc aaggcagcac agtggttctt  20700
tggtgctcag cctagttgtg atttctttct tgctgctctc tgggccagga ccctgatgat  20760
actctccgca ccccctgcca atgctactgg ggaggtcttc ctccctcacc ttgctcctcc  20820
cattctggag gcccctattc ctgcttgact ttgggtcaga ggattctttc tcaagcacat  20880
ttgattatgt ctctatcctg cttaaaatct ggatacaaaa aataatacct tattgttaaa  20940
aagtttgaaa ataaagatga aatagacagc aaaaacccat tacccaaata accagtggtg  21000
ttgctgtgta gtctctaaaa atattttta cagttttgta ttgtgcagct ttccatttat  21060
aacacaatat tcatatttaa aaattcttta taaatatttt taatagctat acatatagta  21120
ctgagtactt tttttaaca ctggagacga cttcagttac cagtggtgaa tgaagtattc  21180
ttaaatttat tgttatctta gaaaactcac aaatgttatc gtgatttaag attattccat  21240
gggtgttctc agatttgatt tatataatta taattttatg caaattcagt gtaggggtgt  21300
gcactgtagt cattctcaaa tgtgtgtctg tgcccttcct tcttacctct gggtcaggtt  21360
gaaagaggaa atacaaatat gctgagcacc cattactgtg gctcctgtgc cgggccagtc  21420
attttattct catgtggtct aatgagctag gtaggatttt cattttatca gcaaggaagg  21480
tgaggccagg aatttaagta atttgcccca agtcatgaag ttagttagtg agtaaattag  21540
gatttgagcc cagattttc tgacttcaag tcagctgtta tccttctact acaccttcgt  21600
tttaatatgg tgaataccag caagaagagt gaagtagagt tgtagttata atagactgta  21660
ggtgggagca agtaaaggaa tatggaaatg ggagatcccg tagaactaaa acagccttgt  21720
actttgggtc ttgatatttc aataaaagtg tctcttcgtc attcagtaac taaattccac  21780
tggcctggat tgaagttgga cctgtcttac ttagcctgtt gtatgatgaa tagtgatctc  21840
taatgaggtt ccattatacc agaacactgt agtattataa cttcctttg gtaaatcaca  21900
cttatgggaa atgtgataga agactttcac agttttaaat actcctgttt aaaatttagg  21960
tatttcaaaa aagttcagct atgtttgtaa aaagtgcaac taaaaaaagc tttgtgtttg  22020
ccttccagct gctagcaagt cctgtgccat tatgtccaca cacattgtgg cttgcctgct  22080
cctctacaga cacaggcagg tatgtctgca atgtcacctg cagttaagta ggaagcagga  22140
gaatgttttg tcagctgctc agatacatac tcaggggcag atttggccca ctcatggcta  22200
gtactatgag gtaaacagta aaataagctg aggaccctgc ccaaaggagc ttatcaactt  22260
ggtggaggaa gaatctacat ttaaaaacaa aacaaaacag actgcttaat atatatagta  22320
ctaagctatt gcttgattaa tactgttaat gtaaataagg tctaactcat taacatgtgg  22380
tatatattct gaaagcaaat gctttccaaa tgaattgact ggcattttag aacccacccct  22440
ttatcctccc aaaatacatt tgtctgagct ttatgatgga agagaccaca ccagtcttgt  22500
tcagtcatat tctcaacacc aaacagtgcc aatatatata ggcaccaaat aaatatttgc  22560
cagataaata tttaaaatga aggaaatttt gctaaaaaat aagcactcct tacttgcaga  22620
tggcttttt cctccccctt gtgatcttat gtgtgcatat catgtgtcat ggctagagtg  22680
ttcactagca tgtgtaatac cttgacattc ctggaggacc agctttttaa gtagttttct  22740
gactcgctct gcattggtgt tctggcccta cttctctatg tgctagcagt gagctgcagg  22800
aaagccaagg caagaagaaa gtcttggaat gttggcctct cagctttttg gaaagtaggt  22860
tttccaccat catgataccg tttccatctt tctttaggga attgatctct ccacattggt  22920
cgaagacttc tttgtgatga aagaggaagt cctggctcgt gattttgacc tggggttctc  22980
```

-continued

```
aggaaattca gaagatgtag taatgcatgc catacagctg ctgggaaatt gtgtcacaat  23040
cacccacact agcaggaacg atgagttttt tatcaccccc agcacaactg tcccatcagt  23100
cttcgaactc aacttctaca gcaatggggt acttcatgtc tttatcatgg aggccatcat  23160
aggtatgtca gaccttgaaa tattttcagt aattttcatg gaaaataaaa aggcctaaaa  23220
cacatagtgg tatctgcttt aatttgggtg atagcccctt gcttgaggga atgtggctat  23280
aattttagtt ttcaaacgaa aatgtaatct cctgttatat cactgtttac aatgagtagt  23340
tactgaatta ccgtttgtat agcattaccc ttatttttca ggagaggtag agtgtcttgc  23400
tatccaggag ctgaaaatct aactgagatg agacatacac agagcagcaa agtgagtgga  23460
gggcctcatt tgtgattaag agaaaagaga ggaaggagag aagagggggc ttatgtcttt  23520
ggagaaggtt tttgatgcag ttgggatcat atggaatcat aagaatttag tcttatggga  23580
tttacttaaa tttctccaaa tacaggccat tatttttgat gtattaataa tctcttaagg  23640
ttattcaagc cagttgaagt ttttcttgga gactttgagc tggcaacttc attgttgctt  23700
ttcttttctt agcttgcagc ctttatgcag ttctgaacaa gaggggactg gggggtccca  23760
ctagcacccc acctaacctg atcagccagg agcagctggt gcggaaggcg gccagcctgt  23820
gctaccttct ctccaatgaa ggcaccatct cactggtgag tgaagaccct tcagtgttgc  23880
ctggtctctt ttcttgagcg ttttcatgaa aacgtaaccc cccgtgtttt tctgttagat  23940
aatgtttgac ccattgttga tactttatat tccactcctg gatttcagtg accaccaaac  24000
caatatgtca tttactatct tggtttgctc tctgggtcac tgctccactg aatctatcct  24060
gcagctatga gccatgatag gacagattgc tcaatgttct caggcagtca catccaaagc  24120
tagtgagcac gtattgtgtg tgaggcactg ggtcagtggt ttgtaaataa ttaacacacc  24180
cacctgtaga tgatggaacc acagatggta agagtcagaa gcagccttaa aaatcatctg  24240
ctcggccagg tgcggtggct cacgcctgta atctcagcac tttgggaggc tgaggcgggc  24300
agatcacgag gtcaggagat cgagaccatc ctggctaacg tggagaaacc ccgtctctac  24360
taaaaataca aaaaaaaatt agccaggtgt agtagcacct gcctgtagtc ccagctactt  24420
tggaggctga ggcaggagga tcacttgaac ctgggaggcg gaggatgcag tgagctgaga  24480
ttgcgccact gttctccagc ctgagtgaca gagcgagact ccatctcaaa aaaaaaaaaa  24540
aaaaaaaaag aaaatcatct gctcaacacc tctcaattta caaatgagga aaaccaagcc  24600
cagcagtact aatgagcatt tatattatat acccaaacac ttttaggcat ttatcatgag  24660
acatatgtat taagtagtag atttccttct tctcaaagtc atcaacatgt agaattcata  24720
ttttatttga attccgatat tttcttttgt atgaatgtgt cttgagatgt tgacgagatg  24780
agtgcatgtg ttaggagtac cgccccctcc atgccatgct ttgtgtgagg tgtgctcgtg  24840
gtcctgttgg ggaatctgtt ttgcatgaac cttgggtggt gggatggaag ggatgagggc  24900
agataagact tccaagattg accttgtcct ttctctggta tttatttact tattccaatg  24960
ttgcctttcc tcaatcacca cttttgtgta cagtatttat tataagataa ctattgcaga  25020
gaaattgtct tataaagtaa aagaaataga tggtgggggg ctgataagca gtcttcagag  25080
ggctttccac actgtgggtg tggggagaga attgagctca ggagtacccc ttgcaggtgg  25140
tgcagtgttg ggtgctctgc caactttaag tgacagaggt cttttcttgg gctttgtcca  25200
tgaccgtgtg tgtatcaaga cagtgggcac tgggaatcac aggacttgct cagtggggtg  25260
atggaggtaa cagaatggaa ggctttggca gctaccttgt accatgtttt ctgcgtttaa  25320
aaaaagaagt ataaaatggt ggcatttata tttaaatgaa ttttcttttc agccttgcca  25380
```

gacattttac caagtctgcc atgaaacagt aggaaagttt atccagtatg gcattcttac 25440
agtggcagag gtaagaggta gagctttcct ttatttgtct ttatacttac tcttcattcc 25500
cttacctttt ctacaactta tttaaaccaa taattggcca ggcatggtgg catgtgcctg 25560
taatcccagc actttgggag gtgaaggcgg gtggatcacc tgaggtcagg agtacgagag 25620
cagcctggcc aacatggcac aaccctgtct ttcctaaaaa tacaaaaatt agctgggcat 25680
ggtggcacac acctgtaatc ccagctactt gggaggctga ggcacaagaa tcggagtggt 25740
ggaggtttca gtgagccaag atcatgtcag tgcactccag cctgggtgac agagtgagac 25800
tcagtctcat aaataagtaa acaaaccaat aattacattt ggtatatagt catgttcaga 25860
tgtagagaag caaaaaataa gaatggggag aataagtgtc ctttgggatt atttaatatt 25920
ttggttccta tttgtaagtt gtgttgtcta aaacatatcc tgacttgatt ccgtgacatc 25980
cagaagtttg tatgctaagt tgagacgtta cacctatcag tatgcttgca gcttgcacat 26040
ctgcagtttt catttttgag attctatttt aattttggta gatttagtgt agaggagatg 26100
gcctggaaaa gtacatatca atttagaaca tgtgggggta cttttatttg atctttcttt 26160
ctggtagctc tcccctccca cctgcccttt cttttgtctc ctgctgtctc ctgactgagt 26220
ttgagtttgg aagggaagtg gactgacatt atgagtggct aaacagagaa gagccaggaa 26280
gggtcagaga agaggactgc cttgtcctgg ctccactggg cagttgtttg tgtgccagtg 26340
catatttatt tactatccat catctccttg gcctagcacg atgaccagga agatatcagt 26400
cctagtcttg ctgagcagca gtgggacaag aagcttccag aacctttgtc ttggagaagt 26460
gatgaagaag atgaagacag tgactttggg gaggaacagc gagattgcta cctgaaggta 26520
cttgggtgaa gaattctggt ggatattaca gggatatgtt gaggtttatg ctgcagtgag 26580
atcagctgga gtcctggtga tgtcttctta tctaaagaat cccccaacta gctctggtac 26640
cttctgtgtg gtaaagacac tcaaactgtt tgagttgaat taatagcatt ttaagtagaa 26700
aaggaaagga gagtctgaaa agtcaggaag atgaatgtca taggtgagac tttcaccatc 26760
cttttatgaa atacacaggt gcatacctgt ttacctacac ctgcacccct catgaggcag 26820
cagttttgct attgagctgc cactgacctg gctgctcttt ttgagtcact cttgctgtcc 26880
ctcccaaaat ttcatatatt aagctctttg ctgtcaatta aaacaaatac cattatagga 26940
gaaaattgag attaaaaaaa aagtccctga tttagaaaaa tcaattttgt ctaatttata 27000
attttagaac ttagtaataa tgacccgtct tttctgaata ctctaagagg attactcttt 27060
tttgacattt agaaattgtc ttctttttca cttgggtggt attagtttag tttcaagatg 27120
gggcagtgat cttgctttca cactccagag gggcttgacc gaaccagtgt gttttgggta 27180
ggtacagtga gagcctctcg gccataaagc accgccgtca cagtggccat cattccccac 27240
agtgctggac tgtgggcaaa ggccatttag gggaggcagg gaataggtgc tgcagaagga 27300
gtgagataat cttggtggtc tcccattggt ctttctgcag acttgagtga ctgttgagcc 27360
caggcttcaa accatggagg gcctggtctt aggagcggct atttttagtg atgacagcgt 27420
atcacaagta gggcattcat ttatgaaaat ttcttctagg tggctgttca atgaacacaa 27480
gcctcaaata ccataaaaaa gtgaatgatt acaataaaga atgtgtttga aagccagcag 27540
ttgtttccag cagagattct ctgcatgagg ggcagggggc cgctttcatg tagtgctgat 27600
gtgagtggcc atcttctcac gttactggct ctccagagaa agtcctctgt ccacttgcct 27660
tgtgtctctt gtcccttcct catgacttca tctcctgctt ttgcacactc aggtgagcca 27720

-continued

```
atccaaggag caccagcagt ttatcacctt cttacagaga ctccttgggc ctttgctgga  27780
ggcctacagc tctgctgcca tctttgttca caacttcagt ggtcctgttc cagaacctga  27840
gtatctgcaa aagttgcaca aatacctaat aaccagaaca gaaagaaatg ttgcagtata  27900
tggtatgtta agtcactatt tattctttta aaatcttttt tttttttttg gatttcagaa  27960
atttgctaat tgtagaaaat tggaaaaatg caaacttatc ctgacctcta acaccgtaga  28020
gtattactat tatcttcttt ggcatgttat ataagttgaa tgatacagtt atacactctt  28080
acatctggct tttttcacgt aacgttattt ttgagattca tacatgttgc atatagttgt  28140
tcctttgttc ttgttgtgta gtgttccatt gtataaatat ttaccacatt ttattcattc  28200
tgctgttgat ggatatttgg gttgttttca gttcacagct gctttgaaca gtgttgctat  28260
gagcatattt gaatatgtct tttggtgaat atctgtgccc ctatatacag catgtatgtg  28320
ggaacagaat tgcctggttg taggctctgg gtatattcgg ctttggtaga taccaccaaa  28380
cagtttccaa gggattatac ctacttgtac tcccacaaca gtgtgtgttt cacttgctgc  28440
acatcttggc cagcgctccg tcttctttgt tttaggaggt gtgattgggg tgggagtact  28500
attttataca gttgtagttt ggagctgaaa ctacttgaat cactttttag agccaaaagg  28560
aatctaatct aatcacctca ttttatagtt gaggaaaata ccccaggtca cactgctaat  28620
taatgggtaa tctcgggatc agaattcttg tttcctaacc tcgaggcctg tgctttctct  28680
ggttccactg atgtacaatc atctgtgtac cactgggtag cttaaagaat atttatacac  28740
tatctcattt gattctcaca acagtcctgg aaaatggatg ttttaggtat ttctacttcc  28800
ctctgttctc cctatttctc tctctacacc ctcttttctt tccccttccc tttcttattt  28860
acctcaatat aggacaaagt aggtgtaagc aaagtaggtt taacagcaag tcatctgaga  28920
actcacaggt tgccagtggt ggaagtgggg ccccaccctt gtctgctgac ttgccctcat  28980
tctcttccta gctccccata ctttcttact gtggctgctg ggattgtcat gatttgttga  29040
gcgtaaccat ttgacagggt tttattctct ctcttcagct gagagtgcca catattgtct  29100
tgtgaagaat gctgtgaaaa tgtttaagga tattggggta ggtgtccacc atttatggta  29160
taaaagctat ctcaacttct gttctcttta gatctagtct gtttgagcta cctttgtggt  29220
ggggtggacc ccgagagaag cagtttctgc tggcttaatg ataaaggcat ttttgggaac  29280
ggggcatgta ggatgggttg ggctatgttg aaggtgaagc ccatcagtgt agatttattt  29340
gaatgttctg gaattttact ggtttcacat ttattcccaa gctgctatat ataactggta  29400
tcaatatgtt tcaaggtgct acaggttgaa tatcccttat ccaaaatgtt gggaccagaa  29460
atgttttgga tttcagattt ttttgggatt ttggaatatg tgcattagac ttacaggttg  29520
agcgtctcta atccaaaacc caaaatgctc tgatgagcat gtcttttgag catcatattg  29580
atgttcaaaa tctttcagat tttggagtac ttcagatttt tgattttggg attaggacca  29640
caatcttggc tcttaattat tccatatgat ttttagttac tttcttgtat ttttacaaga  29700
atttctagaa gtatcctcag gtgtccttta ccttcatgat tcatggggaa tgtaagttct  29760
atagagatac tagcggcctt ttgtgaggga ctgtttgtga ctttattcta agtcatttta  29820
gagtatagtt atgttggttg aaattttaga atatagttaa tgttggttga actccatcaa  29880
aacaaaaaaa aaaaaataga aaaagaaaac cttgtttgca ttggaaactc ccacctcatg  29940
ctcacacaca cccaggcata catttactta atgccaggat atggtttttt gtgcctttac  30000
tgccttctga ggtctaggac accacaggtc aggttggtaa tggaaatttt ttttattttt  30060
tattttttgc ctttaattta atctaaacct tttctttagg ttttcaagga gaccaaacaa  30120
```

aagagagtgt ctgttttaga actgagcagc acttttctac ctcaatgcaa ccgacaaaaa 30180
cttctagaat atattctgag ttttgtggtg ctgtaggtaa cgtgtggcac tgctggcaaa 30240
tgaaggtcat gagatgagtt ccttgtaggt accagcttct ggctcaagag ttgaaggtgc 30300
catcgcaggg tcaggcctgc cctgtcccga agtgatctcc tggaagacaa gtgccttctc 30360
cctccatgga tctgtgatct tcccagctct gcatcaacac agcagcctgc agataacact 30420
tggggggacc tcagcctcta ttcgcaactc ataatccgta gactacaaga tgaaatctca 30480
ataaattatt tttgagttta ttaaagattg acattttaag tacaactttt aaggactaat 30540
tactgtgatg gacacagaaa tgtagctgtg ttctggaact gaatcttaca tggtatactt 30600
agtgctgctg ggtaatttgt tggtatatta tctggttagt ggttaatgct tcctttaaaa 30660
ataattgagt catccattca ctctttttca gttttatctg tcaatagtag ctacattttt 30720
aatgggagca ccttttatcc caaagtgctt tataaattga gtggactgat atatatcaca 30780
cccaggtatc actgtgctgt cctttgctgt cagatttaga aatgttttta agagctatgt 30840
gaaaacagac aatattagtt taggtcggga actgagatat tgtaatcaaa tagttaacat 30900
caggaagtta atttggctgg caaaattcta gggaaacttg gccagaaaac tggtgttgaa 30960
ggcttttgct catataaaca agtgccattg agtttcaaat gaccagcaaa tatatttaga 31020
acccttcctg ttttatgtct gtacctcgtc cacccctcag gtaatacctg cctctcacag 31080
gtacagctgt ttcttggaaa tcctccaacc aaatagcagt tttcctaact tgattagctt 31140
gagctgacag actgttagaa tacagttctc tggccacagc tgatgagggc tttctgtact 31200
gcacacagat tgtgtactgc accccagtcc aggtgactgg tacccactcg agttgtgccg 31260
tgcacaacct gtccagtata tgcatgtggt ggccctactg actggtaatg gttagaggca 31320
tttatggatt tttagctttg aggaaaaacc atgactttta acaaattttt atgggttata 31380
tgcctaaacc cttatgccac atagtggtaa ataattatga aaaatggtct gttcataatt 31440
ggtaggtgcc ttttgtgagc agggagcata attattggtt tattatggta attatggtga 31500
ttttttaaat atcatgtaat gttaaaacgt tttctaacag tttactgttg cttatctcca 31560
agatattatg gaattaagaa tttttccaga tgagtgttac atagattctt tgaatttagt 31620
ataaaagtac tgagaattaa gtttgtactt ccataagctt ggattttaaa cactgatagt 31680
atctcatgag taatgtgtgt tttgggagag ggagggatgc tgattgatat ttcacattgt 31740
atgaaatacc atgtttgaaa ctcatagcaa taatgctatg ctgttgtgat ccctctcaag 31800
ttctgcattt aaaatatatt ttttctttat aggaattgat gtataccatg aagtcattgt 31860
cagttgtagt agctctgatg ttgaatgaga tatcatgttt tagcattcca ttttactgac 31920
tagggtagaa gaacactttt cttggctaca tttggaggat acccagggag tcttgggtgt 31980
tccttatctg gggaagcaaa catttcacta gtctcttttt ttcatccttt aaattgtaaa 32040
ttaaggatta ctcaagctca ccattattca agattgggac tcgcttccca gtcgacactc 32100
tgccctgcct gtcattgctg caaagagctg ctgctttgcc aacctaagca aagaaaatac 32160
ggcttctctt gcattatttt cccttttggt tggtttgttt tctagaagta cgttcagatg 32220
ctttggggaa tgcaatgtat gatttgctag ctctctcacc acttaactca ctgtgaggat 32280
aaatatgcat gctttttgta attaactggt gctttgaaaa tctttttttaa gggagaaaaa 32340
tctcaaccaa agttatgctc atccagacaa gctgaccttt gagttaattt cagcacaact 32400
cattcttcag tgcctcatga ctgaaaacaa aaaacaaaaa aacgaaagca tcttcacaat 32460

```
gaagcttcca gatagcaccg ttttgctaaa agatacattc tcattgtttt ccaacagtga  32520
tggcttccac ataaggttaa acaaactagg tgcttgtaaa taatttatta cagtttactc  32580
tatcgcattt ctgtaacatg aaatgcatgc ccttcttcag gggaagactg tggtcaagtt  32640
aaaaaaaaaa aacaatatta aacaacatga aactgcagtc tgtttttgaa aatgagaatg  32700
tcctaagtga ttcagaagag aggagggaag ttgtgcactc tgaaaatgca tgaaaaacaa  32760
aggcaaaaac tagtgggaaa tgtgtagaac tgttaactga gatggcttcg agtcttcctt  32820
ctggaatctg ttaaatttca caaagtcatg agggtaaatg gagaaaatat ttctgggatt  32880
acaatgaatg taagcccaaa ttgtggaatt gccagtaacc tggatgggga aaagcatttc  32940
ccatagcact ccatgtaata tgagtgctct gtgagatgtt catcagtgtt ttatagaaat  33000
ggtgttgctg ggaaaccaag tttgcacctg gaaacttaca atgcacttta gcgcagtaag  33060
ggcttggcat ccggtagtga aaaactgtct aacccagcat tgcccaaact attttgacac  33120
caggaccttt ttctcctttg ggatacttat gaacctctca ctaatgtcct gtggagaaca  33180
ttttgggaaa cactatgtta gatagttctt taaggagaca aaacggtaat gaacagatag  33240
cactggggca gaatatgcat gcattttgta acgtccagtg tggcgttgaa tagatgtgta  33300
tttcctcccc tgcagaaaat aagcacagaa aattataatg taggtgatcg gagctctttc  33360
ctttgataga gagaacagcc ccaatgatcc tggctttttc actgaacgta tcagaataca  33420
tggatgaatt ggggtaaata aggttttaat tcagatctag aagaaagtat tgtacgtttg  33480
aatgcagatt tttatccaca gatagttgta gtgtttagac atgacaggac ctatcgttga  33540
ggtttctaag acttactatg ggctgtaaac ctgtttttta aaactatttt agaaacctga  33600
gacttgccgt ctggcatttt agtttaatac aaactaatga ttgcatttga aagagattct  33660
tgaccttatt tctaaacgtc tagagctctg aaatgtcttg atggaaggta ttaaactatt  33720
tgcctgttgt acaaagaaat gttaagactc gtgaaaagaa ttactataag gtactgtgaa  33780
ataactgcga ttttgtgagc aaaacatact tggaaatgct gattgatttt tatgcttgtt  33840
agtgtattgc aagaaacaca gaaaatgtag ttttgtttta ataaaccaaa aattgaacat  33900
a                                                                  33901
```

<210> SEQ ID NO 2
<211> LENGTH: 33901
<212> TYPE: DNA
<213> ORGANISM: homo sapien

<400> SEQUENCE: 2

```
gcgccactgc agctggcatt ggccgggact ggaagtgcgg gcttctgcag cagccgaagc     60
tggagctgct agggtgcgaa ctgccagggc aggtgtgggc tgcgggaggc tactcgggcc    120
gggagcgccg ggacaagtgc atggaggtgg tgcgactcct gcaagttgct ggggcagtcg    180
tgtcccctat tccctgacac ccgagctccg gtcttctccc tgagaaatcg gtcgggctcg    240
tgcaggggtg gggatcagga ttcatctctc ctggggagac tgcgctgggg catgggttcc    300
cctgggttgg aaggagtcct tatggactca gtcccctaag tatctgcacg cgcggaggcg    360
ccgccagcca gcccgcctgg gtccctaggg aacattgagg cagtaagggg tactctgaga    420
gcagccggta tgctggagat aattaatgac agcgttacca ttgattggac tgagcgctca    480
ctgtgtgtta cacactgtgg tagacccttt gtttatatta ttccgtcctc tcaacaatcc    540
aggaggttaa gagctatcat tctgcccatt ttccagatgg gaaaactaag gcatagaagt    600
taaccaactt atggtaataa aaaatcacac agatggtaag cagtggaaga tttaaacctc    660
```

-continued

```
acagctggtc ttccagcctc tgtccttttc agatcctcta gtcagcttct ctcagcgcat    720
gctgctggct ggtgcctctg ggatattgct tctttattac tccttgacct agagcgaact    780
gtgcggaggg aggaagtgca aaacgtggac ctcctgttgg cacaaacgag cctctttgtc    840
ctctcctcat cctctcttca cttcattttc tcaggcagca gcggctcccc tgttgtatgg    900
acattctgca cccgaaactg atagctgagt cctgaagttt tatgttatga aacagaagaa    960
ctttcatccc aggtgcattg gtttattctc tcccctagcc tgttatgtta gattgtactt   1020
atgttaaatt tttaaggaca taggtggtta tgccgagaat aacagtgact gtagccaacc   1080
catgtgggga ttgtaaagaa attggaatat gccttccaaa ggaacactgt taatctagac   1140
atgacctttc aggattttaa aggaataatt ttaggccagg tgagaaacag ccaaaagcaa   1200
aaataatgtg aggctagaga ttatgtttga aagtttttat attttggatt aatatctatt   1260
ctaggagttt actcttagtg aatctttttc cttagggtag aaaaaagctt atcgaaaagg   1320
atgaaaactt atacatcaga tatttcaaaa tagtgtgctt ttctttcaga gctttgtagc   1380
tttgtattac ctttgtatta aaagtgaaaa tgttctttta ggacatcaca agaaaattaa   1440
gatcttaatt taagtacggg aacttaaggg gtgccctaat tgccttaatt aaataaacat   1500
gccttccttc tgccaggaac tattcaatta acaaaaatga aataagaata agctcttatt   1560
ttcatttgca aatgactatt catagctatt ttgtttggat acaattcata gctattttgt   1620
ttggatacta ttttgtttgc atactatgtt ttgtttggat actattcata gctattttgt   1680
gtggatacaa aggatacaat gttgtatcct tatatattca ggaagtctta gaatacaaat   1740
gctgattttt ttttttctta gtcagggaag cctaactgtg ttcatataaa cacatcaaag   1800
tcagttttta ccttgtgact caacatggta gaagtctgtc agttcatgtg atatcccatt   1860
gtggagcaaa gtaatgtaga aatcagaatt ttgagttcta gtatttactc tctcgattcc   1920
ttgttaattt aaatggtacc tattttttat agcacatgat ttgggaatta cactttgtga   1980
catggatgaa tctgcactga cccttggtac aatagatgtt tcttatctgc cacattcatc   2040
agaatacagt gttggtcgat gtaagcacac aagtgaggaa tgggtaagtt taggataaga   2100
gttaaaagca ctcagcctaa aaatgttcat ttcaatgatg tttatgaagg tgcaaatact   2160
ggcagcaaca taatatcaca tcaagattaa tagctacaga aactggtatg tttatgaagc   2220
ctaataaaaa attttatggc attatattgg gaagaaaaaa tggttagaaa atttatgtac   2280
actgattatg ttagaaaaca aaataatcat tttgcatagg aaaaaaaccc tagtagtagt   2340
tttgggtcgg taagaaattt ttttttcttt ctttctcttg gtatgtactt tccatgagtt   2400
atacttgaaa agcatgaatt ttataataga agtaaacttt aaaaaattag gaacttatag   2460
tatgaattca atccaaaagg cgtacatttt cttggattgt ttttcctatt tcaatataac   2520
atgacgtatt ttaaatatct taattgtctt tatataaaaa atggtggggt ttttttttt    2580
gcttaatttt gagaatgtta tatctgtata acagagatgt gagcaactga gctcaaagtt   2640
aagcattttt agaatagaag agcaaggttt gaccctaatt gaatagtata gctataattt   2700
aagttctggt ctttaagttc ccttgataag ataaaggaat gttatataag tttacctgtt   2760
ttttatttaa agtaaaatta taaaaacttg ctcactatgt aaggccttta tagttctgta   2820
gtgcgactgt gtgatttaaa agggggtaag gttaattgtt agactagaga tccaggagtc   2880
tgaattgatt tatctagctg tcagaagtct gtttgacctt ctacaattta gtttttaaat   2940
ttttgaatac tgccttcagt gtgtagctat tactatcctt gggtgctcag cttttgctta   3000
```

-continued tgtggtaagc ttttatccaa gtgttgatca tggagggagt acttaaatga aaatcaccca 3060
gaatatgcca taagttttc ttctgttcaa aatactttag attttgagat caagtagaca 3120
agtattctct tgccatttag aaactatatt tttttcttaa tatttgtcag ggtgagtgtg 3180
gctttagacc caccgtcttc agatctgcaa ctttaaaatg gaaagaaagc ctaatgagtc 3240
ggaaaaggcc atttgttgga agatgttgtt actcctgcac tccccagagc tgggtaagaa 3300
ccttactgct tattgaccct aatactcagc ataaaatatt atttccaact ttgtagtagg 3360
cagtcttatt ggactaaatt cactttcaga acagagaccc atgtttatga accaaatatt 3420
tcaagtaaag atgttgacac actttttctt tccatttatt tattcagtaa atattggtcc 3480
cataattgat actaggtaac attctagttc ttttgaggtt ttagtaggat tttaaggggg 3540
agagtagatc ttacttttgg ttaagtcttc aaaggagtta gtgggaacct tcatgaactt 3600
ttaggtgttg aactttagca cttaacatta aaattctagc aagataagaa agagataatg 3660
ggacagaata agaagttaaa gctgtgactt tgctctgagc ctttgctaat ggaaggtgtc 3720
tgttgacttt gtgatagtga aagattgtca ctaaaatgtt agaatgaaga tttaagagag 3780
tgtatatggg tttgttgttt gtattttggt gaaaaaacac aagccatgca atatcttttg 3840
cattacagtg cagtctttga gaagagccaa gtgggtgaga ggtatatttt cggtggtagt 3900
tgaagagaag gacaaattag cacaggaaca agaacttcac gtagttgtgt ttgaaggcag 3960
tagaattgcc ttttaaaagt catatctgga tgttaagctc tctctgggat ccagttatta 4020
ggatgaagaa attctgccgt ttaagtgcct gccatttata gaggttgctt gtaacttgtg 4080
tggctaggta attgtgctgt gtgaattttc tactcaaggt tggtttggca gaaagtagaa 4140
ttctgagtct ggtataaagg ggtttactaa catgggagag atttgtgtgg aacccaagca 4200
gtttatgtta aatgttcaga tctgctgaag aatgtcttgt tataaatatt gcttctttta 4260
aaccacaact accttgttgc aagaatttgg tagaattcaa gaatcacaga aatttctagc 4320
ctaggagtaa agctagttca gattaatagg tcacttgaaa tcaagattta aacagaatgt 4380
cattttcttt ttagatctga catctagtct aattctaatt ttgaatactt aaaacaataa 4440
ctacaatgtg ttcttaagtc agagggtata ggaaataatt tggtggtggt aatggtttgg 4500
agtaaagggt aaaggtagat agtacaacag acaattgatt tttgccctac tatagtacct 4560
gatggagttg aacttgatct tgaattactt ccatgacatg atcatttaaa ataatttgtt 4620
taaaaatgtt tttattggta actgtataat atttgctatc ttttctctga aatcgtattt 4680
tccttttctc taaagagatt ccacttaagt agttttatat ttgttgaggg aacattgtgc 4740
tttttcagca tttaagtgtg gaacagttac ctttttgccc atattgataa agctatagac 4800
tatcttttca gcaaagctat ctctggatta tctttcaaga tcacatgtaa agagggtgac 4860
cagtagacag acgatttctc attaaatgga cagttattta ggggtaatag aaagaccata 4920
ctctttagat caagacataa gattgaatcc taaacctctc ccggtcttag tttctcacct 4980
agaaaatggt gataactctt ttgtgtcagg gattttggga gatttagtaa gcaacaataa 5040
ctgcatggta cttagcgtgg tctttgtatt ttgggaaaac tgaaatctct gacattcttg 5100
tagcttcact tctttcaggg tggagatgag gagtcaagca gcaaggggta ctgtttcctt 5160
tggttttaag gtggtttgtt tgtttgtttg ttttttgttt ttgtttttgt ttttttgaga 5220
tggagtcttg ctttgtcgcc caggctggag tacaatggca tcgtgttggc tcactgcaac 5280
ctccgtctct taggttcaag caattctcct gcctcagcct cccaagtagc tgggattaca 5340
ggcaccgacc accacaccca gctaattttt atatttttgg tagagacgga gtttcaccat 5400

```
gttggccagg ctggtctcaa actaatgacc tcaggtgatc tgcccgcttc ggcctcccaa   5460
agtgctgaga ttacgggtgt gagccactgc gcctggctag ttttaagatt ttaaagatga   5520
atttgagtt tatgacattc tttgaaggct aaaaagtact tttcaataaa actttttct   5580
tccctaagat ttttgaggca atatctgttt ttatgcttga tattaaagtt atcaagaact   5640
cataatgaga gctcttcacc gtcaatctag ttgtgtattt atgtctacat ttactttgtt   5700
ttatatagga caaattttc aaccccagta tcccgtcttt gggtttgcgg aatgttattt   5760
atatcaatga aactcacaca aggtaaaaag aaatttctta tgtttttaat acatctcaaa   5820
agaaaaactt cataataatc agttaacaca ctttaagctg aattgctttg cattactgag   5880
agtgaataga atatgagttt ctgacacaag agagattatc tgaaaattgg aagcagtata   5940
gccacagaga gaactattac tgttaccact tgtgtactta cagataattt caggggagtg   6000
tagatgtcac ttagaatgtt ctttgactta tattgatttg catatgaagt atgccaaaat   6060
gtgggaaata tttgtctgag aagaccggta ggtttgaatc tcttatgatt tattatgact   6120
atttaatact taaaaaaagt ataaattatt gaaatctgcc caatctgtag ggtgttaaaa   6180
gacattttct ctgttgagca aatgttgttt gagttactat ttacccaaga ctttacttag   6240
agttcttaca atttctaggc atatggggat aggcttgtaa gcaccagtgt gagagaaaaa   6300
ggtctttgtt ttatctgact ctaggccagg ggacagggaa ggagggtcga aaggttgtgt   6360
gaatgtctgt gaggcaagag aatcagtagc caaatgctag cagtccttgt aattctaaaa   6420
atagatacct ggagtaggca ggcagatagg ctcagatgag aaatacttga aattctatga   6480
aaattagtgc aagaaatcaa ctacttgaag cccttatgat attacttctc ataatttgat   6540
gatgagatca catatgagaa tgataatact tggatatata gtaaactttt aaaaatagaa   6600
cttaagtcta agtacatgag cagatcattc ccaggctgct ggtctctctc tctctctctt   6660
ttaaatttgc atttaaattt aaatttaaaa aagaggggag agactttggt ccgttgaatt   6720
tttttgata agatgataag atcctaagaa aagggatctc agagtcttcc ttatgtaagt   6780
agatatttta tatataaagc caagaggttt gtttcttgcc ctcaattaga gacagttaag   6840
gaaaatcgca tttgctatga tgacgaggca gaatgaaact attcagtgaa ataagctgca   6900
tgttcagcta tttacttctt ctgtgtattc tatgaagcaa agcctaaaac atttttacac   6960
attcacatag agtcacacac tctgtcactg tcacactcat gcacatgtgc gcacacacac   7020
acaatgcttt cagtcagttg caaagggatt tcatagagag cttggacttt gtacatacca   7080
ataatatttc tgaaaatgtt gactgaagga ggagtttagg attaacattt aatatattgg   7140
gccaaatttt tggaagattt agacaaagga agggaggaag aaaaagagaa tggcaggaag   7200
gagaggtgaa gaaataggtg attcataaac agttctcttt caagttactt tttctctatt   7260
gagggtattc tgggtctttt cagagttact gaattgataa taataatgtg atatcatgta   7320
atcattacaa atgttttcaa agtattacat aatgaaagct tgtagcattc ttattctgaa   7380
actcatctct ccatcctccc atctaaacac cacatagtca tttataactg acaggaatat   7440
gttctatccc tcaggtgtat ttaaaatgtg aagggggaaa aagtgagaaa ttctggcttc   7500
gttagcctag agtacaaata tttagatcat gcttgacttc tttcaactga tctgccttgt   7560
caattcaatt agagaatcag tgattatctt aggaaaaaac aaacaaaaac ttaacaaaaa   7620
aaattagtct ttgatcatag gaaaagactt ccaaatttat ctttttatag cccatagcta   7680
taaatataag ctgtatggtt tatcagaata gatatagctt atatatagca ttaaacattt   7740
```

-continued

```
ttgccttttt aatggtatta ataaagccag atgttcttat ttcttttgtt ttcatattag   7800
ggttattcgg cacagtaaca ctattcaaac attaatacac aaattccaag tttcagtttt   7860
agctgagagt acatgaataa aattggctgc acaacattct gaactactaa ggagaatttg   7920
ctgtaggaga accctaaatc tcagaaagag atgacattag gctttgtttt tatgggcgga   7980
aaattagttt atgatttaag caacttgttt taggggtacc tctaatactt ctctgctaaa   8040
tcattttcac agacaccgcg gatggcttgc aagacgcctt tcttacgttc tttttattca   8100
agagcgagat gtgcataagg gcatgtttgc caccaatgtg actgaaaatg tgctgaacag   8160
cagtaggtaa gggcggggca aggtgtaaag gtgggaagag gcagggatgg gcggtaggag   8220
tgggaggggg aagtaattct tagtaacctt tagtttctct gggactgtgt ctcaagaagt   8280
gttcacattt ccaaacatta aatgttaagc tccaaaggaa actaaagaaa ggcaggagaa   8340
caggtgcttt ggtgacagtg ccatgtggga atagcagcct tgttttatgg attaataatt   8400
gaatgggttt ctaaaacatg aaaggcaaat aagagttcag agatgcacat atttccagag   8460
ttctctgctt tctgtaatat aaatgttgga gacattgtat ttcctatttt atagccgaaa   8520
gagaattgag tttgatattt ttgccagtta ctgagtatct aggtacaaat tcttgtactg   8580
gaaagtcatt gctagaaatc ttaacagaat gaattactgc ctttgctctt acaggagctt   8640
gcttacaata ggaaagactg attggaactc aggtggaatg gggaaataaa tattctagaa   8700
tatgggagtt tgggtgaaga tgttccaaac tcccgtactc tagaatattg attctagagt   8760
actggcctca ttggtgtggc cagtttcaga gatctacctg gatttgggga gcaggagacc   8820
agggtgaatt aaaaggctgc tttaaattca taagtgtcat ctgtagactc ttcgttatgt   8880
ttgttaaggc ctgaacaatg ctggcacata atatgtactc aagaaatact tctcgaatgg   8940
atgagtgagt agttgataat ggaggtgcat cagtcatggt aatgacgtgt agaaacattc   9000
ctggtcagaa tgcaatgaat gctttttagg gaatagactt ggggggcatc agtgtcctgt   9060
ggtattggtc tttttgtatt agtgaattat ggggctatgt ggaattttgc tgtacttcac   9120
tagtccaaaa tcagcaccac tgggataaaa cacaattatg tgaaattctt agattattat   9180
atattctgtt ttcttgttaa aaccttcaag tacatttatt tcatccagat gttttgacta   9240
gtaactggga tgttagaagt ggtttaagga ggttgaacct catgctttct cccctaagtc   9300
agctggaaga tttataaaac tggattaaat gtttcctttt atctcactgc ttattattct   9360
gtgctgtgct cttttgatct tgagctgtgc cttttaaaaa ttactggttt gagttgaaaa   9420
aatttgtaaa tatttatgac catttttggt ccctcccaga gttttacata tagttttact   9480
aatggagtca caatacaaat taaaagtaaa ttaagtcttc aaaagaaaaa tcacacatta   9540
atttggtagt agacttttgg atacctctga attatatgcc taaagggata acctttcttt   9600
ttctctcttc tgctagagta caatttcgtg tccctcatac tttaatggga acattcaaat   9660
tcacccagta aatttgaatt aaattcttag tctgctttcc agattcctca gagattcatt   9720
gatttaggaa tatagtattc ttaatattta atagatagcc agaaagagca cttctagctt   9780
gagcttattc tttcatgtta ccgcatttta aagagaacat acattttgtt ttgtgattta   9840
cagctgcagt ttagaaaata ctgaatacag aatgtagtat agaaacaatt acattgtctc   9900
tttttccatt ttcataccag agtacaagag gcaattgcag aagtggctgc tgaattaaac   9960
cctgatggtt ctgcccagca gcaatcaaaa gccgttaaca aagtgaaaaa gaaagctaaa  10020
aggattcttc aagaaatggt tgccactgtc tcaccggcaa tgatcaggta ttaaaaggca  10080
aggcagaaag ctttcaatca cagccatgct gatttgagca aataagactg aattattgaa  10140
```

```
ctttcctagc acagttctct ttgtccaaaa gatgttttaa tgaatcctga tattaaatta  10200
aactcttctt atattcttat tcagctttcg tgcaaagtag cactgtggta ggcttgaagg  10260
tgccttcata tctgttaatt gatagcagcc aatgtattac tactaacatc tgctcaccta  10320
gactgcttgt gaatcaactt tcacgtatct gagtcataaa aggagtggtt tgtgtacatc  10380
agagggatca ttctgctcac taaatattca ttcgccttgg tcatttgctt ctgcagtata  10440
aaatgttatt agagtgaact atgactgtag tctataataa atggatactt ctgtaagtag  10500
tatatatata tataaaatta gctctagttc agcaattcag acatacgtgc atgcatgtgc  10560
acacacacta agtcatttac aagtactttg aggttgtagg tccataaatt taagtagaca  10620
gaagtcaact gtatgtgctt gtatgtaaaa ataacgtgtg ttcatttatg ttgttttttt  10680
tgtttgtact ttgtttcaga ctgactgggt gggtgctgct aaaactgttc aacagcttct  10740
tttggaacat tcaaattcac aaaggtcaac ttgagatggt taaagctgca actgaggcaa  10800
gaatttctgt gaatctatta ccccattttc ccctcaattg tagagtggtt ttagggttct  10860
tgtggaaatg ttttcttgtg tactgtgatg tatttcaacc catttggaag atttccctca  10920
tttatgataa cttcaatagc tgtgtatttg gggaggagaa atgagataca ggagtactta  10980
ctagcaatat gcaggattcc ttttgtaagt taccttgcaa caaccctgaa aatctggtag  11040
aacaatccct attttgtaga tgaagcaata gagacacaga tagataaata ggttgtctca  11100
agtggcagat aataagtgac ttgccctgga tttcaaatca aaccaagcct gactccaaaa  11160
cctgtgctct ttttatatca gtggagctgc ttctcagaaa gggtataggt caactggaac  11220
tcttgattgc tcttcttccc ccaacttatt tctgttgtta tagttgctct ttttcttttt  11280
agctcagaaa gtattacatt gaaggaagtt cctattattg gaaaatgttt ttaaagagtg  11340
agtcactgat tagccagtgt ttgagtgact ctagccaaat atgcagttgc aaagtgtgat  11400
tgaattttac atttgagttt taaatttggc atttttccct ttgctagacg aatttgccgc  11460
ttctgtttct accagttcat agatcccata ttgactatct gctgctcact ttcattctct  11520
tctgccataa catcaaagca ccatacattg cttcaggcaa taatctcaac atcccaatct  11580
tcaggtaaga tgagcttatt ttggaattta aggaattaaa aagattatgt tttgaatttt  11640
aattttttaa attatagctt tcgatatgtt attgtaaaga tgacattagc ctttttttctt  11700
ttattataaa agtgatacat agttattgtg taaaatttgg agagtgcaaa aatgcattaa  11760
gactatcatc attatttata tattttatat gggatacttg gtgaactgtg actacctaaa  11820
ctttatgggc attgtttatc aaatagataa aaggcaatta gaaaggcaag atagcaaatt  11880
accataccag gctcagcagt agggagttgt ttggtggagg agggggcagt gaagtgggag  11940
aagggttagt gatataaaga caaccatacc tgttactttg acctcataat ttagtagagc  12000
tagaaccact taaaaagtac aatatcatgt gaaaggtatg ttttagaggt tttcaccttt  12060
tgaaaggttt tttagaggtt ttcctcaatg cgttccattc aggggaaata gtatgtgcaa  12120
atgcggagag atacaggagc atggtatggt tgggaagtga tggacaattg ggtaaggtgg  12180
gaatatggga tgcattagga aggatcagag actggaggtg gtagctgtgt aggtagtgaa  12240
agctggatca aaacaatttc taagccaaga gattagagtc tgtcctgtac ttgagaaatg  12300
acatgttcag gtttgtattt tgaaaggtca ttctggatta gaaagaatga aatcaattct  12360
gcttccatta ggatagttca ggcagaagat aatggaggtt taaattgtag tattgttttt  12420
ggacaggagg gcatagattt aaaaagtact tagtagctcg aatttaaaga cccagtgcta  12480
```

-continued

```
gtccctatgg gggctcaata gagggggaga ggaaggagca agattcccag gtgtttacca  12540
cctaggaaac tgggtaggtg gtaggtctga tcaccaacaa agaattggtg aggaactggt  12600
tgagctggtt tgggaaatta aaagtttcaa acctgaaagg acaaagcatc tctaaggtca  12660
gctctgtggg tagagagtgg ataaaaggag catgaattta gaaagagact ggaaggaaag  12720
tgggctggca ggttgtgcag gtggagcttc acaagatggc cttcgtcacc tttgtgtgct  12780
gtgtcctcag tatcacagtc taaggagctc cttcttaatc ccttggttca gagttctata  12840
ggctttcaga gttctgtagc taaccagact cttgtgaccc aactgaagag aagccatgga  12900
ttcatgcagt cagtgatatt tatccagctg tgctttagac aagagagaac aaaatatata  12960
gtccttgcct tcacatagct taatggataa tgtagacaga cagctagctg taatagcgtg  13020
tgatatgatt ctacagggta gatgtgcttt tccaggaatt agaatatctg tgtttgctct  13080
ccaggggacc tctctccagg aacaaggaac cgggaaactg aattagaaag tcatcaggaa  13140
gtttctggtg ggcacagact tagagggaag aggactattc cactggggct ctagagaagc  13200
cttgcttctc ttgtaattag aatatttcct atacccattt ccttcacatt tggttctcaa  13260
ttaggatttc ttggaactgc ttaataaaca ctgataattt tttgtaatcc aacttccctt  13320
tcatggactc tatgccagtg actgtgtagc tcacctgtcc ttcagacaca gcaggctgta  13380
gttagcccag cctgtttttg tgcagctttc ttttgttaca tgacagtcta cccattcaca  13440
aaccacttct caggtgttat ttttgtggat ggctcatctc attcatttta ttctgcagag  13500
ttttactctc aaagagtgat actaagcttt ggcaacacct tactgtggcc tccttctatt  13560
tactgtagag cagtggtccc caaccttttt ggcatcaggg accagtttca tggaagacaa  13620
tttccacaga ccatgggggt ggggaggatg gttttgggat gattcaagca tgttacattt  13680
attgtgcact ttatttctat tattattact ttgtaatata taaagaaata attatacaac  13740
tcatcataat gtagaatcac tagacggtcc caactggggg tgataggaga cagtgacaga  13800
tcatcaggca ttagattctc ataaggaatg cacaacctag atccctcatg ggcagatgtg  13860
cagttcacaa taggatttgc gctcctatcc tatgagaatc taatgctgtt gctgatctga  13920
caggaggcgg agctcagagg gtaatgcaag tgatggggaa tggctgtaaa tatagatgaa  13980
gctttgcttg cttgcctgcc actcatctcc tgctgtgtgg cccggttcct aacaggccgg  14040
ggaccggtat tggtccgtgg ccccggggtt tgggaccact gctgtagagg ataccaaaaa  14100
tatatattaa tgtttatgtt agtatcactc tacttgaaaa gaataggagg ctgtgagttt  14160
ggaaagattg acttagacag tttcaacttc atatcaaaat tagtgttgta gaaagagaca  14220
tagggttagg aaaagaatcg ttttatgcct gtgtatgtgc aaatgaagca catttttgtt  14280
tcatgttttg gaaagatggt tatgcttggt ttcagttgga taaaattgtt tttgtctcac  14340
aaggatcctc tgtaaacaat aattatttga gaaaatttcc cccaaggagc tttcgtaata  14400
aacatcatat tcattttgta gtaaacatgc catgcgcaaa tttcagaatg tctaagggtc  14460
agtgtcttga gaccctgggc aggattttaa aatttagaag tgttctataa tcctcttaaa  14520
atctatacta tcatttttac gggtaatatg tcatgcaaac tccttttggc ttggaacaga  14580
tataatagag gctcattata cacagtgata tcccaaagac tgatgaacaa tgtaaatgac  14640
tgaaacatgt cgataatatg gaaaatgaaa aaaatgcctg catttttact gtcagctgct  14700
caaacggcac atatggcttg tatccacttg gcaaatgttt tcaattaact tggaatgtga  14760
gtattctttt tacatttttc tttgtaaata attcatgtat tctgaattta tagtaccttg  14820
atccataagc ttgggggctt cttcatacga cgaaggctcg atgaaacacc agatggacgg  14880
```

-continued

```
aaagatgttc tctatagagc tttgctccat ggggtatgtg tgatctctaa ttatccttag  14940
ggacattgtg ttggttatca cagtggaagg aaaaatgact cttttgagtt gagattttta  15000
aaaactgctc tttgagtaac tggagtgatt attgcttgag tttggtaatt tgttgttgtt  15060
gttgttgttg ttattaccaa aatatagcat tggaggagct gttttattag tgtgaataag  15120
atactttgtc agtagtgaag ttatcgtttt ttctgttttg cttttaaaga tttaattttt  15180
ctgagctcat tctaagttga gtggtcttga atgtatgttt tactttcttc ttatatccca  15240
gcatatagtt gaattacttc gacagcagca attcttggag atcttcctgg aaggcacacg  15300
ttctaggagt ggaaaaacct cttgtgctcg ggcaggactt ttgtcagttg tggtagatac  15360
tctgtctacc aatgtcatcc cagacatctt gataatacct gttggaatct cctatgatcg  15420
cattatcgaa ggtcactaca atggtgaaca actggtaagg gtacctacac aaaagttttc  15480
tttgcttatc aagtctttta gatttaactt ttagaattta catttgcttt tagaattaag  15540
aatttttttt ggtactccct atgtttaaag cactgtatga aatgtgattg gatgggcatg  15600
gtgagtagct ttcatgccct atctttaact tgattggtag tgcttatgtg gtgttttctt  15660
gagcttggca gaagtgacct ggttagattt atcagtgccg accttggtca tgggattggg  15720
aagtgggaga agacttgcca ccgtgttgcc atctctgctg tggaaggtta tctgcggttt  15780
gttctcccca gggcttaatg aatatgtgca tattttaaat tgggcttgaa gaacttgtgg  15840
ggtcatgttg gcaaaaacac ctacagatta atttgagagg tagcaatgac tttttcagta  15900
tacctttta ttgaagtata atagttacaa aagagtatat aaatcatagg catgtagctt  15960
gaattatcac aaagtgaata catctatgca actagcaccc agatcaagga acaatattac  16020
caggaccttt gaaaccctcc ttgtgcttct cctatcatca tccccgcaag ggtaatgatt  16080
aatttcattt cttacagact gggttagttt tgcatatttt tgcacttacg taaattggat  16140
aacatgtggt ctgtacgcat ctggtttcct ttgcttaagc aggtgtttgt gagattcatc  16200
cacattgttg catgtagtct attccttctc atagctgtgt agtattccag tgtatggtat  16260
accataattt attctactgt taacaaaatg tttggctgta atcattcttg gatattttt  16320
cttgatgacc atatatattc attttgttgg gtatgtgcct aggagaagaa ctgatgggtc  16380
ttaaaaaata tgtattttca gctttagtag gtactgccaa ccactttatc agaatggttt  16440
taccagctta ccactccagt cagcagttag agttcaagag gaatttagtt ttgttcttat  16500
ttattgtgga aattttggct gaggtactta tttcaagctt acggctccag acatgtcaga  16560
aattcaagga cgtctgacaa tcagaggctt tagaaattaa gtgataggct tacaaattaa  16620
gtgatatgat ctgtatgaca ctcttctcct tgtgttctat gaatctgtcc ttgatgtata  16680
ccctactcat cctgactgtg tctcacgagt tcatatctga gtctgtgtcc gttatatgtc  16740
ctgtcattgt gccttatgtg taatagatac taggtattta ctgaatgaat actcagctca  16800
aaggccactg taaggctgga tttgcaatta cttgcctaat attagacatt tagactctgg  16860
tgatcatcag acctcagata aatggcctct ttgatgtttt attcttgttt aagaaccaca  16920
gaagttttcc aggctatgtc attttttcct tcattagttt gcaattgtat ttttgtgaat  16980
tgtgtgaaca tgatactaaa tgaaatagta ttaaatgttt tgtttttcat tgactgaatt  17040
ccatctccca atgacatgat tacatctttg aatactaaac gttttctgac aggccgcagt  17100
taatgattac ctcctttcct tcttcattca ttgttcttct tcaagatgaa cttacagttt  17160
ccataaaaca agttattctg tggataatag aatgtttgtg tatgtgttgg ctttatttct  17220
```

caccatgtta ttctcactat tggaatttag ggcaaaccta agaagaatga gagcctgtgg 17280
agtgtagcaa gaggtgttat tagaatgtta cgaaaaaact atggttgtgt ccgagtggat 17340
tttgcacagc cattttcctt aaaggtgagt gtctgttgaa atgaaaccat gttgaagcat 17400
ctacctggag tcaggaggct ccagtgctga ctcttaacag cacctctctg tgtgacttgg 17460
ggctgcagtt tgctctcctg taaaatgagg actatgataa aggtggtgtt gcctaaattt 17520
ttccacaaaa tttgcctatt gacaaaggag agtgagtatc tgtttttggg agatatcagg 17580
ctcgacattt attgctatta ttattttttt ttaattcatg accatctaag gggaacaaaa 17640
aacaggtaga aggaataagt tttagtattt gatagtacag tagggaaatt atagttagca 17700
gtaatttatt gtatatttca aaataactaa aagagaagaa ttgtaatatt cccaaccccc 17760
cacaaaaagc taagtgtttg aggtgatggt tatcccaatt accctgattt tatcattaca 17820
cattgtatat agatatcaaa atatcacatg taccccaaaa tatgtacaag tattatatat 17880
caattaaccc caaaagtcaa aaaaatttttg agatggatga atgaataaat gaataaataa 17940
ttgtaaaaaa ataaaaattc atgggaatct tgcatgtgcc tttataatac gtatttatat 18000
cttatgtttc aaaattgcct ttaggggaaa tttttccaaa cacctcccct aaaagctggg 18060
taactttttt tttgagacgg agtttcatgt tcttgtagcc caggctggag tgcagtggcg 18120
aaatctcagc tcactgcaac ctctgccccc taggttcaag caattctcct gcgtcagcct 18180
cctaagtagc tgggattaca ggtgcccgct accacacctg gctaattttt gtatttttag 18240
tagagacggg gtttcaccat gttggccagg ctggcctcaa acttctgacc tcaggtgatc 18300
tgcccgcctc ctcatctgcc tcccaaagtg ctgggattac aggtgtgagc cacttcgggc 18360
agccaaagct gggtgaattt gacaggataa tgctctctat gtcctattgt gtagaatcca 18420
gtacccacac atcccaaagg atagtgccat cctcattgaa agtctgggac tggcaggtcc 18480
ctgaggccct tgctggttta aattcttaag gtattcaaat tgtaaaggag aaggagaaaa 18540
atgggtacag aagtagggag cccagggata aggagcagaa ggtcccgcct ctccttttat 18600
tctacttcct ggcttaactt taagagattc cagctgctgt ggtagatgct tgctaacctt 18660
aaatgctttg atcttttaga accttatcat ttcttgccac tttctttctc tttatttttt 18720
aaatggtcac atagcttctc tgtcttgtta tgatttgctt ttagattgag gttcttttga 18780
aaataatgtg acccttgggt tgccagattt ttttaagtat gattatgtct atcatcacta 18840
ttaatgatat taagaatgtc agttttatga tgatgtgtga gaaaagttaa aaatttcttt 18900
taattttaaa atgattttgt ttaagcatcc tattctttgt gtcttcagtg ttcaagttca 18960
gtttcatgct tagcagcatt ctgtgaatca ttctggactt ctgaagacag tttaggatat 19020
agaaagtatt tcccatgctc tatagcatgg cttatttcat aaacaactcc cttttaacct 19080
ttggaagatg aaattacatt ttatatgttg gtgcgaaagt gagggtaaat gatcatgttg 19140
tgtttttttc tccaggaata tttagaaagc caaagtcaga aaccggtgtc tgctctactt 19200
tccctggagc aagcgttgtt accagctata cttccttcaa ggtaaaattt gtagaattgt 19260
ttaatgctaa tcaagctacc aaacatctgt tatttcttgt attgcataga ttaaccttat 19320
taaaaatgcg cacattctta ttttcacttc ttaagtaact tttctcttag tccaataagg 19380
gatattgaga tgacatgttt tcatattagt ttggaagttt ttaattattt gcttataact 19440
ttttgatttt gtgactcata taggagttct taattgattt atgctttttg aatgcttgaa 19500
ctgagttttt ttggtagtag gttatgcata ttgtatgtaa gtgaaccata tgaaagaatt 19560
ttgctgtttg aatttttcgg aattcaaatt gaattcaaat tgaattttaa cttagagaaa 19620
ttgaatatga agcctttcct ttaatatgtg gaagtgttga attttcagaa atgttttaaa 19680
ataaggcatc ttgaattatg tattctttct gccagtggtt ttggaagtgg tgtatcaaca 19740
gactatttag tcataactaa ataacatgtt ttggccaggc cataatgtag tatattatgg 19800
aggaaaataa gccatagaaa taatctgttt gtggtttaaa tttaaaatat atagtaattt 19860
aaagtatcta attcatttaa agatcagttc cacatggttt gccttgtaaa agagtgcggt 19920
tgtgtgttga tttttgaaac actttttaga cccagtgatg ctgctgatga aggtagagac 19980
acgtccatta atgagtccag aaatgcaaca gatgaatccc tacgaaggag gttgattgca 20040
aatctggctg agcatattct attcagtaag tagaatacca gactctttaa ttctacaatt 20100
tagattcatc atggtatggt gcaaactata cagattttgg aatctgctga ggttagtttc 20160
cacttctatt aattcacagg tggtgatagg taagttatta gaaagaaggt gataccgtga 20220
ggatttgaga taattggagt taaacatctt atacagtgtc tggtaattag taggtgttca 20280
tgtggtagtt gttgtacttt ttaaaaatag ttattattaa aatgatttgt tgcctctgtt 20340
gctcattaat gtgttttatt tgaactactt gaactaattt gtggtacaac gtctagattt 20400
atagttgcat gtccatttct cctttgaccc catgagtttt tgtaatgcag caaatatgag 20460
tggccttgta taaagctttg ccttagccgt ggagaataca aaatgaataa ttaatggttc 20520
tgaactcaat gagcttatgt tcttgtcagt gggatggtta tacacaaata attaaagtga 20580
acctagagag gagaggagtg tgagttcact gcaggaccag tcttctttaa gttccaagct 20640
gtacaattgt gtactgttgt ggaggctgct ttaaaatccc aaggcagcac agtggttctt 20700
tggtgctcag cctagttgtg atttctttct tgctgctctc tgggccagga ccctgatgat 20760
actctccgca ccccctgcca atgctactgg ggaggtcttc ctccctcacc ttgctcctcc 20820
cattctggag gcccctattc ctgcttgact ttgggtcaga ggattctttc tcaagcacat 20880
ttgattatgt ctctatcctg cttaaaatct ggatacaaaa aataatacct tattgttaaa 20940
aagtttgaaa ataaagatga aatagacagc aaaaacccat tacccaaata accagtggtg 21000
ttgctgtgta gtctctaaaa atattttta cagttttgta ttgtgcagct ttccatttat 21060
aacacaatat tcatatttaa aaattcttta taaatatttt taatagctat acatatagta 21120
ctgagtactt ttttttaaca ctggagacga cttcagttac cagtggtgaa tgaagtattc 21180
ttaaatttat tgttatctta gaaaactcac aaatgttatc gtgatttaag attattccat 21240
gggtgttctc agatttgatt tatataatta taattttatg caaattcagt gtaggggtgt 21300
gcactgtagt cattctcaaa tgtgtgtctg tgcccttcct tcttacctct gggtcaggtt 21360
gaaagaggaa atacaaatat gctgagcacc cattactgtg gctcctgtgc cgggccagtc 21420
atttattct catgtggtct aatgagctag gtaggatttt cattttatca gcaaggaagg 21480
tgaggccagg aatttaagta atttgcccca agtcatgaag ttagttagtg agtaaattag 21540
gatttgagcc cagatttttc tgacttcaag tcagctgtta tccttctact acaccttcgt 21600
tttaatatgg tgaataccag caagaagagt gaagtagagt tgtagttata atagactgta 21660
ggtgggagca agtaaaggaa tatggaaatg ggagatcccg tagaactaaa acagccttgt 21720
actttgggtc ttgatatttc aataaaagtg tctcttcgtc attcagtaac taaattccac 21780
tggcctggat tgaagttgga cctgtcttac ttagcctgtt gtatgatgaa tagtgatctc 21840
taatgaggtt ccattatacc agaacactgt agtattataa cttcctttg gtaaatcaca 21900
cttatgggaa atgtgataga agactttcac agttttaaat actcctgttt aaaatttagg 21960

-continued

```
tatttcaaaa aagttcagct atgtttgtaa aaagtgcaac taaaaaaagc tttgtgtttg  22020
ccttccagct gctagcaagt cctgtgccat tatgtccaca cacattgtgg cttgcctgct  22080
cctctacaga cacaggcagg tatgtctgca atgtcacctg cagttaagta ggaagcagga  22140
gaatgttttg tcagctgctc agatacatac tcaggggcag atttggccca ctcatggcta  22200
gtactatgag gtaaacagta aaataagctg aggaccctgc ccaaaggagc ttatcaactt  22260
ggtggaggaa gaatctacat ttaaaaacaa aacaaaacag actgcttaat atatatagta  22320
ctaagctatt gcttgattaa tactgttaat gtaaataagg tctaactcat taacatgtgg  22380
tatatattct gaaagcaaat gctttccaaa tgaattgact ggcattttag aacccaccct  22440
ttatcctccc aaaatacatt tgtctgagct ttatgatgga agagaccaca ccagtcttgt  22500
tcagtcatat tctcaacacc aaacagtgcc aatatatata ggcaccaaat aaatatttgc  22560
cagataaata tttaaaatga aggaaatttt gctaaaaaat aagcactcct tacttgcaga  22620
tggctttttt cctcccccttt gtgatcttat gtgtgcatat catgtgtcat ggctagagtg  22680
ttcactagca tgtgtaatac cttgacattc ctggaggacc agctttttaa gtagttttct  22740
gactcgctct gcattggtgt tctggcccta cttctctatg tgctagcagt gagctgcagg  22800
aaagccaagg caagaagaaa gtcttggaat gttggcctct cagctttttg gaaagtaggt  22860
tttccaccat catgataccg tttccatctt tctttaggga attgatctct ccacattggt  22920
cgaagacttc tttgtgatga aagaggaagt cctggctcgt gattttgacc tggggttctc  22980
aggaaattca gaagatgtag taatgcatgc catacagctg ctgggaaatt gtgtcacaat  23040
cacccacact agcaggaacg atgagttttt tatcaccccc agcacaactg tcccatcagt  23100
cttcgaactc aacttctaca gcaatggggt acttcatgtc tttatcatgg aggccatcat  23160
aggtatgtca gaccttgaaa tattttcagt aattttcatg gaaaataaaa aggcctaaaa  23220
cacatagtgg tatctgcttt aatttgggtg atagcccctt gcttgaggga atgtggctat  23280
aattttagtt ttcaaacgaa aatgtaatct cctgttatat cactgtttac aatgagtagt  23340
tactgaatta ccgtttgtat agcattaccc ttatttttca ggagaggtag agtgtcttgc  23400
tatccaggag ctgaaaatct aactgagatg agacatacac agagcagcaa agtgagtgga  23460
gggcctcatt tgtgattaag agaaaagaga ggaaggagag aagaggggc ttatgtcttt  23520
ggagaaggtt tttgatgcag ttgggatcat atggaatcat aagaatttag tcttatggga  23580
tttacttaaa tttctccaaa tacaggccat tatttttgat gtattaataa tctcttaagg  23640
ttattcaagc cagttgaagt ttttcttgga gactttgagc tggcaacttc attgttgctt  23700
ttcttttctt agcttgcagc ctttatgcag ttctgaacaa gaggggactg gggggtccca  23760
ctagcacccc acctaacctg atcagccagg agcagctggt gcggaaggcg gccagcctgt  23820
gctaccttct ctccaatgaa ggcaccatct cactggtgag tgaagaccct tcagtgttgc  23880
ctggtctctt ttcttgagcg ttttcatgaa aacgtaaccc cccgtgtttt tctgttagat  23940
aatgtttgac ccattgttga tactttatat tccactcctg gatttcagtg accaccaaac  24000
caatatgtca tttactatct tggtttgctc tctgggtcac tgctccactg aatctatcct  24060
gcagctatga gccatgatag gacagattgc tcaatgttct caggcagtca catccaaagc  24120
tagtgagcac gtattgtgtg tgaggcactg ggtcagtggt ttgtaaataa ttaacacacc  24180
cacctgtaga tgatggaacc acagatggta agagtcagaa gcagccttaa aaatcatctg  24240
ctcggccagg tgcggtggct cacgcctgta atctcagcac tttgggaggc tgaggcgggc  24300
agatcacgag gtcaggagat cgagaccatc ctggctaacg tggagaaacc ccgtctctac  24360
```

-continued taaaaataca aaaaaaaatt agccaggtgt agtagcacct gcctgtagtc ccagctactt 24420
tggaggctga ggcaggagga tcacttgaac ctgggaggcg gaggatgcag tgagctgaga 24480
ttgcgccact gttctccagc ctgagtgaca gagcgagact ccatctcaaa aaaaaaaaaa 24540
aaaaaaaaag aaaatcatct gctcaacacc tctcaattta caaatgagga aaaccaagcc 24600
cagcagtact aatgagcatt tatattatat acccaaacac ttttaggcat ttatcatgag 24660
acatatgtat taagtagtag atttccttct tctcaaagtc atcaacatgt agaattcata 24720
ttttatttga attccgatat tttcttttgt atgaatgtgt cttgagatgt tgacgagatg 24780
agtgcatgtg ttaggagtac cgccccctcc atgccatgct ttgtgtgagg tgtgctcgtg 24840
gtcctgttgg ggaatctgtt ttgcatgaac cttgggtggt gggatggaag ggatgagggc 24900
agataagact tccaagattg accttgtcct ttctctggta tttatttact tattccaatg 24960
ttgcctttcc tcaatcacca cttttgtgta cagtatttat tataagataa ctattgcaga 25020
gaaattgtct tataaagtaa aagaaataga tggtgggggg ctgataagca gtcttcagag 25080
ggctttccac actgtgggtg tggggagaga attgagctca ggagtacccc ttgcaggtgg 25140
tgcagtgttg ggtgctctgc caactttaag tgacagaggt cttttcttgg gctttgtcca 25200
tgaccgtgtg tgtatcaaga cagtgggcac tgggaatcac aggacttgct cagtggggtg 25260
atggaggtaa cagaatggaa ggctttggca gctaccttgt accatgtttt ctgcgtttaa 25320
aaaaagaagt ataaaatggt ggcatttata tttaaatgaa ttttcttttc agccttgcca 25380
gacattttac caagtctgcc atgaaacagt aggaaagttt atccagtatg gcattcttac 25440
agtggcagag gtaagaggta gagctttcct ttatttgtct ttatacttac tcttcattcc 25500
cttacctttt ctacaactta tttaaaccaa taattggcca ggcatggtgg catgtgcctg 25560
taatcccagc actttgggag gtgaaggcgg gtggatcacc tgaggtcagg agtacgagag 25620
cagcctggcc aacatggcac aaccctgtct ttcctaaaaa tacaaaaatt agctgggcat 25680
ggtggcacac acctgtaatc ccagctactt gggaggctga ggcacaagaa tcggagtggt 25740
ggaggtttca gtgagccaag atcatgtcag tgcactccag cctgggtgac agagtgagac 25800
tcagtctcat aaataagtaa acaaaccaat aattacattt ggtatatagt catgttcaga 25860
tgtagagaag caaaaaataa gaatggggag aataagtgtc ctttgggatt atttaatatt 25920
ttggttccta tttgtaagtt gtgttgtcta aaacatatcc tgacttgatt ccgtgacatc 25980
cagaagtttg tatgctaagt tgagacgtta cacctatcag tatgcttgca gcttgcacat 26040
ctgcagtttt catttttgag attctatttt aattttggta gatttagtgt agaggagatg 26100
gcctggaaaa gtacatatca atttagaaca tgtgggggta cttttatttg atctttcttt 26160
ctggtagctc tcccctccca cctgcccttt cttttgtctc ctgctgtctc ctgactgagt 26220
ttgagtttgg aagggaagtg gactgacatt atgagtggct aaacagagaa gagccaggaa 26280
gggtcagaga agaggactgc cttgtcctgg ctccactggg cagttgtttg tgtgccagtg 26340
catatttatt tactatccat catctccttg gcctagcacg atgaccagga agatatcagt 26400
cctagtcttg ctgagcagca gtgggacaag aagcttccag aacctttgtc ttggagaagt 26460
gatgaagaag atgaagacag tgactttggg gaggaacagc gagattgcta cctgaaggta 26520
cttgggtgaa gaattctggt ggatattaca gggatatgtt gaggtttatg ctgcagtgag 26580
atcagctgga gtcctggtga tgtcttctta tctaaagaat cccccaacta gctctggtac 26640
cttctgtgtg gtaaagacac tcaaactgtt tgagttgaat taatagcatt ttaagtagaa 26700

-continued

```
aaggaaagga gagtctgaaa agtcaggaag atgaatgtca taggtgagac tttcaccatc  26760
cttttatgaa atacacaggt gcatacctgt ttacctacac ctgcacccct catgaggcag  26820
cagttttgct attgagctgc cactgacctg gctgctcttt ttgagtcact cttgctgtcc  26880
ctcccaaaat ttcatatatt aagctctttg ctgtcaatta aaacaaatac cattatagga  26940
gaaaattgag attaaaaaaa aagtccctga tttagaaaaa tcaattttgt ctaatttata  27000
atttagaac ttagtaataa tgacccgtct tttctgaata ctctaagagg attactcttt  27060
tttgacattt agaaattgtc ttctttttca cttgggtggt attagtttag tttcaagatg  27120
gggcagtgat cttgctttca cactccagag gggcttgacc gaaccagtgt gttttgggta  27180
ggtacagtga gagcctctcg gccataaagc accgccgtca cagtggccat cattccccac  27240
agtgctggac tgtgggcaaa ggccatttag gggaggcagg gaataggtgc tgcagaagga  27300
gtgagataat cttggtggtc tcccattggt ctttctgcag acttgagtga ctgttgagcc  27360
caggcttcaa accatggagg gcctggtctt aggagcggct atttttagtg atgacagcgt  27420
atcacaagta gggcattcat ttatgaaaat ttcttctagg tggctgttca atgaacacaa  27480
gcctcaaata ccataaaaaa gtgaatgatt acaataaaga atgtgtttga aagccagcag  27540
ttgtttccag cagagattct ctgcatgagg ggcagggggc cgctttcatg tagtgctgat  27600
gtgagtggcc atcttctcac gttactggct ctccagagaa agtcctctgt ccacttgcct  27660
tgtgtctctt gtcccttcct catgacttca tctcctgctt ttgcacactc aggtgagcca  27720
atccaaggag caccagcagt ttatcacctt cttacagaga ctccttgggc ctttgctgga  27780
ggcctacagc tctgctgcca tctttgttca caacttcagt ggtcctgttc cagaacctga  27840
gtatctgcaa aagttgcaca aatacctaat aaccagaaca gaaagaaatg ttgcagtata  27900
tggtatgtta agtcactatt tattctttta aaatcttttt tttttttttg gatttcagaa  27960
atttgctaat tgtagaaaat tggaaaaatg caaacttatc ctgacctcta acaccgtaga  28020
gtattactat tatcttcttt ggcatgttat ataagttgaa tgatacagtt atacactctt  28080
acatctggct tttttcacgt aacgttattt ttgagattca tacatgttgc atatagttgt  28140
tcctttgttc ttgttgtgta gtgttccatt gtataaatat ttaccacatt ttattcattc  28200
tgctgttgat ggatatttgg gttgttttca gttcacagct gctttgaaca gtgttgctat  28260
gagcatattt gaatatgtct tttggtgaat atctgtgccc ctatatacag catgtatgtg  28320
ggaacagaat tgcctggttg taggctctgg gtatattcgg ctttggtaga taccaccaaa  28380
cagtttccaa gggattatac ctacttgtac tcccacaaca gtgtgtgttt cacttgctgc  28440
acatcttggc cagcgctccg tcttctttgt tttaggaggt gtgattgggg tgggagtact  28500
attttataca gttgtagttt ggagctgaaa ctacttgaat cactttttag agccaaaagg  28560
aatctaatct aatcacctca ttttatagtt gaggaaaata ccccaggtca cactgctaat  28620
taatgggtaa tctcgggatc agaattcttg tttcctaacc tcgaggcctg tgctttctct  28680
ggttccactg atgtacaatc atctgtgtac cactgggtag cttaaagaat atttatacac  28740
tatctcattt gattctcaca acagtcctgg aaaatggatg ttttaggtat ttctacttcc  28800
ctctgttctc cctatttctc tctctacacc ctcttttctt tccccttccc tttcttattt  28860
acctcaatat aggacaaagt aggtgtaagc aaagtaggtt taacagcaag tcatctgaga  28920
actcacaggt tgccagtggt ggaagtgggg ccccaccctt gtctgctgac ttgccctcat  28980
tctcttccta gctccccata ctttcttact gtggctgctg ggattgtcat gatttgttga  29040
gcgtaaccat ttgacagggt tttattctct ctcttcagct gagagtgcca catattgtct  29100
```

-continued

```
tgtgaagaat gctgtgaaaa tgtttaagga tattggggta ggtgtccacc atttatggta  29160
taaaagctat ctcaacttct gttctcttta gatctagtct gtttgagcta cctttgtggt  29220
ggggtggacc ccgagagaag cagtttctgc tggcttaatg ataaaggcat ttttgggaac  29280
ggggcatgta ggatgggttg ggctatgttg aaggtgaagc ccatcagtgt agatttattt  29340
gaatgttctg gaattttact ggtttcacat ttattcccaa gctgctatat ataactggta  29400
tcaatatgtt tcaaggtgct acaggttgaa tatcccttat ccaaaatgtt gggaccagaa  29460
atgttttgga tttcagattt ttttgggatt ttggaatatg tgcattagac ttacaggttg  29520
agcgtctcta atccaaaacc caaaatgctc tgatgagcat gtcttttgag catcatattg  29580
atgttcaaaa tctttcagat tttggagtac ttcagatttt tgattttggg attaggacca  29640
caatcttggc tcttaattat tccatatgat ttttagttac tttcttgtat ttttacaaga  29700
atttctagaa gtatcctcag gtgtccttta ccttcatgat tcatggggaa tgtaagttct  29760
atagagatac tagcggcctt ttgtgaggga ctgtttgtga ctttattcta agtcatttta  29820
gagtatagtt atgttggttg aaattttaga atatagttaa tgttggttga actccatcaa  29880
aacaaaaaaa aaaaaataga aaaagaaaac cttgtttgca ttggaaactc ccacctcatg  29940
ctcacacaca cccaggcata catttactta atgccaggat atggtttttt gtgcctttac  30000
tgccttctga ggtctaggac accacaggtc aggttggtaa tggaaatttt ttttattttt  30060
tattttttgc ctttaattta atctaaacct tttctttagg ttttcaagga gaccaaacaa  30120
aagagagtgt ctgttttaga actgagcagc acttttctac ctcaatgcaa ccgacaaaaa  30180
cttctagaat atattctgag ttttgtggtg ctgtaggtaa cgtgtggcac tgctggcaaa  30240
tgaaggtcat gagatgagtt ccttgtaggt accagcttct ggctcaagag ttgaaggtgc  30300
catcgcaggg tcaggcctgc cctgtcccga agtgatctcc tggaagacaa gtgccttctc  30360
cctccatgga tctgtgatct tcccagctct gcatcaacac agcagcctgc agataacact  30420
tggggggacc tcagcctcta ttcgcaactc ataatccgta gactacaaga tgaaatctca  30480
ataaattatt tttgagttta ttaaagattg acattttaag tacaactttt aaggactaat  30540
tactgtgatg gacacagaaa tgtagctgtg ttctggaact gaatcttaca tggtatactt  30600
agtgctgctg ggtaatttgt tggtatatta tctggttagt ggttaatgct tcctttaaaa  30660
ataattgagt catccattca ctctttttca gttttatctg tcaatagtag ctacattttt  30720
aatgggagca ccttttatcc caaagtgctt tataaattga gtggactgat atatatcaca  30780
cccaggtatc actgtgctgt cctttgctgt cagatttaga aatgttttta agagctatgt  30840
gaaaacagac aatattagtt taggtcggga actgagatat tgtaatcaaa tagttaacat  30900
caggaagtta atttggctgg caaaattcta gggaaacttg gccagaaaac tggtgttgaa  30960
ggcttttgct catataaaca agtgccattg agtttcaaat gaccagcaaa tatatttaga  31020
acccttcctg ttttatgtct gtacctcgtc cacccctcag gtaatacctg cctctcacag  31080
gtacagctgt ttcttggaaa tcctccaacc aaatagcagt tttcctaact tgattagctt  31140
gagctgacag actgttagaa tacagttctc tggccacagc tgatgagggc tttctgtact  31200
gcacacagat tgtgtactgc accccagtcc aggtgactgg tacccactcg agttgtgccg  31260
tgcacaacct gtccagtata tgcatgtggt ggccctactg actggtaatg gttagaggca  31320
tttatggatt tttagctttg aggaaaaacc atgactttta acaaattttt atgggttata  31380
tgcctaaacc cttatgccac atagtggtaa ataattatga aaaatggtct gttcataatt  31440
```

-continued

```
ggtaggtgcc ttttgtgagc agggagcata attattggtt tattatggta attatggtga  31500
tttttaaat atcatgtaat gttaaaacgt tttctaacag tttactgttg cttatctcca  31560
agatattatg gaattaagaa tttttccaga tgagtgttac atagattctt tgaatttagt  31620
ataaaagtac tgagaattaa gtttgtactt ccataagctt ggattttaaa cactgatagt  31680
atctcatgag taatgtgtgt tttgggagag ggagggatgc tgattgatat ttcacattgt  31740
atgaaatacc atgtttgaaa ctcatagcaa taatgctatg ctgttgtgat ccctctcaag  31800
ttctgcattt aaaatatatt ttttctttat aggaattgat gtataccatg aagtcattgt  31860
cagttgtagt agctctgatg ttgaatgaga tatcatgttt tagcattcca ttttactgac  31920
tagggtagaa gaacactttt cttggctaca tttggaggat acccagggag tcttgggtgt  31980
tccttatctg ggaagcaaa catttcacta gtctcttttt ttcatccttt aaattgtaaa  32040
ttaaggatta ctcaagctca ccattattca agattgggac tcgcttccca gtcgacactc  32100
tgccctgcct gtcattgctg caaagagctg ctgctttgcc aacctaagca aagaaaatac  32160
ggcttctctt gcattatttt cccttttggt tggtttgttt tctagaagta cgttcagatg  32220
ctttggggaa tgcaatgtat gatttgctag ctctctcacc acttaactca ctgtgaggat  32280
aaatatgcat gctttttgta attaactggt gctttgaaaa tctttttaa gggagaaaaa  32340
tctcaaccaa agttatgctc atccagacaa gctgaccttt gagttaattt cagcacaact  32400
cattcttcag tgcctcatga ctgaaaacaa aaaacaaaaa aacgaaagca tcttcacaat  32460
gaagcttcca gatagcaccg ttttgctaaa agatacattc tcattgtttt ccaacagtga  32520
tggcttccac ataaggttaa acaaactagg tgcttgtaaa taatttatta cagtttactc  32580
tatcgcattt ctgtaacatg aaatgcatgc ccttcttcag gggaagactg tggtcaagtt  32640
aaaaaaaaaa aacaatatta aacaacatga aactgcagtc tgtttttgaa aatgagaatg  32700
tcctaagtga ttcagaagag aggagggaag ttgtgcactc tgaaaatgca tgaaaaacaa  32760
aggcaaaaac tagtgggaaa tgtgtagaac tgttaactga gatggcttcg agtcttcctt  32820
ctggaatctg ttaaatttca caaagtcatg agggtaaatg gagaaaatat ttctgggatt  32880
acaatgaatg taagcccaaa ttgtggaatt gccagtaacc tggatgggga aaagcatttc  32940
ccatagcact ccatgtaata tgagtgctct gtgagatgtt catcagtgtt ttatagaaat  33000
ggtgttgctg ggaaaccaag tttgcacctg gaaacttaca atgcacttta gcgcagtaag  33060
ggcttggcat ccggtagtga aaaactgtct aacccagcat tgcccaaact attttgacac  33120
caggaccttt ttctcctttg ggatacttat gaacctctca ctaatgtcct gtggagaaca  33180
ttttgggaaa cactatgtta gatagttctt taaggagaca aaacggtaat gaacagatag  33240
cactggggca gaatatgcat gcattttgta acgtccagtg tggcgttgaa tagatgtgta  33300
tttcctcccc tgcagaaaat aagcacagaa aattataatg taggtgatcg gagctctttc  33360
ctttgataga gagaacagcc ccaatgatcc tggctttttc actgaacgta tcagaataca  33420
tggatgaatt ggggtaaata aggttttaat tcagatctag aagaaagtat tgtacgtttg  33480
aatgcagatt tttatccaca gatagttgta gtgtttagac atgacaggac ctatcgttga  33540
ggtttctaag acttactatg ggctgtaaac ctgtttttta aaactatttt agaaacctga  33600
gacttgccgt ctggcatttt agtttaatac aaactaatga ttgcatttga aagagattct  33660
tgaccttatt tctaaacgtc tagagctctg aaatgtcttg atggaaggta ttaaactatt  33720
tgcctgttgt acaaagaaat gttaagactc gtgaaaagaa ttactataag gtactgtgaa  33780
ataactgcga ttttgtgagc aaaacatact tggaaatgct gattgatttt tatgcttgtt  33840
```

-continued agtgtattgc aagaaacaca gaaaatgtag ttttgtttta ataaaccaaa aattgaacat 33900
a 33901

<210> SEQ ID NO 3
<211> LENGTH: 6372
<212> TYPE: RNA
<213> ORGANISM: homo sapien

<400> SEQUENCE: 3
gcgccacugc agcuggcauu ggccgggacu ggaagugcgg gcuucugcag cagccgaagc 60
uggagcugcu agggcagcag cggcuccccu guuguaugga cauucugcac ccgaaacuga 120
uagcugaguc cugaaguuuu auguuaugaa acagaagaac uuucauccca gcacaugauu 180
ugggaauuac acuuugugac auggaugaau cugcacugac ccuugguaca auagauguuu 240
cuuaucugcc acauucauca gaauacagug uuggucgaug uaagcacaca agugaggaau 300
ggggugagug uggcuuuaga cccaccaucu ucagaucugc aacuuuaaaa uggaaagaaa 360
gccuaaugag ucggaaaagg ccauuuguug gaagauguug uuacuccugc acuccccaga 420
gcugggacaa auuuuucaac cccaguaucc cgucuuuggg uuugcggaau guuauuuaua 480
ucaaugaaac ucacacaaga caccgcggau ggcuugcaag acgccuuucu uacguucuuu 540
uuauucaaga gcgagaugug cauaagggca uguuugccac caaugugacu gaaaaugugc 600
ugaacagcag uagaguacaa gaggcaauug cagaaguggc ugcugaauua aacccugaug 660
guucugccca gcagcaauca aaagccguua acaaagugaa aaagaaagcu aaaaggauuc 720
uucaagaaau gguugccacu gucucaccgg caaugaucag acugacuggg ugggugcugc 780
uaaaacuguu caacagcuuc uuuuggaaca uucaaauuca caaaggucaa cuugagaugg 840
uuaaagcugc aacugagacg aauuugccgc uucuguuucu accaguucau agaucccaua 900
uugacuaucu gcugcucacu uucauucucu ucugccauaa caucaaagca ccauacauug 960
cuucaggcaa uaaucucaac aucccaaucu ucaguaccuu gauccauaag cuuggggggcu 1020 ucuucauacg acgaaggcuc gaugaaacac cagauggacg gaaagauguu cucuauagag 1080
cuuugcucca ugggcauaua guugaauuac uucgacagca gcaauucuug gagaucuucc 1140
uggaaggcac acguucuagg aguggaaaaa ccucuugugc ucgggcagga cuuuugucag 1200
uugugguaga uacucugucu accaauguca ucccagacau cuugauaaua ccuguuggaa 1260
ucuccuauga ucgcauuauc gaaggucacu acaaugguga acaacugggc aaaccuaaga 1320
agaaugagag ccuguggagu guagcaagag guguuauuag aauguuacga aaaaacuaug 1380
guuguguccg aguggauuuu gcacagccau uuuccuuaaa ggaauauuua gaaagccaaa 1440
gucagaaacc ggugucugcu cuacuuuccc uggagcaagc guuguuacca gcuauacuuc 1500
cuucaagacc cagugaugcu gcugaugaag guagagacac guccauuaau gaguccagaa 1560
augcaacaga ugaaucccua cgaaggaggu ugauugcaaa ucuggcugag cauauucuau 1620
ucacugcuag caaguccugu gccauuaugu ccacacacau uguggcuugc cugcuccucu 1680
acagacacag gcagggaauu gaucucucca cauuggucga agacuucuuu gugaugaaag 1740
aggaaguccu ggcucgugau uuugaccugg gguucucagg aaauucagaa gauguaguaa 1800
ugcaugccau acagcugcug ggaaauugug ucacaaucac ccacacuagc aggaacgaug 1860
aguuuuuuau cacccccagc acaacugucc caucagucuu cgaacucaac uucuacagca 1920
augggguacu ucaugucuuu aucauggagg ccaucauagc uugcagccuu uaugcaguuc 1980

-continued ugaacaagag gggacugggg ggucccacua gcaccccacc uaaccugauc agccaggagc 2040
agcuggugcg gaaggcggcc agccugugcu accuucucuc caaugaaggc accaucucac 2100
ugccuugcca gacauuuuac caagucugcc augaaacagu aggaaaguuu auccaguaug 2160
gcauucuuac aguggcagag cacgaugacc aggaagauau caguccuagu cuugcugagc 2220
agcaguggga caagaagcuu ccagaaccuu ugucuuggag aagugaugaa gaagaugaag 2280
acagugacuu uggggaggaa cagcgagauu gcuaccugaa ggugagccaa uccaaggagc 2340
accagcaguu uaucaccuuc uuacagagac uccuugggcc uuugcuggag gccuacagcu 2400
cugcugccau cuuuguucac aacuucagug guccuguucc agaaccugag uaucugcaaa 2460
aguugcacaa auaccuaaua accagaacag aaagaaaugu ugcaguauau gcugagagug 2520
ccacauauug ucuugugaag aaugcuguga aaauguuuaa ggauauuggg guuuucaagg 2580
agaccaaaca aaagagagug ucuguuuuag aacugagcag cacuuuucua ccucaaugca 2640
accgacaaaa acuucuagaa uauauucuga guuuuguggu gcuguaggua acguguggca 2700
cugcuggcaa augaagguca ugagaugagu uccuuguagg uaccagcuuc uggcucaaga 2760
guugaaggug ccaucgcagg gucaggccug cccugucccg aagugaucuc cuggaagaca 2820
agugccuucu cccuccaugg aucugugauc uucccagcuc ugcaucaaca cagcagccug 2880
cagauaacac uuggggggac cucagccucu auucgcaacu cauaauccgu agacuacaag 2940
augaaaucuc aauaaauuau uuuugaguuu auuaaagauu gacauuuuaa guacaacuuu 3000
uaaggacuaa uuacugugau ggacacagaa auguagcugu guucuggaac ugaaucuuac 3060
augguauacu uagugcugcu ggguaauuug uugguauauu aucugguuag ugguuaaugc 3120
uuccuuuaaa aauaauugag ucauccauuc acucuuuuuc aguuuuaucu gucaauagua 3180
gcuacauuuu uaaugggagc accuuuuauc ccaaagugcu uuauaaauug aguggacuga 3240
uauauaucac acccagguau cacugugcug uccuuugcug ucagauuuag aaauguuuuu 3300
aagagcuaug ugaaaacaga caauauuagu uuaggucggg aacugagaua uuguaaucaa 3360
auaguuaaca ucaggaaguu aauuuggcug gcaaaauucu agggaaacuu ggccagaaaa 3420
cugguguuga aggcuuuugc ucauauaaac aagugccauu gaguuucaaa ugaccagcaa 3480
auauauuuag aacccuuccu guuuuauguc uguaccucgu ccaccccuca gguaauaccu 3540
gccucucaca gguacagcug uuucuuggaa auccuccaac caaauagcag uuuuccuaac 3600
uugauuagcu ugagcugaca gacuguuaga auacaguucu cuggccacag cugaugaggg 3660
cuuucuguac ugcacacaga uuguguacug caccccaguc caggugacug guacccacuc 3720
gaguugugcc gugcacaacc uguccaguau augcaugugg uggcccuacu gacugguaau 3780
gguuagaggc auuuauggau uuuuagcuuu gaggaaaaac caugacuuuu aacaaauuuu 3840 uaugguuau augccuaaac ccuuaugcca cauaguggua aauaauuaug aaaaaugguc 3900
uguucauaau ugguaggugc cuuuugugag cagggagcau aauuauuggu uuauuauggu 3960
aauuauggug auuuuuuaaa uaucauguaa uguuaaaacg uuuucuaaca guuuacuguu 4020
gcuuaucucc aagauauuau ggaauuaaga auuuuuccag augaguguua cauagauucu 4080
uugaauuuag uauaaaagua cugagaauua aguuuguacu uccauaagcu uggauuuuaa 4140
acacugauag uaucucauga guaaugugug uuuugggaga gggagggaug cugauugaua 4200
uuucacauug uaugaaauac cauguuugaa acucauagca auaaaugcuau gcuguuguga 4260 ucccucucaa guucugcauu uaaaauauau uuuuucuuua uaggaauuga uguauaccau 4320
gaagucauug ucaguuguag uagcucugau guugaaugag auaucauguu uuagcauucc 4380
auuuuacuga cuaggguaga agaacacuuu ucuuggcuac auuuggagga uacccaggga 4440
gucuugggug uuccuuaucu ggggaagcaa acauuucacu agucucuuuu uuucauccuu 4500 uaaaauuguaa auuaaggauu acucaagcuc accauuauuc aagauuggga cucgcuuccc 4560
agucgacacu cugcccugcc ugucauugcu gcaaagagcu gcugcuuugc caaccuaagc 4620
aaagaaaaua cggcuucucu ugcauuauuu ucccuuuugg uugguuuguu uucuagaagu 4680
acguucagau gcuuugggga augcaaugua ugauuugcua gcucucucac cacuuaacuc 4740
acugugagga uaaauaugca ugcuuuuugu aauuaacugg ugcuuugaaa aucuuuuuua 4800
agggagaaaa aucucaacca aaguuaugcu cauccagaca agcugaccuu ugaguuaauu 4860
ucagcacaac ucauucuuca gugccucaug acugaaaaca aaaaacaaaa aaacgaaagc 4920
aucuucacaa ugaagcuucc agauagcacc guuuugcuaa aagauacauu cucauuguuu 4980
uccaacagug auggcuucca cauaagguua aacaaacuag gugcuuguaa auaaauuauu 5040
acaguuuacu cuaucgcauu ucuguaacau gaaaugcaug cccuucuuca ggggaagacu 5100
guggucaagu uaaaaaaaaa aaacaauauu aaacaacaug aaacugcagu cuguuuuuga 5160
aaaugagaau guccuaagug auucagaaga gaggagggaa guugugcacu cugaaaaugc 5220
augaaaaaca aaggcaaaaa cuagugggaa auguguagaa cuguuaacug agauggcuuc 5280
gagucuuccu ucuggaaucu guuaaauuuc acaaagucau gaggguaaau ggagaaaaua 5340
uuucugggau uacaaugaau guaagcccaa auuguggaau ugccaguaac cuggaugggg 5400
aaaagcauuu cccauagcac uccauguaau augagugcuc ugugagaugu ucaucagugu 5460
uuuauagaaa ugguguugcu gggaaaccaa guuugcaccu ggaaacuuac aaugcacuuu 5520
agcgcaguaa gggcuuggca uccgguagug aaaaacuguc uaacccagca uugcccaaac 5580
uauuuugaca ccaggaccuu uuucuccuuu gggauacuua ugaaccucuc acuaaugucc 5640
uguggagaac auuuugggaa acacuauguu agauaguucu uuaaggagac aaaacgguaa 5700
ugaacagaua gcacuggggc agaauaugca ugcauuuugu aacguccagu guggcguuga 5760
auagaugugu auuuccuccc cugcagaaaa uaagcacaga aaauuauaau guaggugauc 5820
ggagcucuuu ccuuugauag agagaacagc cccaaugauc cuggcuuuuu cacugaacgu 5880
aucagaauac auggaugaau uggggguaaau aagguuuuaa uucagaucua gaagaaagua 5940
uuguacguuu gaaugcagau uuuuauccac agauaguugu aguguuuaga caugacagga 6000
ccuaucguug agguuucuaa gacuuacuau gggcuguaaa ccuguuuuuu aaaacuauuu 6060
uagaaaccug agacuugccg ucuggcauuu uaguuuaaua caaacuaaug auugcauuug 6120
aaagagauuc uugaccuuau uucuaaacgu cuagagcucu gaaaugucuu gauggaaggu 6180
auuaaacuau uugccuguug uacaaagaaa uguuaagacu cgugaaaaga auuacuauaa 6240
gguacuguga aauaacugcg auuuugugag caaaacauac uuggaaaugc ugauugauuu 6300
uuaugcuugu uaguguauug caagaaacac agaaaaugua guuuuguuuu aauaaaccaa 6360
aaauugaaca ua 6372

<210> SEQ ID NO 4
<211> LENGTH: 5664
<212> TYPE: RNA
<213> ORGANISM: homo sapien

<400> SEQUENCE: 4
gaagcuggag cugcuagggu gcgaacugcc agggcaggca gcagcggcuc cccuguugua 60

-continued

```
uggacauucu gcacccgaaa cugauagcug aguccugaag uuuuauguua ugaaacagaa    120
gaacuuucau cccagcacau gauuugggaa uuacacuuug ugacauggau gaaucugcac    180
ugacccuugg uacaauagau guuucuuauc ugccacauuc aucagaauac aguguugguc    240
gauguaagca cacaagugag gaauggggug aguguggcuu uagacccacc aucuucagau    300
cugcaacuuu aaaauggaaa gaaagccuaa ugagucggaa aaggccauuu guuggaagau    360
guuguuacuc cugcacuccc cagagcuggg acaaauuuuu caaccccagu aucccgucuu    420
ugggguuugcg gaauguuauu uauaucaaug aaacucacac aagacaccgc ggauggcuug    480
caagacgccu uucuuacguu cuuuuuauuc aagagcgaga ugugcauaag ggcauguuug    540
ccaccaaugu gacugaaaau gugcugaaca gcaguagagu acaagaggca auugcagaag    600
uggcugcuga auuaaacccu gaugguucug cccagcagca aucaaaagcc guuaacaaag    660
ugaaaaagaa agcuaaaagg auucuucaag aaaugguugc cacugucuca ccggcaauga    720
ucagacugac ugggugggug cugcuaaaac uguucaacag cuucuuuugg aacauucaaa    780
uucacaaagg ucaacuugag augguuaaag cugcaacuga gacgaauuug ccgcuucugu    840
uucuaccagu ucauagaucc cauauugacu aucugcugcu cacuuucauu cucuucugcc    900
auaacaucaa agcaccauac auugcuucag gcaauaaucu caacauccca aucuucagua    960
ccuugaucca uaagcuuggg ggcuucuuca uacgacgaag gcucgaugaa acaccagaug   1020
gacggaaaga uguucucuau agagcuuugc uccaugggca uauaguugaa uuacuucgac   1080
agcagcaauu cuuggagauc uuccuggaag gcacacguuc uaggagugga aaaaccucuu   1140
gugcucgggc aggacuuuug ucaguugugg uagauacucu gucuaccaau gucaucccag   1200
acaucuugau aauaccuguu ggaaucuccu augaucgcau uaucgaaggu cacuacaaug   1260
gugaacaacu gggcaaaccu aagaagaaug agagccugug gaguguagca agaggguguua   1320
uuagaauguu acgaaaaaac uaugguugug uccgagugga uuuugcacag ccauuuuccu   1380
uaaaggaaua uuuagaaagc caaagucaga aaccggugucc ugcucuacuu ucccuggagc   1440
aagcguuguu accagcuaua cuuccuucaa gacccaguga ugcugcugau gaagguagag   1500
acacguccau uaaugagucc agaaaugcaa cagaugaauc ccuacgaagg agguugauug   1560
caaaucuggc ugagcauauu cuauucacug cuagcaaguc cugugccauu auguccacac   1620
acauuguggc uugccugcuc cucuacagac acaggcaggg aauugaucuc uccacauugg   1680
ucgaagacuu cuuugugaug aaagaggaag uccuggcucg ugauuuugac cugggguucu   1740
caggaaauuc agaagaugua guaaugcaug ccauacagcu gcugggaaau ugugucacaa   1800
ucacccacac uagcaggaac gaugaguuuu uuaucacccc cagcacaacu gucccaucag   1860
ucuucgaacu caacuucuac agcaaugggg uacuucaugu cuuuaucaug gaggccauca   1920
uagcuugcag ccuuuaugca guucugaaca agaggggacu gggggguccc acuagcaccc   1980
caccuaaccu gaucagccag gagcagcugg ugcggaaggc ggccagccug ugcuaccuuc   2040
ucuccaauga aggcaccauc ucacugccuu gccagacauu uuaccaaguc ugccaugaaa   2100
caguaggaaa guuuauccag uauggcauuc uuacaguggc agagcacgau gaccaggaag   2160
auaucagucc uagucuugcu gagcagcagu gggacaagaa gcuuccagaa ccuuugucuu   2220
ggagaaguga ugaagaagau gaagacagug acuuugggga ggaacagcga gauugcuacc   2280
ugaagguacu ugggugaaga auucuggugg auauuacagg gauauguuga gguuuaugcu   2340
gcagugagau cagcuggagu ccuggugaug ucuucuuauc uaaagaaucc cccaacuagc   2400
ucugguaccu ucugugugu aaagacacuc aaacuguuug aguugaauua auagcauuuu   2460
```

-continued aaguagaaaa ggaaaggaga gucugaaaag ucaggaagau gaaugucaua ggugagacuu 2520
ucaccauccu uuuaugaaau acacaggugc auaccuguuu accuacaccu gcaccccuca 2580
ugaggcagca guuuugcuau ugagcugcca cugaccuggc ugcucuuuuu gagucacucu 2640
ugcugucccu cccaaaauuu cauauauuaa gcucuuugcu gucaauuaaa acaaauacca 2700
uuauaggaga aaauugagau uaaaaaaaaa gucccugauu uagaaaaauc aauuuugucu 2760
aauuuauaau uuuagaacuu aguaauaaug acccgucuuu ucugaauacu cuaagaggau 2820
uacucuuuuu ugacauuuag aaauugucuu cuuuuucacu ugggugguau uaguuuaguu 2880
ucaagauggg gcagugaucu ugcuuucaca cuccagaggg gcuugaccga accagugugu 2940
uuuggguagg uacagugaga gccucucggc cauaaagcac cgccgucaca guggccauca 3000
uuccccacag ugcuggacug ugggcaaagg ccauuuaggg gaggcaggga auaggugcug 3060
cagaaggagu gagauaaucu ugguggucuc ccauuggucu uucugcagac uugagugacu 3120
guugagccca ggcuucaaac cauggagggc cuggucuuag gagcggcuau uuuuagugau 3180
gacagcguau cacaaguagg gcauucauuu augaaaauuu cuucuaggug gcuguucaau 3240
gaacacaagc cucaaauacc auaaaaaagu gaaugauuac aauaaagaau guguuugaaa 3300
gccagcaguu guuuccagca gagauucucu gcaugagggg cagggggccg cuuucaugua 3360
gugcugaugu gaguggccau cuucucacgu uacuggcucu ccagagaaag uccucugucc 3420
acuugccuug ugucucuugu cccuuccuca ugacuucauc uccugcuuuu gcacacucag 3480
gugagccaau ccaaggagca ccagcaguuu aucaccuucu uacagagacu ccuugggccu 3540
uugcuggagg ccuacagcuc ugcugccauc uuuguucaca acuucagugg uccuguucca 3600
gaaccugagu aucugcaaaa guugcacaaa uaccuaauaa ccagaacaga aagaaauguu 3660
gcaguauaug guauguuaag ucacuauuua uucuuuuaaa aucuuuuuuu uuuuuuugga 3720
uuucagaaau uugcuaauug uagaaaauug gaaaaaugca aacuuauccu gaccucuaac 3780
accguagagu auuacuauua ucuucuuugg cauguuauau aaguugaaug auacaguuau 3840
acacucuuac aucuggcuuu uuucacguaa cguuauuuuu gagauucaua cauguugcau 3900
auaguuguuc cuuuguucuu guuguguagu guuccauugu auaaauauuu accacauuuu 3960
auucauucug cuguugaugg auauuugggu uguuuucagu ucacagcugc uuugaacagu 4020
guugcuauga gcauauuuga auaugucuuu uggugaauau cugugccccu auauacagca 4080
uguauguggg aacagaauug ccugguugua ggcucugggu auauucggcu uugguagaua 4140
ccaccaaaca guuuccaagg gauuauaccu acuuguacuc ccacaacagu guguguuuca 4200
cuugcugcac aucuuggcca gcgcuccguc uucuuuguuu uaggaggugu gauuggggug 4260
ggaguacuau uuuauacagu uguaguuugg agcugaaacu acuugaauca cuuuuuagag 4320
ccaaaaggaa ucuaaucuaa ucaccucauu uuauaguuga ggaaaauacc ccaggucaca 4380
cugcuaauua augguaauc ucgggaucag aauucuuguu uccuaaccuc gaggccugug 4440
cuuucucugg uuccacugau guacaaucau cuguguacca cuggguagcu uaaagaauau 4500
uuauacacua ucucauuuga uucucacaac aguccuggaa aauggauguu uuagguauuu 4560
cuacuucccu cuguucuccc uauuucucuc ucuacacccu cuuuucuuuc cccuucccuu 4620
ucuuauuuac cucaauauag gacaaaguag guguaagcaa aguagguuua acagcaaguc 4680
aucugagaac ucacagguug ccaguggugg aaguggggcc ccacccuugu cugcugacuu 4740
gcccucauuc ucuuccuagc uccccauacu uucuuacugu ggcugcuggg auugucauga 4800

```
uuuguugagc guaaccauuu gacaggguuu uauucucucu cuucagcuga gagugccaca   4860

uauugucuug ugaagaaugc ugugaaaaug uuuaaggaua uuggggguagg uguccaccau   4920

uuaugguaua aaagcuaucu caacuucugu ucucuuuaga ucuagucugu uugagcuacc   4980

uuuguggugg gguggacccc gagagaagca guuucugcug gcuuaaugau aaaggcauuu   5040

uugggaacgg ggcauguagg augguuuggg cuauguugaa ggugaagccc aucaguguag   5100

auuuauuuga auguucugga auuuuacugg uuucacauuu auucccaagc ugcuauauau   5160

aacugguauc aauauguuuc aaggugcuac agguugaaua ucccuuaucc aaaauguugg   5220

gaccagaaau guuuuggauu ucagauuuuu uugggauuuu ggaauaugug cauuagacuu   5280

acagguugag cgucucuaau ccaaaaccca aaaugcucug augagcaugu cuuuugagca   5340

ucauauugau guucaaaauc uuucagauuu uggaguacuu cagauuuuug auuuugggau   5400

uaggaccaca aucuuggcuc uuaauuauuc cauaugauuu uuaguuacuu ucuuguauuu   5460

uuacaagaau uucuagaagu auccucaggu guccuuuacc uucaugauuc auggggaaug   5520

uaaguucuau agagauacua gcggccuuuu gugagggacu guuugugacu uuauucuaag   5580

ucauuuuaga guauaguuau guugguugaa auuuuagaau auaguuaaug uugguugaac   5640

uccaucaaaa caaaaaaaaa aaaa                                          5664
```

<210> SEQ ID NO 5
<211> LENGTH: 6368
<212> TYPE: RNA
<213> ORGANISM: homo sapien

<400> SEQUENCE: 5

```
gcgccacugc agcuggcauu ggccgggacu ggaagugcgg gcuucugcag cagccgaagc     60

uggagcugcu aggcagcggc uccccuguug uauggacauu cugcacccga aacugauagc    120

ugaguccuga aguuuuaugu uaugaaacag aagaacuuuc aucccagcac augauuuggg    180

aauuacacuu ugugacaugg augaaucugc acugacccuu gguacaauag auguuucuua    240

ucugccacau ucaucagaau acaguguugg ucgauguaag cacacaagug aggaaugggg    300

ugaguguggc uuuagaccca ccaucuucag aucugcaacu uuaaaaugga aagaaagccu    360

aaugagucgg aaaaggccau uuguuggaag auguuguuac uccugcacuc cccagagcug    420

ggacaaauuu uucaacccca guaucccguc uuugggguuug cggaauguua uuuauaucaa    480

ugaaacucac acaagacacc gcggauggcu ugcaagacgc cuuucuuacg uucuuuuuau    540

ucaagagcga gaugugcaua agggcauguu ugccaccaau gugacugaaa augugcugaa    600

cagcaguaga guacaagagg caauugcaga aguggcugcu gaauuaaacc cugaugguuc    660

ugcccagcag caaucaaaag ccguuaacaa agugaaaaag aaagcuaaaa ggauucuuca    720

agaaaugguu gccacugucu caccggcaau gaucagacug acuggguggg ugcugcuaaa    780

acuguucaac agcuucuuuu ggaacauuca aauucacaaa ggucaacuug agaugguuaa    840

agcugcaacu gagacgaauu ugccgcuucu guuucuacca guucauagau cccauauuga    900

cuaucugcug cucacuuuca uucucuucug ccauaacauc aaagcaccau acauugcuuc    960

aggcaauaau cucaacaucc caaucuucag uaccuugauc cauaagcuug ggggcuucuu   1020

cauacgacga aggcucgaug aaacaccaga uggacggaaa gauguucucu auagagcuuu   1080

gcuccauggg cauauaguug aauuacuucg acagcagcaa uucuuggaga ucuuccugga   1140

aggcacacgu ucuaggagug gaaaaaccuc uugugcucgg gcaggacuuu ugucaguugu   1200

gguagauacu cugucuacca augucauccc agacaucuug auaauaccug uuggaaucuc   1260
```

-continued cuaugaucgc auuaucgaag gucacuacaa uggugaacaa cugggcaaac cuaagaagaa 1320
ugagagccug uggaguguag caagaggugu uauuagaaug uuacgaaaaa acuaugguug 1380
uguccgagug gauuuugcac agccauuuuc cuuaaaggaa uauuuagaaa gccaaaguca 1440
gaaaccggug ucugcucuac uuucccugga gcaagcguug uuaccagcua uacuuccuuc 1500
aagacccagu gaugcugcug augaagguag agacacgucc auuaaugagu ccagaaaugc 1560
aacagaugaa ucccuacgaa ggagguugau ugcaaaucug gcugagcaua uucuauucac 1620
ugcuagcaag uccugugcca uuauguccac acacauugug gcuugccugc uccucuacag 1680
acacaggcag ggaauugauc ucuccacauu ggucgaagac uucuuuguga ugaaagagga 1740
aguccuggcu cgugauuuug accuggggau cucaggaaau ucagaagaug uaguaaugca 1800
ugccauacag cugcugggaa auugugucac aaucacccac acuagcagga acgaugaguu 1860
uuuuaucacc cccagcacaa cugucccauc agucuucgaa cucaacuucu acagcaaugg 1920
gguacuucau gucuuuauca uggaggccau cauagcuugc agccuuuaug caguucugaa 1980
caagagggga cugggggguc ccacuagcac cccaccuaac cugaucagcc aggagcagcu 2040
ggugcggaag gcggccagcc ugugcuaccu ucucuccaau gaaggcacca ucucacugcc 2100
uugccagaca uuuuaccaag ucugccauga aacaguagga aaguuuaucc aguauggcau 2160
ucuuacagug gcagagcacg augaccagga agauaucagu ccuagucuug cugagcagca 2220
gugggacaag aagcuuccag aaccuuuguc uuggagaagu gaugaagaag augaagacag 2280
ugacuuuggg gaggaacagc gagauugcua ccugaaggug agccaaucca aggagcacca 2340
gcaguuuauc accuucuuac agagacuccu ugggccuuug cuggaggccu acagcucugc 2400
ugccaucuuu guucacaacu ucaguggucc uguuccagaa ccugaguauc ugcaaaaguu 2460
gcacaaauac cuaauaacca gaacagaaag aaauguugca guauaugcug agagugccac 2520
auauugucuu gugaagaaug cugugaaaau guuuaaggau auuggggguuu ucaaggagac 2580 caaacaaaag agagugucug uuuuagaacu gagcagcacu uuucuaccuc aaugcaaccg 2640
acaaaaacuu cuagaauaua uucugaguuu uguggugcug uagguaacgu guggcacugc 2700
uggcaaauga aggucaugag augaguuccu uguagguacc agcuucuggc ucaagaguug 2760
aaggugccau cgcaggguca ggccugcccu gucccgaagu gaucuccugg aagacaagug 2820
ccuucucccu ccauggaucu gugaucuucc cagcucugca ucaacacagc agccugcaga 2880
uaacacuugg ggggaccuca gccucuauuc gcaacucaua auccguagac uacaagauga 2940
aaucucaaua aauuauuuuu gaguuuauua aagauugaca uuuuaaguac aacuuuuaag 3000
gacuaauuac ugugauggac acagaaaugu agcuguguuc uggaacugaa ucuuacaugg 3060
uauacuuagu gcugcugggu aauuuguugg uauauuaucu gguuaguggu uaaugcuucc 3120
uuuaaaaaua auugagucau ccauucacuc uuuuucaguu uuaucuguca auaguagcua 3180
cauuuuuaau gggagcaccu uuuaucccaa agugcuuuau aaauugagug gacugauaua 3240
uaucacaccc agguaucacu gugcuguccu uugcugucag auuuagaaau guuuuuaaga 3300
gcuaugugaa aacagacaau auuaguuuag gucgggaacu gagauauugu aaucaaauag 3360
uuaacaucag gaaguuaauu uggcuggcaa aauucuaggg aaacuuggcc agaaaacugg 3420
uguugaaggc uuuugcucau auaaacaagu gccauugagu uucaaaugac cagcaaauau 3480
auuuagaacc cuuccuguuu uaugucugua ccucguccac ccccucaggua auaccugccu 3540 cucacaggua cagcuguuuc uuggaaaucc uccaaccaaa uagcaguuuu ccuaacuuga 3600

-continued uuagcuugag cugacagacu guuagaauac aguucucugg ccacagcuga ugagggcuuu 3660
cuguacugca cacagauugu guacugcacc ccaguccagg ugacugguac ccacucgagu 3720
ugugccgugc acaaccuguc caguauaugc augugguggc ccuacugacu gguaaugguu 3780
agaggcauuu auggauuuuu agcuuugagg aaaaaccaug acuuuuaaca aauuuuuaug 3840
gguuauaugc cuaaacccuu augccacaua gugguaaaua auuaugaaaa auggucuguu 3900
cauaauuggu aggugccuuu ugugagcagg gagcauaauu auugguuuau uaugguaauu 3960
auggugauuu uuuaaauauc auguaauguu aaaacguuuu cuaacaguuu acuguugcuu 4020
aucuccaaga uauuauggaa uuaagaauuu uuccagauga guguuacaua gauucuuuga 4080
auuuaguaua aaaguacuga gaauuaaguu uguacuucca uaagcuugga uuuuaaacac 4140
ugauaguauc ucaugaguaa uguguguuuu gggagaggga gggaugcuga uugauauuuc 4200
acauuguaug aaauaccaug uuugaaacuc auagcaauaa ugcuaugcug uugugauccc 4260
ucucaaguuc ugcauuuaaa auauauuuuu ucuuuauagg aauugaugua uaccaugaag 4320
ucauugucag uuguaguagc ucugauguug aaugagauau cauguuuuag cauuccauuu 4380
uacugacuag gguagaagaa cacuuuucuu ggcuacauuu ggaggauacc cagggagucu 4440
ugggguguucc uuaucugggg aagcaaacau uucacuaguc ucuuuuuuuc auccuuuaaa 4500
uuguaaauua aggauuacuc aagcucacca uuauucaaga uugggacucg cuucccaguc 4560
gacacucugc ccugccuguc auugcugcaa agagcugcug cuuugccaac cuaagcaaag 4620
aaaauacggc uucucuugca uuauuuuccc uuuugguugg uuuguuuucu agaaguacgu 4680
ucagaugcuu uggggaaugc aauguaugau uugcuagcuc ucucaccacu uaacucacug 4740
ugaggauaaa uaugcaugcu uuuuguaauu aacuggugcu uugaaaaucu uuuuuaaggg 4800
agaaaaaucu caaccaaagu uaugcucauc cagacaagcu gaccuuugag uuaauuucag 4860
cacaacucau ucuucagugc cucaugacug aaaacaaaaa acaaaaaaac gaaagcaucu 4920
ucacaaugaa gcuuccagau agcaccguuu ugcuaaaaga uacauucuca uuguuuucca 4980
acagugaugg cuuccacaua agguuaaaca aacuaggugc uuguaaauaa uuuauuacag 5040
uuuacucuau cgcauuucug uaacaugaaa ugcaugcccu ucuucagggg aagacugugg 5100
ucaaguuaaa aaaaaaaaac aauauuaaac aacaugaaac ugcagucugu uuuugaaaau 5160
gagaaugucc uaagugauuc agaagagagg agggaaguug ugcacucuga aaaugcauga 5220
aaaacaaagg caaaaacuag ugggaaaugu guagaacugu uaacugagau ggcuucgagu 5280
cuuccuucug gaaucuguua aauuucacaa agucaugagg guaaauggag aaaauauuuc 5340
ugggauuaca augaauguaa gcccaaauug uggaauugcc aguaaccugg auggggaaaa 5400
gcauuuccca uagcacucca uguaauauga gugcucugug agauguucau caguguuuua 5460
uagaaauggu guugcuggga aaccaaguuu gcaccuggaa acuuacaaug cacuuuagcg 5520
caguaagggc uuggcauccg guagugaaaa acugucuaac ccagcauugc ccaaacuauu 5580
uugacaccag gaccuuuuuc uccuuuggga uacuuaugaa ccucucacua auguccugug 5640
gagaacauuu ugggaaacac uauguuagau aguucuuuaa ggagacaaaa cgguaaugaa 5700
cagauagcac uggggcagaa uaugcaugca uuuuguaacg uccagugugg cguugaauag 5760
auguguauuu ccucccccugc agaaaauaag cacagaaaau uauaauguag gugaucggag 5820
cucuuuccuu ugauagagag aacagcccca augauccugg cuuuuucacu gaacguauca 5880
gaauacaugg augaauuggg guaaauaagg uuuuaauuca gaucuagaag aaaguauugu 5940
acguuugaau gcagauuuuu auccacagau aguuguagug uuuagacaug acaggaccua 6000
ucguugaggu uucuaagacu uacuaugggc uguaaaccug uuuuuuaaaa cuauuuuaga 6060
aaccugagac uugccgucug gcauuuuagu uuaauacaaa cuaaugauug cauuugaaag 6120
agauucuuga ccuuauuucu aaacgucuag agcucugaaa ugucuugaug gaagguauua 6180
aacuauuugc cuguuguaca aagaaauguu aagacucgug aaaagaauua cuauaaggua 6240
cugugaaaua acugcgauuu ugugagcaaa acauacuugg aaaugcugau ugauuuuuau 6300
gcuuguuagu guauugcaag aaacacagaa aauguaguuu uguuuuaaua aaccaaaaau 6360
ugaacaua 6368

<210> SEQ ID NO 6
<211> LENGTH: 4918
<212> TYPE: RNA
<213> ORGANISM: homo sapien

<400> SEQUENCE: 6
ggccacugca gcuggcauug gccgggacug gaagugcggg cuucugcagc agccgaagcu 60
ggagcugcua gggcagcagc ggcuccccug uuguauggac auucugcacc cgaaacugau 120
agcugagucc ugaaguuuua uguuaugaaa cagaagaacu uucaucccag cacaugauuu 180
gggaauuaca cuuugugaca uggaugaauc ugcacugacc cuugguacaa uagauguuuc 240
uuaucugcca cauucaucag aauacagugu uggucgaugu aagcacacaa gugaggaaug 300
gggugagugu ggcuuuagac ccaccaucuu cagaucugca acuuuaaaau ggaaagaaag 360
ccuaaugagu cggaaaaggc cauuuguugg aagauguugu uacuccugca cuccccagag 420
cugggacaaa uuuuucaacc ccaguauccc gucuuugggu uugcggaaug uuauuuauau 480
caaugaaacu cacacaagac accgcggaug gcuugcaaga cgccuuucuu acguucuuuu 540
uauucaagag cgagaugugc auaagggcau guuugccacc aaugugacug aaaaugugcu 600
gaacagcagu agaguacaag aggcaauugc agaaguggcu gcugaauuaa acccugaugg 660
uucugcccag cagcaaucaa aagccguuaa caaagugaaa aagaaagcua aaaggauucu 720
ucaagaaaug guugccacug ucucaccggc aaugaucaga cugacugggu gggugcugcu 780
aaaacuguuc aacagcuucu uuuggaacuu ucaaauucac aaaggucaac uugagauggu 840
uaaagcugca acugagacga auuugccgcu ucuguuucua ccaguucaua gaucccauau 900
ugacuaucug cugcucacuu ucauucucuu cugccauaac aucaaagcac cauacauugc 960
uucaggcaau aaucucaaca ucccaaucuu caguaccuug auccauaagc uuggggggcuu 1020 cuucauacga cgaaggcucg augaaacacc agauggacgg aaagauguuc ucuauagagc 1080
uuugcuccau gggcauauag uugaauuacu ucgacagcag caauucuugg agaucuuccu 1140
ggaaggcaca cguucuagga guggaaaaac cucuugugcu cgggcaggac uuuugucagu 1200
ugugguagau acucugucua ccaaugucau cccagacauc uugauaauac cuguuggaau 1260
cuccuaugau cgcauuaucg aaggucacua caauggugaa caacugggca aaccuaagaa 1320
gaaugagagc cuguggagug uagcaagagg uguuauuaga auguuacgaa aaaacuaugg 1380
uuguguccga guggauuuug cacagccauu uuccuuaaag gaauauuuag aaagccaaag 1440
ucagaaaccg gugucugcuc uacuuucccu ggagcaagcg uuguuaccag cuauacuucc 1500
uucaagaccc agugaugcug cugaugaagg uagagacacg uccauuaaug aguccagaaa 1560
ugcaacagau gaaucccuac gaaggagguu gauugcaaau cuggcugagc auauucuauu 1620
cacugcuagc aaguccugug ccauuauguc cacacacauu guggcuugcc ugcuccucua 1680

-continued

```
cagacacagg cagggaauug aucucuccac auuggucgaa gacuucuuug ugaugaaaga   1740
ggaaguccug gcucgugauu uugaccuggg guucucagga aauucagaag auguaguaau   1800
gcaugccaua cagcugcugg gaaauugugu cacaaucacc cacacuagca ggaacgauga   1860
guuuuuuauc acccccagca caacuguccc aucagucuuc gaacucaacu ucuacagcaa   1920
uggggguacuu caugucuuua ucauggaggc caucauagcu ugcagccuuu augcaguucu   1980
gaacaagagg ggacuggggg gucccacuag caccccaccu aaccugauca gccaggagca   2040
gcuggugcgg aaggcggcca gccugugcua ccuucucucc aaugaaggca ccaucucacu   2100
gccuugccag acauuuuacc aagucugcca ugaaacagua ggaaaguuua uccgguaugg   2160
cauucuuaca guggcagagc acgaugacca ggaagauauc aguccuaguc uugcugagca   2220
gcagugggac aagaagcuuc cagaaccuuu gucuuggaga agugaugaag aagaugaaga   2280
cagugacuuu ggggaggaac agcgagauug cuaccugaag gugagccaau ccaaggagca   2340
ccagcaguuu aucaccuucu uacagagacu ccuugggccu uugcuggagg ccuacagcuc   2400
ugcugccauc uuuguucaca acuucagugg uccuguucca gaaccugagu aucugcaaaa   2460
guugcacaaa uaccuaauaa ccagaacaga aagaaauguu gcaguauaug cugagagugc   2520
cacauauugu cuugugaaga augcugugaa aauguuuaag gauauugggg uuuucaagga   2580
gaccaaacaa aagagagugu cuguuuuaga acugagcagc acuuuucuac cucaaugcaa   2640
ccgacaaaaa cuucuagaau auauucugag uuuuguggug cuguagguaa cguguggcac   2700
ugcuggcaaa ugaaggucau gagaugaguu ccuuguaggu accagcuucu ggcucaagag   2760
uugaaggugc caucgcaggg ucaggccugc ccugucccga agugaucucc uggaagacaa   2820
gugccuucuc ccuccaugga ucugugaucu ucccagcucu gcaucaacac agcagccugc   2880
agauaacacu ugggggggacc ucagccucua uucgcaacuc auaauccgua gacuacaaga   2940
ugaaaucuca auaaaauauu uuugaguuua uuaaagauug acauuuuaag uacaacuuuu   3000
aaggacuaau uacugugaug gacacagaaa uguagcugug uucuggaacu gaaucuuaca   3060
ugguauacuu agugcugcug gguaauuugu ugguauauua ucugguuagu gguuaaugcu   3120
uccuuuaaaa auaaauugagu cauccauuca cucuuuuuca guuuuaucug ucaauaguag   3180
cuacauuuuu aaugggagca ccuuuuaucc caaagugcuu uauaaauuga guggacugau   3240
auauaucaca cccagguauc acugugcugu ccuuugcugu cagauuuaga aauguuuuua   3300
agagcuaugu gaaaacagac aauauuaguu uaggucggga acugagauau uguaaucaaa   3360
uaguuaacau caggaaguua auuuggcugg caaaauucua gggaaacuug gccagaaaac   3420
uggguguugaa ggcuuuugcu cauauaaaca agugccauug aguuucaaau gaccagcaaa   3480
uauauuuaga acccuuccug uuuuaugucu guaccucguc caccccucag guaauaccug   3540
ccucucacag guacagcugu uucuuggaaa ucccuccaacc aaauagcagu uuuccuaacu   3600
ugauuagcuu gagcugacag acuguuagaa uacaguucuc uggccacagc ugaugagggc   3660
uuucuguacu gcacacagau uguguacugc accccagucc aggugacugg uacccacucg   3720
aguugugccg ugcacaaccu guccaguaua ugcauguggu ggcccuacug acugguaaug   3780
guuagaggca uuuauggauu uuuagcuuug aggaaaaacc augacuuuua acaaauuuuu   3840
auggguuaua ugccuaaacc cuuaugccac auagugguaa auaauuauga aaaauggucu   3900
guucauaauu gguaggugcc uuuugugagc agggagcaua auuauugguu uauuauggua   3960
auuaugguga uuuuuuaaau aucauguaau guuaaaacgu uuucuaacag uuuacuguug   4020
cuuaucucca agauauuaug gaauuaagaa uuuuuccaga ugaguguuac auagauucuu   4080
```

ugaauuuagu auaaaaguac ugagaauuaa guuuguacuu ccauaagcuu ggauuuuaaa 4140
cacugauagu aucucaugag uaaugugugu uuugggagag ggagggaugc ugauugauau 4200
uucacauugu augaaauacc auguuugaaa cucauagcaa uaaugcuaug cuguugugau 4260
cccucccaag uucugcauuu aaaauauauu uuuucuuuau aggaauugau guauaccaug 4320
aagucauugu caguuguagu agcucugaug uugaaugaga uaucauguuu uagcauucca 4380
uuuuacugac uaggguagaa gaacacucuu cuuggcuaca uuuggaggau acccagggag 4440
ucuugggugu uccuuaucug gggaagcaaa cauuucacua gucucuuuuu uucauccuuu 4500
aaauuguaaa uuaaggauua cucaagcuca ccauuauuca agauugggac ucgcuuccca 4560
gucgacacuc ugcccugccu gucauugcug caaagagcug cugcuuugcc aaccuaagca 4620
aagaaaauac ggcuucucuu gcauuauuuu cccuuuuggu ugguuuguuu ucuagaagua 4680
cguucagaug cuuuggggaa ugcaauguau gauuugcuag cucucucacc acuuaacuca 4740
cugugaggau aaauaugcau gcuuuuugua auuaacuggu gcuuugaaaa ucuuuuuuaa 4800
gggagaaaaa ucucaaccaa aguuaugcuc auccagacaa gcugaccuuu gaguuaauuu 4860
cagcacaacu cauucuucag ugccucauga cugaaaacaa aaaaaaaaaa aaaaaaa 4918

<210> SEQ ID NO 7
<211> LENGTH: 3490
<212> TYPE: RNA
<213> ORGANISM: homo sapien

<400> SEQUENCE: 7
agcgggcugg aagugcgggc uucugcagca gccgaagcug gagcugcuag ggcagcagcg 60
gcuccccugu uguauggaca uucugcaccc gaaacugaua gcugaguccu gaaguuuuau 120
guuaugaaac agaagaacuu ucaucccagc acaugauuug ggaauuacac uuugugacau 180
ggaugaauau gcacugaccc uugguacaau agauguuucu uaucugccac auucaucaga 240
auacaguguu ggucgaugua agcacacaag ugaggaaugg ggugagugug gcuuuagacc 300
caccaucuuc agaucugcaa cuuuaaaaug gaaagaaagc cuaaugaguc ggaaaaggcc 360
auuuguugga agauguuguu acuccugcac uccccagagc ugggacaaau uuuucaacac 420
caguaucccg ucuuuggguu ugcggaaugu uauuuauauc aaugaaacuc acacaagaca 480
ccgcggaugg cuugcaagac gccuuucuua cguucuuuuu auucaagagc gagaugugca 540
uaagggcaug uuugccacca augugacuga aaaugugcug aacagcagua gaguacaaga 600
ggcaauugca gaaguggcug cugaauuaaa cccugauggu ucugcccagc agcaaucaaa 660
agccguuaac aaagugaaaa agaaagcuaa aaggauucuu caagaaaugg uugccacugu 720
cucaccggca augaucagac ugacugggug ggugcugcua aaacuguuca acagcuucuu 780
uuggaacauu caaauucaca aaggucaacu ugagauggu aaagcugcaa cugagacgaa 840
uuugccgcuu cuguuucuac caguucauag aucccauauu gacuaucugc ugcucacuuu 900
cauucucuuc ugccauaaca ucaaagcacc auacauugcu ucaggcaaua aucucaacau 960
cccaaucuuc aguaccuuga uccauaagcu ugggggcuuc uucauacgac gaaggcucga 1020
ugaaacacca gauggacgga aagauguucu cuauagagcu uugcuccaug ggcauauagu 1080
ugaauuacuu cgacagcagc aauucuugga gaucuuccug gaaggcacac guucuaggag 1140
uggaaaaacc ucuugugcuc gggcaggacu uuugucaguu gugguagaua cucugucuac 1200
caaugucauc ccagacaucu ugauaauacc uguuggaauc uccuaugauc gcauuaucga 1260

-continued

```
aggucacuac aauggugaac aacugggcaa accuaagaag aaugagagcc uguggagugu   1320
agcaagaggu guuauuagaa uguuacgaaa aaacuauggu uguguccgag uggauuuugc   1380
acagccauuu uccuuaaagg aauauuuaga aagccaaagu cagaaaccgg ugucugcucu   1440
acuuucccug gagcaagcgu uguuaccagc uauacuuccu ucaagaccca gugaugcugc   1500
ugaugaaggu agagacacgu ccauuaauga guccagaaau gcaacagaug aaucccuacg   1560
aaggagguug auugcaaauc uggcugagca uauucuauuc acugcuagca aguccugugc   1620
cauuaugucc acacacauug uggcuugccu gcuccucuac agacacaggc agggaauuga   1680
ucucuccaca uuggucgaag acuucuuugu gaugaaagag gaaguccugg cucgugauuu   1740
ugaccugggg uucucaggaa auucagaaga uguaguaaug caugccauac agcugcuggg   1800
aaauuguguc acaaucaccc acacuagcag gaacgaugag uuuuuuauca cccccagcac   1860
aacuguccca ucagucuucg aacucaacuu cuacagcaau gggguacuuc augucuuuau   1920
cauggaggcc aucauagcuu gcagccuuua ugcaguucug aacaagaggg gacugggggg   1980
ucccacuagc accccaccua accugaucag ccaggagcag cuggugcgga aggcggccag   2040
ccugugcuac cuucucucca augaaggcac caucucacug ccuugccaga cauuuuacca   2100
agucugccau gaaacaguag gaaaguuuau ccaguauggc auucuuacag uggcagagca   2160
cgaugaccag gaagauauca guccuagucu ugcugagcag caguggggaca agaagcuucc   2220
agaaccuuug ucuuggagaa gugaugaaga agaugaagac agugacuuug gggaggaaca   2280
gcgagauugc uaccugaagg ugagccaauc caaggagcac cagcaguuua ucaccuucuu   2340
acagagacuc cuugggccuu ugcuggaggc cuacagcucu gcugccaucu uuguucacaa   2400
cuucagugguu ccuguuccag aaccugagua ucugcaaaag uugcacaaau accuaauaac   2460
cagaacagaa agaaauguug caguauaugc ugagagugcc acauauuguc uugugaagaa   2520
ugcugugaaa auguuuaagg auauuggggu uuucaaggag accaaacaaa agagagguguc   2580
uguuuuagaa cugagcagca cuuuucuacc ucaaugcaac cgacaaaaac uucuagaaua   2640
uauucugagu uuuguggugc uguagguaac guguggcacu gcuggcaaau gaaggucaug   2700
agaugaguuc cuuguaggua caagcuucug gcucaagagu ugaaggugcc aucgcagggu   2760
caggccugcc cugucccgaa gugaucuccu ggaagacaag ugccuucucc auccauggau   2820
cugugaucuu cccagcucug caucaacaca gcagccugca gauaacacuu gggggggaccu   2880
cagccucuau ucgcaacuca uaauccguag acuacaagau gaaaucucaa uaaauuauuu   2940
uugaguuuau uaaagauuga cauuuuaagu acaacuuuua aggacuaauu acugugaugg   3000
acacagaaau guagcugugu ucuggaacug aaucuuacau gguauacuua gugcugcugg   3060
guaauuuguu gguauauuau cugguuagug guuaaugcuu ccuuuaaaaa uaauugaguc   3120
auccauucac ucuuuuucag uuuuaucugu caauaguagc uacauuuuua augggagcac   3180
cuuuuauccc aaagugcuuu auaaauugag uggacugaua uauaucacac ccagguauca   3240
cugugcuguc cuuugcuguc agauuuagaa auguuuuuaa gagcuaugug aaaacagaca   3300
auauuaguuu aggucgggaa cugagauauu guaaucaaau aguuaacauc aggaaguuaa   3360
uuuggcuggc aaaauucuag ggaaacuugg ccagaaaacu ggguguugaag gcuuuugcuc   3420
auauaaacaa gugccauuga guuucaaaug accagcaaau auauuuagaa cucaaaaaaa   3480
aaaaaaaaaa                                                          3490
```

<210> SEQ ID NO 8
<211> LENGTH: 2855

-continued

<212> TYPE: RNA
<213> ORGANISM: homo sapien

<400> SEQUENCE: 8
aacuuucauc ccagcacaug auuugggaau uacacuuugu gacauggaug aaucugcacu 60
gacccuuggu acaauagaug uuucuuaucu gccacauuca ucagaauaca guguuggucg 120
auguaagcac acaagugagg aaugggguga guguggcuuu agacccacca ucuucagauc 180
ugcaacuuua aaauggaaag aaagccuaau gagucggaaa aggccauuug uuggaagaug 240
uuguuacucc ugcacucccc agagcuggga caaauuuuuc aaccccagua ucccgucuuu 300
ggguuugcgg aauguuauuu auaucaauga aacucacaca agacaccgcg gauggcuugc 360
aagacgccuu ucuuacguuc uuuuuauuca agagcgagau gugcauaagg gcauguuugc 420
caccaaugug acugaaaaug ugcugaacag caguagagua caagaggcaa uugcagaagu 480
ggcugcugaa uuaaacccug augguucugc ccagcagcaa ucaaaagccg uuaacaaagu 540
gaaaaagaaa gcuaaaagga uucuucaaga aaugguugcc acugucucac cggcaaugau 600
cagacugacu gggugggugc ugcuaaaacu guucaacagc uucuuuugga acauucaaau 660
ucacaaaggu caacuugaga ugguuaaagc ugcaacugag acgaauuugc cgcuucuguu 720
ucuaccaguu cauagauccc auauugacua ucugcugcuc acuuucauuc ucuucugcca 780
uaacaucaaa gcaccauaca uugcuucagg caauaaaucuc aacaucccaa ucuucaguac 840
cuugauccau aagcuugggg gcuucuucau acgacgaagg cucgaugaaa caccagaugg 900
acggaaagau guucucuaua gagcuuugcu ccaugggcau auaguugaau uacuucgaca 960
gcagcaauuc uuggagaucu uccuggaagg cacacguucu aggaguggaa aaaccucuug 1020
ugcucgggca ggacuuuugu caguuguggu agauacucug ucuaccaaug ucaucccaga 1080
caucuugaua auaccuguug gaaucuccua ugaucgcauu aucgaaggucc acuacaaugg 1140 ugaacaacug ggcaaaccua agaagaauga gagccugugg aguguagcaa gagguguuac 1200
uagaauguua cgaaaaaacu augguugugu ccgaguggau uuugcacagc cauuuuccuu 1260
aaaggaauau uuagaaagcc aaagucagaa accggugucu gcucuacuuu cccuggagca 1320
agcguuguua ccagcuauac uuccuucaag acccagugau gcugcugaug aagguagaga 1380
cacguccauu aaugagucca gaaaugcaac agaugaaucc cuacgaagga gguugauugc 1440
aaaucuggcu gagcauauuc uauucacugc uagcaagucc ugugccauua uguccacaca 1500
cauuguggcu ugccugcucc ucuacagaca caggcaggga auugaucucu ccacauuggu 1560
cgaagacuuc uuugugauga aagaggaagu ccuggcucgu gauuuugacc uggggguucuc 1620 aggaaauuca gaagauguag uaaugcaugc cauacagcug cugggaaauu gugucacaau 1680
cacccacacu agcaggaacg augaguuuuu uaucaccccc agcacaacug ucccaucagu 1740
cuucgaacuc aacuucuaca gcaaugggu acuucauguc uuuaucaugg aggccaucau 1800
agcuugcagc cuuuaugcag uucugaacaa gaggggacug gggggucca cuagcacccc 1860 accuaaccug aucagccagg agcagcuggu gcggaaggcg gccagccugu gcuaccuucu 1920
cuccaaugaa ggcaccaucu cacugccuug ccagacauuu uaccaagucu gccaugaaac 1980
aguaggaaag uuuauccagu auggcauucu uacaguggca gagcacgaug accaggaaga 2040
uaucaguccu agucuugcug agcagcagug ggacaagaag cuuccugaac cuuugucuug 2100
gagaagugau gaagaagaug aagacaguga cuuuggggag gaacagcgag auugcuaccu 2160
gaaggugagc caauccaagg agcaccagca guuuaucacc uucuuacaga gacuccuugg 2220

```
gccuuugcug gaggccuaca gcucugcugc caucuuuguu cacaacuuca gugguccugu   2280
uccagaaccu gaguaucugc aaaaguugca caaauaccua auaaccagaa cagaaagaaa   2340
uguugcagua uaugcugaga gugccacaua uugucuugug aagaaugcug ugaaaauguu   2400
uaaggauauu gggguuuuca aggagaccaa acaaaagaga gugucuguuu uagaacugag   2460
cagcacuuuu cuaccucaau gcaaccgaca aaaacuucua gaauauauuc ugaguuuugu   2520
ggugcuguag guaacgugug gcacugcugg caaaugaagg ucaugagaug aguuccuugu   2580
agguaccagc uucuggcuca agaguugaag gugccgucgc agggucaggc cugcccuguc   2640
ccgaggugau cuccuggaag acaagugccu ucucccucca uggaucugug aucuucccag   2700
cucugcauca acacagcagc cugcagauaa cacuuggggg gaccucagcc ucuauucgca   2760
acucauaauc cguagacuac aagaugaaau cucaauaaau uauuuuugag uuuauuaaag   2820
aggucuuuua aggcaaaaaa aaaaaaaaaa aaaaa                              2855
```

<210> SEQ ID NO 9
<211> LENGTH: 6372
<212> TYPE: RNA
<213> ORGANISM: homo sapien

<400> SEQUENCE: 9

```
gcgccacugc agcuggcauu ggccgggacu ggaagugcgg gcuucugcag cagccgaagc     60
uggagcugcu agggcagcag cggcuccccu guuguaugga cauucugcac ccgaaacuga    120
uagcugaguc cugaaguuuu auguuaugaa acagaagaac uuucauccca gcacaugauu    180
ugggaauuac acuuugugac auggaugaau cugcacugac ccuugguaca auagauguuu    240
cuuaucugcc acauucauca gaauacagug uuggucgaug uaagcacaca agugaggaau    300
ggggugagug uggcuuuaga cccaccgucu ucagaucugc aacuuuaaaa uggaaagaaa    360
gccuaaugag ucggaaaagg ccauuuguug gaagauguug uuacuccugc acuccccaga    420
gcugggacaa auuuuucaac cccaguaucc cgucuuuggg uuugcggaau guuauuuaua    480
ucaaugaaac ucacacaaga caccgcggau ggcuugcaag acgccuuucu uacguucuuu    540
uuauucaaga gcgagaugug cauaagggca uguuugccac caaugugacu gaaaaugugc    600
ugaacagcag uagaguacaa gaggcaauug cagaaguggc ugcugaauua aacccugaug    660
guucugccca gcagcaauca aaagccguua acaaagugaa aaagaaagcu aaaaggauuc    720
uucaagaaau gguugccacu gucucaccgg caaugaucag acugacuggg ugggugcugc    780
uaaaacuguu caacagcuuc uuuuggaaca uucaaauuca caaaggucaa cuugagaugg    840
uuaaagcugc aacugagacg aauuugccgc uucuguuucu accaguucau agaucccaua    900
uugacuaucu gcugcucacu uucauucucu ucugccauaa caucaaagca ccauacauug    960
cuucaggcaa uaaucucaac aucccaaucu ucaguaccuu gauccauaag cuugggggcu   1020
ucuucauacg acgaaggcuc gaugaaacac cagauggacg gaaagauguu cucuauagag   1080
cuuugcucca ugggcauaua guugaauuac uucgacagca gcaauucuug gagaucuucc   1140
uggaaggcac acguucuagg aguggaaaaa ccucuugugc ucgggcagga cuuuugucag   1200
uugugguaga uacucugucu accaauguca ucccagacau cuugauaaua ccuguuggaa   1260
ucuccuauga ucgcauuauc gaaggucacu acaaugguga acaacugggc aaaccuaaga   1320
agaaugagag ccuguggagu guagcaagag guguuauuag aauguuacga aaaaacuaug   1380
guuguguccg aguggauuuu gcacagccau uuuccuuaaa ggaauauuua gaaagccaaa   1440
gucagaaacc ggugucugcu cuacuuuccc uggagcaagc guuguuacca gcuauacuuc   1500
```

-continued

```
cuucaagacc cagugaugcu gcugaugaag guagagacac guccauuaau gaguccagaa   1560
augcaacaga ugaaucccua cgaaggaggu ugauugcaaa ucuggcugag cauauucuau   1620
ucacugcuag caaguccugu gccauuaugu ccacacacau uguggcuugc cugcuccucu   1680
acagacacag gcagggaauu gaucucucca cauuggucga agacuucuuu gugaugaaag   1740
aggaagaccu ggcucgugau uuugaccugg gguucucagg aaauucagaa gauguaguaa   1800
ugcaugccau acagcugcug ggaaauugug ucacaaucac ccacacuagc aggaacgaug   1860
aguuuuuuau cacccccagc acaacugucc caucagucuu cgaacucaac uucuacagca   1920
auggggguacu ucaugucuuu aucauggagg ccaucauagc uugcagccuu uaugcaguuc   1980
ugaacaagag gggacugggg ggucccacua gcacccccacc uaaccugauc agccaggagc   2040
agcuggugcg gaaggcggcc agccugugcu accuucucuc caaugaaggc accaucucac   2100
ugccuugcca gacauuuuac caagucugcc augaaacagu aggaaaguuu auccaguaug   2160
gcauucuuac aguggcagag cacgaugacc aggaagauau caguccuagu cuugcugagc   2220
agcaguggga caagaagcuu ccagaaccuu ugucuuggag aagugaugaa gaagaugaag   2280
acagugacuu uggggaggaa cagcgagauu gcuaccugaa ggugagccaa uccaaggagc   2340
accagcaguu uaucaccuuc uuacagagac uccuugggcc uuugcuggag gccuacagcu   2400
cugcugccau cuuuguucac aacuucagug guccuguucc agaaccugag uaucugcaaa   2460
aguugcacaa auaccuaaua accagaacag aaagaaaugu ugcaguauau gcugagagug   2520
ccacauauug ucuugugaag aaugcuguga aaauguuuaa ggauauuggg guuuucaagg   2580
agaccaaaca aaagagagug ucuguuuuag aacugagcag cacuuuucua ccucaaugca   2640
accgacaaaa acuucuagaa uauauucuga guuuuguggu gcuguaggua acguguggca   2700
cugcuggcaa augaagguca ugagaugagu uccuuguagg uaccagcuuc uggcucaaga   2760
guugaaggug ccaucgcagg gucaggccug cccugucccg aagugaucuc cuggaagaca   2820
agugccuucu cccuccaugg aucugugauc uucccagcuc ugcaucaaca cagcagccug   2880
cagauaacac uugggggggac cucagccucu auucgcaacu cauaauccgu agacuacaag   2940
augaaaucuc aauaaaauau uuuugaguuu auuaaagauu gacauuuuaa guacaacuuu   3000
uaaggacuaa uuacugugau ggacacagaa auguagcugu guucuggaac ugaaucuuac   3060
augguauacu uagugcugcu ggguaauuug uugguauauu aucugguuag ugguuaaugc   3120
uuccuuuaaa aauaauugag ucauccauuc acucuuuuuc aguuuuaucu gucaauagua   3180
gcuacauuuu uaaugggagc accuuuuauc ccaaagugcu uuauaaauug aguggacuga   3240
uauauaucac acccagguau cacugugcug uccuuugcug ucagauuuag aaauguuuuu   3300
aagagcuaug ugaaaacaga caauauuagu uuaggucggg aacugagaua uuguaaucaa   3360
auaguuaaca ucaggaaguu aauuuggcug gcaaaauucu agggaaacuu ggccagaaaa   3420
cuggguguuga aggcuuuugc ucauauaaac aagugccauu gaguuucaaa ugaccagcaa   3480
auauauuuag aacccuuccu guuuuauguc uguaccucgu ccacccccuca gguaauaccu   3540
gccucucaca gguacagcug uuucuuggaa auccuccaac caaauagcag uuuuccuaac   3600
uugauuagcu ugagcugaca gacuguuaga auacaguucu cuggccacag cugaugaggg   3660
cuuucuguac ugcacacaga uuguguacug caccccaguc caggugacug guacccacuc   3720
gaguugugcc gugcacaacc uguccaguau augcaugugg uggcccuacu gacugguaau   3780
gguuagaggc auuuauggau uuuuagcuuu gaggaaaaac caugacuuuu aacaaauuuu   3840
```

-continued

```
uaugggguuau augccuaaac ccuuaugcca cauaguggua aauaauuaug aaaaaugguc   3900
uguucauaau ugguaggugc cuuuugugag cagggagcau aauuauuggu uuauuauggu   3960
aauuauggug auuuuuuaaa uaucauguaa uguuaaaacg uuuucuaaca guuuacuguu   4020
gcuuaucucc aagauauuau ggaauuaaga auuuuuccag augaguguua cauagauucu   4080
uugaauuuag uauaaaagua cugagaauua aguuuguacu uccauaagcu uggauuuuaa   4140
acacugauag uaucucauga guaaugugug uuuugggaga gggagggaug cugauugaua   4200
uuucacauug uaugaaauac cauguuugaa acucauagca auaaaugcuau gcuguuguga   4260
ucccucucaa guucugcauu uaaaauauau uuuuucuuua uaggaauuga uguauaccau   4320
gaagucauug ucaguuguag uagcucugau guugaaugag auaucauguu uuagcauucc   4380
auuuuacuga cuaggguaga agaacacuuu ucuuggcuac auuuggagga uacccaggga   4440
gucuugggug uuccuuaucu ggggaagcaa acauuucacu agucucuuuu uuucauccuu   4500
uaaauuguaa auuaaggauu acucaagcuc accauuauuc aagauuggga cucgcuuccc   4560
agucgacacu cugcccugcc ugucauugcu gcaaagagcu gcugcuuugc caaccuaagc   4620
aaagaaaaua cggcuucucu ugcauuauuu ucccuuuugg uugguuuguu uucuagaagu   4680
acguucagau gcuuugggga augcaaugua ugauuugcua gcucucucac cacuuaacuc   4740
acugugagga uaaauaugca ugcuuuuugu aauuaacugg ugcuuugaaa aucuuuuuua   4800
agggagaaaa aucucaacca aaguuaugcu cauccagaca agcugaccuu ugaguuaauu   4860
ucagcacaac ucauucuuca gugccucaug acugaaaaca aaaaacaaaa aaacgaaagc   4920
aucuucacaa ugaagcuucc agauagcacc guuuugcuaa aagauacauu cucauuguuu   4980
uccaacagug auggcuucca cauaagguua aacaaacuag gugcuuguaa auaauuuauu   5040
acaguuuacu cuaucgcauu ucuguaacau gaaaugcaug cccuucuuca ggggaagacu   5100
guggucaagu uaaaaaaaaa aaacaauauu aaacaacaug aaacugcagu cuguuuuuga   5160
aaaugagaau guccuaagug auucagaaga gaggagggaa guugugcacu cugaaaaugc   5220
augaaaaaca aaggcaaaaa cuagugggaa auguguagaa cuguuaacug agauggcuuc   5280
gagucuuccu ucuggaaucu guuaaauuuc acaaagucau gaggguaaau ggagaaaaua   5340
uuucugggau uacaaugaau guaagcccaa auuguggaau ugccaguaac cuggaugggg   5400
aaaagcauuu cccauagcac uccauguaau augagugcuc ugugagaugu ucaucagugu   5460
uuuauagaaa ugguguugcu gggaaaccaa guuugcaccu ggaaacuuac aaugcacuuu   5520
agcgcaguaa gggcuuggca uccgguagug aaaaacuguc uaacccagca uugcccaaac   5580
uauuuugaca ccaggaccuu uuucuccuuu gggauacuua ugaaccucuc acuaaugucc   5640
uguggagaac auuuugggaa acacuauguu agauaguucu uuaaggagac aaaacgguaa   5700
ugaacagaua gcacuggggc agaauaugca ugcauuuugu aacguccagu guggcguuga   5760
auagaugugu auuuccuccc cugcagaaaa uaagcacaga aaauuauaau guaggugauc   5820
ggagcucuuu ccuuugauag agagaacagc cccaaugauc cuggcuuuuu cacugaacgu   5880
aucagaauac auggaugaau uggggguaaau aagguuuuaa uucagaucua gaagaaagua   5940
uuguacguuu gaaugcagau uuuuauccac agauaguugu aguguuuaga caugacagga   6000
ccuaucguug agguuucuaa gacuuacuau gggcuguaaa ccuguuuuuu aaaacuauuu   6060
uagaaaccug agacuugccg ucuggcauuu uaguuuaaua caaacuaaug auugcauuug   6120
aaagagauuc uugaccuuau uucuaaacgu cuagagcucu gaaaugucuu gauggaaggu   6180
auuaaacuau uugccuguug uacaaagaaa uguuaagacu cgugaaaaga auuacuauaa   6240
```

gguacuguga aauaacugcg auuuugugag caaaacauac uuggaaaugc ugauugauuu 6300
uuaugcuugu uaguguauug caagaaacac agaaaaugua guuuuguuuu aauaaaccaa 6360
aaauugaaca ua 6372

<210> SEQ ID NO 10
<211> LENGTH: 5664
<212> TYPE: RNA
<213> ORGANISM: homo sapien

<400> SEQUENCE: 10
gaagcuggag cugcuagggu gcgaacugcc agggcaggca gcagcggcuc cccuguugua 60
uggacauucu gcacccgaaa cugauagcug aguccugaag uuuuauguua ugaaacagaa 120
gaacuuucau cccagcacau gauuugggaa uuacacuuug ugacauggau gaaucugcac 180
ugacccuugg uacaauagau guuucuuauc ugccacauuc aucagaauac aguguugguc 240
gauguaagca cacaagugag gaaugggug aguguggcuu uagacccacc gucuucagau 300
cugcaacuuu aaaauggaaa gaaagccuaa ugagucggaa aaggccauuu guuggaagau 360
guuguuacuc cugcacuccc cagagcuggg acaaauuuuu caaccccagu aucccgucuu 420
uggguuugcg gaauguuauu uauaucaaug aaacucacac aagacaccgc ggauggcuug 480
caagacgccu uucuuacguu cuuuuuauuc aagagcgaga ugugcauaag ggcauguuug 540
ccaccaaugu gacugaaaau gugcugaaca gcaguagagu acaagaggca auugcagaag 600
uggcugcuga auuaaacccu gaugguucug cccagcagca aucaaaagcc guuaacaaag 660
ugaaaaagaa agcuaaaagg auucuucaag aaaugguugc cacugucuca ccggcaauga 720
ucagacugac uggguggguG cugcuaaaac uguucaacag cuucuuuugg aacauucaaa 780
uucacaaagg ucaacuugag augguuaaag cugcaacuga gacgaauuug ccgcuucugu 840
uucuaccagu ucauagaucc cauauugacu aucugcugcu cacuuucauu cucuucugcc 900
auaacaucaa agcaccauac auugcuucag gcaauaaucu caacauccca aucuucagua 960
ccuugaucca uaagcuuggg ggcuucuuca uacgacgaag gcucgaugaa acaccagaug 1020
gacggaaaga uguucucuau agagcuuugc uccaugggca uauaguugaa uuacuucgac 1080
agcagcaauu cuuggagauc uuccuggaag gcacacguuc uaggagugga aaaaccucuu 1140
gugcucgggc aggacuuuug ucaguugugg uagauacucu gucuaccaau gucaucccag 1200
acaucuugau aauaccuguu ggaaucuccu augaucgcau uaucgaaggu cacuacaaug 1260
gugaacaacu gggcaaaccu aagaagaaug agagccugug gaguguagca agagguguua 1320
uuagaauguu acgaaaaaac uaugguugug uccgagugga uuuugcacag ccauuuuccu 1380
uaaaggaaua uuuagaaagc caaagucaga aaccggugucugcucuacuu ucccuggagc 1440 aagcguuguu accagcuaua cuuccuucaa gacccaguga ugcugcugau gaagguagag 1500
acacguccau uaaugagucc agaaaugcaa cagaugaauc ccuacgaagg agguugauug 1560
caaaucuggc ugagcauauu cuauucacug cuagcaaguc cugugccauu auguccacac 1620
acauuguggc uugccugcuc cucuacagac acaggcaggg aauugaucuc uccacauugg 1680
ucgaagacuu cuuugugaug aaagaggaag uccuggcucg ugauuuugac cugggguucu 1740
caggaaauuc agaagaugua guaaugcaug ccauacagcu gcugggaaau ugugucacaa 1800
ucacccacac uagcaggaac gaugaguuuu uuaucacccc cagcacaacu gucccaucag 1860
ucuucgaacu caacuucuac agcaaugggg uacuucaugu cuuuaucaug gaggccauca 1920

-continued

```
uagcuugcag ccuuuaugca guucugaaca agaggggacu gggggguccc acuagcaccc   1980
caccuaaccu gaucagccag gagcagcugg ugcggaaggc ggccagccug ugcuaccuuc   2040
ucuccaauga aggcaccauc ucacugccuu gccagacauu uuaccaaguc ugccaugaaa   2100
caguaggaaa guuuauccag uauggcauuc uuacaguggc agagcacgau gaccaggaag   2160
auaucagucc uagucuugcu gagcagcagu gggacaagaa gcuuccagaa ccuuugucuu   2220
ggagaaguga ugaagaagau gaagacagug acuuugggga ggaacagcga gauugcuacc   2280
ugaagguacu ugggugaaga auucuggugg auauuacagg gauauguuga gguuuaugcu   2340
gcagugagau cagcuggagu ccuggugaug ucuucuuauc uaaagaaucc cccaacuagc   2400
ucugguaccu ucuguguggu aaagacacuc aaacuguuug aguugaauua auagcauuuu   2460
aaguagaaaa ggaaaggaga gucugaaaag ucaggaagau gaaugucaua ggugagacuu   2520
ucaccauccu uuuaugaaau acacaggugc auaccuguuu accuacaccu gcacccccuca  2580
ugaggcagca guuuugcuau ugagcugcca cugaccuggc ugcucuuuuu gagucacucu   2640
ugcugucccu cccaaaauuu cauauauuaa gcucuuugcu gucaauuaaa acaaauacca   2700
uuauaggaga aaauugagau uaaaaaaaaa gucccugauu uagaaaaauc aauuuugucu   2760
aauuuauaau uuuagaacuu aguaauaaug acccgucuuu ucugaauacu cuaagaggau   2820
uacucuuuuu ugacauuuag aaauugucuu cuuuuucacu ugggugguau uaguuuaguu   2880
ucaagauggg gcagugaucu ugcuuucaca cuccagaggg gcuugaccga accagugugu   2940
uuuggguagg uacagugaga gccucucggc cauaaagcac cgccgucaca guggccauca   3000
uuccccacag ugcuggacug ugggcaaagg ccauuuaggg gaggcaggga auaggugcug   3060
cagaaggagu gagauaaucu ugguggucuc ccauuggucu uucugcagac uugagugacu   3120
guugagccca ggcuucaaac cauggagggc cuggucuuag gagcggcuau uuuuagugau   3180
gacagcguau cacaaguagg gcauucauuu augaaaauuu cuucuaggug gcuguucaau   3240
gaacacaagc cucaaauacc auaaaaaagu gaaugauuac aauaaagaau guguuugaaa   3300
gccagcaguu guuuccagca gagauucucu gcaugagggg cagggggccg cuuucaugua   3360
gugcugaugu gaguggccau cuucucacgu uacuggcucu ccagagaaag uccucugucc   3420
acuugccuug ugucucuugu cccuuccuca ugacuucauc uccugcuuuu gcacacucag   3480
gugagccaau ccaaggagca ccagcaguuu aucaccuucu uacagagacu ccuugggccu   3540
uugcuggagg ccuacagcuc ugcugccauc uuuguucaca acuucagugg uccuguucca   3600
gaaccugagu aucugcaaaa guugcacaaa uaccuaauaa ccagaacaga aagaaauguu   3660
gcaguauaug guauguuaag ucacuauuua uucuuuuaaa aucuuuuuuu uuuuuuugga   3720
uuucagaaau uugcuaauug uagaaaauug gaaaaaugca aacuuauccu gaccucuaac   3780
accguagagu auuacuauua ucuucuuugg cauguuauau aaguugaaug auacaguuau   3840
acacucuuac aucuggcuuu uuucacguaa cguuauuuuu gagauucaua cauguugcau   3900
auaguuguuc cuuuguucuu guuguguagu guuccauugu auaaaauauu accacauuuu   3960
auucauucug cuguugaugg auauuugggu uguuuucagu ucacagcugc uuugaacagu   4020
guugcuauga gcauauuuga auaugucuuu uggugaauau cugugccccu auauacagca   4080
uguauguggg aacagaauug ccugguugua ggcucugggu auauucggcu uugguagaua   4140
ccaccaaaca guuuccaagg gauuauaccu acuuguacuc ccacaacagu guguguuuca   4200
cuugcugcac aucuuggcca gcgcuccguc uucuuuguuu uaggaggugu gauuggggug   4260
ggaguacuau uuuauacagu uguaguuugg agcugaaacu acuugaauca cuuuuuagag   4320
```

```
ccaaaaggaa ucuaaucuaa ucaccucauu uuauaguuga ggaaaauacc ccaggucaca   4380

cugcuaauua augggguaauc ucgggaucag aauucuuguu uccuaaccuc gaggccugug   4440

cuuucucugg uuccacugau guacaaucau cuguguacca cuggguagcu uaaagaauau   4500

uuauacacua ucucauuuga uucucacaac aguccuggaa aauggauguu uuagguauuu   4560

cuacuucccu cuguucuccc uauuucucuc ucuacacccu cuuuucuuuc cccuucccuu   4620

ucuuauuuac cucaauauag gacaaaguag guguaagcaa aguagguuua acagcaaguc   4680

aucugagaac ucacagguug ccaguggugg aaguggggcc ccacccuugu cugcugacuu   4740

gcccucauuc ucuuccuagc uccccauacu uucuuacugu ggcugcuggg auugucauga   4800

uuuguugagc guaaccauuu gacaggguuu uauucucucu cuucagcuga gagugccaca   4860

uauugucuug ugaagaaugc ugugaaaaug uuuaaggaua uuggggguagg uguccaccau   4920

uuaugguaua aaagcuaucu caacuucugu ucucuuuaga ucuagucugu uugagcuacc   4980

uuuguggugg gguggacccc gagagaagca guuucugcug gcuuaaugau aaaggcauuu   5040

uugggaacgg ggcauguagg augggguuggg cuauguugaa ggugaagccc aucaguguag   5100

auuuauuuga auguucugga auuuuacugg uuucacauuu auucccaagc ugcuauauau   5160

aacugguauc aauauguuuc aaggugcuac agguugaaua ucccuuaucc aaaauguugg   5220

gaccagaaau guuuuggauu ucagauuuuu uugggauuuu ggaauaugug cauuagacuu   5280

acagguugag cgucucuaau ccaaaaccca aaaugcucug augagcaugu cuuuugagca   5340

ucauauugau guucaaaauc uuucagauuu uggaguacuu cagauuuuug auuuugggau   5400

uaggaccaca aucuuggcuc uuaauuauuc cauaugauuu uuaguuacuu ucuuguauuu   5460

uuacaagaau uucuagaagu auccucaggu guccuuuacc uucaugauuc auggggaaug   5520

uaaguucuau agagauacua gcggccuuuu gugagggacu guuugugacu uuauucuaag   5580

ucauuuuaga guauaguuau guugguugaa auuuuagaau auaguuaaug uugguugaac   5640

uccaucaaaa caaaaaaaaa aaaa                                          5664
```

<210> SEQ ID NO 11
<211> LENGTH: 6368
<212> TYPE: RNA
<213> ORGANISM: homo sapien

<400> SEQUENCE: 11

```
gcgccacugc agcuggcauu ggccgggacu ggaagugcgg gcuucugcag cagccgaagc     60

uggagcugcu aggcagcggc uccccuguug uauggacauu cugcacccga aacugauagc    120

ugaguccuga aguuuuaugu uaugaaacag aagaacuuuc aucccagcac augauuuggg    180

aauuacacuu ugugacaugg augaaucugc acugacccuu gguacaauag auguuucuua    240

ucugccacau ucaucagaau acaguguugg ucgauguaag cacacaagug aggaaugggg    300

ugaguguggc uuuagaccca ccgucuucag aucugcaacu uuaaaaugga aagaaagccu    360

aaugagucgg aaaaggccau uuguuggaag auguuguuac uccugcacuc cccagagcug    420

ggacaaauuu uucaacccca guaucccguc uuuggguuug cggaauguua uuuauaucaa    480

ugaaacucac acaagacacc gcggauggcu ugcaagacgc cuuucuuacg uucuuuuuau    540

ucaagagcga gaugugcaua agggcauguu ugccaccaau gugacugaaa augugcugaa    600

cagcaguaga guacaagagg caauugcaga aguggcugcu gaauuaaacc cugaugguuc    660

ugcccagcag caaucaaaag ccguuaacaa agugaaaaag aaagcuaaaa ggauucuuca    720
```

-continued

```
agaaaugguu gccacugucu caccggcaau gaucagacug acugggu ggg ugcugcuaaa    780
acuguucaac agcuucuuuu ggaacauuca aauucacaaa ggucaacuug agaugguuaa    840
agcugcaacu gagacgaauu ugccgcuucu guuucuacca guucauagau cccauauuga    900
cuaucugcug cucacuuuca uucucuucug ccauaacauc aaagcaccau acauugcuuc    960
aggcaauaau cucaacaucc caaucuucag uaccuugauc cauaagcuug ggggcuucuu   1020
cauacgacga aggcucgaug aaacaccaga uggacggaaa gauguucucu auagagcuuu   1080
gcuccauggg cauauaguug aauuacuucg acagcagcaa uucuuggaga ucuuccugga   1140
aggcacacgu ucuaggagug gaaaaaccuc uugugcucgg gcaggacuuu ugucaguugu   1200
gguagauacu cugucuacca augucauccc agacaucuug auaauaccug uuggaaucuc   1260
cuaugaucgc auuaucgaag gucacuacaa uggugaacaa cugggcaaac cuaagaagaa   1320
ugagagccug uggaguguag caagaggugu uauuagaaug uuacgaaaaa acuaugguug   1380
uguccgagug gauuuugcac agccauuuuc cuuaaaggaa uauuuagaaa gccaaaguca   1440
gaaaccggug ucugcucuac uuucccugga gcaagcguug uuaccagcua uacuuccuuc   1500
aagacccagu gaugcugcug augaagguag agacacgucc auuaaugagu ccagaaaugc   1560
aacagaugaa ucccuacgaa ggagguugau ugcaaaucug gcugagcaua uucuauucac   1620
ugcuagcaag uccugugcca uuauguccac acacauugug gcuugccugc uccucuacag   1680
acacaggcag ggaauugauc ucuccacauu ggucgaagac uucuuuguga ugaaagagga   1740
aguccuggcu cgugauuuug accugggguu cucaggaaau ucagaagaug uaguaaugca   1800
ugccauacag cugcugggaa auugugucac aaucacccac acuagcagga acgaugaguu   1860
uuuuaucacc cccagcacaa cugucccauc agucuucgaa cucaacuucu acagcaaugg   1920
gguacuucau gucuuuauca uggaggccau cauagcuugc agccuuuaug caguucugaa   1980
caagagggga cuggggguc ccacuagcac cccaccuaac cugaucagcc aggagcagcu   2040
ggugcggaag gcggccagcc ugugcuaccu ucucuccaau gaaggcacca ucucacugcc   2100
uugccagaca uuuuaccaag ucugccauga aacaguagga aaguuuaucc aguauggcau   2160
ucuuacagug gcagagcacg augaccagga agauaucagu ccuagucuug cugagcagca   2220
gugggacaag aagcuuccag aaccuuuguc uuggagaagu gaugaagaag augaagacag   2280
ugacuuuggg gaggaacagc gagauugcua ccugaaggug agccaaucca aggagcacca   2340
gcaguuuauc accuucuuac agagacuccu ugggccuuug cuggaggccu acagcucugc   2400
ugccaucuuu guucacaacu ucaguggucc uguuccagaa ccugaguauc ugcaaaaguu   2460
gcacaaauac cuaauaacca gaacagaaag aaauguugca guauaugcug agagugccac   2520
auauugucuu gugaagaaug cugugaaaau guuuaaggau auuggggguuu ucaaggagac   2580
caaacaaaag agagugucug uuuuagaacu gagcagcacu uuucuaccuc aaugcaaccg   2640
acaaaaacuu cuagaauaua uucugaguuu ugugguggcug uagguaacgu guggcacugc   2700
uggcaaauga aggucaugag augaguuccu uguagguacc agcuucuggc ucaagaguug   2760
aaggugccau cgcaggguca ggccugcccu gucccgaagu gaucuccugg aagacaagug   2820
ccuucucccu ccauggaucu gugaucuucc cagcucugca ucaacacagc agccugcaga   2880
uaacacuugg ggggaccuca gccucuauuc gcaacucaua auccguagac uacaagauga   2940
aaucucaaua aauuauuuuu gaguuuauua aagauugaca uuuuaaguac aacuuuuaag   3000
gacuaauuac ugugauggac acagaaaugu agcuguguuc uggaacugaa ucuuacaugg   3060
uauacuuagu gcugcugggu aauuuguugg uauauuaucu gguuaguggu uaaugcuucc   3120
```

-continued

```
uuuaaaaaua auugagucau ccauucacuc uuuuucaguu uuaucuguca auaguagcua   3180
cauuuuuaau gggagcaccu uuuaucccaa agugcuuuau aaauugagug gacugauaua   3240
uaucacaccc agguaucacu gugcuguccu uugcugucag auuuagaaau guuuuuaaga   3300
gcuaugugaa aacagacaau auuaguuuag gucgggaacu gagauauugu aaucaaauag   3360
uuaacaucag gaaguuaauu uggcuggcaa aauucuaggg aaacuuggcc agaaaacugg   3420
uguugaaggc uuuugcucau auaaacaagu gccauugagu uucaaaugac cagcaaauau   3480
auuuagaacc cuuccuguuu uaugucugua ccucguccac cccucaggua auaccugccu   3540
cucacaggua cagcuguuuc uuggaaaucc uccaaccaaa uagcaguuuu ccuaacuuga   3600
uuagcuugag cugacagacu guuagaauac aguucucugg ccacagcuga ugagggcuuu   3660
cuguacugca cacagauugu guacugcacc ccaguccagg ugacugguac ccacucgagu   3720
ugugccgugc acaaccuguc caguauaugc auguggugc ccuacugacu gguaaugguu   3780
agaggcauuu auggauuuuu agcuuugagg aaaaaccaug acuuuuaaca aauuuuuaug   3840
gguuauaugc cuaaacccuu augccacaua gugguaaaua auuaugaaaa auggucuguu   3900
cauaauuggu aggugccuuu ugugagcagg gagcauaauu auugguuuau uaugguaauu   3960
auggugauuu uuuaaauauc auguaauguu aaaacguuuu cuaacaguuu acuguugcuu   4020
aucuccaaga uauuauggaa uuaagaauuu uuccagauga guguuacaua gauucuuuga   4080
auuuaguaua aaaguacuga gaauuaaguu uguacuucca uaagcuugga uuuuaaacac   4140
ugauaguauc ucaugaguaa ugugguuuu gggagaggga gggaugcuga uugauauuuc   4200
acauuguaug aaauaccaug uuugaaacuc auagcaauaa ugcuaugcug uugugauccc   4260
ucucaaguuc ugcauuuaaa auauauuuuu ucuuuauagg aauugaugua uaccaugaag   4320
ucauugucag uuguaguagc ucugauguug aaugagauau cauguuuuag cauuccauuu   4380
uacugacuag gguagaagaa cacuuuucuu ggcuacauuu ggaggauacc cagggagucu   4440
uggguguucc uuaucugggg aagcaaacau uucacuaguc ucuuuuuuuc auccuuuaaa   4500
uuguaaauua aggauuacuc aagcucacca uuauucaaga uugggacucg cuucccaguc   4560
gacacucugc ccugccuguc auugcugcaa agagcugcug cuuugccaac cuaagcaaag   4620
aaaauacggc uucucuugca uuauuuuccc uuuugguugg uuuguuuucu agaaguacgu   4680
ucagaugcuu uggggaaugc aauguaugau uugcuagcuc ucucaccacu uaacucacug   4740
ugaggauaaa uaugcaugcu uuuuguaauu aacuggugcu uugaaaaucu uuuuuaaggg   4800
agaaaaaucu caaccaaagu uaugcucauc cagacaagcu gaccuuugag uuaauuucag   4860
cacaacucau ucuucagugc cucaugacug aaaacaaaaa acaaaaaaac gaaagcaucu   4920
ucacaaugaa gcuuccagau agcaccguuu ugcuaaaaga uacauucuca uuguuuucca   4980
acagugaugg cuuccacaua agguuaaaca aacuaggugc uuguaaauaa uuuauuacag   5040
uuuacucuau cgcauuucug uaacaugaaa ugcaugcccu ucuucagggg aagacugugg   5100
ucaaguuaaa aaaaaaaaac aauauuaaac aacaugaaac ugcagucugu uuuugaaaau   5160
gagaaugucc uaagugauuc agaagagagg agggaaguug ugcacucuga aaaugcauga   5220
aaaacaaagg caaaaacuag ugggaaaugu guagaacugu uaacugagau ggcuucgagu   5280
cuuccuucug gaaucuguua aauuucacaa agucaugagg guaaauggag aaaauauuuc   5340
ugggauuaca augaauguaa gcccaaauug uggaauugcc aguaaccugg augggggaaaa   5400
gcauuuccca uagcacucca uguaauauga gugcucugug agauguucau caguguuuua   5460
```

-continued uagaaauggu guugcuggga aaccaaguuu gcaccuggaa acuuacaaug cacuuuagcg 5520
caguaagggc uuggcauccg guagugaaaa acugucuaac ccagcauugc ccaaacuauu 5580
uugacaccag gaccuuuuuc uccuuuggga uacuuaugaa ccucucacua auguccugug 5640
gagaacauuu ugggaaacac uauguuagau aguucuuuaa ggagacaaaa cgguaaugaa 5700
cagauagcac uggggcagaa uaugcaugca uuuuguaacg uccagugugg cguugaauag 5760
auguguauuu ccucccccugc agaaaauaag cacagaaaau uauaauguag gugaucggag 5820
cucuuuccuu ugauagagag aacagcccca augauccugg cuuuuucacu gaacguauca 5880
gaauacaugg augaauuggg guaaauaagg uuuuaauuca gaucuagaag aaaguauugu 5940
acguuugaau gcagauuuuu auccacagau aguuguagug uuuagacaug acaggaccua 6000
ucguugaggu uucuaagacu uacuaugggc uguaaaccug uuuuuuaaaa cuauuuuaga 6060
aaccugagac uugccgucug gcauuuuagu uuaauacaaa cuaaugauug cauuugaaag 6120
agauucuuga ccuuauuucu aaacgucuag agcucugaaa ugucuugaug gaagguauua 6180
aacuauuugc cuguuguaca aagaaauguu aagacucgug aaaagaauua cuauaaggua 6240
cugugaaaua acugcgauuu ugugagcaaa acauacuugg aaaugcugau ugauuuuuau 6300
gcuuguuagu guauugcaag aaacacagaa aauguaguuu uguuuuaaua aaccaaaaau 6360
ugaacaua 6368

<210> SEQ ID NO 12
<211> LENGTH: 4918
<212> TYPE: RNA
<213> ORGANISM: homo sapien

<400> SEQUENCE: 12
ggccacugca gcuggcauug gccgggacug gaagugcggg cuucugcagc agccgaagcu 60
ggagcugcua gggcagcagc ggcuccccug uuguauggac auucugcacc cgaaacugau 120
agcugagucc ugaaguuuua uguuaugaaa cagaagaacu uucaucccag cacaugauuu 180
gggaauuaca cuuugugaca uggaugaauc ugcacugacc cuugguacaa uagauguuuc 240
uuaucugcca cauucaucag aauacagugu uggucgaugu aagcacacaa gugaggaaug 300
gggugagugu ggcuuuagac ccaccgucuu cagaucugca acuuuaaaau ggaaagaaag 360
ccuaaugagu cggaaaaggc cauuuguugg aagauguugu uacuccugca cuccccagag 420
cugggacaaa uuuuucaacc ccaguauccc gucuuugggu uugcggaaug uuauuuauau 480
caaugaaacu cacacaagac accgcggaug gcuugcaaga cgccuuucuu acguucuuuu 540
uauucaagag cgagaugugc auaagggcau guuugccacc aaugugacug aaaaugugcu 600
gaacagcagu agaguacaag aggcaauugc agaaguggcu gcugaauuaa acccugaugg 660
uucugcccag cagcaaucaa aagccguuaa caaagugaaa aagaaagcua aaaggauucu 720
ucaagaaaug guugccacug ucucaccggc aaugaucaga cugacugggu gggugcugcu 780
aaaacuguuc aacagcuucu uuuggaacuu ucaaauucac aaaggucaac uugagauggu 840
uaaagcugca acugagacga auuugccgcu ucuguuucua ccaguucaua gaucccauau 900
ugacuaucug cugcucacuu ucauucucuu cugccauaac aucaaagcac cauacauugc 960
uucaggcaau aaucucaaca ucccaaucuu caguaccuug auccauaagc uuggggggcuu 1020 cuucauacga cgaaggcucg augaaacacc agauggacgg aaagauguuc ucuauagagc 1080
uuugcuccau gggcauauag uugaauuacu ucgacagcag caauucuugg agaucuuccu 1140
ggaaggcaca cguucuagga guggaaaaac cucuugugcu cgggcaggac uuuugucagu 1200

-continued

```
ugugguagau acucugucua ccaaugucau cccagacauc uugauaauac cuguuggaau   1260
cuccuaugau cgcauuaucg aaggucacua caauggugaa caacugggca aaccuaagaa   1320
gaaugagagc cuguggagug uagcaagagg uguuauuaga auguuacgaa aaaacuaugg   1380
uuguguccga guggauuuug cacagccauu uuccuuaaag gaauauuuag aaagccaaag   1440
ucagaaaccg gugucugcuc uacuuucccu ggagcaagcg uuguuaccag cuauacuucc   1500
uucaagaccc agugaugcug cugaugaagg uagagacacg uccauuaaug aguccagaaa   1560
ugcaacagau gaaucccuac gaaggagguu gauugcaaau cuggcugagc auauucuauu   1620
cacugcuagc aaguccugug ccauuauguc cacacacauu guggcuugcc ugcuccucua   1680
cagacacagg cagggaauug aucucuccac auuggucgaa gacuucuuug ugaugaaaga   1740
ggaaguccug gcucgugauu uugaccuggg guucucagga aauucagaag auguaguaau   1800
gcaugccaua cagcugcugg gaaauugugu cacaaucacc cacacuagca ggaacgauga   1860
guuuuuuauc acccccagca caacuguccc aucagucuuc gaacucaacu ucuacagcaa   1920
uggggguacuu caugucuuua ucauggaggc caucauagcu ugcagccuuu augcaguucu   1980
gaacaagagg ggacuggggg gucccacuag caccccaccu aaccugauca gccaggagca   2040
gcuggugcgg aaggcggcca gccugugcua ccuucucucc aaugaaggca ccaucucacu   2100
gccuugccag acauuuuacc aagucugcca ugaaacagua ggaaaguuua uccgguaugg   2160
cauucuuaca guggcagagc acgaugacca ggaagauauc aguccuaguc uugcugagca   2220
gcagugggac aagaagcuuc cagaaccuuu gucuuggaga agugaugaag aagaugaaga   2280
cagugacuuu ggggaggaac agcgagauug cuaccugaag gugagccaau ccaaggagca   2340
ccagcaguuu aucaccuucu uacagagacu ccuugggccu uugcuggagg ccuacagcuc   2400
ugcugccauc uuuguucaca acuucagugg uccuguucca gaaccugagu aucugcaaaa   2460
guugcacaaa uaccuaauaa ccagaacaga aagaaauguu gcaguauaug cugagagugc   2520
cacauauugu cuugugaaga augcugugaa aauguuuaag gauauugggg uuuucaagga   2580
gaccaaacaa aagagagugu cuguuuuaga acugagcagc acuuuucuac cucaaugcaa   2640
ccgacaaaaa cuucuagaau auauucugag uuuugugguug cuguagguaa cguguggcac   2700
ugcuggcaaa ugaaggucau gagaugaguu ccuuguaggu accagcuucu ggcucaagag   2760
uugaaggugc caucgcaggg ucaggccugc ccugucccga agugaucucc uggaagacaa   2820
gugccuucuc ccuccaugga ucugugaucu ucccagcucu gcaucaacac agcagccugc   2880
agauaacacu ugggggggacc ucagccucua uucgcaacuc auaauccgua gacuacaaga   2940
ugaaaucuca auaaauuauu uuugaguuua uuaaagauug acauuuuaag uacaacuuuu   3000
aaggacuaau uacugugaug gacacagaaa uguagcugug uucuggaacu gaaucuuaca   3060
ugguauacuu agugcugcug gguaauuugu ugguauauua ucugguuagu gguuaaugcu   3120
uccuuuaaaa auaauugagu cauccauuca cucuuuuuca guuuuaucug ucaauaguag   3180
cuacauuuuu aaugggagca ccuuuuaucc caaagugcuu uauaaauuga guggacugau   3240
auauaucaca cccagguauc acugugcugu ccuuugcugu cagauuuaga aauguuuuua   3300
agagcuaugu gaaaacagac aauauuaguu uaggucggga acugagauau uguaaucaaa   3360
uaguuaacau caggaaguua auuuggcugg caaaauucua gggaaacuug gccagaaaac   3420
uggguguugaa ggcuuuugcu cauauaaaca agugccauug aguuucaaau gaccagcaaa   3480
uauauuuaga acccuuccug uuuuaugucu guaccucguc caccccucag guaauaccug   3540
```

-continued ccucucacag guacagcugu uucuuggaaa ucccuccaacc aaauagcagu uuuccuaacu 3600
ugauuagcuu gagcugacag acuguuagaa uacaguucuc uggccacagc ugaugagggc 3660
uuucuguacu gcacacagau uguguacugc accccagucc aggugacugg uacccacucg 3720
aguugugccg ugcacaaccu guccaguaua ugcauguggu ggcccuacug acugguaaug 3780
guuagaggca uuuauggauu uuuagcuuug aggaaaaacc augacuuuua acaaauuuuu 3840 augggguuaua ugccuaaacc cuuaugccac auaguggtaa auaauuauga aaaauggucu 3900
guucauaauu gguaggugcc uuuugugagc agggagcaua auuauugguu uauuauggua 3960
auuaugguga uuuuuuaaau aucauguaau guuaaaacgu uuucuaacag uuuacuguug 4020
cuuaucucca agauauuaug gaauuaagaa uuuuuccaga ugaguguuac auagauucuu 4080
ugaauuuagu auaaaaguac ugagaauuaa guuuguacuu ccauaagcuu ggauuuuaaa 4140
cacugauagu aucucaugag uaaugugugu uuugggagag ggagggaugc ugauugauau 4200
uucacauugu augaaauacc auguuugaaa cucauagcaa uaaugcuaug cuguugugau 4260
cccucccaag uucugcauuu aaaauauauu uuuucuuuau aggaauugau guauaccaug 4320
aagucauugu caguuguagu agcucugaug uugaaugaga uaucauguuu uagcauucca 4380
uuuuacugac uaggguagaa gaacacucuu cuuggcuaca uuuggaggau acccagggag 4440
ucuugggugu uccuuaucug gggaagcaaa cauuucacua gucucuuuuu uucauccuuu 4500
aaauuguaaa uuaaggauua cucaagcuca ccauuauuca agauugggac ucgcuuccca 4560
gucgacacuc ugcccugccu gucauugcug caaagagcug cugcuuugcc aaccuaagca 4620
aagaaaauac ggcuucucuu gcauuauuuu cccuuuuggu ugguuuguuu ucuagaagua 4680
cguucagaug cuuuggggaa ugcaauguau gauuugcuag cucucucacc acuuaacuca 4740
cugugaggau aaauaugcau gcuuuuugua auuaacuggu gcuuugaaaa ucuuuuuuaa 4800
gggagaaaaa ucucaaccaa aguuaugcuc auccagacaa gcugaccuuu gaguuaauuu 4860
cagcacaacu cauucuucag ugccucauga cugaaaacaa aaaaaaaaaa aaaaaaa 4918

<210> SEQ ID NO 13
<211> LENGTH: 3490
<212> TYPE: RNA
<213> ORGANISM: homo sapien

<400> SEQUENCE: 13
agcgggcugg aagugcgggc uucugcagca gccgaagcug gagcugcuag ggcagcagcg 60
gcuccccugu uguauggaca uucugcaccc gaaacugaua gcugaguccu gaaguuuuau 120
guuaugaaac agaagaacuu ucaucccagc acaugauuug ggaauuacac uuugugacau 180
ggaugaauau gcacugaccc uugguacaau agauguuucu uaucugccac auucaucaga 240
auacaguguu ggucgaugua agcacacaag ugaggaaugg ggugagugug gcuuuagacc 300
caccgucuuc agaucugcaa cuuuaaaaug gaaagaaagc cuaaugaguc ggaaaaggcc 360
auuuguugga agauguuguu acuccugcac uccccagagc ugggacaaau uuuucaacac 420
caguaucccg ucuuuggguu ugcggaaugu uauuuauauc aaugaaacuc acacaagaca 480
ccgcggaugg cuugcaagac gccuuucuua cguucuuuuu auucaagagc gagaugugca 540
uaagggcaug uuugccacca augugacuga aaaugugcug aacagcagua gaguacaaga 600
ggcaauugca gaaguggcug cugaauuaaa cccugauggu ucugcccagc agcaaucaaa 660
agccguuaac aaagugaaaa agaaagcuaa aaggauucuu caagaaaugg uugccacugu 720
cucaccggca augaucagac ugacugggug ggugcugcua aaacuguuca acagcuucuu 780
uuggaacauu caaauucaca aaggucaacu ugagaugguu aaagcugcaa cugagacgaa 840
uuugccgcuu cuguuucuac caguucauag aucccauauu gacuaucugc ugcucacuuu 900
cauucucuuc ugccauaaca ucaaagcacc auacauugcu ucaggcaaua aucucaacau 960
cccaaucuuc aguaccuuga uccauaagcu ugggggcuuc uucauacgac gaaggcucga 1020
ugaaacacca gauggacgga aagauguucu cuauagagcu uugcuccaug ggcauauagu 1080
ugaauuacuu cgacagcagc aauucuugga gaucuuccug gaaggcacac guucuaggag 1140
uggaaaaacc ucuugugcuc gggcaggacu uuugucaguu gugguagaua cucugucuac 1200
caaugucauc ccagacaucu ugauaauacc uguuggaauc ucccuaugauc gcauuaucga 1260
aggucacuac aauggugaac aacugggcaa accuaagaag aaugagagcc uguggagugu 1320
agcaagaggu guuauuagaa uguuacgaaa aaacuauggu uguguccgag uggauuuugc 1380
acagccauuu uccuuaaagg aauauuuaga aagccaaagu cagaaaccgg ugucugcucu 1440
acuuucccug gagcaagcgu uguuaccagc uauacuuccu ucaagaccca gugaugcugc 1500
ugaugaaggu agagacacgu ccauuaauga guccagaaau gcaacagaug aaucccuacg 1560
aaggagguug auugcaaauc uggcugagca uauucuauuc acugcuagca aguccugugc 1620
cauuaugucc acacacauug uggcuugccu gcuccucuac agacacaggc agggaauuga 1680
ucucuccaca uuggucgaag acuucuuugu gaugaaagag gaaguccugg cucgugauuu 1740
ugaccugggg uucucaggaa auucagaaga uguaguaaug caugccauac agcugcuggg 1800
aaauugugucc acaaucaccc acacuagcag gaacgaugag uuuuuuauca cccccagcac 1860
aacugucccaa ucagucuucg aacucaacuu cuacagcaau gggguacuuc augucuuuau 1920
cauggaggcc aucauagcuu gcagccuuua ugcaguucug aacaagaggg gacugggggg 1980
ucccacuagc accccaccua accugaucag ccaggagcag cuggugcgga aggcggccag 2040
ccugugcuac cuucucucca augaaggcac caucucacug ccuugccaga cauuuuacca 2100
agucugccau gaaacaguag gaaaguuuau ccaguauggc auucuuacag uggcagagca 2160
cgaugaccag gaagauauca guccuagucu ugcugagcag caguggggaca agaagcuucc 2220
agaaccuuug ucuuggagaa gugaugaaga agaugaagac agugacuuug gggaggaaca 2280
gcgagauugc uaccugaagg ugagccaauc caaggagcac cagcaguuua ucaccuucuu 2340
acagagacuc cuugggccuu ugcuggaggc cuacagcucu gcugccaucu uuguucacaa 2400
cuucaguggu ccuguuccag aaccugagua ucugcaaaag uugcacaaau accuaauaac 2460
cagaacagaa agaaauguug caguauaugc ugagagugcc acauauuguc uugugaagaa 2520
ugcugugaaa auguuuaagg auauuggggu uuucaaggag accaaacaaa agagaguguc 2580
uguuuuagaa cugagcagca cuuuucuacc ucaaugcaac cgacaaaaac uucuagaaua 2640
uauucugagu uuuguggugc uguagguaac guguggcacu gcuggcaaau gaaggucaug 2700
agaugaguuc cuuguaggua caagcuucug gcucaagagu ugaaggugcc aucgcagggu 2760
caggccugcc cugucccgaa gugaucuccu ggaagacaag ugccuucucc auccauggau 2820
cugugaucuu cccagcucug caucaacaca gcagccugca gauaacacuu ggggggaccu 2880
cagccucuau ucgcaacuca uaauccguag acuacaagau gaaaucucaa uaaauuauuu 2940
uugaguuuau uaaagauuga cauuuuaagu acaacuuuua aggacuaauu acugugaugg 3000
acacagaaau guagcugugu ucuggaacug aaucuuacau gguauacuua gugcugcugg 3060
guaauuuguu gguauauuau cugguuagug guuaaugcuu ccuuuaaaaa uaauugaguc 3120

-continued auccauucac ucuuuuucag uuuuaucugu caauaguagc uacauuuuua augggagcac 3180
cuuuuauccc aaagugcuuu auaaaauugag uggacugaua uauaucacac ccagguauca 3240
cugugcuguc cuuugcuguc agauuuagaa auguuuuuaa gagcuaugug aaaacagaca 3300
auauuaguuu aggucgggaa cugagauauu guaaucaaau aguuaacauc aggaaguuaa 3360
uuuggcuggc aaaauucuag ggaaacuugg ccagaaaacu gguguugaag gcuuuugcuc 3420
auauaaacaa gugccauuga guuucaaaug accagcaaau auauuuagaa cucaaaaaaa 3480
aaaaaaaaaa 3490

<210> SEQ ID NO 14
<211> LENGTH: 2855
<212> TYPE: RNA
<213> ORGANISM: homo sapien

<400> SEQUENCE: 14
aacuuucauc ccagcacaug auuugggaau uacacuuugu gacauggaug aaucugcacu 60
gacccuuggu acaauagaug uuucuuaucu gccacauuca ucagaauaca guguuggucg 120
auguaagcac acaagugagg aaugggguga guguggcuuu agacccaccg ucuucagauc 180
ugcaacuuua aaauggaaag aaagccuaau gagucggaaa aggccauuug uuggaagaug 240
uuguuacucc ugcacucccc agagcuggga caaauuuuuc aaccccagua ucccgucuuu 300
ggguuugcgg aauguuauuu auaucaauga aacucacaca agacaccgcg gauggcuugc 360
aagacgccuu ucuuacguuc uuuuuauuca agagcgagau gugcauaagg gcauguuugc 420
caccaaugug acugaaaaug ugcugaacag caguagagua caagaggcaa uugcagaagu 480
ggcugcugaa uuaaacccug augguucugc ccagcagcaa ucaaaagccg uuaacaaagu 540
gaaaaagaaa gcuaaaagga uucuucaaga aaugguugcc acugucucac cggcaaugau 600
cagacugacu gggugggugc ugcuaaaacu guucaacagc uucuuuugga acauucaaau 660
ucacaaaggu caacuugaga ugguuaaagc ugcaacugag acgaauuugc cgcuucuguu 720
ucuaccaguu cauagauccc auauugacua ucugcugcuc acuuucauuc ucuucugcca 780
uaacaucaaa gcaccauaca uugcuucagg caauaaucuc aacaucccaa ucuucaguac 840
cuugauccau aagcuugggg gcuucuucau acgacgaagg cucgaugaaa caccagaugg 900
acggaaagau guucucuaua gagcuuugcu ccaugggcau auaguugaau uacuucgaca 960
gcagcaauuc uuggagaucu uccuggaagg cacacguucu aggaguggaa aaaccucuug 1020
ugcucgggca ggacuuuugu caguugugggu agauacucug ucuaccaaug ucaucccaga 1080
caucuugaua auaccuguug gaaucuccua ugaucgcauu aucgaagguc acuacaaugg 1140
ugaacaacug ggcaaaccua agaagaauga gagccugugg aguguagcaa gagguguuac 1200
uagaauguua cgaaaaaacu augguuguguu ccgaguggau uuugcacagc cauuuuccuu 1260
aaaggaauau uuagaaagcc aaagucagaa accggugucu gcucuacuuu cccuggagca 1320
agcguuguua ccagcuauac uuccuucaag acccagugau gcugcugaug aagguagaga 1380
cacguccauu aaugagucca gaaaugcaac agaugaaucc cuacgaagga gguugauugc 1440
aaaucuggcu gagcauauuc uauucacugc uagcaagucc ugugccauua uguccacaca 1500
cauuguggcu ugccugcucc ucuacagaca caggcaggga auugaucucu ccacauuggu 1560
cgaagacuuc uuugugauga aagaggaagu ccuggcucgu gauuuugacc ugggguucuc 1620
aggaaauuca gaagauguag uaaugcaugc cauacagcug cugggaaauu gugucacaau 1680
cacccacacu agcaggaacg augaguuuuu uaucaccccc agcacaacug ucccaucagu 1740

```
cuucgaacuc aacuucuaca gcaaugggu acuucauguc uuuaucaugg aggccaucau   1800

agcuugcagc cuuuaugcag uucugaacaa gaggggacug gggggucca cuagcacccc   1860

accuaaccug aucagccagg agcagcuggu gcggaaggcg gccagccugu gcuaccuucu   1920

cuccaaugaa ggcaccaucu cacugccuug ccagacauuu uaccaagucu gccaugaaac   1980

aguaggaaag uuuauccagu auggcauucu uacaguggca gagcacgaug accaggaaga   2040

uaucaguccu agucuugcug agcagcagug ggacaagaag cuuccugaac cuuugucuug   2100

gagaagugau gaagaagaug aagacaguga cuuuggggag gaacagcgag auugcuaccu   2160

gaaggugagc caauccaagg agcaccagca guuuaucacc uucuuacaga gacuccuugg   2220

gccuuugcug gaggccuaca gcucugcugc caucuuuguu cacaacuuca guggguccugu   2280

uccagaaccu gaguaucugc aaaaguugca caaauaccua auaaccagaa cagaaagaaa   2340

uguugcagua uaugcugaga gugccacaua uugucuugug aagaaugcug ugaaaauguu   2400

uaaggauauu gggguuuuca aggagaccaa acaaaagaga gugucuguuu uagaacugag   2460

cagcacuuuu cuaccucaau gcaaccgaca aaaacuucua gaauauauuc ugaguuuugu   2520

ggugcuguag guaacgugug gcacugcugg caaaugaagg ucaugagaug aguuccuugu   2580

agguaccagc uucuggcuca agaguugaag gugccgucgc agggucaggc cugcccuguc   2640

ccgaggugau cuccuggaag acaagugccu ucucccucca uggaucugug aucuucccag   2700

cucugcauca acacagcagc cugcagauaa cacuuggggg gaccucagcc ucuauucgca   2760

acucauaauc cguagacuac aagaugaaau cucaauaaau uauuuuugag uuuauuaaag   2820

aggucuuuua aggcaaaaaa aaaaaaaaaa aaaaa                             2855
```

<210> SEQ ID NO 15
<211> LENGTH: 6372
<212> TYPE: DNA
<213> ORGANISM: homo sapien

<400> SEQUENCE: 15

```
gcgccactgc agctggcatt ggccgggact ggaagtgcgg gcttctgcag cagccgaagc     60

tggagctgct agggcagcag cggctcccct gttgtatgga cattctgcac ccgaaactga    120

tagctgagtc ctgaagtttt atgttatgaa acagaagaac tttcatccca gcacatgatt    180

tgggaattac actttgtgac atggatgaat ctgcactgac ccttggtaca atagatgttt    240

cttatctgcc acattcatca gaatacagtg ttggtcgatg taagcacaca agtgaggaat    300

ggggtgagtg tggctttaga cccaccatct tcagatctgc aactttaaaa tggaaagaaa    360

gcctaatgag tcggaaaagg ccatttgttg gaagatgttg ttactcctgc actccccaga    420

gctgggacaa atttttcaac cccagtatcc cgtctttggg tttgcggaat gttatttata    480

tcaatgaaac tcacacaaga caccgcggat ggcttgcaag acgcctttct tacgttcttt    540

ttattcaaga gcgagatgtg cataagggca tgtttgccac caatgtgact gaaaatgtgc    600

tgaacagcag tagagtacaa gaggcaattg cagaagtggc tgctgaatta aaccctgatg    660

gttctgccca gcagcaatca aaagccgtta acaaagtgaa aaagaaagct aaaaggattc    720

ttcaagaaat ggttgccact gtctcaccgg caatgatcag actgactggg tgggtgctgc    780

taaaactgtt caacagcttc ttttggaaca ttcaaattca caaaggtcaa cttgagatgg    840

ttaaagctgc aactgagacg aatttgccgc ttctgtttct accagttcat agatcccata    900

ttgactatct gctgctcact ttcattctct tctgccataa catcaaagca ccatacattg    960
```

-continued

```
cttcaggcaa taatctcaac atcccaatct tcagtacctt gatccataag cttgggggct   1020
tcttcatacg acgaaggctc gatgaaacac cagatggacg gaaagatgtt ctctatagag   1080
ctttgctcca tgggcatata gttgaattac ttcgacagca gcaattcttg gagatcttcc   1140
tggaaggcac acgttctagg agtggaaaaa cctcttgtgc tcgggcagga cttttgtcag   1200
ttgtggtaga tactctgtct accaatgtca tcccagacat cttgataata cctgttggaa   1260
tctcctatga tcgcattatc gaaggtcact acaatggtga acaactgggc aaacctaaga   1320
agaatgagag cctgtggagt gtagcaagag gtgttattag aatgttacga aaaaactatg   1380
gttgtgtccg agtggatttt gcacagccat tttccttaaa ggaatattta gaaagccaaa   1440
gtcagaaacc ggtgtctgct ctactttccc tggagcaagc gttgttacca gctatacttc   1500
cttcaagacc cagtgatgct gctgatgaag gtagagacac gtccattaat gagtccagaa   1560
atgcaacaga tgaatcccta cgaaggaggt tgattgcaaa tctggctgag catattctat   1620
tcactgctag caagtcctgt gccattatgt ccacacacat tgtggcttgc ctgctcctct   1680
acagacacag gcagggaatt gatctctcca cattggtcga agacttcttt gtgatgaaag   1740
aggaagtcct ggctcgtgat tttgacctgg ggttctcagg aaattcagaa gatgtagtaa   1800
tgcatgccat acagctgctg ggaaattgtg tcacaatcac ccacactagc aggaacgatg   1860
agtttttat caccccagc acaactgtcc catcagtctt cgaactcaac ttctacagca   1920
atggggtact tcatgtcttt atcatggagg ccatcatagc ttgcagcctt tatgcagttc   1980
tgaacaagag gggactgggg ggtcccacta gcaccccacc taacctgatc agccaggagc   2040
agctggtgcg gaaggcggcc agcctgtgct accttctctc caatgaaggc accatctcac   2100
tgccttgcca gacattttac caagtctgcc atgaaacagt aggaaagttt atccagtatg   2160
gcattcttac agtggcagag cacgatgacc aggaagatat cagtcctagt cttgctgagc   2220
agcagtggga caagaagctt ccagaacctt tgtcttggag aagtgatgaa gaagatgaag   2280
acagtgactt tggggaggaa cagcgagatt gctacctgaa ggtgagccaa tccaaggagc   2340
accagcagtt tatcaccttc ttacagagac tccttgggcc tttgctggag gcctacagct   2400
ctgctgccat ctttgttcac aacttcagtg gtcctgttcc agaacctgag tatctgcaaa   2460
agttgcacaa atacctaata accagaacag aaagaaatgt tgcagtatat gctgagagtg   2520
ccacatattg tcttgtgaag aatgctgtga aaatgtttaa ggatattggg gttttcaagg   2580
agaccaaaca aaagagagtg tctgttttag aactgagcag cacttttcta cctcaatgca   2640
accgacaaaa acttctagaa tatattctga gttttgtggt gctgtaggta acgtgtggca   2700
ctgctggcaa atgaaggtca tgagatgagt tccttgtagg taccagcttc tggctcaaga   2760
gttgaaggtg ccatcgcagg gtcaggcctg ccctgtcccg aagtgatctc ctggaagaca   2820
agtgccttct ccctccatgg atctgtgatc ttcccagctc tgcatcaaca cagcagcctg   2880
cagataacac ttggggggac ctcagcctct attcgcaact cataatccgt agactacaag   2940
atgaaatctc aataaattat ttttgagttt attaaagatt gacattttaa gtacaacttt   3000
taaggactaa ttactgtgat ggacacagaa atgtagctgt gttctggaac tgaatcttac   3060
atggtatact tagtgctgct gggtaatttg ttggtatatt atctggttag tggttaatgc   3120
ttcctttaaa aataattgag tcatccattc actcttttc agttttatct gtcaatagta   3180
gctacatttt taatgggagc accttttatc ccaaagtgct ttataaattg agtggactga   3240
tatatatcac acccaggtat cactgtgctg tcctttgctg tcagatttag aaatgttttt   3300
aagagctatg tgaaaacaga caatattagt ttaggtcggg aactgagata ttgtaatcaa   3360
```

-continued

```
atagttaaca tcaggaagtt aatttggctg gcaaaattct agggaaactt ggccagaaaa   3420
ctggtgttga aggcttttgc tcatataaac aagtgccatt gagtttcaaa tgaccagcaa   3480
atatatttag aacccttcct gttttatgtc tgtacctcgt ccacccctca ggtaatacct   3540
gcctctcaca ggtacagctg tttcttggaa atcctccaac caaatagcag ttttcctaac   3600
ttgattagct tgagctgaca gactgttaga atacagttct ctggccacag ctgatgaggg   3660
ctttctgtac tgcacacaga ttgtgtactg caccccagtc caggtgactg gtacccactc   3720
gagttgtgcc gtgcacaacc tgtccagtat atgcatgtgg tggccctact gactggtaat   3780
ggttagaggc atttatggat ttttagcttt gaggaaaaac catgactttt aacaaatttt   3840
tatgggttat atgcctaaac ccttatgcca catagtggta aataattatg aaaaatggtc   3900
tgttcataat tggtaggtgc cttttgtgag cagggagcat aattattggt ttattatggt   3960
aattatggtg attttttaaa tatcatgtaa tgttaaaacg ttttctaaca gtttactgtt   4020
gcttatctcc aagatattat ggaattaaga atttttccag atgagtgtta catagattct   4080
ttgaatttag tataaaagta ctgagaatta agtttgtact tccataagct tggattttaa   4140
acactgatag tatctcatga gtaatgtgtg ttttgggaga gggagggatg ctgattgata   4200
tttcacattg tatgaaatac catgtttgaa actcatagca ataatgctat gctgttgtga   4260
tccctctcaa gttctgcatt taaaatatat tttttcttta taggaattga tgtataccat   4320
gaagtcattg tcagttgtag tagctctgat gttgaatgag atatcatgtt ttagcattcc   4380
attttactga ctagggtaga agaacacttt tcttggctac atttggagga tacccaggga   4440
gtcttgggtg ttccttatct ggggaagcaa acatttcact agtctctttt tttcatcctt   4500
taaattgtaa attaaggatt actcaagctc accattattc aagattggga ctcgcttccc   4560
agtcgacact ctgccctgcc tgtcattgct gcaaagagct gctgctttgc caacctaagc   4620
aaagaaaata cggcttctct tgcattattt tccctttttgg ttggtttgtt ttctagaagt   4680
acgttcagat gctttgggga atgcaatgta tgatttgcta gctctctcac cacttaactc   4740
actgtgagga taaatatgca tgctttttgt aattaactgg tgctttgaaa atcttttttta   4800
agggagaaaa atctcaacca aagttatgct catccagaca agctgacctt tgagttaatt   4860
tcagcacaac tcattcttca gtgcctcatg actgaaaaca aaaaacaaaa aaacgaaagc   4920
atcttcacaa tgaagcttcc agatagcacc gttttgctaa aagatacatt ctcattgttt   4980
tccaacagtg atggcttcca cataaggtta aacaaactag gtgcttgtaa ataatttatt   5040
acagtttact ctatcgcatt tctgtaacat gaaatgcatg cccttcttca ggggaagact   5100
gtggtcaagt taaaaaaaaa aaacaatatt aaacaacatg aaactgcagt ctgtttttga   5160
aaatgagaat gtcctaagtg attcagaaga gaggagggaa gttgtgcact ctgaaaatgc   5220
atgaaaaaca aaggcaaaaa ctagtgggaa atgtgtagaa ctgttaactg agatggcttc   5280
gagtcttcct tctggaatct gttaaatttc acaaagtcat gagggtaaat ggagaaaata   5340
tttctgggat tacaatgaat gtaagcccaa attgtggaat tgccagtaac ctggatgggg   5400
aaaagcattt cccatagcac tccatgtaat atgagtgctc tgtgagatgt tcatcagtgt   5460
tttatagaaa tggtgttgct gggaaaccaa gtttgcacct ggaaacttac aatgcacttt   5520
agcgcagtaa gggcttggca tccggtagtg aaaaactgtc taacccagca ttgcccaaac   5580
tattttgaca ccaggacctt tttctccttt gggatactta tgaacctctc actaatgtcc   5640
tgtggagaac attttgggaa acactatgtt agatagttct ttaaggagac aaaacggtaa   5700
```

-continued

```
tgaacagata gcactggggc agaatatgca tgcattttgt aacgtccagt gtggcgttga   5760

atagatgtgt atttcctccc ctgcagaaaa taagcacaga aaattataat gtaggtgatc   5820

ggagctcttt cctttgatag agagaacagc cccaatgatc ctggcttttt cactgaacgt   5880

atcagaatac atggatgaat tggggtaaat aaggttttaa ttcagatcta gaagaaagta   5940

ttgtacgttt gaatgcagat ttttatccac agatagttgt agtgtttaga catgacagga   6000

cctatcgttg aggtttctaa gacttactat gggctgtaaa cctgtttttt aaaactattt   6060

tagaaacctg agacttgccg tctggcattt tagtttaata caaactaatg attgcatttg   6120

aaagagattc ttgaccttat ttctaaacgt ctagagctct gaaatgtctt gatggaaggt   6180

attaaactat ttgcctgttg tacaaagaaa tgttaagact cgtgaaaaga attactataa   6240

ggtactgtga aataactgcg attttgtgag caaaacatac ttggaaatgc tgattgattt   6300

ttatgcttgt tagtgtattg caagaaacac agaaaatgta gttttgtttt aataaaccaa   6360

aaattgaaca ta                                                        6372
```

```
<210> SEQ ID NO 16
<211> LENGTH: 5664
<212> TYPE: DNA
<213> ORGANISM: homo sapien

<400> SEQUENCE: 16

gaagctggag ctgctagggt gcgaactgcc agggcaggca gcagcggctc ccctgttgta     60

tggacattct gcacccgaaa ctgatagctg agtcctgaag ttttatgtta tgaaacagaa    120

gaactttcat cccagcacat gatttgggaa ttacactttg tgacatggat gaatctgcac    180

tgacccttgg tacaatagat gtttcttatc tgccacattc atcagaatac agtgttggtc    240

gatgtaagca cacaagtgag gaatggggtg agtgtggctt tagacccacc atcttcagat    300

ctgcaacttt aaaatggaaa gaaagcctaa tgagtcggaa aaggccattt gttggaagat    360

gttgttactc ctgcactccc cagagctggg acaaattttt caaccccagt atcccgtctt    420

tgggtttgcg gaatgttatt tatatcaatg aaactcacac aagacaccgc ggatggcttg    480

caagacgcct ttcttacgtt ctttttattc aagagcgaga tgtgcataag ggcatgtttg    540

ccaccaatgt gactgaaaat gtgctgaaca gcagtagagt acaagaggca attgcagaag    600

tggctgctga attaaaccct gatggttctg cccagcagca atcaaaagcc gttaacaaag    660

tgaaaaagaa agctaaaagg attcttcaag aaatggttgc cactgtctca ccggcaatga    720

tcagactgac tgggtgggtg ctgctaaaac tgttcaacag cttcttttgg aacattcaaa    780

ttcacaaagg tcaacttgag atggttaaag ctgcaactga gacgaatttg ccgcttctgt    840

ttctaccagt tcatagatcc catattgact atctgctgct cactttcatt ctcttctgcc    900

ataacatcaa agcaccatac attgcttcag gcaataatct caacatccca atcttcagta    960

ccttgatcca taagcttggg ggcttcttca tacgacgaag gctcgatgaa acaccagatg   1020

gacggaaaga tgttctctat agagctttgc tccatgggca tatagttgaa ttacttcgac   1080

agcagcaatt cttggagatc ttcctggaag gcacacgttc taggagtgga aaaacctctt   1140

gtgctcgggc aggacttttg tcagttgtgg tagatactct gtctaccaat gtcatcccag   1200

acatcttgat aatacctgtt ggaatctcct atgatcgcat tatcgaaggt cactacaatg   1260

gtgaacaact gggcaaacct aagaagaatg agagcctgtg gagtgtagca agaggtgtta   1320

ttagaatgtt acgaaaaaac tatggttgtg tccgagtgga ttttgcacag ccattttcct   1380

taaaggaata tttagaaagc caaagtcaga aaccggtgtc tgctctactt tccctggagc   1440
```

-continued

```
aagcgttgtt accagctata cttccttcaa gacccagtga tgctgctgat gaaggtagag   1500
acacgtccat taatgagtcc agaaatgcaa cagatgaatc cctacgaagg aggttgattg   1560
caaatctggc tgagcatatt ctattcactg ctagcaagtc ctgtgccatt atgtccacac   1620
acattgtggc ttgcctgctc ctctacagac acaggcaggg aattgatctc tccacattgg   1680
tcgaagactt ctttgtgatg aaagaggaag tcctggctcg tgattttgac ctggggttct   1740
caggaaattc agaagatgta gtaatgcatg ccatacagct gctgggaaat tgtgtcacaa   1800
tcacccacac tagcaggaac gatgagtttt ttatcacccc cagcacaact gtcccatcag   1860
tcttcgaact caacttctac agcaatgggg tacttcatgt ctttatcatg gaggccatca   1920
tagcttgcag cctttatgca gttctgaaca agaggggact ggggggtccc actagcaccc   1980
cacctaacct gatcagccag gagcagctgg tgcggaaggc ggccagcctg tgctaccttc   2040
tctccaatga aggcaccatc tcactgcctt gccagacatt ttaccaagtc tgccatgaaa   2100
cagtaggaaa gtttatccag tatggcattc ttacagtggc agagcacgat gaccaggaag   2160
atatcagtcc tagtcttgct gagcagcagt gggacaagaa gcttccagaa cctttgtctt   2220
ggagaagtga tgaagaagat gaagacagtg actttgggga ggaacagcga gattgctacc   2280
tgaaggtact tgggtgaaga attctggtgg atattacagg gatatgttga ggtttatgct   2340
gcagtgagat cagctggagt cctggtgatg tcttcttatc taaagaatcc cccaactagc   2400
tctggtacct tctgtgtggt aaagacactc aaactgtttg agttgaatta atagcatttt   2460
aagtagaaaa ggaaaggaga gtctgaaaag tcaggaagat gaatgtcata ggtgagactt   2520
tcaccatcct tttatgaaat acacaggtgc atacctgttt acctacacct gcacccctca   2580
tgaggcagca gttttgctat tgagctgcca ctgacctggc tgctcttttt gagtcactct   2640
tgctgtccct cccaaaattt catatattaa gctctttgct gtcaattaaa acaaatacca   2700
ttataggaga aaattgagat taaaaaaaaa gtccctgatt tagaaaaatc aattttgtct   2760
aatttataat tttagaactt agtaataatg acccgtcttt tctgaatact ctaagaggat   2820
tactcttttt tgacatttag aaattgtctt ctttttcact tgggtggtat tagtttagtt   2880
tcaagatggg gcagtgatct tgctttcaca ctccagaggg gcttgaccga accagtgtgt   2940
tttgggtagg tacagtgaga gcctctcggc cataaagcac cgccgtcaca gtggccatca   3000
ttccccacag tgctggactg tgggcaaagg ccatttaggg gaggcaggga ataggtgctg   3060
cagaaggagt gagataatct tggtggtctc ccattggtct ttctgcagac ttgagtgact   3120
gttgagccca ggcttcaaac catggagggc ctggtcttag gagcggctat ttttagtgat   3180
gacagcgtat cacaagtagg gcattcattt atgaaaattt cttctaggtg gctgttcaat   3240
gaacacaagc ctcaaatacc ataaaaaagt gaatgattac aataaagaat gtgtttgaaa   3300
gccagcagtt gtttccagca gagattctct gcatgagggg caggggggccg ctttcatgta   3360
gtgctgatgt gagtggccat cttctcacgt tactggctct ccagagaaag tcctctgtcc   3420
acttgccttg tgtctcttgt cccttcctca tgacttcatc tcctgctttt gcacactcag   3480
gtgagccaat ccaaggagca ccagcagttt atcaccttct tacagagact ccttgggcct   3540
ttgctggagg cctacagctc tgctgccatc tttgttcaca acttcagtgg tcctgttcca   3600
gaacctgagt atctgcaaaa gttgcacaaa tacctaataa ccagaacaga aagaaatgtt   3660
gcagtatatg gtatgttaag tcactattta ttcttttaaa atcttttttt tttttttgga   3720
tttcagaaat ttgctaattg tagaaaattg gaaaaatgca aacttatcct gacctctaac   3780
```

accgtagagt attactatta tcttctttgg catgttatat aagttgaatg atacagttat 3840
acactcttac atctggcttt tttcacgtaa cgttattttt gagattcata catgttgcat 3900
atagttgttc ctttgttctt gttgtgtagt gttccattgt ataaatattt accacatttt 3960
attcattctg ctgttgatgg atatttgggt tgttttcagt tcacagctgc tttgaacagt 4020
gttgctatga gcatatttga atatgtcttt tggtgaatat ctgtgcccct atatacagca 4080
tgtatgtggg aacagaattg cctggttgta ggctctgggt atattcggct ttggtagata 4140
ccaccaaaca gtttccaagg gattatacct acttgtactc ccacaacagt gtgtgtttca 4200
cttgctgcac atcttggcca gcgctccgtc ttctttgttt taggaggtgt gattggggtg 4260
ggagtactat tttatacagt tgtagtttgg agctgaaact acttgaatca ctttttagag 4320
ccaaaaggaa tctaatctaa tcacctcatt ttatagttga ggaaaatacc ccaggtcaca 4380
ctgctaatta atgggtaatc tcgggatcag aattcttgtt tcctaacctc gaggcctgtg 4440
ctttctctgg ttccactgat gtacaatcat ctgtgtacca ctgggtagct taaagaatat 4500
ttatacacta tctcatttga ttctcacaac agtcctggaa aatggatgtt ttaggtattt 4560
ctacttccct ctgttctccc tatttctctc tctacaccct cttttctttc cccttccctt 4620
tcttatttac ctcaatatag gacaaagtag gtgtaagcaa agtaggttta acagcaagtc 4680
atctgagaac tcacaggttg ccagtggtgg aagtggggcc ccacccttgt ctgctgactt 4740
gccctcattc tcttcctagc tccccatact ttcttactgt ggctgctggg attgtcatga 4800
tttgttgagc gtaaccattt gacagggttt tattctctct cttcagctga gagtgccaca 4860
tattgtcttg tgaagaatgc tgtgaaaatg tttaaggata ttggggtagg tgtccaccat 4920
ttatggtata aaagctatct caacttctgt tctctttaga tctagtctgt ttgagctacc 4980
tttgtggtgg ggtggacccc gagagaagca gtttctgctg gcttaatgat aaaggcattt 5040
ttgggaacgg ggcatgtagg atgggttggg ctatgttgaa ggtgaagccc atcagtgtag 5100
atttatttga atgttctgga attttactgg tttcacattt attcccaagc tgctatatat 5160
aactggtatc aatatgtttc aaggtgctac aggttgaata tcccttatcc aaaatgttgg 5220
gaccagaaat gttttggatt tcagattttt ttgggatttt ggaatatgtg cattagactt 5280
acaggttgag cgtctctaat ccaaaaccca aaatgctctg atgagcatgt cttttgagca 5340
tcatattgat gttcaaaatc tttcagattt tggagtactt cagatttttg attttgggat 5400
taggaccaca atcttggctc ttaattattc catatgattt ttagttactt tcttgtattt 5460
ttacaagaat ttctagaagt atcctcaggt gtcctttacc ttcatgattc atggggaatg 5520
taagttctat agagatacta gcggcctttt gtgagggact gtttgtgact ttattctaag 5580
tcattttaga gtatagttat gttggttgaa attttagaat atagttaatg ttggttgaac 5640
tccatcaaaa caaaaaaaaa aaaa 5664

<210> SEQ ID NO 17
<211> LENGTH: 6368
<212> TYPE: DNA
<213> ORGANISM: homo sapien

<400> SEQUENCE: 17
gcgccactgc agctggcatt ggccgggact ggaagtgcgg gcttctgcag cagccgaagc 60
tggagctgct aggcagcggc tcccctgttg tatggacatt ctgcacccga aactgatagc 120
tgagtcctga agttttatgt tatgaaacag aagaactttc atcccagcac atgatttggg 180
aattacactt tgtgacatgg atgaatctgc actgaccctt ggtacaatag atgtttctta 240

-continued

```
tctgccacat tcatcagaat acagtgttgg tcgatgtaag cacacaagtg aggaatgggg    300
tgagtgtggc tttagaccca ccatcttcag atctgcaact ttaaaatgga aagaaagcct    360
aatgagtcgg aaaaggccat ttgttggaag atgttgttac tcctgcactc cccagagctg    420
ggacaaattt ttcaacccca gtatcccgtc tttgggtttg cggaatgtta tttatatcaa    480
tgaaactcac acaagacacc gcggatggct tgcaagacgc ctttcttacg ttctttttat    540
tcaagagcga gatgtgcata agggcatgtt tgccaccaat gtgactgaaa atgtgctgaa    600
cagcagtaga gtacaagagg caattgcaga agtggctgct gaattaaacc ctgatggttc    660
tgcccagcag caatcaaaag ccgttaacaa agtgaaaaag aaagctaaaa ggattcttca    720
agaaatggtt gccactgtct caccggcaat gatcagactg actgggtggg tgctgctaaa    780
actgttcaac agcttctttt ggaacattca aattcacaaa ggtcaacttg agatggttaa    840
agctgcaact gagacgaatt tgccgcttct gtttctacca gttcatagat cccatattga    900
ctatctgctg ctcactttca ttctcttctg ccataacatc aaagcaccat acattgcttc    960
aggcaataat ctcaacatcc caatcttcag taccttgatc cataagcttg gggcttctt    1020
catacgacga aggctcgatg aaacaccaga tggacggaaa gatgttctct atagagcttt   1080
gctccatggg catatagttg aattacttcg acagcagcaa ttcttggaga tcttcctgga   1140
aggcacacgt tctaggagtg gaaaaacctc ttgtgctcgg gcaggacttt tgtcagttgt   1200
ggtagatact ctgtctacca atgtcatccc agacatcttg ataatacctg ttggaatctc   1260
ctatgatcgc attatcgaag gtcactacaa tggtgaacaa ctgggcaaac ctaagaagaa   1320
tgagagcctg tggagtgtag caagaggtgt tattagaatg ttacgaaaaa actatggttg   1380
tgtccgagtg gattttgcac agccattttc cttaaaggaa tatttagaaa gccaaagtca   1440
gaaaccggtg tctgctctac tttccctgga gcaagcgttg ttaccagcta tacttccttc   1500
aagacccagt gatgctgctg atgaaggtag agacacgtcc attaatgagt ccagaaatgc   1560
aacagatgaa tccctacgaa ggaggttgat tgcaaatctg gctgagcata ttctattcac   1620
tgctagcaag tcctgtgcca ttatgtccac acacattgtg gcttgcctgc tcctctacag   1680
acacaggcag ggaattgatc tctccacatt ggtcgaagac ttctttgtga tgaaagagga   1740
agtcctggct cgtgattttg acctggggtt ctcaggaaat tcagaagatg tagtaatgca   1800
tgccatacag ctgctgggaa attgtgtcac aatcacccac actagcagga acgatgagtt   1860
ttttatcacc cccagcacaa ctgtcccatc agtcttcgaa ctcaacttct acagcaatgg   1920
ggtacttcat gtctttatca tggaggccat catagcttgc agcctttatg cagttctgaa   1980
caagagggga ctggggggtc ccactagcac cccacctaac ctgatcagcc aggagcagct   2040
ggtgcggaag gcggccagcc tgtgctacct tctctccaat gaaggcacca tctcactgcc   2100
ttgccagaca ttttaccaag tctgccatga aacagtagga aagtttatcc agtatggcat   2160
tcttacagtg gcagagcacg atgaccagga agatatcagt cctagtcttg ctgagcagca   2220
gtgggacaag aagcttccag aacctttgtc ttggagaagt gatgaagaag atgaagacag   2280
tgactttggg gaggaacagc gagattgcta cctgaaggtg agccaatcca aggagcacca   2340
gcagtttatc accttcttac agagactcct tgggcctttg ctggaggcct acagctctgc   2400
tgccatcttt gttcacaact tcagtggtcc tgttccagaa cctgagtatc tgcaaaagtt   2460
gcacaaatac ctaataacca gaacagaaag aaatgttgca gtatatgctg agagtgccac   2520
atattgtctt gtgaagaatg ctgtgaaaat gtttaaggat attggggttt tcaaggagac   2580
```

-continued

```
caaacaaaag agagtgtctg ttttagaact gagcagcact tttctacctc aatgcaaccg   2640
acaaaaactt ctagaatata ttctgagttt tgtggtgctg taggtaacgt gtggcactgc   2700
tggcaaatga aggtcatgag atgagttcct tgtaggtacc agcttctggc tcaagagttg   2760
aaggtgccat cgcagggtca ggcctgccct gtcccgaagt gatctcctgg aagacaagtg   2820
ccttctccct ccatggatct gtgatcttcc cagctctgca tcaacacagc agcctgcaga   2880
taacacttgg ggggacctca gcctctattc gcaactcata atccgtagac tacaagatga   2940
aatctcaata aattattttt gagtttatta aagattgaca ttttaagtac aacttttaag   3000
gactaattac tgtgatggac acagaaatgt agctgtgttc tggaactgaa tcttacatgg   3060
tatacttagt gctgctgggt aatttgttgg tatattatct ggttagtggt taatgcttcc   3120
tttaaaaata attgagtcat ccattcactc tttttcagtt ttatctgtca atagtagcta   3180
catttttaat gggagcacct tttatcccaa agtgctttat aaattgagtg gactgatata   3240
tatcacaccc aggtatcact gtgctgtcct ttgctgtcag atttagaaat gtttttaaga   3300
gctatgtgaa aacagacaat attagtttag gtcgggaact gagatattgt aatcaaatag   3360
ttaacatcag gaagttaatt tggctggcaa aattctaggg aaacttggcc agaaaactgg   3420
tgttgaaggc ttttgctcat ataaacaagt gccattgagt ttcaaatgac cagcaaatat   3480
atttagaacc cttcctgttt tatgtctgta cctcgtccac ccctcaggta atacctgcct   3540
ctcacaggta cagctgtttc ttggaaatcc tccaaccaaa tagcagtttt cctaacttga   3600
ttagcttgag ctgacagact gttagaatac agttctctgg ccacagctga tgagggcttt   3660
ctgtactgca cacagattgt gtactgcacc ccagtccagg tgactggtac ccactcgagt   3720
tgtgccgtgc acaacctgtc cagtatatgc atgtggtggc cctactgact ggtaatggtt   3780
agaggcattt atggattttt agctttgagg aaaaaccatg acttttaaca aatttttatg   3840
ggttatatgc ctaaaccctt atgccacata gtggtaaata attatgaaaa atggtctgtt   3900
cataattggt aggtgccttt tgtgagcagg gagcataatt attggtttat tatggtaatt   3960
atggtgattt tttaaatatc atgtaatgtt aaaacgtttt ctaacagttt actgttgctt   4020
atctccaaga tattatggaa ttaagaattt ttccagatga gtgttacata gattctttga   4080
atttagtata aaagtactga gaattaagtt tgtacttcca taagcttgga ttttaaacac   4140
tgatagtatc tcatgagtaa tgtgtgtttt gggagaggga gggatgctga ttgatatttc   4200
acattgtatg aaataccatg tttgaaactc atagcaataa tgctatgctg ttgtgatccc   4260
tctcaagttc tgcatttaaa atatattttt tctttatagg aattgatgta taccatgaag   4320
tcattgtcag ttgtagtagc tctgatgttg aatgagatat catgttttag cattccattt   4380
tactgactag ggtagaagaa cacttttctt ggctacattt ggaggatacc cagggagtct   4440
tgggtgttcc ttatctgggg aagcaaacat ttcactagtc tcttttttttc atcctttaaa   4500
ttgtaaatta aggattactc aagctcacca ttattcaaga ttgggactcg cttcccagtc   4560
gacactctgc cctgcctgtc attgctgcaa agagctgctg ctttgccaac ctaagcaaag   4620
aaaatacggc ttctcttgca ttattttccc ttttggttgg tttgttttct agaagtacgt   4680
tcagatgctt tggggaatgc aatgtatgat ttgctagctc tctcaccact taactcactg   4740
tgaggataaa tatgcatgct ttttgtaatt aactggtgct ttgaaaatct tttttaaggg   4800
agaaaaatct caaccaaagt tatgctcatc cagacaagct gacctttgag ttaatttcag   4860
cacaactcat tcttcagtgc ctcatgactg aaaacaaaaa acaaaaaaac gaaagcatct   4920
tcacaatgaa gcttccagat agcaccgttt tgctaaaaga tacattctca ttgttttcca   4980
```

acagtgatgg cttccacata aggttaaaca aactaggtgc ttgtaaataa tttattacag 5040
tttactctat cgcatttctg taacatgaaa tgcatgccct tcttcagggg aagactgtgg 5100
tcaagttaaa aaaaaaaaac aatattaaac aacatgaaac tgcagtctgt ttttgaaaat 5160
gagaatgtcc taagtgattc agaagagagg agggaagttg tgcactctga aaatgcatga 5220
aaaacaaagg caaaaactag tgggaaatgt gtagaactgt taactgagat ggcttcgagt 5280
cttccttctg gaatctgtta aatttcacaa agtcatgagg gtaaatggag aaaatatttc 5340
tgggattaca atgaatgtaa gcccaaattg tggaattgcc agtaacctgg atggggaaaa 5400
gcatttccca tagcactcca tgtaatatga gtgctctgtg agatgttcat cagtgtttta 5460
tagaaatggt gttgctggga aaccaagttt gcacctggaa acttacaatg cactttagcg 5520
cagtaagggc ttggcatccg gtagtgaaaa actgtctaac ccagcattgc ccaaactatt 5580
ttgacaccag gaccttttc tcctttggga tacttatgaa cctctcacta atgtcctgtg 5640
gagaacattt tgggaaacac tatgttagat agttctttaa ggagacaaaa cggtaatgaa 5700
cagatagcac tggggcagaa tatgcatgca ttttgtaacg tccagtgtgg cgttgaatag 5760
atgtgtattt cctcccctgc agaaaataag cacagaaaat tataatgtag gtgatcggag 5820
ctctttcctt tgatagagag aacagcccca atgatcctgg ctttttcact gaacgtatca 5880
gaatacatgg atgaattggg gtaaataagg ttttaattca gatctagaag aaagtattgt 5940
acgtttgaat gcagattttt atccacagat agttgtagtg tttagacatg acaggaccta 6000
tcgttgaggt ttctaagact tactatgggc tgtaaacctg ttttttaaaa ctattttaga 6060
aacctgagac ttgccgtctg gcattttagt ttaatacaaa ctaatgattg catttgaaag 6120
agattcttga ccttatttct aaacgtctag agctctgaaa tgtcttgatg gaaggtatta 6180
aactatttgc ctgttgtaca aagaaatgtt aagactcgtg aaaagaatta ctataaggta 6240
ctgtgaaata actgcgattt tgtgagcaaa acatacttgg aaatgctgat tgatttttat 6300
gcttgttagt gtattgcaag aaacacagaa aatgtagttt tgttttaata aaccaaaaat 6360
tgaacata 6368

<210> SEQ ID NO 18
<211> LENGTH: 4918
<212> TYPE: DNA
<213> ORGANISM: homo sapien

<400> SEQUENCE: 18
ggccactgca gctggcattg gccgggactg gaagtgcggg cttctgcagc agccgaagct 60
ggagctgcta gggcagcagc ggctcccctg ttgtatggac attctgcacc cgaaactgat 120
agctgagtcc tgaagtttta tgttatgaaa cagaagaact ttcatcccag cacatgattt 180
gggaattaca ctttgtgaca tggatgaatc tgcactgacc cttggtacaa tagatgtttc 240
ttatctgcca cattcatcag aatacagtgt tggtcgatgt aagcacacaa gtgaggaatg 300
gggtgagtgt ggctttagac ccaccatctt cagatctgca actttaaaat ggaaagaaag 360
cctaatgagt cggaaaaggc catttgttgg aagatgttgt tactcctgca ctccccagag 420
ctgggacaaa tttttcaacc ccagtatccc gtctttgggt ttgcggaatg ttatttatat 480
caatgaaact cacacaagac accgcggatg gcttgcaaga cgcctttctt acgttctttt 540
tattcaagag cgagatgtgc ataagggcat gtttgccacc aatgtgactg aaaatgtgct 600
gaacagcagt agagtacaag aggcaattgc agaagtggct gctgaattaa accctgatgg 660

-continued

```
ttctgcccag cagcaatcaa aagccgttaa caaagtgaaa aagaaagcta aaaggattct    720
tcaagaaatg gttgccactg tctcaccggc aatgatcaga ctgactgggt gggtgctgct    780
aaaactgttc aacagcttct tttggaactt tcaaattcac aaaggtcaac ttgagatggt    840
taaagctgca actgagacga atttgccgct tctgtttcta ccagttcata gatcccatat    900
tgactatctg ctgctcactt tcattctctt ctgccataac atcaaagcac catacattgc    960
ttcaggcaat aatctcaaca tcccaatctt cagtaccttg atccataagc ttgggggctt   1020
cttcatacga cgaaggctcg atgaaacacc agatggacgg aaagatgttc tctatagagc   1080
tttgctccat gggcatatag ttgaattact tcgacagcag caattcttgg agatcttcct   1140
ggaaggcaca cgttctagga gtggaaaaac ctcttgtgct cgggcaggac ttttgtcagt   1200
tgtggtagat actctgtcta ccaatgtcat cccagacatc ttgataatac ctgttggaat   1260
ctcctatgat cgcattatcg aaggtcacta caatggtgaa caactgggca aacctaagaa   1320
gaatgagagc ctgtggagtg tagcaagagg tgttattaga atgttacgaa aaaactatgg   1380
ttgtgtccga gtggattttg cacagccatt ttccttaaag gaatatttag aaagccaaag   1440
tcagaaaccg gtgtctgctc tactttccct ggagcaagcg ttgttaccag ctatacttcc   1500
ttcaagaccc agtgatgctg ctgatgaagg tagagacacg tccattaatg agtccagaaa   1560
tgcaacagat gaatccctac gaaggaggtt gattgcaaat ctggctgagc atattctatt   1620
cactgctagc aagtcctgtg ccattatgtc cacacacatt gtggcttgcc tgctcctcta   1680
cagacacagg cagggaattg atctctccac attggtcgaa gacttctttg tgatgaaaga   1740
ggaagtcctg gctcgtgatt ttgacctggg gttctcagga aattcagaag atgtagtaat   1800
gcatgccata cagctgctgg gaaattgtgt cacaatcacc cacactagca ggaacgatga   1860
gtttttttatc acccccagca caactgtccc atcagtcttc gaactcaact tctacagcaa   1920
tggggtactt catgtcttta tcatggaggc catcatagct tgcagccttt atgcagttct   1980
gaacaagagg ggactggggg gtcccactag caccccacct aacctgatca gccaggagca   2040
gctggtgcgg aaggcggcca gcctgtgcta ccttctctcc aatgaaggca ccatctcact   2100
gccttgccag acattttacc aagtctgcca tgaaacagta ggaaagttta tccggtatgg   2160
cattcttaca gtggcagagc acgatgacca ggaagatatc agtcctagtc ttgctgagca   2220
gcagtgggac aagaagcttc cagaaccttt gtcttggaga agtgatgaag aagatgaaga   2280
cagtgacttt ggggaggaac agcgagattg ctacctgaag gtgagccaat ccaaggagca   2340
ccagcagttt atcaccttct tacagagact ccttgggcct ttgctggagg cctacagctc   2400
tgctgccatc tttgttcaca acttcagtgg tcctgttcca gaacctgagt atctgcaaaa   2460
gttgcacaaa tacctaataa ccagaacaga aagaaatgtt gcagtatatg ctgagagtgc   2520
cacatattgt cttgtgaaga atgctgtgaa aatgtttaag gatattgggg ttttcaagga   2580
gaccaaacaa aagagagtgt ctgttttaga actgagcagc acttttctac ctcaatgcaa   2640
ccgacaaaaa cttctagaat atattctgag ttttgtggtg ctgtaggtaa cgtgtggcac   2700
tgctggcaaa tgaaggtcat gagatgagtt ccttgtaggt accagcttct ggctcaagag   2760
ttgaaggtgc catcgcaggg tcaggcctgc cctgtcccga agtgatctcc tggaagacaa   2820
gtgccttctc cctccatgga tctgtgatct tcccagctct gcatcaacac agcagcctgc   2880
agataacact tggggggacc tcagcctcta ttcgcaactc ataatccgta gactacaaga   2940
tgaaatctca ataaattatt tttgagttta ttaaagattg acattttaag tacaactttt   3000
aaggactaat tactgtgatg gacacagaaa tgtagctgtg ttctggaact gaatcttaca   3060
```

-continued tggtatactt agtgctgctg ggtaatttgt tggtatatta tctggttagt ggttaatgct 3120
tcctttaaaa ataattgagt catccattca ctctttttca gttttatctg tcaatagtag 3180
ctacattttt aatgggagca ccttttatcc caaagtgctt tataaattga gtggactgat 3240
atatatcaca cccaggtatc actgtgctgt cctttgctgt cagatttaga aatgttttta 3300
agagctatgt gaaaacagac aatattagtt taggtcggga actgagatat tgtaatcaaa 3360
tagttaacat caggaagtta atttggctgg caaaattcta gggaaacttg gccagaaaac 3420
tggtgttgaa ggcttttgct catataaaca agtgccattg agtttcaaat gaccagcaaa 3480
tatatttaga acccttcctg ttttatgtct gtacctcgtc cacccctcag gtaatacctg 3540
cctctcacag gtacagctgt ttcttggaaa tcctccaacc aaatagcagt tttcctaact 3600
tgattagctt gagctgacag actgttagaa tacagttctc tggccacagc tgatgagggc 3660
tttctgtact gcacacagat tgtgtactgc accccagtcc aggtgactgg tacccactcg 3720
agttgtgccg tgcacaacct gtccagtata tgcatgtggt ggccctactg actggtaatg 3780
gttagaggca tttatggatt tttagctttg aggaaaaacc atgactttta acaaattttt 3840
atgggttata tgcctaaacc cttatgccac atagtggtaa ataattatga aaaatggtct 3900
gttcataatt ggtaggtgcc ttttgtgagc agggagcata attattggtt tattatggta 3960
attatggtga ttttttaaat atcatgtaat gttaaaacgt tttctaacag tttactgttg 4020
cttatctcca agatattatg gaattaagaa tttttccaga tgagtgttac atagattctt 4080
tgaatttagt ataaaagtac tgagaattaa gtttgtactt ccataagctt ggattttaaa 4140
cactgatagt atctcatgag taatgtgtgt tttgggagag ggagggatgc tgattgatat 4200
ttcacattgt atgaaatacc atgtttgaaa ctcatagcaa taatgctatg ctgttgtgat 4260
ccctcccaag ttctgcattt aaaatatatt ttttctttat aggaattgat gtataccatg 4320
aagtcattgt cagttgtagt agctctgatg ttgaatgaga tatcatgttt tagcattcca 4380
ttttactgac tagggtagaa gaacactctt cttggctaca tttggaggat acccagggag 4440
tcttgggtgt tccttatctg gggaagcaaa catttcacta gtctcttttt ttcatccttt 4500
aaattgtaaa ttaaggatta ctcaagctca ccattattca agattgggac tcgcttccca 4560
gtcgacactc tgccctgcct gtcattgctg caaagagctg ctgctttgcc aacctaagca 4620
aagaaaatac ggcttctctt gcattatttt ccccttttggt tggtttgttt tctagaagta 4680
cgttcagatg ctttggggaa tgcaatgtat gatttgctag ctctctcacc acttaactca 4740
ctgtgaggat aaatatgcat gctttttgta attaactggt gctttgaaaa tcttttttaa 4800
gggagaaaaa tctcaaccaa agttatgctc atccagacaa gctgaccttt gagttaattt 4860
cagcacaact cattcttcag tgcctcatga ctgaaaacaa aaaaaaaaaa aaaaaaa 4918

<210> SEQ ID NO 19
<211> LENGTH: 3490
<212> TYPE: DNA
<213> ORGANISM: homo sapien

<400> SEQUENCE: 19
agcgggctgg aagtgcgggc ttctgcagca gccgaagctg gagctgctag ggcagcagcg 60
gctcccctgt tgtatggaca ttctgcaccc gaaactgata gctgagtcct gaagttttat 120
gttatgaaac agaagaactt tcatcccagc acatgatttg ggaattacac tttgtgacat 180
ggatgaatat gcactgaccc ttggtacaat agatgtttct tatctgccac attcatcaga 240

-continued

```
atacagtgtt ggtcgatgta agcacacaag tgaggaatgg ggtgagtgtg gctttagacc    300
caccatcttc agatctgcaa ctttaaaatg gaaagaaagc ctaatgagtc ggaaaaggcc    360
atttgttgga agatgttgtt actcctgcac tccccagagc tgggacaaat ttttcaacac    420
cagtatcccg tctttgggtt tgcggaatgt tatttatatc aatgaaactc acacaagaca    480
ccgcggatgg cttgcaagac gcctttctta cgttcttttt attcaagagc gagatgtgca    540
taagggcatg tttgccacca atgtgactga aaatgtgctg aacagcagta gagtacaaga    600
ggcaattgca gaagtggctg ctgaattaaa ccctgatggt tctgcccagc agcaatcaaa    660
agccgttaac aaagtgaaaa agaaagctaa aaggattctt caagaaatgg ttgccactgt    720
ctcaccggca atgatcagac tgactgggtg ggtgctgcta aaactgttca acagcttctt    780
ttggaacatt caaattcaca aaggtcaact tgagatggtt aaagctgcaa ctgagacgaa    840
tttgccgctt ctgtttctac cagttcatag atcccatatt gactatctgc tgctcacttt    900
cattctcttc tgccataaca tcaaagcacc atacattgct tcaggcaata atctcaacat    960
cccaatcttc agtaccttga tccataagct tgggggcttc ttcatacgac gaaggctcga   1020
tgaaacacca gatggacgga aagatgttct ctatagagct ttgctccatg ggcatatagt   1080
tgaattactt cgacagcagc aattcttgga gatcttcctg gaaggcacac gttctaggag   1140
tggaaaaacc tcttgtgctc gggcaggact tttgtcagtt gtggtagata ctctgtctac   1200
caatgtcatc ccagacatct tgataatacc tgttggaatc tcctatgatc gcattatcga   1260
aggtcactac aatggtgaac aactgggcaa acctaagaag aatgagagcc tgtggagtgt   1320
agcaagaggt gttattagaa tgttacgaaa aaactatggt tgtgtccgag tggattttgc   1380
acagccattt tccttaaagg aatatttaga aagccaaagt cagaaaccgg tgtctgctct   1440
actttccctg gagcaagcgt tgttaccagc tatacttcct tcaagaccca gtgatgctgc   1500
tgatgaaggt agagacacgt ccattaatga gtccagaaat gcaacagatg aatccctacg   1560
aaggaggttg attgcaaatc tggctgagca tattctattc actgctagca agtcctgtgc   1620
cattatgtcc acacacattg tggcttgcct gctcctctac agacacaggc agggaattga   1680
tctctccaca ttggtcgaag acttctttgt gatgaaagag gaagtcctgg ctcgtgattt   1740
tgacctgggg ttctcaggaa attcagaaga tgtagtaatg catgccatac agctgctggg   1800
aaattgtgtc acaatcaccc acactagcag gaacgatgag ttttttatca cccccagcac   1860
aactgtccca tcagtcttcg aactcaactt ctacagcaat ggggtacttc atgtctttat   1920
catggaggcc atcatagctt gcagccttta tgcagttctg aacaagaggg gactgggggg   1980
tcccactagc accccaccta acctgatcag ccaggagcag ctggtgcgga aggcggccag   2040
cctgtgctac cttctctcca atgaaggcac catctcactg ccttgccaga catttttacca   2100
agtctgccat gaaacagtag gaaagtttat ccagtatggc attcttacag tggcagagca   2160
cgatgaccag gaagatatca gtcctagtct tgctgagcag cagtgggaca agaagcttcc   2220
agaacctttg tcttggagaa gtgatgaaga agatgaagac agtgactttg gggaggaaca   2280
gcgagattgc tacctgaagg tgagccaatc caaggagcac cagcagttta tcaccttctt   2340
acagagactc cttgggcctt tgctggaggc ctacagctct gctgccatct ttgttcacaa   2400
cttcagtggt cctgttccag aacctgagta tctgcaaaag ttgcacaaat acctaataac   2460
cagaacagaa agaaatgttg cagtatatgc tgagagtgcc acatattgtc ttgtgaagaa   2520
tgctgtgaaa atgtttaagg atattggggt tttcaaggag accaaacaaa agagagtgtc   2580
tgttttagaa ctgagcagca cttttctacc tcaatgcaac cgacaaaaac ttctagaata   2640
```

-continued tattctgagt tttgtggtgc tgtaggtaac gtgtggcact gctggcaaat gaaggtcatg 2700
agatgagttc cttgtaggta caagcttctg gctcaagagt tgaaggtgcc atcgcagggt 2760
caggcctgcc ctgtcccgaa gtgatctcct ggaagacaag tgccttctcc atccatggat 2820
ctgtgatctt cccagctctg catcaacaca gcagcctgca gataacactt ggggggacct 2880
cagcctctat tcgcaactca taatccgtag actacaagat gaaatctcaa taaattattt 2940
ttgagtttat taaagattga cattttaagt acaactttta aggactaatt actgtgatgg 3000
acacagaaat gtagctgtgt tctggaactg aatcttacat ggtatactta gtgctgctgg 3060
gtaatttgtt ggtatattat ctggttagtg gttaatgctt cctttaaaaa taattgagtc 3120
atccattcac tctttttcag ttttatctgt caatagtagc tacattttta atgggagcac 3180
cttttatccc aaagtgcttt ataaattgag tggactgata tatatcacac ccaggtatca 3240
ctgtgctgtc ctttgctgtc agatttagaa atgtttttaa gagctatgtg aaaacagaca 3300
atattagttt aggtcgggaa ctgagatatt gtaatcaaat agttaacatc aggaagttaa 3360
tttggctggc aaaattctag ggaaacttgg ccagaaaact ggtgttgaag gcttttgctc 3420
atataaacaa gtgccattga gtttcaaatg accagcaaat atatttagaa ctcaaaaaaa 3480
aaaaaaaaaa 3490

<210> SEQ ID NO 20
<211> LENGTH: 2855
<212> TYPE: DNA
<213> ORGANISM: homo sapien

<400> SEQUENCE: 20
aactttcatc ccagcacatg atttgggaat tacactttgt gacatggatg aatctgcact 60
gacccttggt acaatagatg tttcttatct gccacattca tcagaataca gtgttggtcg 120
atgtaagcac acaagtgagg aatggggtga gtgtggcttt agacccacca tcttcagatc 180
tgcaacttta aaatggaaag aaagcctaat gagtcggaaa aggccatttg ttggaagatg 240
ttgttactcc tgcactcccc agagctggga caaatttttc aaccccagta tcccgtcttt 300
gggtttgcgg aatgttattt atatcaatga aactcacaca agacaccgcg gatggcttgc 360
aagacgcctt tcttacgttc tttttattca agagcgagat gtgcataagg gcatgtttgc 420
caccaatgtg actgaaaatg tgctgaacag cagtagagta caagaggcaa ttgcagaagt 480
ggctgctgaa ttaaaccctg atggttctgc ccagcagcaa tcaaaagccg ttaacaaagt 540
gaaaaagaaa gctaaaagga ttcttcaaga aatggttgcc actgtctcac cggcaatgat 600
cagactgact gggtgggtgc tgctaaaact gttcaacagc ttcttttgga acattcaaat 660
tcacaaaggt caacttgaga tggttaaagc tgcaactgag acgaatttgc cgcttctgtt 720
tctaccagtt catagatccc atattgacta tctgctgctc actttcattc tcttctgcca 780
taacatcaaa gcaccataca ttgcttcagg caataatctc aacatcccaa tcttcagtac 840
cttgatccat aagcttgggg gcttcttcat acgacgaagg ctcgatgaaa caccagatgg 900
acggaaagat gttctctata gagctttgct ccatgggcat atagttgaat tacttcgaca 960
gcagcaattc ttggagatct tcctggaagg cacacgttct aggagtggaa aaacctcttg 1020
tgctcgggca ggacttttgt cagttgtggt agatactctg tctaccaatg tcatcccaga 1080
catcttgata atacctgttg gaatctccta tgatcgcatt atcgaaggtc actacaatgg 1140
tgaacaactg ggcaaaccta agaagaatga gagcctgtgg agtgtagcaa gaggtgttac 1200

```
tagaatgtta cgaaaaaact atggttgtgt ccgagtggat tttgcacagc cattttcctt   1260
aaaggaatat ttagaaagcc aaagtcagaa accggtgtct gctctacttt ccctggagca   1320
agcgttgtta ccagctatac ttccttcaag acccagtgat gctgctgatg aaggtagaga   1380
cacgtccatt aatgagtcca gaaatgcaac agatgaatcc ctacgaagga ggttgattgc   1440
aaatctggct gagcatattc tattcactgc tagcaagtcc tgtgccatta tgtccacaca   1500
cattgtggct tgcctgctcc tctacagaca caggcaggga attgatctct ccacattggt   1560
cgaagacttc tttgtgatga aagaggaagt cctggctcgt gattttgacc tggggttctc   1620
aggaaattca gaagatgtag taatgcatgc catacagctg ctgggaaatt gtgtcacaat   1680
cacccacact agcaggaacg atgagttttt tatcaccccc agcacaactg tcccatcagt   1740
cttcgaactc aacttctaca gcaatggggt acttcatgtc tttatcatgg aggccatcat   1800
agcttgcagc ctttatgcag ttctgaacaa gaggggactg gggggtccca ctagcacccc   1860
acctaacctg atcagccagg agcagctggt gcggaaggcg gccagcctgt gctaccttct   1920
ctccaatgaa ggcaccatct cactgccttg ccagacattt taccaagtct gccatgaaac   1980
agtaggaaag tttatccagt atggcattct tacagtggca gagcacgatg accaggaaga   2040
tatcagtcct agtcttgctg agcagcagtg ggacaagaag cttcctgaac ctttgtcttg   2100
gagaagtgat gaagaagatg aagacagtga ctttggggag gaacagcgag attgctacct   2160
gaaggtgagc caatccaagg agcaccagca gtttatcacc ttcttacaga gactccttgg   2220
gcctttgctg gaggcctaca gctctgctgc catctttgtt cacaacttca gtggtcctgt   2280
tccagaacct gagtatctgc aaaagttgca caaataccta ataaccagaa cagaaagaaa   2340
tgttgcagta tatgctgaga gtgccacata ttgtcttgtg aagaatgctg tgaaaatgtt   2400
taaggatatt ggggttttca aggagaccaa acaaaagaga gtgtctgttt tagaactgag   2460
cagcactttt ctacctcaat gcaaccgaca aaaacttcta gaatatattc tgagttttgt   2520
ggtgctgtag gtaacgtgtg gcactgctgg caaatgaagg tcatgagatg agttccttgt   2580
aggtaccagc ttctggctca agagttgaag gtgccgtcgc agggtcaggc ctgccctgtc   2640
ccgaggtgat ctcctggaag acaagtgcct tctccctcca tggatctgtg atcttcccag   2700
ctctgcatca acacagcagc ctgcagataa cacttggggg gacctcagcc tctattcgca   2760
actcataatc cgtagactac aagatgaaat ctcaataaat tatttttgag tttattaaag   2820
aggtctttta aggcaaaaaa aaaaaaaaaa aaaaa                              2855
```

<210> SEQ ID NO 21
<211> LENGTH: 6372
<212> TYPE: DNA
<213> ORGANISM: homo sapien

<400> SEQUENCE: 21

```
gcgccactgc agctggcatt ggccgggact ggaagtgcgg gcttctgcag cagccgaagc     60
tggagctgct agggcagcag cggctcccct gttgtatgga cattctgcac ccgaaactga    120
tagctgagtc ctgaagtttt atgttatgaa acagaagaac tttcatccca gcacatgatt    180
tgggaattac actttgtgac atggatgaat ctgcactgac ccttggtaca atagatgttt    240
cttatctgcc acattcatca gaatacagtg ttggtcgatg taagcacaca agtgaggaat    300
ggggtgagtg tggctttaga cccaccgtct tcagatctgc aactttaaaa tggaaagaaa    360
gcctaatgag tcggaaaagg ccatttgttg gaagatgttg ttactcctgc actccccaga    420
gctgggacaa atttttcaac cccagtatcc cgtctttggg tttgcggaat gttatttata    480
```

```
tcaatgaaac tcacacaaga caccgcggat ggcttgcaag acgcctttct tacgttcttt    540
ttattcaaga gcgagatgtg cataagggca tgtttgccac caatgtgact gaaaatgtgc    600
tgaacagcag tagagtacaa gaggcaattg cagaagtggc tgctgaatta aaccctgatg    660
gttctgccca gcagcaatca aaagccgtta acaaagtgaa aaagaaagct aaaaggattc    720
ttcaagaaat ggttgccact gtctcaccgg caatgatcag actgactggg tgggtgctgc    780
taaaactgtt caacagcttc ttttggaaca ttcaaattca caaaggtcaa cttgagatgg    840
ttaaagctgc aactgagacg aatttgccgc ttctgtttct accagttcat agatcccata    900
ttgactatct gctgctcact ttcattctct tctgccataa catcaaagca ccatacattg    960
cttcaggcaa taatctcaac atcccaatct tcagtacctt gatccataag cttgggggct   1020
tcttcatacg acgaaggctc gatgaaacac cagatggacg gaaagatgtt ctctatagag   1080
ctttgctcca tgggcatata gttgaattac ttcgacagca gcaattcttg gagatcttcc   1140
tggaaggcac acgttctagg agtggaaaaa cctcttgtgc tcgggcagga cttttgtcag   1200
ttgtggtaga tactctgtct accaatgtca tcccagacat cttgataata cctgttggaa   1260
tctcctatga tcgcattatc gaaggtcact acaatggtga acaactgggc aaacctaaga   1320
agaatgagag cctgtggagt gtagcaagag gtgttattag aatgttacga aaaaactatg   1380
gttgtgtccg agtggatttt gcacagccat tttccttaaa ggaatattta gaaagccaaa   1440
gtcagaaacc ggtgtctgct ctactttccc tggagcaagc gttgttacca gctatacttc   1500
cttcaagacc cagtgatgct gctgatgaag gtagagacac gtccattaat gagtccagaa   1560
atgcaacaga tgaatcccta cgaaggaggt tgattgcaaa tctggctgag catattctat   1620
tcactgctag caagtcctgt gccattatgt ccacacacat tgtggcttgc ctgctcctct   1680
acagacacag gcagggaatt gatctctcca cattggtcga agacttcttt gtgatgaaag   1740
aggaagtcct ggctcgtgat tttgacctgg ggttctcagg aaattcagaa gatgtagtaa   1800
tgcatgccat acagctgctg ggaaattgtg tcacaatcac ccacactagc aggaacgatg   1860
agtttttat caccccccagc acaactgtcc catcagtctt cgaactcaac ttctacagca   1920
atggggtact tcatgtcttt atcatggagg ccatcatagc ttgcagcctt tatgcagttc   1980
tgaacaagag gggactgggg ggtcccacta gcaccccacc taacctgatc agccaggagc   2040
agctggtgcg gaaggcggcc agcctgtgct accttctctc caatgaaggc accatctcac   2100
tgccttgcca gacattttac caagtctgcc atgaaacagt aggaaagttt atccagtatg   2160
gcattcttac agtggcagag cacgatgacc aggaagatat cagtcctagt cttgctgagc   2220
agcagtggga caagaagctt ccagaacctt tgtcttggag aagtgatgaa gaagatgaag   2280
acagtgactt tggggaggaa cagcgagatt gctacctgaa ggtgagccaa tccaaggagc   2340
accagcagtt tatcaccttc ttacagagac tccttgggcc tttgctggag gcctacagct   2400
ctgctgccat ctttgttcac aacttcagtg gtcctgttcc agaacctgag tatctgcaaa   2460
agttgcacaa atacctaata accagaacag aaagaaatgt tgcagtatat gctgagagtg   2520
ccacatattg tcttgtgaag aatgctgtga aaatgtttaa ggatattggg gttttcaagg   2580
agaccaaaca aaagagagtg tctgttttag aactgagcag cacttttcta cctcaatgca   2640
accgacaaaa acttctagaa tatattctga gttttgtggt gctgtaggta acgtgtggca   2700
ctgctggcaa atgaaggtca tgagatgagt tccttgtagg taccagcttc tggctcaaga   2760
gttgaaggtg ccatcgcagg gtcaggcctg ccctgtcccg aagtgatctc ctggaagaca   2820
```

-continued

```
agtgccttct ccctccatgg atctgtgatc ttcccagctc tgcatcaaca cagcagcctg   2880
cagataacac ttggggggac ctcagcctct attcgcaact cataatccgt agactacaag   2940
atgaaatctc aataaattat ttttgagttt attaaagatt gacattttaa gtacaacttt   3000
taaggactaa ttactgtgat ggacacagaa atgtagctgt gttctggaac tgaatcttac   3060
atggtatact tagtgctgct gggtaatttg ttggtatatt atctggttag tggttaatgc   3120
ttcctttaaa aataattgag tcatccattc actctttttc agttttatct gtcaatagta   3180
gctacatttt taatgggagc accttttatc ccaaagtgct ttataaattg agtggactga   3240
tatatatcac acccaggtat cactgtgctg tcctttgctg tcagatttag aaatgttttt   3300
aagagctatg tgaaaacaga caatattagt ttaggtcggg aactgagata ttgtaatcaa   3360
atagttaaca tcaggaagtt aatttggctg gcaaaattct agggaaactt ggccagaaaa   3420
ctggtgttga aggcttttgc tcatataaac aagtgccatt gagtttcaaa tgaccagcaa   3480
atatatttag aacccttcct gttttatgtc tgtacctcgt ccacccctca ggtaatacct   3540
gcctctcaca ggtacagctg tttcttggaa atcctccaac caaatagcag ttttcctaac   3600
ttgattagct tgagctgaca gactgttaga atacagttct ctggccacag ctgatgaggg   3660
ctttctgtac tgcacacaga ttgtgtactg caccccagtc caggtgactg gtacccactc   3720
gagttgtgcc gtgcacaacc tgtccagtat atgcatgtgg tggccctact gactggtaat   3780
ggttagaggc atttatggat ttttagcttt gaggaaaaac catgactttt aacaaatttt   3840
tatgggttat atgcctaaac ccttatgcca catagtggta aataattatg aaaaatggtc   3900
tgttcataat tggtaggtgc cttttgtgag cagggagcat aattattggt ttattatggt   3960
aattatggtg atttttttaaa tatcatgtaa tgttaaaacg ttttctaaca gtttactgtt   4020
gcttatctcc aagatattat ggaattaaga atttttccag atgagtgtta catagattct   4080
ttgaatttag tataaaagta ctgagaatta agtttgtact tccataagct tggattttaa   4140
acactgatag tatctcatga gtaatgtgtg ttttgggaga gggagggatg ctgattgata   4200
tttcacattg tatgaaatac catgtttgaa actcatagca ataatgctat gctgttgtga   4260
tccctctcaa gttctgcatt taaaatatat tttttcttta taggaattga tgtataccat   4320
gaagtcattg tcagttgtag tagctctgat gttgaatgag atatcatgtt ttagcattcc   4380
attttactga ctagggtaga agaacacttt tcttggctac atttggagga tacccaggga   4440
gtcttgggtg ttccttatct ggggaagcaa acatttcact agtctctttt tttcatcctt   4500
taaattgtaa attaaggatt actcaagctc accattattc aagattggga ctcgcttccc   4560
agtcgacact ctgccctgcc tgtcattgct gcaaagagct gctgctttgc caacctaagc   4620
aaagaaaata cggcttctct tgcattattt tcccttttgg ttggtttgtt ttctagaagt   4680
acgttcagat gctttgggga atgcaatgta tgatttgcta gctctctcac cacttaactc   4740
actgtgagga taaatatgca tgctttttgt aattaactgg tgctttgaaa atcttttta    4800
agggagaaaa atctcaacca aagttatgct catccagaca agctgacctt tgagttaatt   4860
tcagcacaac tcattcttca gtgcctcatg actgaaaaca aaaaacaaaa aaacgaaagc   4920
atcttcacaa tgaagcttcc agatagcacc gttttgctaa aagatacatt ctcattgttt   4980
tccaacagtg atggcttcca cataaggtta aacaaactag gtgcttgtaa ataatttatt   5040
acagtttact ctatcgcatt tctgtaacat gaaatgcatg cccttcttca ggggaagact   5100
gtggtcaagt taaaaaaaaa aaacaatatt aaacaacatg aaactgcagt ctgtttttga   5160
aaatgagaat gtcctaagtg attcagaaga gaggagggaa gttgtgcact ctgaaaatgc   5220
```

atgaaaaaca aaggcaaaaa ctagtgggaa atgtgtagaa ctgttaactg agatggcttc 5280
gagtcttcct tctggaatct gttaaatttc acaaagtcat gagggtaaat ggagaaaata 5340
tttctgggat tacaatgaat gtaagcccaa attgtggaat tgccagtaac ctggatgggg 5400
aaaagcattt cccatagcac tccatgtaat atgagtgctc tgtgagatgt tcatcagtgt 5460
tttatagaaa tggtgttgct gggaaaccaa gtttgcacct ggaaacttac aatgcacttt 5520
agcgcagtaa gggcttggca tccggtagtg aaaaactgtc taacccagca ttgcccaaac 5580
tattttgaca ccaggacctt tttctccttt gggatactta tgaacctctc actaatgtcc 5640
tgtggagaac attttgggaa acactatgtt agatagttct ttaaggagac aaaacggtaa 5700
tgaacagata gcactggggc agaatatgca tgcattttgt aacgtccagt gtggcgttga 5760
atagatgtgt atttcctccc ctgcagaaaa taagcacaga aaattataat gtaggtgatc 5820
ggagctcttt cctttgatag agagaacagc cccaatgatc ctggcttttt cactgaacgt 5880
atcagaatac atggatgaat tggggtaaat aaggttttaa ttcagatcta gaagaaagta 5940
ttgtacgttt gaatgcagat ttttatccac agatagttgt agtgtttaga catgacagga 6000
cctatcgttg aggtttctaa gacttactat gggctgtaaa cctgtttttt aaaactattt 6060
tagaaacctg agacttgccg tctggcattt tagtttaata caaactaatg attgcatttg 6120
aaagagattc ttgaccttat ttctaaacgt ctagagctct gaaatgtctt gatggaaggt 6180
attaaactat ttgcctgttg tacaaagaaa tgttaagact cgtgaaaaga attactataa 6240
ggtactgtga aataactgcg attttgtgag caaaacatac ttggaaatgc tgattgattt 6300
ttatgcttgt tagtgtattg caagaaacac agaaaatgta gttttgtttt aataaaccaa 6360
aaattgaaca ta 6372

<210> SEQ ID NO 22
<211> LENGTH: 5664
<212> TYPE: DNA
<213> ORGANISM: homo sapien

<400> SEQUENCE: 22
gaagctggag ctgctagggt gcgaactgcc agggcaggca gcagcggctc ccctgttgta 60
tggacattct gcacccgaaa ctgatagctg agtcctgaag ttttatgtta tgaaacagaa 120
gaactttcat cccagcacat gatttgggaa ttacactttg tgacatggat gaatctgcac 180
tgacccttgg tacaatagat gtttcttatc tgccacattc atcagaatac agtgttggtc 240
gatgtaagca cacaagtgag gaatggggtg agtgtggctt tagacccacc gtcttcagat 300
ctgcaacttt aaaatggaaa gaaagcctaa tgagtcggaa aaggccattt gttggaagat 360
gttgttactc ctgcactccc cagagctggg acaaattttt caaccccagt atcccgtctt 420
tgggtttgcg gaatgttatt tatatcaatg aaactcacac aagacaccgc ggatggcttg 480
caagacgcct ttcttacgtt ctttttattc aagagcgaga tgtgcataag ggcatgtttg 540
ccaccaatgt gactgaaaat gtgctgaaca gcagtagagt acaagaggca attgcagaag 600
tggctgctga attaaaccct gatggttctg cccagcagca atcaaaagcc gttaacaaag 660
tgaaaaagaa agctaaaagg attcttcaag aaatggttgc cactgtctca ccggcaatga 720
tcagactgac tgggtgggtg ctgctaaaac tgttcaacag cttcttttgg aacattcaaa 780
ttcacaaagg tcaacttgag atggttaaag ctgcaactga gacgaatttg ccgcttctgt 840
ttctaccagt tcatagatcc catattgact atctgctgct cactttcatt ctcttctgcc 900

-continued

```
ataacatcaa agcaccatac attgcttcag gcaataatct caacatccca atcttcagta    960
ccttgatcca taagcttggg ggcttcttca tacgacgaag gctcgatgaa acaccagatg   1020
gacggaaaga tgttctctat agagctttgc tccatgggca tatagttgaa ttacttcgac   1080
agcagcaatt cttggagatc ttcctggaag gcacacgttc taggagtgga aaaacctctt   1140
gtgctcgggc aggacttttg tcagttgtgg tagatactct gtctaccaat gtcatcccag   1200
acatcttgat aatacctgtt ggaatctcct atgatcgcat tatcgaaggt cactacaatg   1260
gtgaacaact gggcaaacct aagaagaatg agagcctgtg gagtgtagca agaggtgtta   1320
ttagaatgtt acgaaaaaac tatggttgtg tccgagtgga ttttgcacag ccatttcct    1380
taaaggaata tttagaaagc caaagtcaga aaccggtgtc tgctctactt tccctggagc   1440
aagcgttgtt accagctata cttccttcaa gacccagtga tgctgctgat gaaggtagag   1500
acacgtccat taatgagtcc agaaatgcaa cagatgaatc cctacgaagg aggttgattg   1560
caaatctggc tgagcatatt ctattcactg ctagcaagtc ctgtgccatt atgtccacac   1620
acattgtggc ttgcctgctc ctctacagac acaggcaggg aattgatctc tccacattgg   1680
tcgaagactt ctttgtgatg aaagaggaag tcctggctcg tgattttgac ctggggttct   1740
caggaaattc agaagatgta gtaatgcatg ccatacagct gctgggaaat tgtgtcacaa   1800
tcacccacac tagcaggaac gatgagtttt ttatcacccc cagcacaact gtcccatcag   1860
tcttcgaact caacttctac agcaatgggg tacttcatgt ctttatcatg gaggccatca   1920
tagcttgcag cctttatgca gttctgaaca agaggggact ggggggtccc actagcaccc   1980
cacctaacct gatcagccag gagcagctgg tgcggaaggc ggccagcctg tgctaccttc   2040
tctccaatga aggcaccatc tcactgcctt gccagacatt ttaccaagtc tgccatgaaa   2100
cagtaggaaa gtttatccag tatggcattc ttacagtggc agagcacgat gaccaggaag   2160
atatcagtcc tagtcttgct gagcagcagt gggacaagaa gcttccagaa cctttgtctt   2220
ggagaagtga tgaagaagat gaagacagtg actttgggga ggaacagcga gattgctacc   2280
tgaaggtact tgggtgaaga attctggtgg atattacagg gatatgttga ggtttatgct   2340
gcagtgagat cagctggagt cctggtgatg tcttcttatc taaagaatcc cccaactagc   2400
tctggtacct tctgtgtggt aaagacactc aaactgtttg agttgaatta atagcatttt   2460
aagtagaaaa ggaaaggaga gtctgaaaag tcaggaagat gaatgtcata ggtgagactt   2520
tcaccatcct tttatgaaat acacaggtgc atacctgttt acctacacct gcacccctca   2580
tgaggcagca gttttgctat tgagctgcca ctgacctggc tgctcttttt gagtcactct   2640
tgctgtccct cccaaaattt catatattaa gctctttgct gtcaattaaa acaaatacca   2700
ttataggaga aaattgagat taaaaaaaaa gtccctgatt tagaaaaatc aattttgtct   2760
aatttataat tttagaactt agtaataatg acccgtcttt tctgaatact ctaagaggat   2820
tactcttttt tgacatttag aaattgtctt ctttttcact tgggtggtat tagtttagtt   2880
tcaagatggg gcagtgatct tgctttcaca ctccagaggg gcttgaccga accagtgtgt   2940
tttgggtagg tacagtgaga gcctctcggc cataaagcac cgccgtcaca gtggccatca   3000
ttccccacag tgctggactg tgggcaaagg ccatttaggg gaggcaggga ataggtgctg   3060
cagaaggagt gagataatct tggtggtctc ccattggtct ttctgcagac ttgagtgact   3120
gttgagccca ggcttcaaac catggagggc ctggtcttag gagcggctat ttttagtgat   3180
gacagcgtat cacaagtagg gcattcattt atgaaaattt cttctaggtg gctgttcaat   3240
gaacacaagc ctcaaatacc ataaaaaagt gaatgattac aataaagaat gtgtttgaaa   3300
```

-continued

```
gccagcagtt gtttccagca gagattctct gcatgagggg cagggggccg ctttcatgta   3360
gtgctgatgt gagtggccat cttctcacgt tactggctct ccagagaaag tcctctgtcc   3420
acttgccttg tgtctcttgt cccttcctca tgacttcatc tcctgctttt gcacactcag   3480
gtgagccaat ccaaggagca ccagcagttt atcaccttct tacagagact ccttgggcct   3540
ttgctggagg cctacagctc tgctgccatc tttgttcaca acttcagtgg tcctgttcca   3600
gaacctgagt atctgcaaaa gttgcacaaa tacctaataa ccagaacaga aagaaatgtt   3660
gcagtatatg gtatgttaag tcactattta ttcttttaaa atcttttttt ttttttttgga   3720
tttcagaaat ttgctaattg tagaaaattg gaaaaatgca aacttatcct gacctctaac   3780
accgtagagt attactatta tcttctttgg catgttatat aagttgaatg atacagttat   3840
acactcttac atctggcttt tttcacgtaa cgttattttt gagattcata catgttgcat   3900
atagttgttc ctttgttctt gttgtgtagt gttccattgt ataaatattt accacatttt   3960
attcattctg ctgttgatgg atatttgggt tgttttcagt tcacagctgc tttgaacagt   4020
gttgctatga gcatatttga atatgtcttt tggtgaatat ctgtgcccct atatacagca   4080
tgtatgtggg aacagaattg cctggttgta ggctctgggt atattcggct ttggtagata   4140
ccaccaaaca gtttccaagg gattatacct acttgtactc ccacaacagt gtgtgtttca   4200
cttgctgcac atcttggcca gcgctccgtc ttctttgttt taggaggtgt gattggggtg   4260
ggagtactat tttatacagt tgtagtttgg agctgaaact acttgaatca ctttttagag   4320
ccaaaaggaa tctaatctaa tcacctcatt ttatagttga ggaaaatacc ccaggtcaca   4380
ctgctaatta atgggtaatc tcgggatcag aattcttgtt tcctaacctc gaggcctgtg   4440
ctttctctgg ttccactgat gtacaatcat ctgtgtacca ctgggtagct taaagaatat   4500
ttatacacta tctcatttga ttctcacaac agtcctggaa aatggatgtt ttaggtattt   4560
ctacttccct ctgttctccc tatttctctc tctacaccct cttttctttc cccttccctt   4620
tcttatttac ctcaatatag gacaaagtag gtgtaagcaa agtaggttta acagcaagtc   4680
atctgagaac tcacaggttg ccagtggtgg aagtggggcc ccacccttgt ctgctgactt   4740
gccctcattc tcttcctagc tccccatact ttcttactgt ggctgctggg attgtcatga   4800
tttgttgagc gtaaccattt gacagggttt tattctctct cttcagctga gagtgccaca   4860
tattgtcttg tgaagaatgc tgtgaaaatg tttaaggata ttggggtagg tgtccaccat   4920
ttatggtata aaagctatct caacttctgt tctctttaga tctagtctgt ttgagctacc   4980
tttgtggtgg ggtggacccc gagagaagca gtttctgctg gcttaatgat aaaggcattt   5040
ttgggaacgg ggcatgtagg atgggttggg ctatgttgaa ggtgaagccc atcagtgtag   5100
atttatttga atgttctgga attttactgg tttcacattt attcccaagc tgctatatat   5160
aactggtatc aatatgtttc aaggtgctac aggttgaata tcccttatcc aaaatgttgg   5220
gaccagaaat gttttggatt tcagattttt ttgggatttt ggaatatgtg cattagactt   5280
acaggttgag cgtctctaat ccaaaaccca aaatgctctg atgagcatgt cttttgagca   5340
tcatattgat gttcaaaatc tttcagattt tggagtactt cagatttttg attttgggat   5400
taggaccaca atcttggctc ttaattattc catatgattt ttagttactt tcttgtattt   5460
ttacaagaat ttctagaagt atcctcaggt gtcctttacc ttcatgattc atggggaatg   5520
taagttctat agagatacta gcggcctttt gtgagggact gtttgtgact ttattctaag   5580
tcattttaga gtatagttat gttggttgaa attttagaat atagttaatg ttggttgaac   5640
```

-continued tccatcaaaa caaaaaaaaa aaaa 5664

<210> SEQ ID NO 23
<211> LENGTH: 6368
<212> TYPE: DNA
<213> ORGANISM: homo sapien

<400> SEQUENCE: 23
gcgccactgc agctggcatt ggccgggact ggaagtgcgg gcttctgcag cagccgaagc 60
tggagctgct aggcagcggc tcccctgttg tatggacatt ctgcacccga aactgatagc 120
tgagtcctga agttttatgt tatgaaacag aagaactttc atcccagcac atgatttggg 180
aattacactt tgtgacatgg atgaatctgc actgaccctt ggtacaatag atgtttctta 240
tctgccacat tcatcagaat acagtgttgg tcgatgtaag cacacaagtg aggaatgggg 300
tgagtgtggc tttagaccca ccgtcttcag atctgcaact ttaaaatgga aagaaagcct 360
aatgagtcgg aaaaggccat ttgttggaag atgttgttac tcctgcactc cccagagctg 420
ggacaaattt ttcaacccca gtatcccgtc tttgggtttg cggaatgtta tttatatcaa 480
tgaaactcac acaagacacc gcggatggct tgcaagacgc ctttcttacg ttctttttat 540
tcaagagcga gatgtgcata agggcatgtt tgccaccaat gtgactgaaa atgtgctgaa 600
cagcagtaga gtacaagagg caattgcaga agtggctgct gaattaaacc ctgatggttc 660
tgcccagcag caatcaaaag ccgttaacaa agtgaaaaag aaagctaaaa ggattcttca 720
agaaatggtt gccactgtct caccggcaat gatcagactg actgggtggg tgctgctaaa 780
actgttcaac agcttctttt ggaacattca aattcacaaa ggtcaacttg agatggttaa 840
agctgcaact gagacgaatt tgccgcttct gtttctacca gttcatagat cccatattga 900
ctatctgctg ctcactttca ttctcttctg ccataacatc aaagcaccat acattgcttc 960
aggcaataat ctcaacatcc caatcttcag taccttgatc cataagcttg gggcttctt 1020 catacgacga aggctcgatg aaacaccaga tggacggaaa gatgttctct atagagcttt 1080
gctccatggg catatagttg aattacttcg acagcagcaa ttcttggaga tcttcctgga 1140
aggcacacgt tctaggagtg gaaaaacctc ttgtgctcgg gcaggacttt tgtcagttgt 1200
ggtagatact ctgtctacca atgtcatccc agacatcttg ataatacctg ttggaatctc 1260
ctatgatcgc attatcgaag gtcactacaa tggtgaacaa ctgggcaaac ctaagaagaa 1320
tgagagcctg tggagtgtag caagaggtgt tattagaatg ttacgaaaaa actatggttg 1380
tgtccgagtg gattttgcac agccattttc cttaaaggaa tatttagaaa gccaaagtca 1440
gaaaccggtg tctgctctac tttccctgga gcaagcgttg ttaccagcta tacttccttc 1500
aagacccagt gatgctgctg atgaaggtag agacacgtcc attaatgagt ccagaaatgc 1560
aacagatgaa tccctacgaa ggaggttgat tgcaaatctg gctgagcata ttctattcac 1620
tgctagcaag tcctgtgcca ttatgtccac acacattgtg gcttgcctgc tcctctacag 1680
acacaggcag ggaattgatc tctccacatt ggtcgaagac ttctttgtga tgaaagagga 1740
agtcctggct cgtgattttg acctggggtt ctcaggaaat tcagaagatg tagtaatgca 1800
tgccatacag ctgctgggaa attgtgtcac aatcacccac actagcagga acgatgagtt 1860
ttttatcacc cccagcacaa ctgtcccatc agtcttcgaa ctcaacttct acagcaatgg 1920
ggtacttcat gtctttatca tggaggccat catagcttgc agcctttatg cagttctgaa 1980 caagaggga ctgggggtc ccactagcac cccacctaac ctgatcagcc aggagcagct 2040
ggtgcggaag gcggccagcc tgtgctacct tctctccaat gaaggcacca tctcactgcc 2100

```
ttgccagaca ttttaccaag tctgccatga aacagtagga aagtttatcc agtatggcat   2160
tcttacagtg gcagagcacg atgaccagga agatatcagt cctagtcttg ctgagcagca   2220
gtgggacaag aagcttccag aacctttgtc ttggagaagt gatgaagaag atgaagacag   2280
tgactttggg gaggaacagc gagattgcta cctgaaggtg agccaatcca aggagcacca   2340
gcagtttatc accttcttac agagactcct tgggcctttg ctggaggcct acagctctgc   2400
tgccatcttt gttcacaact tcagtggtcc tgttccagaa cctgagtatc tgcaaaagtt   2460
gcacaaatac ctaataacca gaacagaaag aaatgttgca gtatatgctg agagtgccac   2520
atattgtctt gtgaagaatg ctgtgaaaat gtttaaggat attggggttt tcaaggagac   2580
caaacaaaag agagtgtctg ttttagaact gagcagcact tttctacctc aatgcaaccg   2640
acaaaaactt ctagaatata ttctgagttt tgtggtgctg taggtaacgt gtggcactgc   2700
tggcaaatga aggtcatgag atgagttcct tgtaggtacc agcttctggc tcaagagttg   2760
aaggtgccat cgcagggtca ggcctgccct gtcccgaagt gatctcctgg aagacaagtg   2820
ccttctccct ccatggatct gtgatcttcc cagctctgca tcaacacagc agcctgcaga   2880
taacacttgg ggggacctca gcctctattc gcaactcata atccgtagac tacaagatga   2940
aatctcaata aattattttt gagtttatta aagattgaca ttttaagtac aacttttaag   3000
gactaattac tgtgatggac acagaaatgt agctgtgttc tggaactgaa tcttacatgg   3060
tatacttagt gctgctgggt aatttgttgg tatattatct ggttagtggt taatgcttcc   3120
tttaaaaata attgagtcat ccattcactc tttttcagtt ttatctgtca atagtagcta   3180
catttttaat gggagcacct tttatcccaa agtgctttat aaattgagtg gactgatata   3240
tatcacaccc aggtatcact gtgctgtcct ttgctgtcag atttagaaat gtttttaaga   3300
gctatgtgaa aacagacaat attagtttag gtcgggaact gagatattgt aatcaaatag   3360
ttaacatcag gaagttaatt tggctggcaa aattctaggg aaacttggcc agaaaactgg   3420
tgttgaaggc ttttgctcat ataaacaagt gccattgagt ttcaaatgac cagcaaatat   3480
atttagaacc cttcctgttt tatgtctgta cctcgtccac ccctcaggta atacctgcct   3540
ctcacaggta cagctgtttc ttggaaatcc tccaaccaaa tagcagtttt cctaacttga   3600
ttagcttgag ctgacagact gttagaatac agttctctgg ccacagctga tgagggcttt   3660
ctgtactgca cacagattgt gtactgcacc ccagtccagg tgactggtac ccactcgagt   3720
tgtgccgtgc acaacctgtc cagtatatgc atgtggtggc cctactgact ggtaatggtt   3780
agaggcattt atggattttt agctttgagg aaaaaccatg acttttaaca aatttttatg   3840
ggttatatgc ctaaaccctt atgccacata gtggtaaata attatgaaaa atggtctgtt   3900
cataattggt aggtgccttt tgtgagcagg gagcataatt attggtttat tatggtaatt   3960
atggtgattt tttaaatatc atgtaatgtt aaaacgtttt ctaacagttt actgttgctt   4020
atctccaaga tattatggaa ttaagaattt ttccagatga gtgttacata gattctttga   4080
atttagtata aaagtactga gaattaagtt tgtacttcca taagcttgga ttttaaacac   4140
tgatagtatc tcatgagtaa tgtgtgtttt gggagaggga gggatgctga ttgatatttc   4200
acattgtatg aaataccatg tttgaaactc atagcaataa tgctatgctg ttgtgatccc   4260
tctcaagttc tgcatttaaa atatattttt tctttatagg aattgatgta taccatgaag   4320
tcattgtcag ttgtagtagc tctgatgttg aatgagatat catgttttag cattccattt   4380
tactgactag ggtagaagaa cacttttctt ggctacattt ggaggatacc cagggagtct   4440
```

-continued

```
tgggtgttcc ttatctgggg aagcaaacat ttcactagtc tcttttttttc atcctttaaa   4500

ttgtaaatta aggattactc aagctcacca ttattcaaga ttgggactcg cttcccagtc   4560

gacactctgc cctgcctgtc attgctgcaa agagctgctg ctttgccaac ctaagcaaag   4620

aaaatacggc ttctcttgca ttattttccc ttttggttgg tttgttttct agaagtacgt   4680

tcagatgctt tggggaatgc aatgtatgat ttgctagctc tctcaccact taactcactg   4740

tgaggataaa tatgcatgct ttttgtaatt aactggtgct ttgaaaatct tttttaaggg   4800

agaaaaatct caaccaaagt tatgctcatc cagacaagct gacctttgag ttaatttcag   4860

cacaactcat tcttcagtgc ctcatgactg aaaacaaaaa acaaaaaaac gaaagcatct   4920

tcacaatgaa gcttccagat agcaccgttt tgctaaaaga tacattctca ttgttttcca   4980

acagtgatgg cttccacata aggttaaaca aactaggtgc ttgtaaataa tttattacag   5040

tttactctat cgcatttctg taacatgaaa tgcatgccct tcttcagggg aagactgtgg   5100

tcaagttaaa aaaaaaaaac aatattaaac aacatgaaac tgcagtctgt ttttgaaaat   5160

gagaatgtcc taagtgattc agaagagagg agggaagttg tgcactctga aaatgcatga   5220

aaaacaaagg caaaaactag tgggaaatgt gtagaactgt taactgagat ggcttcgagt   5280

cttccttctg gaatctgtta aatttcacaa agtcatgagg gtaaatggag aaaatatttc   5340

tgggattaca atgaatgtaa gcccaaattg tggaattgcc agtaacctgg atggggaaaa   5400

gcatttccca tagcactcca tgtaatatga gtgctctgtg agatgttcat cagtgtttta   5460

tagaaatggt gttgctggga aaccaagttt gcacctggaa acttacaatg cactttagcg   5520

cagtaagggc ttggcatccg gtagtgaaaa actgtctaac ccagcattgc ccaaactatt   5580

ttgacaccag gaccttttttc tcctttggga tacttatgaa cctctcacta atgtcctgtg   5640

gagaacattt tgggaaacac tatgttagat agttctttaa ggagacaaaa cggtaatgaa   5700

cagatagcac tggggcagaa tatgcatgca ttttgtaacg tccagtgtgg cgttgaatag   5760

atgtgtattt cctcccctgc agaaaataag cacagaaaat tataatgtag gtgatcggag   5820

ctctttcctt tgatagagag aacagcccca atgatcctgg ctttttcact gaacgtatca   5880

gaatacatgg atgaattggg gtaaataagg ttttaattca gatctagaag aaagtattgt   5940

acgtttgaat gcagattttt atccacagat agttgtagtg tttagacatg acaggaccta   6000

tcgttgaggt ttctaagact tactatgggc tgtaaacctg ttttttaaaa ctattttaga   6060

aacctgagac ttgccgtctg gcattttagt ttaatacaaa ctaatgattg catttgaaag   6120

agattcttga ccttatttct aaacgtctag agctctgaaa tgtcttgatg gaaggtatta   6180

aactatttgc ctgttgtaca aagaaatgtt aagactcgtg aaaagaatta ctataaggta   6240

ctgtgaaata actgcgattt tgtgagcaaa acatacttgg aaatgctgat tgatttttat   6300

gcttgttagt gtattgcaag aaacacagaa aatgtagttt tgttttaata aaccaaaaat   6360

tgaacata                                                             6368
```

<210> SEQ ID NO 24
<211> LENGTH: 4918
<212> TYPE: DNA
<213> ORGANISM: homo sapien

<400> SEQUENCE: 24

```
ggccactgca gctggcattg gccgggactg gaagtgcggg cttctgcagc agccgaagct     60

ggagctgcta gggcagcagc ggctcccctg ttgtatggac attctgcacc cgaaactgat    120

agctgagtcc tgaagtttta tgttatgaaa cagaagaact ttcatcccag cacatgattt    180
```

-continued

```
gggaattaca ctttgtgaca tggatgaatc tgcactgacc cttggtacaa tagatgtttc    240
ttatctgcca cattcatcag aatacagtgt tggtcgatgt aagcacacaa gtgaggaatg    300
gggtgagtgt ggctttagac ccaccgtctt cagatctgca actttaaaat ggaaagaaag    360
cctaatgagt cggaaaaggc catttgttgg aagatgttgt tactcctgca ctccccagag    420
ctgggacaaa tttttcaacc ccagtatccc gtctttgggt ttgcggaatg ttatttatat    480
caatgaaact cacacaagac accgcggatg gcttgcaaga cgcctttctt acgttctttt    540
tattcaagag cgagatgtgc ataagggcat gtttgccacc aatgtgactg aaaatgtgct    600
gaacagcagt agagtacaag aggcaattgc agaagtggct gctgaattaa accctgatgg    660
ttctgcccag cagcaatcaa aagccgttaa caaagtgaaa aagaaagcta aaaggattct    720
tcaagaaatg gttgccactg tctcaccggc aatgatcaga ctgactgggt gggtgctgct    780
aaaactgttc aacagcttct tttggaactt tcaaattcac aaaggtcaac ttgagatggt    840
taaagctgca actgagacga atttgccgct tctgtttcta ccagttcata gatcccatat    900
tgactatctg ctgctcactt tcattctctt ctgccataac atcaaagcac catacattgc    960
ttcaggcaat aatctcaaca tcccaatctt cagtaccttg atccataagc ttgggggctt   1020
cttcatacga cgaaggctcg atgaaacacc agatggacgg aaagatgttc tctatagagc   1080
tttgctccat gggcatatag ttgaattact tcgacagcag caattcttgg agatcttcct   1140
ggaaggcaca cgttctagga gtggaaaaac ctcttgtgct cgggcaggac ttttgtcagt   1200
tgtggtagat actctgtcta ccaatgtcat cccagacatc ttgataatac ctgttggaat   1260
ctcctatgat cgcattatcg aaggtcacta caatggtgaa caactgggca aacctaagaa   1320
gaatgagagc ctgtggagtg tagcaagagg tgttattaga atgttacgaa aaaactatgg   1380
ttgtgtccga gtggattttg cacagccatt ttccttaaag gaatatttag aaagccaaag   1440
tcagaaaccg gtgtctgctc tactttccct ggagcaagcg ttgttaccag ctatacttcc   1500
ttcaagaccc agtgatgctg ctgatgaagg tagagacacg tccattaatg agtccagaaa   1560
tgcaacagat gaatccctac gaaggaggtt gattgcaaat ctggctgagc atattctatt   1620
cactgctagc aagtcctgtg ccattatgtc cacacacatt gtggcttgcc tgctcctcta   1680
cagacacagg cagggaattg atctctccac attggtcgaa gacttctttg tgatgaaaga   1740
ggaagtcctg gctcgtgatt ttgacctggg gttctcagga aattcagaag atgtagtaat   1800
gcatgccata cagctgctgg gaaattgtgt cacaatcacc cacactagca ggaacgatga   1860
gtttttttatc acccccagca caactgtccc atcagtcttc gaactcaact tctacagcaa   1920
tggggtactt catgtcttta tcatggaggc catcatagct tgcagccttt atgcagttct   1980
gaacaagagg ggactggggg gtcccactag caccccacct aacctgatca gccaggagca   2040
gctggtgcgg aaggcggcca gcctgtgcta ccttctctcc aatgaaggca ccatctcact   2100
gccttgccag acattttacc aagtctgcca tgaaacagta ggaaagttta tccggtatgg   2160
cattcttaca gtggcagagc acgatgacca ggaagatatc agtcctagtc ttgctgagca   2220
gcagtgggac aagaagcttc cagaaccttt gtcttggaga agtgatgaag aagatgaaga   2280
cagtgacttt ggggaggaac agcgagattg ctacctgaag gtgagccaat ccaaggagca   2340
ccagcagttt atcaccttct tacagagact ccttgggcct ttgctggagg cctacagctc   2400
tgctgccatc tttgttcaca acttcagtgg tcctgttcca gaacctgagt atctgcaaaa   2460
gttgcacaaa tacctaataa ccagaacaga aagaaatgtt gcagtatatg ctgagagtgc   2520
```

-continued

```
cacatattgt cttgtgaaga atgctgtgaa aatgtttaag gatattgggg ttttcaagga   2580
gaccaaacaa aagagagtgt ctgttttaga actgagcagc acttttctac ctcaatgcaa   2640
ccgacaaaaa cttctagaat atattctgag ttttgtggtg ctgtaggtaa cgtgtggcac   2700
tgctggcaaa tgaaggtcat gagatgagtt ccttgtaggt accagcttct ggctcaagag   2760
ttgaaggtgc catcgcaggg tcaggcctgc cctgtcccga agtgatctcc tggaagacaa   2820
gtgccttctc cctccatgga tctgtgatct tcccagctct gcatcaacac agcagcctgc   2880
agataacact tggggggacc tcagcctcta ttcgcaactc ataatccgta gactacaaga   2940
tgaaatctca ataaattatt tttgagttta ttaaagattg acattttaag tacaactttt   3000
aaggactaat tactgtgatg gacacagaaa tgtagctgtg ttctggaact gaatcttaca   3060
tggtatactt agtgctgctg ggtaatttgt tggtatatta tctggttagt ggttaatgct   3120
tcctttaaaa ataattgagt catccattca ctctttttca gttttatctg tcaatagtag   3180
ctacattttt aatgggagca ccttttatcc caaagtgctt tataaattga gtggactgat   3240
atatatcaca cccaggtatc actgtgctgt cctttgctgt cagatttaga aatgttttta   3300
agagctatgt gaaaacagac aatattagtt taggtcggga actgagatat tgtaatcaaa   3360
tagttaacat caggaagtta atttggctgg caaaattcta gggaaacttg gccagaaaac   3420
tggtgttgaa ggcttttgct catataaaca agtgccattg agtttcaaat gaccagcaaa   3480
tatatttaga acccttcctg ttttatgtct gtacctcgtc caccccctcag gtaatacctg   3540
cctctcacag gtacagctgt ttcttggaaa tcctccaacc aaatagcagt tttcctaact   3600
tgattagctt gagctgacag actgttagaa tacagttctc tggccacagc tgatgagggc   3660
tttctgtact gcacacagat tgtgtactgc accccagtcc aggtgactgg tacccactcg   3720
agttgtgccg tgcacaacct gtccagtata tgcatgtggt ggccctactg actggtaatg   3780
gttagaggca tttatggatt tttagctttg aggaaaaacc atgactttta acaaattttt   3840
atgggttata tgcctaaacc cttatgccac atagtggtaa ataattatga aaaatggtct   3900
gttcataatt ggtaggtgcc ttttgtgagc agggagcata attattggtt tattatggta   3960
attatggtga ttttttaaat atcatgtaat gttaaaacgt tttctaacag tttactgttg   4020
cttatctcca agatattatg gaattaagaa tttttccaga tgagtgttac atagattctt   4080
tgaatttagt ataaaagtac tgagaattaa gtttgtactt ccataagctt ggattttaaa   4140
cactgatagt atctcatgag taatgtgtgt tttgggagag ggagggatgc tgattgatat   4200
ttcacattgt atgaaatacc atgtttgaaa ctcatagcaa taatgctatg ctgttgtgat   4260
ccctcccaag ttctgcattt aaaatatatt ttttctttat aggaattgat gtataccatg   4320
aagtcattgt cagttgtagt agctctgatg ttgaatgaga tatcatgttt tagcattcca   4380
ttttactgac tagggtagaa gaacactctt cttggctaca tttggaggat acccagggag   4440
tcttgggtgt tccttatctg gggaagcaaa catttcacta gtctcttttt ttcatccttt   4500
aaattgtaaa ttaaggatta ctcaagctca ccattattca agattgggac tcgcttccca   4560
gtcgacactc tgccctgcct gtcattgctg caaagagctg ctgctttgcc aacctaagca   4620
aagaaaatac ggcttctctt gcattatttt cccttttggt tggtttgttt tctagaagta   4680
cgttcagatg ctttggggaa tgcaatgtat gatttgctag ctctctcacc acttaactca   4740
ctgtgaggat aaatatgcat gctttttgta attaactggt gctttgaaaa tcttttttaa   4800
gggagaaaaa tctcaaccaa agttatgctc atccagacaa gctgaccttt gagttaattt   4860
cagcacaact cattcttcag tgcctcatga ctgaaaacaa aaaaaaaaaa aaaaaaaa     4918
```

<210> SEQ ID NO 25
<211> LENGTH: 3490
<212> TYPE: DNA
<213> ORGANISM: homo sapien

<400> SEQUENCE: 25
agcgggctgg aagtgcgggc ttctgcagca gccgaagctg gagctgctag ggcagcagcg 60
gctcccctgt tgtatggaca ttctgcaccc gaaactgata gctgagtcct gaagttttat 120
gttatgaaac agaagaactt tcatcccagc acatgatttg ggaattacac tttgtgacat 180
ggatgaatat gcactgaccc ttggtacaat agatgtttct tatctgccac attcatcaga 240
atacagtgtt ggtcgatgta agcacacaag tgaggaatgg ggtgagtgtg gctttagacc 300
caccgtcttc agatctgcaa ctttaaaatg gaaagaaagc ctaatgagtc ggaaaaggcc 360
atttgttgga agatgttgtt actcctgcac tccccagagc tgggacaaat ttttcaacac 420
cagtatcccg tctttgggtt tgcggaatgt tatttatatc aatgaaactc acacaagaca 480
ccgcggatgg cttgcaagac gcctttctta cgttcttttt attcaagagc gagatgtgca 540
taagggcatg tttgccacca atgtgactga aaatgtgctg aacagcagta gagtacaaga 600
ggcaattgca gaagtggctg ctgaattaaa ccctgatggt tctgcccagc agcaatcaaa 660
agccgttaac aaagtgaaaa agaaagctaa aaggattctt caagaaatgg ttgccactgt 720
ctcaccggca atgatcagac tgactgggtg ggtgctgcta aaactgttca acagcttctt 780
ttggaacatt caaattcaca aaggtcaact tgagatggtt aaagctgcaa ctgagacgaa 840
tttgccgctt ctgtttctac cagttcatag atcccatatt gactatctgc tgctcacttt 900
cattctcttc tgccataaca tcaaagcacc atacattgct tcaggcaata atctcaacat 960
cccaatcttc agtaccttga tccataagct tgggggcttc ttcatacgac gaaggctcga 1020
tgaaacacca gatggacgga aagatgttct ctatagagct ttgctccatg ggcatatagt 1080
tgaattactt cgacagcagc aattcttgga gatcttcctg gaaggcacac gttctaggag 1140
tggaaaaacc tcttgtgctc gggcaggact tttgtcagtt gtggtagata ctctgtctac 1200
caatgtcatc ccagacatct tgataatacc tgttggaatc tcctatgatc gcattatcga 1260
aggtcactac aatggtgaac aactgggcaa acctaagaag aatgagagcc tgtggagtgt 1320
agcaagaggt gttattagaa tgttacgaaa aaactatggt tgtgtccgag tggattttgc 1380
acagccattt tccttaaagg aatatttaga aagccaaagt cagaaaccgg tgtctgctct 1440
actttccctg gagcaagcgt tgttaccagc tatacttcct tcaagaccca gtgatgctgc 1500
tgatgaaggt agagacacgt ccattaatga gtccagaaat gcaacagatg aatccctacg 1560
aaggaggttg attgcaaatc tggctgagca tattctattc actgctagca agtcctgtgc 1620
cattatgtcc acacacattg tggcttgcct gctcctctac agacacaggc agggaattga 1680
tctctccaca ttggtcgaag acttctttgt gatgaaagag gaagtcctgg ctcgtgattt 1740
tgacctgggg ttctcaggaa attcagaaga tgtagtaatg catgccatac agctgctggg 1800
aaattgtgtc acaatcaccc acactagcag gaacgatgag tttttttatca cccccagcac 1860 aactgtccca tcagtcttcg aactcaactt ctacagcaat ggggtacttc atgtctttat 1920
catggaggcc atcatagctt gcagcottta tgcagttctg aacaagaggg gactgggggg 1980
tcccactagc accccaccta acctgatcag ccaggagcag ctggtgcgga aggcggccag 2040
cctgtgctac cttctctcca atgaaggcac catctcactg ccttgccaga cattttacca 2100

-continued

```
agtctgccat gaaacagtag gaaagtttat ccagtatggc attcttacag tggcagagca   2160

cgatgaccag gaagatatca gtcctagtct tgctgagcag cagtgggaca agaagcttcc   2220

agaacctttg tcttggagaa gtgatgaaga agatgaagac agtgactttg gggaggaaca   2280

gcgagattgc tacctgaagg tgagccaatc caaggagcac cagcagttta tcaccttctt   2340

acagagactc cttgggcctt tgctggaggc ctacagctct gctgccatct ttgttcacaa   2400

cttcagtggt cctgttccag aacctgagta tctgcaaaag ttgcacaaat acctaataac   2460

cagaacagaa agaaatgttg cagtatatgc tgagagtgcc acatattgtc ttgtgaagaa   2520

tgctgtgaaa atgtttaagg atattggggt tttcaaggag accaaacaaa agagagtgtc   2580

tgttttagaa ctgagcagca cttttctacc tcaatgcaac cgacaaaaac ttctagaata   2640

tattctgagt tttgtggtgc tgtaggtaac gtgtggcact gctggcaaat gaaggtcatg   2700

agatgagttc cttgtaggta caagcttctg gctcaagagt tgaaggtgcc atcgcagggt   2760

caggcctgcc ctgtcccgaa gtgatctcct ggaagacaag tgccttctcc atccatggat   2820

ctgtgatctt cccagctctg catcaacaca gcagcctgca gataacactt ggggggacct   2880

cagcctctat tcgcaactca taatccgtag actacaagat gaaatctcaa taaattattt   2940

ttgagtttat taaagattga cattttaagt acaactttta aggactaatt actgtgatgg   3000

acacagaaat gtagctgtgt tctggaactg aatcttacat ggtatactta gtgctgctgg   3060

gtaatttgtt ggtatattat ctggttagtg gttaatgctt cctttaaaaa taattgagtc   3120

atccattcac tctttttcag ttttatctgt caatagtagc tacattttta atgggagcac   3180

cttttatccc aaagtgcttt ataaattgag tggactgata tatatcacac ccaggtatca   3240

ctgtgctgtc ctttgctgtc agatttagaa atgtttttaa gagctatgtg aaaacagaca   3300

atattagttt aggtcgggaa ctgagatatt gtaatcaaat agttaacatc aggaagttaa   3360

tttggctggc aaaattctag ggaaacttgg ccagaaaact ggtgttgaag gcttttgctc   3420

atataaacaa gtgccattga gtttcaaatg accagcaaat atatttagaa ctcaaaaaaa   3480

aaaaaaaaaa                                                          3490
```

```
<210> SEQ ID NO 26
<211> LENGTH: 2855
<212> TYPE: DNA
<213> ORGANISM: homo sapien

<400> SEQUENCE: 26

aactttcatc ccagcacatg atttgggaat tacactttgt gacatggatg aatctgcact     60

gacccttggt acaatagatg tttcttatct gccacattca tcagaataca gtgttggtcg    120

atgtaagcac acaagtgagg aatggggtga gtgtggcttt agacccaccg tcttcagatc    180

tgcaacttta aaatggaaag aaagcctaat gagtcggaaa aggccatttg ttggaagatg    240

ttgttactcc tgcactcccc agagctggga caaatttttc aaccccagta tcccgtcttt    300

gggtttgcgg aatgttattt atatcaatga aactcacaca agacaccgcg gatggcttgc    360

aagacgcctt tcttacgttc tttttattca agagcgagat gtgcataagg gcatgtttgc    420

caccaatgtg actgaaaatg tgctgaacag cagtagagta caagaggcaa ttgcagaagt    480

ggctgctgaa ttaaaccctg atggttctgc ccagcagcaa tcaaaagccg ttaacaaagt    540

gaaaaagaaa gctaaaagga ttcttcaaga aatggttgcc actgtctcac cggcaatgat    600

cagactgact gggtgggtgc tgctaaaact gttcaacagc ttcttttgga acattcaaat    660

tcacaaaggt caacttgaga tggttaaagc tgcaactgag acgaatttgc cgcttctgtt    720
```

```
tctaccagtt catagatccc atattgacta tctgctgctc actttcattc tcttctgcca    780

taacatcaaa gcaccataca ttgcttcagg caataatctc aacatcccaa tcttcagtac    840

cttgatccat aagcttgggg gcttcttcat acgacgaagg ctcgatgaaa caccagatgg    900

acggaaagat gttctctata gagctttgct ccatgggcat atagttgaat tacttcgaca    960

gcagcaattc ttggagatct tcctggaagg cacacgttct aggagtggaa aaacctcttg   1020

tgctcgggca ggacttttgt cagttgtggt agatactctg tctaccaatg tcatcccaga   1080

catcttgata atacctgttg gaatctccta tgatcgcatt atcgaaggtc actacaatgg   1140

tgaacaactg ggcaaaccta agaagaatga gagcctgtgg agtgtagcaa gaggtgttac   1200

tagaatgtta cgaaaaaact atggttgtgt ccgagtggat tttgcacagc cattttcctt   1260

aaaggaatat ttagaaagcc aaagtcagaa accggtgtct gctctacttt ccctggagca   1320

agcgttgtta ccagctatac ttccttcaag acccagtgat gctgctgatg aaggtagaga   1380

cacgtccatt aatgagtcca gaaatgcaac agatgaatcc ctacgaagga ggttgattgc   1440

aaatctggct gagcatattc tattcactgc tagcaagtcc tgtgccatta tgtccacaca   1500

cattgtggct tgcctgctcc tctacagaca caggcaggga attgatctct ccacattggt   1560

cgaagacttc tttgtgatga aagaggaagt cctggctcgt gattttgacc tggggttctc   1620

aggaaattca gaagatgtag taatgcatgc catacagctg ctgggaaatt gtgtcacaat   1680

cacccacact agcaggaacg atgagttttt tatcaccccc agcacaactg tcccatcagt   1740

cttcgaactc aacttctaca gcaatggggt acttcatgtc tttatcatgg aggccatcat   1800

agcttgcagc ctttatgcag ttctgaacaa gaggggactg gggggtccca ctagcacccc   1860

acctaacctg atcagccagg agcagctggt gcggaaggcg gccagcctgt gctaccttct   1920

ctccaatgaa ggcaccatct cactgccttg ccagacattt taccaagtct gccatgaaac   1980

agtaggaaag tttatccagt atggcattct tacagtggca gagcacgatg accaggaaga   2040

tatcagtcct agtcttgctg agcagcagtg ggacaagaag cttcctgaac ctttgtcttg   2100

gagaagtgat gaagaagatg aagacagtga ctttggggag gaacagcgag attgctacct   2160

gaaggtgagc caatccaagg agcaccagca gtttatcacc ttcttacaga gactccttgg   2220

gcctttgctg gaggcctaca gctctgctgc catctttgtt cacaacttca gtggtcctgt   2280

tccagaacct gagtatctgc aaaagttgca caaataccta ataaccagaa cagaaagaaa   2340

tgttgcagta tatgctgaga gtgccacata ttgtcttgtg aagaatgctg tgaaaatgtt   2400

taaggatatt ggggttttca aggagaccaa acaaaagaga gtgtctgttt tagaactgag   2460

cagcactttt ctacctcaat gcaaccgaca aaaacttcta gaatatattc tgagttttgt   2520

ggtgctgtag gtaacgtgtg gcactgctgg caaatgaagg tcatgagatg agttccttgt   2580

aggtaccagc ttctggctca agagttgaag gtgccgtcgc agggtcaggc ctgccctgtc   2640

ccgaggtgat ctcctggaag acaagtgcct tctccctcca tggatctgtg atcttcccag   2700

ctctgcatca acacagcagc ctgcagataa cacttggggg gacctcagcc tctattcgca   2760

actcataatc cgtagactac aagatgaaat ctcaataaat tatttttgag tttattaaag   2820

aggtctttta aggcaaaaaa aaaaaaaaaa aaaaa                              2855
```

<210> SEQ ID NO 27
<211> LENGTH: 828
<212> TYPE: PRT
<213> ORGANISM: homo sapien

<400> SEQUENCE: 27

```
Met Asp Glu Ser Ala Leu Thr Leu Gly Thr Ile Asp Val Ser Tyr Leu
1               5                   10                  15

Pro His Ser Ser Glu Tyr Ser Val Gly Arg Cys Lys His Thr Ser Glu
            20                  25                  30

Glu Trp Gly Glu Cys Gly Phe Arg Pro Thr Ile Phe Arg Ser Ala Thr
        35                  40                  45

Leu Lys Trp Lys Glu Ser Leu Met Ser Arg Lys Arg Pro Phe Val Gly
    50                  55                  60

Arg Cys Cys Tyr Ser Cys Thr Pro Gln Ser Trp Asp Lys Phe Phe Asn
65                  70                  75                  80

Pro Ser Ile Pro Ser Leu Gly Leu Arg Asn Val Ile Tyr Ile Asn Glu
                85                  90                  95

Thr His Thr Arg His Arg Gly Trp Leu Ala Arg Arg Leu Ser Tyr Val
            100                 105                 110

Leu Phe Ile Gln Glu Arg Asp Val His Lys Gly Met Phe Ala Thr Asn
        115                 120                 125

Val Thr Glu Asn Val Leu Asn Ser Ser Arg Val Gln Glu Ala Ile Ala
    130                 135                 140

Glu Val Ala Ala Glu Leu Asn Pro Asp Gly Ser Ala Gln Gln Gln Ser
145                 150                 155                 160

Lys Ala Val Asn Lys Val Lys Lys Lys Ala Lys Arg Ile Leu Gln Glu
                165                 170                 175

Met Val Ala Thr Val Ser Pro Ala Met Ile Arg Leu Thr Gly Trp Val
            180                 185                 190

Leu Leu Lys Leu Phe Asn Ser Phe Phe Trp Asn Ile Gln Ile His Lys
        195                 200                 205

Gly Gln Leu Glu Met Val Lys Ala Ala Thr Glu Thr Asn Leu Pro Leu
    210                 215                 220

Leu Phe Leu Pro Val His Arg Ser His Ile Asp Tyr Leu Leu Leu Thr
225                 230                 235                 240

Phe Ile Leu Phe Cys His Asn Ile Lys Ala Pro Tyr Ile Ala Ser Gly
                245                 250                 255

Asn Asn Leu Asn Ile Pro Ile Phe Ser Thr Leu Ile His Lys Leu Gly
            260                 265                 270

Gly Phe Phe Ile Arg Arg Arg Leu Asp Glu Thr Pro Asp Gly Arg Lys
        275                 280                 285

Asp Val Leu Tyr Arg Ala Leu Leu His Gly His Ile Val Glu Leu Leu
    290                 295                 300

Arg Gln Gln Gln Phe Leu Glu Ile Phe Leu Glu Gly Thr Arg Ser Arg
305                 310                 315                 320

Ser Gly Lys Thr Ser Cys Ala Arg Ala Gly Leu Leu Ser Val Val Val
                325                 330                 335

Asp Thr Leu Ser Thr Asn Val Ile Pro Asp Ile Leu Ile Ile Pro Val
            340                 345                 350

Gly Ile Ser Tyr Asp Arg Ile Ile Glu Gly His Tyr Asn Gly Glu Gln
        355                 360                 365

Leu Gly Lys Pro Lys Lys Asn Glu Ser Leu Trp Ser Val Ala Arg Gly
    370                 375                 380

Val Ile Arg Met Leu Arg Lys Asn Tyr Gly Cys Val Arg Val Asp Phe
385                 390                 395                 400

Ala Gln Pro Phe Ser Leu Lys Glu Tyr Leu Glu Ser Gln Ser Gln Lys
                405                 410                 415
```

```
Pro Val Ser Ala Leu Leu Ser Leu Glu Gln Ala Leu Leu Pro Ala Ile
            420                 425                 430

Leu Pro Ser Arg Pro Ser Asp Ala Ala Asp Glu Gly Arg Asp Thr Ser
        435                 440                 445

Ile Asn Glu Ser Arg Asn Ala Thr Asp Glu Ser Leu Arg Arg Arg Leu
    450                 455                 460

Ile Ala Asn Leu Ala Glu His Ile Leu Phe Thr Ala Ser Lys Ser Cys
465                 470                 475                 480

Ala Ile Met Ser Thr His Ile Val Ala Cys Leu Leu Leu Tyr Arg His
                485                 490                 495

Arg Gln Gly Ile Asp Leu Ser Thr Leu Val Glu Asp Phe Phe Val Met
            500                 505                 510

Lys Glu Glu Val Leu Ala Arg Asp Phe Asp Leu Gly Phe Ser Gly Asn
        515                 520                 525

Ser Glu Asp Val Val Met His Ala Ile Gln Leu Leu Gly Asn Cys Val
    530                 535                 540

Thr Ile Thr His Thr Ser Arg Asn Asp Glu Phe Phe Ile Thr Pro Ser
545                 550                 555                 560

Thr Thr Val Pro Ser Val Phe Glu Leu Asn Phe Tyr Ser Asn Gly Val
                565                 570                 575

Leu His Val Phe Ile Met Glu Ala Ile Ile Ala Cys Ser Leu Tyr Ala
            580                 585                 590

Val Leu Asn Lys Arg Gly Leu Gly Gly Pro Thr Ser Thr Pro Pro Asn
        595                 600                 605

Leu Ile Ser Gln Glu Gln Leu Val Arg Lys Ala Ala Ser Leu Cys Tyr
    610                 615                 620

Leu Leu Ser Asn Glu Gly Thr Ile Ser Leu Pro Cys Gln Thr Phe Tyr
625                 630                 635                 640

Gln Val Cys His Glu Thr Val Gly Lys Phe Ile Gln Tyr Gly Ile Leu
                645                 650                 655

Thr Val Ala Glu His Asp Asp Gln Glu Asp Ile Ser Pro Ser Leu Ala
            660                 665                 670

Glu Gln Gln Trp Asp Lys Lys Leu Pro Glu Pro Leu Ser Trp Arg Ser
        675                 680                 685

Asp Glu Glu Asp Glu Asp Ser Asp Phe Gly Glu Glu Gln Arg Asp Cys
    690                 695                 700

Tyr Leu Lys Val Ser Gln Ser Lys Glu His Gln Gln Phe Ile Thr Phe
705                 710                 715                 720

Leu Gln Arg Leu Leu Gly Pro Leu Leu Glu Ala Tyr Ser Ser Ala Ala
                725                 730                 735

Ile Phe Val His Asn Phe Ser Gly Pro Val Pro Glu Pro Glu Tyr Leu
            740                 745                 750

Gln Lys Leu His Lys Tyr Leu Ile Thr Arg Thr Glu Arg Asn Val Ala
        755                 760                 765

Val Tyr Ala Glu Ser Ala Thr Tyr Cys Leu Val Lys Asn Ala Val Lys
    770                 775                 780

Met Phe Lys Asp Ile Gly Val Phe Lys Glu Thr Lys Gln Lys Arg Val
785                 790                 795                 800

Ser Val Leu Glu Leu Ser Ser Thr Phe Leu Pro Gln Cys Asn Arg Gln
                805                 810                 815

Lys Leu Leu Glu Tyr Ile Leu Ser Phe Val Val Leu
            820                 825
```

<210> SEQ ID NO 28
<211> LENGTH: 710
<212> TYPE: PRT
<213> ORGANISM: homo sapien

<400> SEQUENCE: 28

Met Asp Glu Ser Ala Leu Thr Leu Gly Thr Ile Asp Val Ser Tyr Leu
1 5 10 15

Pro His Ser Ser Glu Tyr Ser Val Gly Arg Cys Lys His Thr Ser Glu
20 25 30

Glu Trp Gly Glu Cys Gly Phe Arg Pro Thr Ile Phe Arg Ser Ala Thr
35 40 45

Leu Lys Trp Lys Glu Ser Leu Met Ser Arg Lys Arg Pro Phe Val Gly
50 55 60

Arg Cys Cys Tyr Ser Cys Thr Pro Gln Ser Trp Asp Lys Phe Phe Asn
65 70 75 80

Pro Ser Ile Pro Ser Leu Gly Leu Arg Asn Val Ile Tyr Ile Asn Glu
85 90 95

Thr His Thr Arg His Arg Gly Trp Leu Ala Arg Arg Leu Ser Tyr Val
100 105 110

Leu Phe Ile Gln Glu Arg Asp Val His Lys Gly Met Phe Ala Thr Asn
115 120 125

Val Thr Glu Asn Val Leu Asn Ser Ser Arg Val Gln Glu Ala Ile Ala
130 135 140

Glu Val Ala Ala Glu Leu Asn Pro Asp Gly Ser Ala Gln Gln Gln Ser
145 150 155 160

Lys Ala Val Asn Lys Val Lys Lys Lys Ala Lys Arg Ile Leu Gln Glu
165 170 175

Met Val Ala Thr Val Ser Pro Ala Met Ile Arg Leu Thr Gly Trp Val
180 185 190

Leu Leu Lys Leu Phe Asn Ser Phe Phe Trp Asn Ile Gln Ile His Lys
195 200 205

Gly Gln Leu Glu Met Val Lys Ala Ala Thr Glu Thr Asn Leu Pro Leu
210 215 220

Leu Phe Leu Pro Val His Arg Ser His Ile Asp Tyr Leu Leu Leu Thr
225 230 235 240

Phe Ile Leu Phe Cys His Asn Ile Lys Ala Pro Tyr Ile Ala Ser Gly
245 250 255

Asn Asn Leu Asn Ile Pro Ile Phe Ser Thr Leu Ile His Lys Leu Gly
260 265 270

Gly Phe Phe Ile Arg Arg Arg Leu Asp Glu Thr Pro Asp Gly Arg Lys
275 280 285

Asp Val Leu Tyr Arg Ala Leu Leu His Gly His Ile Val Glu Leu Leu
290 295 300

Arg Gln Gln Gln Phe Leu Glu Ile Phe Leu Glu Gly Thr Arg Ser Arg
305 310 315 320

Ser Gly Lys Thr Ser Cys Ala Arg Ala Gly Leu Leu Ser Val Val Val
325 330 335

Asp Thr Leu Ser Thr Asn Val Ile Pro Asp Ile Leu Ile Ile Pro Val
340 345 350

Gly Ile Ser Tyr Asp Arg Ile Ile Glu Gly His Tyr Asn Gly Glu Gln
355 360 365

Leu Gly Lys Pro Lys Lys Asn Glu Ser Leu Trp Ser Val Ala Arg Gly
370 375 380

```
Val Ile Arg Met Leu Arg Lys Asn Tyr Gly Cys Val Arg Val Asp Phe
385                 390                 395                 400

Ala Gln Pro Phe Ser Leu Lys Glu Tyr Leu Glu Ser Gln Ser Gln Lys
                405                 410                 415

Pro Val Ser Ala Leu Leu Ser Leu Glu Gln Ala Leu Leu Pro Ala Ile
            420                 425                 430

Leu Pro Ser Arg Pro Ser Asp Ala Ala Asp Glu Gly Arg Asp Thr Ser
        435                 440                 445

Ile Asn Glu Ser Arg Asn Ala Thr Asp Glu Ser Leu Arg Arg Arg Leu
    450                 455                 460

Ile Ala Asn Leu Ala Glu His Ile Leu Phe Thr Ala Ser Lys Ser Cys
465                 470                 475                 480

Ala Ile Met Ser Thr His Ile Val Ala Cys Leu Leu Leu Tyr Arg His
                485                 490                 495

Arg Gln Gly Ile Asp Leu Ser Thr Leu Val Glu Asp Phe Phe Val Met
            500                 505                 510

Lys Glu Glu Val Leu Ala Arg Asp Phe Asp Leu Gly Phe Ser Gly Asn
        515                 520                 525

Ser Glu Asp Val Val Met His Ala Ile Gln Leu Leu Gly Asn Cys Val
    530                 535                 540

Thr Ile Thr His Thr Ser Arg Asn Asp Glu Phe Phe Ile Thr Pro Ser
545                 550                 555                 560

Thr Thr Val Pro Ser Val Phe Glu Leu Asn Phe Tyr Ser Asn Gly Val
                565                 570                 575

Leu His Val Phe Ile Met Glu Ala Ile Ile Ala Cys Ser Leu Tyr Ala
            580                 585                 590

Val Leu Asn Lys Arg Gly Leu Gly Gly Pro Thr Ser Thr Pro Pro Asn
        595                 600                 605

Leu Ile Ser Gln Glu Gln Leu Val Arg Lys Ala Ala Ser Leu Cys Tyr
    610                 615                 620

Leu Leu Ser Asn Glu Gly Thr Ile Ser Leu Pro Cys Gln Thr Phe Tyr
625                 630                 635                 640

Gln Val Cys His Glu Thr Val Gly Lys Phe Ile Gln Tyr Gly Ile Leu
                645                 650                 655

Thr Val Ala Glu His Asp Asp Gln Glu Asp Ile Ser Pro Ser Leu Ala
            660                 665                 670

Glu Gln Gln Trp Asp Lys Lys Leu Pro Glu Pro Leu Ser Trp Arg Ser
        675                 680                 685

Asp Glu Glu Asp Glu Asp Ser Asp Phe Gly Glu Glu Gln Arg Asp Cys
    690                 695                 700

Tyr Leu Lys Val Leu Gly
705                 710


<210> SEQ ID NO 29
<211> LENGTH: 828
<212> TYPE: PRT
<213> ORGANISM: homo sapien

<400> SEQUENCE: 29

Met Asp Glu Ser Ala Leu Thr Leu Gly Thr Ile Asp Val Ser Tyr Leu
1               5                   10                  15

Pro His Ser Ser Glu Tyr Ser Val Gly Arg Cys Lys His Thr Ser Glu
            20                  25                  30

Glu Trp Gly Glu Cys Gly Phe Arg Pro Thr Val Phe Arg Ser Ala Thr
```

```
        35                  40                  45

Leu Lys Trp Lys Glu Ser Leu Met Ser Arg Lys Arg Pro Phe Val Gly
    50                  55                  60

Arg Cys Cys Tyr Ser Cys Thr Pro Gln Ser Trp Asp Lys Phe Phe Asn
65                  70                  75                  80

Pro Ser Ile Pro Ser Leu Gly Leu Arg Asn Val Ile Tyr Ile Asn Glu
                85                  90                  95

Thr His Thr Arg His Arg Gly Trp Leu Ala Arg Arg Leu Ser Tyr Val
            100                 105                 110

Leu Phe Ile Gln Glu Arg Asp Val His Lys Gly Met Phe Ala Thr Asn
        115                 120                 125

Val Thr Glu Asn Val Leu Asn Ser Ser Arg Val Gln Glu Ala Ile Ala
    130                 135                 140

Glu Val Ala Ala Glu Leu Asn Pro Asp Gly Ser Ala Gln Gln Gln Ser
145                 150                 155                 160

Lys Ala Val Asn Lys Val Lys Lys Lys Ala Lys Arg Ile Leu Gln Glu
                165                 170                 175

Met Val Ala Thr Val Ser Pro Ala Met Ile Arg Leu Thr Gly Trp Val
            180                 185                 190

Leu Leu Lys Leu Phe Asn Ser Phe Phe Trp Asn Ile Gln Ile His Lys
        195                 200                 205

Gly Gln Leu Glu Met Val Lys Ala Ala Thr Glu Thr Asn Leu Pro Leu
    210                 215                 220

Leu Phe Leu Pro Val His Arg Ser His Ile Asp Tyr Leu Leu Leu Thr
225                 230                 235                 240

Phe Ile Leu Phe Cys His Asn Ile Lys Ala Pro Tyr Ile Ala Ser Gly
                245                 250                 255

Asn Asn Leu Asn Ile Pro Ile Phe Ser Thr Leu Ile His Lys Leu Gly
            260                 265                 270

Gly Phe Phe Ile Arg Arg Arg Leu Asp Glu Thr Pro Asp Gly Arg Lys
        275                 280                 285

Asp Val Leu Tyr Arg Ala Leu Leu His Gly His Ile Val Glu Leu Leu
    290                 295                 300

Arg Gln Gln Gln Phe Leu Glu Ile Phe Leu Glu Gly Thr Arg Ser Arg
305                 310                 315                 320

Ser Gly Lys Thr Ser Cys Ala Arg Ala Gly Leu Leu Ser Val Val Val
                325                 330                 335

Asp Thr Leu Ser Thr Asn Val Ile Pro Asp Ile Leu Ile Ile Pro Val
            340                 345                 350

Gly Ile Ser Tyr Asp Arg Ile Ile Glu Gly His Tyr Asn Gly Glu Gln
        355                 360                 365

Leu Gly Lys Pro Lys Lys Asn Glu Ser Leu Trp Ser Val Ala Arg Gly
    370                 375                 380

Val Ile Arg Met Leu Arg Lys Asn Tyr Gly Cys Val Arg Val Asp Phe
385                 390                 395                 400

Ala Gln Pro Phe Ser Leu Lys Glu Tyr Leu Glu Ser Gln Ser Gln Lys
                405                 410                 415

Pro Val Ser Ala Leu Leu Ser Leu Glu Gln Ala Leu Leu Pro Ala Ile
            420                 425                 430

Leu Pro Ser Arg Pro Ser Asp Ala Ala Asp Glu Gly Arg Asp Thr Ser
        435                 440                 445

Ile Asn Glu Ser Arg Asn Ala Thr Asp Glu Ser Leu Arg Arg Arg Leu
    450                 455                 460
```

Ile Ala Asn Leu Ala Glu His Ile Leu Phe Thr Ala Ser Lys Ser Cys
465 470 475 480

Ala Ile Met Ser Thr His Ile Val Ala Cys Leu Leu Leu Tyr Arg His
485 490 495

Arg Gln Gly Ile Asp Leu Ser Thr Leu Val Glu Asp Phe Phe Val Met
500 505 510

Lys Glu Glu Val Leu Ala Arg Asp Phe Asp Leu Gly Phe Ser Gly Asn
515 520 525

Ser Glu Asp Val Val Met His Ala Ile Gln Leu Leu Gly Asn Cys Val
530 535 540

Thr Ile Thr His Thr Ser Arg Asn Asp Glu Phe Phe Ile Thr Pro Ser
545 550 555 560

Thr Thr Val Pro Ser Val Phe Glu Leu Asn Phe Tyr Ser Asn Gly Val
565 570 575

Leu His Val Phe Ile Met Glu Ala Ile Ile Ala Cys Ser Leu Tyr Ala
580 585 590

Val Leu Asn Lys Arg Gly Leu Gly Gly Pro Thr Ser Thr Pro Pro Asn
595 600 605

Leu Ile Ser Gln Glu Gln Leu Val Arg Lys Ala Ala Ser Leu Cys Tyr
610 615 620

Leu Leu Ser Asn Glu Gly Thr Ile Ser Leu Pro Cys Gln Thr Phe Tyr
625 630 635 640

Gln Val Cys His Glu Thr Val Gly Lys Phe Ile Gln Tyr Gly Ile Leu
645 650 655

Thr Val Ala Glu His Asp Asp Gln Glu Asp Ile Ser Pro Ser Leu Ala
660 665 670

Glu Gln Gln Trp Asp Lys Lys Leu Pro Glu Pro Leu Ser Trp Arg Ser
675 680 685

Asp Glu Glu Asp Glu Asp Ser Asp Phe Gly Glu Glu Gln Arg Asp Cys
690 695 700

Tyr Leu Lys Val Ser Gln Ser Lys Glu His Gln Gln Phe Ile Thr Phe
705 710 715 720

Leu Gln Arg Leu Leu Gly Pro Leu Leu Glu Ala Tyr Ser Ser Ala Ala
725 730 735

Ile Phe Val His Asn Phe Ser Gly Pro Val Pro Glu Pro Glu Tyr Leu
740 745 750

Gln Lys Leu His Lys Tyr Leu Ile Thr Arg Thr Glu Arg Asn Val Ala
755 760 765

Val Tyr Ala Glu Ser Ala Thr Tyr Cys Leu Val Lys Asn Ala Val Lys
770 775 780

Met Phe Lys Asp Ile Gly Val Phe Lys Glu Thr Lys Gln Lys Arg Val
785 790 795 800

Ser Val Leu Glu Leu Ser Ser Thr Phe Leu Pro Gln Cys Asn Arg Gln
805 810 815

Lys Leu Leu Glu Tyr Ile Leu Ser Phe Val Val Leu
820 825

<210> SEQ ID NO 30
<211> LENGTH: 710
<212> TYPE: PRT
<213> ORGANISM: homo sapien

<400> SEQUENCE: 30

Met Asp Glu Ser Ala Leu Thr Leu Gly Thr Ile Asp Val Ser Tyr Leu

-continued

```
1               5                   10                  15

Pro His Ser Ser Glu Tyr Ser Val Gly Arg Cys Lys His Thr Ser Glu
            20                  25                  30

Glu Trp Gly Glu Cys Gly Phe Arg Pro Thr Val Phe Arg Ser Ala Thr
        35                  40                  45

Leu Lys Trp Lys Glu Ser Leu Met Ser Arg Lys Arg Pro Phe Val Gly
    50                  55                  60

Arg Cys Cys Tyr Ser Cys Thr Pro Gln Ser Trp Asp Lys Phe Phe Asn
65                  70                  75                  80

Pro Ser Ile Pro Ser Leu Gly Leu Arg Asn Val Ile Tyr Ile Asn Glu
                85                  90                  95

Thr His Thr Arg His Arg Gly Trp Leu Ala Arg Arg Leu Ser Tyr Val
            100                 105                 110

Leu Phe Ile Gln Glu Arg Asp Val His Lys Gly Met Phe Ala Thr Asn
        115                 120                 125

Val Thr Glu Asn Val Leu Asn Ser Ser Arg Val Gln Glu Ala Ile Ala
    130                 135                 140

Glu Val Ala Ala Glu Leu Asn Pro Asp Gly Ser Ala Gln Gln Gln Ser
145                 150                 155                 160

Lys Ala Val Asn Lys Val Lys Lys Lys Ala Lys Arg Ile Leu Gln Glu
                165                 170                 175

Met Val Ala Thr Val Ser Pro Ala Met Ile Arg Leu Thr Gly Trp Val
            180                 185                 190

Leu Leu Lys Leu Phe Asn Ser Phe Phe Trp Asn Ile Gln Ile His Lys
        195                 200                 205

Gly Gln Leu Glu Met Val Lys Ala Ala Thr Glu Thr Asn Leu Pro Leu
    210                 215                 220

Leu Phe Leu Pro Val His Arg Ser His Ile Asp Tyr Leu Leu Leu Thr
225                 230                 235                 240

Phe Ile Leu Phe Cys His Asn Ile Lys Ala Pro Tyr Ile Ala Ser Gly
                245                 250                 255

Asn Asn Leu Asn Ile Pro Ile Phe Ser Thr Leu Ile His Lys Leu Gly
            260                 265                 270

Gly Phe Phe Ile Arg Arg Arg Leu Asp Glu Thr Pro Asp Gly Arg Lys
        275                 280                 285

Asp Val Leu Tyr Arg Ala Leu Leu His Gly His Ile Val Glu Leu Leu
    290                 295                 300

Arg Gln Gln Gln Phe Leu Glu Ile Phe Leu Glu Gly Thr Arg Ser Arg
305                 310                 315                 320

Ser Gly Lys Thr Ser Cys Ala Arg Ala Gly Leu Leu Ser Val Val Val
                325                 330                 335

Asp Thr Leu Ser Thr Asn Val Ile Pro Asp Ile Leu Ile Ile Pro Val
            340                 345                 350

Gly Ile Ser Tyr Asp Arg Ile Ile Glu Gly His Tyr Asn Gly Glu Gln
        355                 360                 365

Leu Gly Lys Pro Lys Lys Asn Glu Ser Leu Trp Ser Val Ala Arg Gly
    370                 375                 380

Val Ile Arg Met Leu Arg Lys Asn Tyr Gly Cys Val Arg Val Asp Phe
385                 390                 395                 400

Ala Gln Pro Phe Ser Leu Lys Glu Tyr Leu Glu Ser Gln Ser Gln Lys
                405                 410                 415

Pro Val Ser Ala Leu Leu Ser Leu Glu Gln Ala Leu Leu Pro Ala Ile
            420                 425                 430
```

```
Leu Pro Ser Arg Pro Ser Asp Ala Ala Asp Glu Gly Arg Asp Thr Ser
        435                 440                 445

Ile Asn Glu Ser Arg Asn Ala Thr Asp Glu Ser Leu Arg Arg Arg Leu
    450                 455                 460

Ile Ala Asn Leu Ala Glu His Ile Leu Phe Thr Ala Ser Lys Ser Cys
465                 470                 475                 480

Ala Ile Met Ser Thr His Ile Val Ala Cys Leu Leu Leu Tyr Arg His
                485                 490                 495

Arg Gln Gly Ile Asp Leu Ser Thr Leu Val Glu Asp Phe Phe Val Met
            500                 505                 510

Lys Glu Glu Val Leu Ala Arg Asp Phe Asp Leu Gly Phe Ser Gly Asn
        515                 520                 525

Ser Glu Asp Val Val Met His Ala Ile Gln Leu Leu Gly Asn Cys Val
    530                 535                 540

Thr Ile Thr His Thr Ser Arg Asn Asp Glu Phe Phe Ile Thr Pro Ser
545                 550                 555                 560

Thr Thr Val Pro Ser Val Phe Glu Leu Asn Phe Tyr Ser Asn Gly Val
                565                 570                 575

Leu His Val Phe Ile Met Glu Ala Ile Ile Ala Cys Ser Leu Tyr Ala
            580                 585                 590

Val Leu Asn Lys Arg Gly Leu Gly Gly Pro Thr Ser Thr Pro Pro Asn
        595                 600                 605

Leu Ile Ser Gln Glu Gln Leu Val Arg Lys Ala Ala Ser Leu Cys Tyr
    610                 615                 620

Leu Leu Ser Asn Glu Gly Thr Ile Ser Leu Pro Cys Gln Thr Phe Tyr
625                 630                 635                 640

Gln Val Cys His Glu Thr Val Gly Lys Phe Ile Gln Tyr Gly Ile Leu
                645                 650                 655

Thr Val Ala Glu His Asp Asp Gln Glu Asp Ile Ser Pro Ser Leu Ala
            660                 665                 670

Glu Gln Gln Trp Asp Lys Lys Leu Pro Glu Pro Leu Ser Trp Arg Ser
        675                 680                 685

Asp Glu Glu Asp Glu Asp Ser Asp Phe Gly Glu Glu Gln Arg Asp Cys
    690                 695                 700

Tyr Leu Lys Val Leu Gly
705                 710
```

<210> SEQ ID NO 31
<211> LENGTH: 20
<212> TYPE: DNA
<213> ORGANISM: artificial sequence
<220> FEATURE:
<223> OTHER INFORMATION: gRNA Recognition Sequence

<400> SEQUENCE: 31
atggcctttt ccgactcatt 20

<210> SEQ ID NO 32
<211> LENGTH: 20
<212> TYPE: DNA
<213> ORGANISM: artificial sequence
<220> FEATURE:
<223> OTHER INFORMATION: gRNA Recognition Sequence

<400> SEQUENCE: 32
aaagcctaat gagtcggaaa 20

<210> SEQ ID NO 33
<211> LENGTH: 20
<212> TYPE: DNA
<213> ORGANISM: artificial sequence
<220> FEATURE:
<223> OTHER INFORMATION: gRNA Recognition Sequence

<400> SEQUENCE: 33
gtaaggttct tacccagctc 20

<210> SEQ ID NO 34
<211> LENGTH: 20
<212> TYPE: DNA
<213> ORGANISM: artificial sequence
<220> FEATURE:
<223> OTHER INFORMATION: gRNA Recognition Sequence

<400> SEQUENCE: 34
attagggtca ataagcagta 20

<210> SEQ ID NO 35
<211> LENGTH: 20
<212> TYPE: DNA
<213> ORGANISM: artificial sequence
<220> FEATURE:
<223> OTHER INFORMATION: gRNA Recognition Sequence

<400> SEQUENCE: 35
agtcggaaaa ggccatttgt 20

<210> SEQ ID NO 36
<211> LENGTH: 20
<212> TYPE: DNA
<213> ORGANISM: artificial sequence
<220> FEATURE:
<223> OTHER INFORMATION: gRNA Recognition Sequence

<400> SEQUENCE: 36
taaggttctt acccagctct 20

<210> SEQ ID NO 37
<211> LENGTH: 20
<212> TYPE: DNA
<213> ORGANISM: artificial sequence
<220> FEATURE:
<223> OTHER INFORMATION: gRNA Recognition Sequence

<400> SEQUENCE: 37
aatatttgtc agggtgagtg 20

<210> SEQ ID NO 38
<211> LENGTH: 20
<212> TYPE: DNA
<213> ORGANISM: artificial sequence
<220> FEATURE:
<223> OTHER INFORMATION: gRNA Recognition Sequence

<400> SEQUENCE: 38
gttgcagatc tgaagatggt 20

<210> SEQ ID NO 39
<211> LENGTH: 20
<212> TYPE: DNA
<213> ORGANISM: artificial sequence
<220> FEATURE:
<223> OTHER INFORMATION: gRNA Recognition Sequence

<400> SEQUENCE: 39
tacccagctc tggggagtgc 20

<210> SEQ ID NO 40
<211> LENGTH: 20
<212> TYPE: DNA
<213> ORGANISM: artificial sequence
<220> FEATURE:
<223> OTHER INFORMATION: gRNA Recognition Sequence

<400> SEQUENCE: 40
ggaaagaaag cctaatgagt 20

<210> SEQ ID NO 41
<211> LENGTH: 20
<212> TYPE: DNA
<213> ORGANISM: artificial sequence
<220> FEATURE:
<223> OTHER INFORMATION: gRNA Recognition Sequence

<400> SEQUENCE: 41
aaggttctta cccagctctg 20

<210> SEQ ID NO 42
<211> LENGTH: 20
<212> TYPE: DNA
<213> ORGANISM: artificial sequence
<220> FEATURE:
<223> OTHER INFORMATION: gRNA Recognition Sequence

<400> SEQUENCE: 42
agttgcagat ctgaagatgg 20

<210> SEQ ID NO 43
<211> LENGTH: 20
<212> TYPE: DNA
<213> ORGANISM: artificial sequence
<220> FEATURE:
<223> OTHER INFORMATION: gRNA Recognition Sequence

<400> SEQUENCE: 43
attatttcca actttgtagt 20

<210> SEQ ID NO 44
<211> LENGTH: 20
<212> TYPE: DNA
<213> ORGANISM: artificial sequence
<220> FEATURE:
<223> OTHER INFORMATION: gRNA Recognition Sequence

<400> SEQUENCE: 44
taacaacatc ttccaacaaa 20